US009283276B2

(12) United States Patent
Johns et al.

(10) Patent No.: US 9,283,276 B2
(45) Date of Patent: Mar. 15, 2016

(54) MONOCLONAL ANTIBODY 175 TARGETING THE EGF RECEPTOR AND DERIVATIVES AND USES THEREOF

(75) Inventors: Terrance Grant Johns, Clayton (AU); Elizabeth Stockert, Vienna (AT); Stephen Stockert, legal representative, Vienna (AT); Lloyd J. Old, New York, NY (US); Andrew M. Scott, Kew East (AU); Veronika M. Rayzman, Bentleigh (AU)

(73) Assignee: Ludwig Institute for Cancer Research Ltd., New York, NY (US)

( * ) Notice: Subject to any disclaimer, the term of this patent is extended or adjusted under 35 U.S.C. 154(b) by 1526 days.

(21) Appl. No.: 12/733,146

(22) PCT Filed: Aug. 14, 2008

(86) PCT No.: PCT/US2008/009771
§ 371 (c)(1),
(2), (4) Date: Mar. 1, 2011

(87) PCT Pub. No.: WO2009/023265
PCT Pub. Date: Feb. 19, 2009

(65) Prior Publication Data
US 2011/0150759 A1 Jun. 23, 2011

Related U.S. Application Data

(60) Provisional application No. 60/964,692, filed on Aug. 14, 2007.

(51) Int. Cl.
*C12P 21/08* (2006.01)
*A61K 45/06* (2006.01)
*G01N 33/574* (2006.01)
*G01N 33/74* (2006.01)
*A61K 39/395* (2006.01)
*C07K 16/28* (2006.01)
*G01N 33/50* (2006.01)
*A61K 39/00* (2006.01)

(52) U.S. Cl.
CPC .............. *A61K 45/06* (2013.01); *A61K 39/395* (2013.01); *C07K 16/2863* (2013.01); *G01N 33/5091* (2013.01); *G01N 33/57492* (2013.01); *G01N 33/74* (2013.01); *A61K 2039/505* (2013.01); *C07K 2299/00* (2013.01); *C07K 2317/33* (2013.01); *C07K 2317/34* (2013.01); *C07K 2317/55* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,137,230 A | 1/1979 | Hashimoto |
| 4,151,042 A | 4/1979 | Higashide |
| 4,169,888 A | 10/1979 | Hanka |
| 4,190,580 A | 2/1980 | Hashimoto |
| 4,225,494 A | 9/1980 | Higashide |
| 4,248,870 A | 2/1981 | Miyashita |
| 4,256,746 A | 3/1981 | Miyashita |
| 4,260,608 A | 4/1981 | Miyashita |
| 4,263,294 A | 4/1981 | Miyashita |
| 4,264,596 A | 4/1981 | Miyashita |
| 4,265,814 A | 5/1981 | Hashimoto |
| 4,294,757 A | 10/1981 | Asai |
| 4,307,016 A | 12/1981 | Asai |
| 4,308,268 A | 12/1981 | Miyashita |
| 4,308,269 A | 12/1981 | Miyashita |
| 4,309,428 A | 1/1982 | Miyashita |
| 4,313,946 A | 2/1982 | Powell |
| 4,317,821 A | 3/1982 | Miyashita |
| 4,322,348 A | 3/1982 | Asai |
| 4,331,598 A | 5/1982 | Hasegawa |
| 4,342,566 A | 8/1982 | Theofilopoulos |
| 4,360,462 A | 11/1982 | Higashide |
| 4,361,650 A | 11/1982 | Asai |
| 4,362,663 A | 12/1982 | Kida |
| 4,364,866 A | 12/1982 | Asai |
| 4,371,533 A | 2/1983 | Akimoto |
| 4,413,132 A | 11/1983 | Wierenga |

(Continued)

FOREIGN PATENT DOCUMENTS

| | | |
|---|---|---|
| EP | 0120694 A2 | 10/1984 |
| EP | 0125023 A1 | 11/1984 |

(Continued)

OTHER PUBLICATIONS

Mariuzza et al. (Annu. Rev. Biophys. Biophys. Chem., 16: 139-159, 1987).*

(Continued)

*Primary Examiner* — Brad Duffy
(74) *Attorney, Agent, or Firm* — McCarter & English, LLP; Cristin H. Cowles; Maneesh Gulati, Esq.

(57) ABSTRACT

The present invention relates to antibodies, particularly antibody 175, and fragments thereof or antibodies derived therefrom, which bind to the EGF receptor, particularly to amplified or overexpressed epidermal growth factor receptor (EGFR) and to the de2-7 EGFR truncation of the EGFR. These antibodies are useful in the diagnosis and treatment of cancer. Recombinant or hybrid antibodies having the variable region heavy or light chain sequence(s) of antibody 175 are also provided. The antibodies of the present invention may also be used in therapy in combination with chemotherapeutics or anti-cancer agents and/or with other antibodies or fragments thereof.

18 Claims, 10 Drawing Sheets

(56) References Cited

U.S. PATENT DOCUMENTS

| | | |
|---|---|---|
| 4,418,064 A | 11/1983 | Powell |
| 4,671,958 A | 6/1987 | Rodwell |
| 4,762,707 A | 8/1988 | Jansen |
| 4,816,567 A | 3/1989 | Cabilly et al. |
| 4,867,973 A | 9/1989 | Goers |
| 4,933,294 A | 6/1990 | Waterfield |
| 4,937,183 A | 6/1990 | Ultee |
| 4,943,533 A | 7/1990 | Mendelsohn et al. |
| 4,952,394 A | 8/1990 | Senter |
| 4,997,913 A | 3/1991 | Hellstrom |
| 5,013,547 A | 5/1991 | Sweet |
| 5,028,697 A | 7/1991 | Johnson |
| 5,034,223 A | 7/1991 | Abrams |
| 5,047,324 A | 9/1991 | Fredrickson |
| 5,087,616 A | 2/1992 | Myers |
| 5,106,951 A | 4/1992 | Morgan |
| 5,122,368 A | 6/1992 | Greenfield |
| 5,130,116 A | 7/1992 | Woo |
| 5,141,736 A | 8/1992 | Iwasa |
| 5,164,311 A | 11/1992 | Gupta |
| 5,171,563 A | 12/1992 | Abrams |
| 5,208,020 A | 5/1993 | Chari |
| 5,212,290 A | 5/1993 | Vogelstein |
| 5,217,713 A | 6/1993 | Iwasa |
| 5,225,539 A | 7/1993 | Winter |
| 5,306,809 A | 4/1994 | Boon |
| 5,332,837 A | 7/1994 | Kelly |
| 5,401,828 A | 3/1995 | Vogelstein |
| 5,416,064 A | 5/1995 | Chari |
| 5,457,105 A | 10/1995 | Barker |
| 5,459,061 A | 10/1995 | Sato |
| 5,475,092 A | 12/1995 | Chari |
| 5,541,339 A | 7/1996 | Kelly |
| 5,556,623 A | 9/1996 | Barton |
| 5,558,864 A | 9/1996 | Bendig |
| 5,563,250 A | 10/1996 | Hylarides |
| 5,585,499 A | 12/1996 | Chari |
| 5,606,017 A | 2/1997 | Willner |
| 5,612,474 A | 3/1997 | Patel |
| 5,622,929 A | 4/1997 | Willner |
| 5,635,483 A | 6/1997 | Pettit |
| 5,635,603 A | 6/1997 | Hansen |
| 5,639,641 A | 6/1997 | Pedersen |
| 5,643,573 A | 7/1997 | Barton |
| 5,665,358 A | 9/1997 | Barton |
| 5,674,977 A | 10/1997 | Gariepy |
| 5,677,171 A | 10/1997 | Hudziak |
| 5,708,146 A | 1/1998 | Willner |
| 5,708,156 A | 1/1998 | Ilekis |
| 5,720,954 A | 2/1998 | Hudziak |
| 5,739,350 A | 4/1998 | Kelly |
| 5,760,041 A | 6/1998 | Wissner |
| 5,770,195 A | 6/1998 | Hudziak |
| 5,780,588 A | 7/1998 | Pettit |
| 5,795,965 A | 8/1998 | Tsuchiya |
| 5,807,715 A | 9/1998 | Morrison |
| 5,814,317 A | 9/1998 | Vogelstein |
| 5,824,805 A | 10/1998 | King |
| 5,844,093 A | 12/1998 | Kettleborough |
| 5,846,545 A | 12/1998 | Chari |
| 5,851,526 A | 12/1998 | Welt |
| 5,869,045 A | 2/1999 | Hellstrom |
| 5,869,619 A | 2/1999 | Studnicka |
| 5,880,270 A | 3/1999 | Berninger |
| 5,891,996 A | 4/1999 | De Acosta Del Rio |
| 5,911,995 A | 6/1999 | Uckun |
| 5,942,602 A | 8/1999 | Wels et al. |
| 5,980,896 A | 11/1999 | Hellstrom |
| 6,010,902 A | 1/2000 | Ledbetter |
| 6,060,608 A | 5/2000 | Boger |
| 6,214,345 B1 | 4/2001 | Firestone |
| 6,217,866 B1 | 4/2001 | Schlessinger et al. |
| 6,224,868 B1 | 5/2001 | Wong |
| 6,235,883 B1 | 5/2001 | Jakobovits |
| 6,281,354 B1 | 8/2001 | Boger |
| 6,306,393 B1 | 10/2001 | Goldenberg |
| 6,331,175 B1 | 12/2001 | Goldenberg |
| 6,331,415 B1 | 12/2001 | Cabilly |
| 6,333,410 B1 | 12/2001 | Chari |
| 6,340,701 B1 | 1/2002 | Chari |
| 6,372,738 B2 | 4/2002 | Chari |
| 6,395,272 B1 | 5/2002 | Deo |
| 6,436,931 B1 | 8/2002 | Chari |
| 6,441,163 B1 | 8/2002 | Chari |
| 6,506,883 B2 | 1/2003 | De Acosta Del Rio |
| 6,512,101 B1 | 1/2003 | King |
| RE38,008 E | 2/2003 | Abrams |
| 6,534,660 B1 | 3/2003 | Yongxin |
| 6,548,530 B1 | 4/2003 | Boger |
| 6,570,024 B2 | 5/2003 | Eldridge |
| 6,586,618 B1 | 7/2003 | Zhao |
| 6,596,757 B1 | 7/2003 | Chari |
| 6,630,579 B2 | 10/2003 | Chari |
| 6,660,742 B2 | 12/2003 | Lee |
| 6,699,715 B1 | 3/2004 | Ledbetter |
| 6,706,708 B2 | 3/2004 | Chari |
| 6,716,821 B2 | 4/2004 | Zhao |
| 6,756,397 B2 | 6/2004 | Zhao |
| 6,759,509 B1 | 7/2004 | King |
| 6,790,954 B2 | 9/2004 | Chung |
| 6,797,492 B2 | 9/2004 | Daugherty |
| 6,884,869 B2 | 4/2005 | Senter |
| 6,884,874 B2 | 4/2005 | Eldridge |
| 6,913,748 B2 | 7/2005 | Widdison |
| 6,946,543 B2 | 9/2005 | Ward |
| 6,989,452 B2 | 1/2006 | Ng |
| 7,008,942 B2 | 3/2006 | Chari |
| 7,049,316 B2 | 5/2006 | Zhao |
| 7,060,808 B1 | 6/2006 | Goldstein |
| 7,091,186 B2 | 8/2006 | Senter |
| 7,097,840 B2 | 8/2006 | Erickson |
| 7,098,308 B2 | 8/2006 | Senter |
| 7,129,261 B2 | 10/2006 | Ng |
| 7,129,332 B2 | 10/2006 | Pastan |
| 7,132,511 B2 | 11/2006 | Carr |
| 7,132,554 B2 | 11/2006 | Rose |
| 7,192,750 B2 | 3/2007 | Chung |
| 7,214,685 B2 | 5/2007 | Tietze |
| 7,217,819 B2 | 5/2007 | Chari |
| 7,223,837 B2 | 5/2007 | De Groot |
| 7,226,592 B2 | 6/2007 | Kreysch |
| 7,247,301 B2 | 7/2007 | Van De Winkel |
| 7,256,257 B2 | 8/2007 | Doronina |
| 7,276,497 B2 | 10/2007 | Chari |
| 7,276,499 B2 | 10/2007 | Chari |
| 7,276,585 B2 | 10/2007 | Lazar |
| 7,301,019 B2 | 11/2007 | Widdison |
| 7,303,749 B1 | 12/2007 | Chari |
| 7,329,760 B2 | 2/2008 | Zhao |
| 7,368,565 B2 | 5/2008 | Chari |
| 7,374,762 B2 | 5/2008 | Amphlett |
| 7,375,078 B2 | 5/2008 | Feng |
| 7,388,026 B2 | 6/2008 | Zhao |
| 7,390,898 B2 | 6/2008 | Baloglu |
| 7,411,063 B2 | 8/2008 | Widdison |
| 7,414,073 B2 | 8/2008 | Baloglu |
| 7,423,116 B2 | 9/2008 | Doronina |
| 7,432,088 B2 | 10/2008 | Kuo |
| 7,449,559 B2 | 11/2008 | Ward |
| 7,473,796 B2 | 1/2009 | Chari |
| 7,476,669 B2 | 1/2009 | Chari |
| 7,494,649 B2 | 2/2009 | Amphlett |
| 7,495,114 B2 | 2/2009 | Baloglu |
| 7,498,298 B2 | 3/2009 | Doronina |
| 7,498,302 B2 | 3/2009 | Ng |
| 7,501,120 B2 | 3/2009 | Amphlett |
| 7,514,080 B2 | 4/2009 | Amphlett |
| 7,517,903 B2 | 4/2009 | Chen |
| 7,521,541 B2 | 4/2009 | Eigenbrot |
| 7,528,130 B2 | 5/2009 | Chari |
| 7,550,609 B2 | 6/2009 | Chari |
| 7,553,816 B2 | 6/2009 | Senter |
| 7,575,748 B1 | 8/2009 | Erickson |
| 7,585,857 B2 | 9/2009 | Chari |

(56) References Cited

U.S. PATENT DOCUMENTS

| | | |
|---|---|---|
| 7,589,180 B2 | 9/2009 | Old |
| 7,595,378 B2 | 9/2009 | Van De Winkel |
| 7,598,290 B2 | 10/2009 | Miller |
| 7,598,375 B2 | 10/2009 | Ho |
| 7,601,354 B2 | 10/2009 | Chari |
| 7,628,986 B2 | 12/2009 | Weber |
| 7,635,570 B2 | 12/2009 | Siena |
| 7,651,687 B2 | 1/2010 | Buck |
| 7,655,660 B2 | 2/2010 | Zhao |
| 7,655,661 B2 | 2/2010 | Zhao |
| 7,659,241 B2 | 2/2010 | Senter |
| 7,667,054 B2 | 2/2010 | Miller |
| 7,691,962 B2 | 4/2010 | Boyd |
| 7,723,484 B2 | 5/2010 | Beidler |
| 7,736,644 B2 | 6/2010 | Weber |
| 7,745,394 B2 | 6/2010 | Doronina |
| 7,750,116 B1 | 7/2010 | Doronina |
| 7,754,681 B2 | 7/2010 | Feng |
| 7,767,792 B2 | 8/2010 | Johns |
| 7,790,164 B2 | 9/2010 | Cao |
| 7,807,798 B2 | 10/2010 | Jakobovits |
| 2001/0005747 A1 | 6/2001 | Ball |
| 2001/0036923 A1 | 11/2001 | Chari |
| 2001/0046686 A1 | 11/2001 | Wong |
| 2001/0048922 A1 | 12/2001 | Romet-Lemonne |
| 2001/0055595 A1 | 12/2001 | Goldenberg |
| 2002/0001587 A1 | 1/2002 | Erickson |
| 2002/0004587 A1 | 1/2002 | Miller |
| 2002/0006379 A1 | 1/2002 | Hansen |
| 2002/0012663 A1 | 1/2002 | Waksal |
| 2002/0013485 A1 | 1/2002 | Chari |
| 2002/0049335 A1 | 4/2002 | Boger |
| 2002/0062009 A1 | 5/2002 | Taylor |
| 2002/0064785 A1 | 5/2002 | Mass |
| 2002/0082424 A1 | 6/2002 | Boger |
| 2002/0156274 A1 | 10/2002 | Terfloth |
| 2002/0173629 A1 | 11/2002 | Jakobovits |
| 2003/0050331 A1 | 3/2003 | Ng |
| 2003/0055226 A1 | 3/2003 | Chari |
| 2003/0073731 A1 | 4/2003 | Lee |
| 2003/0073852 A1 | 4/2003 | Ng |
| 2003/0083263 A1 | 5/2003 | Doronina |
| 2003/0091561 A1 | 5/2003 | Van De Winkel |
| 2003/0096743 A1 | 5/2003 | Senter |
| 2003/0109682 A1 | 6/2003 | Santi |
| 2003/0130189 A1 | 7/2003 | Senter |
| 2003/0194403 A1 | 10/2003 | Van De Winkel |
| 2003/0195365 A1 | 10/2003 | Zhao |
| 2003/0199519 A1 | 10/2003 | Zhao |
| 2003/0211097 A1 | 11/2003 | Pastan |
| 2003/0211112 A1 | 11/2003 | Debinski |
| 2003/0215387 A1 | 11/2003 | Harrison |
| 2003/0224001 A1 | 12/2003 | Goldstein |
| 2004/0006212 A1 | 1/2004 | Goldstein |
| 2004/0033543 A1 | 2/2004 | Schwab |
| 2004/0086943 A1 | 5/2004 | Andres |
| 2004/0109867 A1 | 6/2004 | Yongxin |
| 2004/0131611 A1 | 7/2004 | Oliver |
| 2004/0147428 A1 | 7/2004 | Pluenneke |
| 2004/0157782 A1 | 8/2004 | Doronina |
| 2004/0202666 A1 | 10/2004 | Griffiths |
| 2004/0235074 A1 | 11/2004 | Siegall |
| 2004/0235840 A1 | 11/2004 | Chari |
| 2004/0248196 A1 | 12/2004 | Adams |
| 2004/0253645 A1 | 12/2004 | Daugherty |
| 2005/0009751 A1 | 1/2005 | Senter |
| 2005/0014700 A1 | 1/2005 | Boger |
| 2005/0026987 A1 | 2/2005 | Boger |
| 2005/0031627 A1 | 2/2005 | Mazzola |
| 2005/0032860 A1 | 2/2005 | Boger |
| 2005/0053608 A1 | 3/2005 | Weber |
| 2005/0059087 A1 | 3/2005 | Weber |
| 2005/0064492 A1 | 3/2005 | Desauvage |
| 2005/0100546 A1 | 5/2005 | Jakobovits |
| 2005/0106644 A1 | 5/2005 | Cairns |
| 2005/0107595 A1 | 5/2005 | Cairns |
| 2005/0113308 A1 | 5/2005 | Senter |
| 2005/0113571 A1 | 5/2005 | Terfloth |
| 2005/0142133 A1 | 6/2005 | Lazar |
| 2005/0152913 A1 | 7/2005 | Eldridge |
| 2005/0169933 A1 | 8/2005 | Steeves |
| 2005/0214310 A1 | 9/2005 | Toki |
| 2005/0227324 A1 | 10/2005 | Huang |
| 2005/0238640 A1 | 10/2005 | Sliwkowski |
| 2005/0238649 A1 | 10/2005 | Doronina |
| 2005/0255555 A1 | 11/2005 | Johns |
| 2005/0256030 A1 | 11/2005 | Feng |
| 2005/0271671 A1 | 12/2005 | Griffiths |
| 2005/0272083 A1 | 12/2005 | Seshagiri |
| 2005/0272798 A1 | 12/2005 | Ng |
| 2005/0276812 A1 | 12/2005 | Ebens |
| 2006/0004081 A1 | 1/2006 | Chen |
| 2006/0009462 A1 | 1/2006 | Yongxin |
| 2006/0024317 A1 | 2/2006 | Boyd |
| 2006/0074008 A1 | 4/2006 | Senter |
| 2006/0084141 A1 | 4/2006 | Floss |
| 2006/0088523 A1 | 4/2006 | Andya |
| 2006/0116422 A1 | 6/2006 | DeGroot |
| 2006/0121044 A1 | 6/2006 | Amler |
| 2006/0147959 A1 | 7/2006 | Bell |
| 2006/0154334 A1 | 7/2006 | Tarnowski |
| 2006/0165685 A1 | 7/2006 | Kreysch |
| 2006/0182750 A1 | 8/2006 | Chari |
| 2006/0183887 A1 | 8/2006 | Jakobovits |
| 2006/0229253 A1 | 10/2006 | Doronina |
| 2006/0234343 A1 | 10/2006 | Ward |
| 2006/0247295 A1 | 11/2006 | Gangwar |
| 2007/0031402 A1 | 2/2007 | Zhang |
| 2007/0037972 A1 | 2/2007 | Ho |
| 2007/0048314 A1 | 3/2007 | Dai |
| 2007/0071675 A1 | 3/2007 | Wu |
| 2007/0092940 A1 | 4/2007 | Eigenbrot |
| 2007/0112188 A1 | 5/2007 | Widdison |
| 2007/0116707 A1 | 5/2007 | Goldstein |
| 2007/0134243 A1 | 6/2007 | Gazzard |
| 2007/0135346 A1 | 6/2007 | Zhao |
| 2007/0202101 A1 | 8/2007 | Rosen |
| 2007/0264266 A1 | 11/2007 | Chari |
| 2007/0269447 A1 | 11/2007 | Chari |
| 2007/0270585 A1 | 11/2007 | Chari |
| 2008/0008704 A1 | 1/2008 | Rubin |
| 2008/0025983 A1 | 1/2008 | Adams |
| 2008/0114153 A1 | 5/2008 | Steeves |
| 2008/0145374 A1 | 6/2008 | Steeves |
| 2008/0171040 A1 | 7/2008 | Ebens |
| 2008/0171856 A1 | 7/2008 | Steeves |
| 2008/0171865 A1 | 7/2008 | Steeves |
| 2008/0226657 A1 | 9/2008 | Doronina |
| 2008/0226659 A1 | 9/2008 | Erickson |
| 2008/0241128 A1 | 10/2008 | Jeffrey |
| 2008/0248051 A1 | 10/2008 | Doronina |
| 2008/0248053 A1 | 10/2008 | Doronina |
| 2008/0249085 A1 | 10/2008 | Cassady |
| 2008/0260685 A1 | 10/2008 | Zhao |
| 2008/0267960 A1 | 10/2008 | Drachman |
| 2008/0279868 A1 | 11/2008 | Boyd |
| 2008/0281102 A1 | 11/2008 | Gangwar |
| 2008/0293800 A1 | 11/2008 | Gangwar |
| 2008/0300192 A1 | 12/2008 | Doronina |
| 2008/0305044 A1 | 12/2008 | McDonagh |
| 2008/0311136 A1 | 12/2008 | Beusker |
| 2009/0010945 A1 | 1/2009 | Alley |
| 2009/0018086 A1 | 1/2009 | Doronina |
| 2009/0028821 A1 | 1/2009 | Zhao |
| 2009/0041791 A1 | 2/2009 | Feng |
| 2009/0047296 A1 | 2/2009 | Doronina |
| 2009/0053240 A1 | 2/2009 | Lazar |
| 2009/0111756 A1 | 4/2009 | Doronina |
| 2009/0137782 A1 | 5/2009 | Old |
| 2009/0142361 A1 | 6/2009 | Amphlett |
| 2009/0155282 A1 | 6/2009 | Weber |
| 2009/0156790 A1 | 6/2009 | Weber |
| 2009/0175865 A1 | 7/2009 | Eigenbrot |
| 2009/0175887 A1 | 7/2009 | Weber |

(56) References Cited

U.S. PATENT DOCUMENTS

| | | |
|---|---|---|
| 2009/0175888 A1 | 7/2009 | Ng |
| 2009/0202536 A1 | 8/2009 | Ebens |
| 2009/0214541 A1 | 8/2009 | Gillies |
| 2009/0220510 A1 | 9/2009 | Old |
| 2009/0240038 A1 | 9/2009 | Weber |
| 2009/0269343 A1 | 10/2009 | Bigner |
| 2009/0274713 A1 | 11/2009 | Chari |
| 2009/0280503 A1 | 11/2009 | Fiore |
| 2009/0281158 A1 | 11/2009 | Zhao |
| 2009/0304693 A1 | 12/2009 | Ghayur |
| 2009/0306101 A1 | 12/2009 | Solca |
| 2009/0318668 A1 | 12/2009 | Beusker |
| 2009/0324621 A1 | 12/2009 | Senter |
| 2010/0008929 A1 | 1/2010 | Van De Winkel |
| 2010/0056762 A1 | 3/2010 | Old |
| 2010/0092475 A1 | 4/2010 | Johns |
| 2010/0166744 A1 | 7/2010 | Wong |
| 2010/0196265 A1 | 8/2010 | Adams |
| 2010/0203007 A1 | 8/2010 | Li |
| 2010/0322937 A1 | 12/2010 | Johns |
| 2011/0008766 A1 | 1/2011 | Ghayur |
| 2011/0076232 A1 | 3/2011 | Old |
| 2011/0150759 A1 | 6/2011 | Johns |

FOREIGN PATENT DOCUMENTS

| | | |
|---|---|---|
| EP | 0519596 A1 | 12/1992 |
| EP | 0586002 A2 | 3/1994 |
| EP | 0699755 A2 | 3/1996 |
| EP | 1392359 A4 | 9/2005 |
| EP | 1722808 A4 | 7/2009 |
| EP | 1392359 B1 | 10/2009 |
| EP | 2163256 A3 | 2/2010 |
| EP | 2068929 A4 | 3/2010 |
| EP | 2163256 A1 | 3/2010 |
| EP | 1392359 B1 | 7/2010 |
| EP | 2134854 A4 | 1/2011 |
| EP | 10186053 A3 | 5/2011 |
| WO | WO 85/03357 A1 | 8/1985 |
| WO | WO 91/03489 A1 | 3/1991 |
| WO | WO 91/16350 A1 | 10/1991 |
| WO | WO 92/15683 A1 | 9/1992 |
| WO | WO 9311161 | 6/1993 |
| WO | WO 9413804 | 6/1994 |
| WO | WO 95/25167 A1 | 9/1995 |
| WO | WO 96/16988 A1 | 6/1996 |
| WO | WO 9640210 | 12/1996 |
| WO | WO 99/44645 A1 | 9/1999 |
| WO | WO 02/11677 A2 | 2/2002 |
| WO | WO 02092771 | 11/2002 |
| WO | WO 03/014159 A1 | 2/2003 |
| WO | WO 03/068920 A2 | 8/2003 |
| WO | WO 02/092771 A1 | 11/2003 |
| WO | WO 2004/003019 A2 | 1/2004 |
| WO | WO 2004/056847 A2 | 7/2004 |
| WO | WO 2004/085474 A2 | 10/2004 |
| WO | WO 2005/081854 A2 | 9/2005 |
| WO | WO 2005081854 A2 | 9/2005 |
| WO | WO 2005/094357 A2 | 10/2005 |
| WO | WO 2005/081854 A1 | 11/2005 |
| WO | WO 2005/081854 A1 | 8/2006 |
| WO | WO 2007/089149 A2 | 8/2007 |
| WO | WO 2007/103288 A2 | 9/2007 |
| WO | WO 2008/033495 A2 | 3/2008 |
| WO | WO 2008/033495 A1 | 4/2008 |
| WO | WO 2008/091701 A2 | 7/2008 |
| WO | WO 2008/091701 A1 | 8/2008 |
| WO | WO 2008/115404 A1 | 8/2008 |
| WO | WO 2008/115404 A1 | 9/2008 |
| WO | WO 2008/154927 A1 | 12/2008 |
| WO | WO 2009/017394 A1 | 2/2009 |
| WO | WO 2009023265 A1 | 2/2009 |
| WO | WO 2008/033495 A1 | 3/2009 |
| WO | WO 2008/115404 A1 | 9/2009 |
| WO | WO 2009/023265 A1 | 2/2010 |
| WO | WO 2010/096434 | 4/2010 |
| WO | WO 2010/096434 A2 | 8/2010 |
| WO | WO 2010/096434 A3 | 8/2010 |
| WO | WO 2011/035465 A1 | 3/2011 |
| WO | WO 2011/041319 A2 | 4/2011 |
| WO | WO 2011/041319 A1 | 5/2011 |
| WO | WO 2010/096434 A1 | 8/2011 |

OTHER PUBLICATIONS

Gussow et al (Methods in Enzymology, 203: 99-121, 1991).*
Winkler et al (J. Imm., 265:4505-4514, 2000).*
Rudikoff et al (Proc. Natl. Acad. Sci. USA 1982 vol. 79: p. 1979-1983).*
MacCallum et al. (J. Mol. Biol. Oct. 11, 1996; 262 (5): 732-745).*
Holm et al. (Mol. Immunol. Feb. 2007; 44 (6): 1075-1084).*
[Fundamental Immunology p. 242 (William E. Paul, M.D. ed., 3d ed; 1993].*
U.S. Appl. No. 60/290,410, filed May 11, 2001.
U.S. Appl. No. 60/326,019, filed Sep. 28, 2001.
U.S. Appl. No. 60/342,258, filed Dec. 21, 2001.
Abbruzzese et al., "Phase II study of anti-epidermal growth factor receptor (EGFR) antibody cetuximab (IMC-C225) in combination with gemcitabine in patients with advanced pancreatic cancer (Abstract 518)" *Proceedings of the American Society of Clinical Oncology* (2001) 130a, 20.
Aboud-Pirak et al., "Efficacy of antibodies to epidermal growth factor receptor against KB carcinoma in vitro and in nude mice" *Chemical Abstracts* (1989) 69068k, 110(9).
Adams et al., "Monoclonal antibody therapy of cancer." *Nat. Biotechnol.* (2005) 1147-1157, 23(9).
Aden et al., "Cell Surface Antigens Coded for by the Human Chromosome 7" *Immunogenetics* (1976)209-221, 3.
Aghajanian et al., "A phase II study of cetuximab/ paclitaxel/ carboplatin for the initial treatment of advanced stage ovarian, primary peritoneal, and fallopian tube cancer" *Journal of Clinical Oncology, 2005 ASCO Annual Meeting Proceedings* (2005) Abstract 5047, 23(16S; Part I of II: Jun. 1 Supplement).
Agosti et al., "Expression of the epidermal growth factor-receptor in astrocytic tumours is specifically associated with glioblastoma multiforme." *Virchows Archiv. A, Pathological Anatomy and Histopathology* (1992) 321-325, 420(4).
Agulnik et al., "Predictive and pharmacodynamic biomarker studies in tumor and skin tissue samples of patients with recurrent or metastatic squamous cell carcinoma of the head and neck treated with erlotinib." *Journal of Clinical Oncology* (2007) 2184-2190, 25(16).
Agus et al., "Phase I clinical study of pertuzumab, a novel HER dimerization inhibitor, in patients with advanced cancer." *J. Clin. Oncol.* (2005) 2534-2543, 23(11).
Agus et al., "Targeting ligand-activated ErbB2 signaling inhibits breast and prostate tumor growth." *Cancer Cell* (2002) 127-137, 2(2).
Akiyama et al., "Genistein, a specific inhibitor of tyrosine-specific protein kinases." *Journal of Biological Chemistry* (1987) 5592-5595, 262(12).
Albanell et al., "Activated extracellular signal-regulated kinases: association with epidermal growth factor receptor/transforming growth factor alpha expression in head and neck squamous carcinoma and inhibition by anti-epidermal growth factor receptor treatments." *Cancer Res.* (2001) 6500-6510, 61(17).
Albanell et al., "Pharmacodynamic studies of the epidermal growth factor receptor inhibitor ZD1839 in skin from cancer patients: histopathologic and molecular consequences of receptor inhibition." *J. Clin. Oncol.* (2002) 110-124, 20(1).
Albanell et al., "Pharmacodynamic studies with the epidermal growth factor tyrosine kinase inhibitor ZD1839" *Seminars in Oncology* (2001) 56-66, 28.
Aldape et al., "Immunohistochemical detection of EGFRvIII in high malignancy grade astrocytomas and evaluation of prognostic significance." *Journal of neuropathology and experimental neurology* (2004) 700-707, 63(7).
Alimirah et al:, "DU-145 and PC-3 human prostate cancer cell lines express androgen receptor: implications for the androgen receptor functions and regulation." *FEBS letters* (2006) 2294-2300, 580(9).

(56) References Cited

OTHER PUBLICATIONS

Alroy et al., "The ErbB signaling network in embryogenesis and oncogenesis: signal diversification through combinatorial ligand-receptor interactions." *FEBS letters* (1997) 83-86, 410(1).
Anderson et al., "ZD1839 (Iressa), a novel epidermal growth factor receptor (EGFR) tyrosine kinase inhibitor, potently inhibits the growth of EGFR-positive cancer cell lines with or without erbB2 overexpression." *Int. J. Cancer* (2001) 774-782, 94(6).
Andrews et al., "Cellular pharmacology of cisplatin: perspectives on mechanisms of acquired resistance." *Cancer Cells)* (1990) 35-43, 2(2).
Ang et al., "Epidermal growth factor receptor and response of head-and-neck carcinoma to therapy." *Int. J. Radiat. Oncol. Biol. Phys.* (2004) 959-965, 58(3).
Ang et al., "Impact of epidermal growth factor receptor expression on survival and pattern of relapse in patients with advanced head and neck carcinoma." *Cancer Res.* (2002) 7350-7356, 62(24).
Anido et al., "ZD1839, a specific epidermal growth factor receptor (EGFR) tyrosine kinase inhibitor, induces the formation of inactive EGFR/HER2 and EGFR/HER3 heterodimers and prevents heregulin signaling in HER2-overexpressing breast cancer cells." *Clin. Cancer Res.* (2003) 1274-1283, 9(4).
Archer et al., "Regional treatment of epidermal growth factor receptor vIII-expressing neoplastic meningitis with a single-chain immunotoxin, MR-1." *Clin. Cancer Res.* (1999) 2646-2652, 5(9).
Arteaga et al., "Antibodies Against p185HER2 Enhance Etoposide-Induced Cytotoxicity Against Human Breast Carcinoma Cells." *Proceedings of the American Society of Clinical Oncology* (1993) 75 (Abstract 101), 12.
Artega et al., "Tyrosine kinase inhibitors-ZD1839 (Iressa)." *Current opinion in oncology* (2001) 491-498, 13(6).
Arteaga, "The epidermal growth factor receptor: from mutant oncogene in nonhuman cancers to therapeutic target in human neoplasia." *J. Clin. Oncol.* (2001) 32S-40S, 19(18; Supplement).
Arteaga et al., "Unliganded epidermal growth factor receptor dimerization induced by direct interaction of quinazolines with ATP binding site." *Journal of Biological Chemisry* (1997) 23247-23254, 272(37).
Arteaga, "ErbB-targeted therapeutic approaches in human cancer." *Exp. Cell Res.* (2003) 122-130, 284(1).
Arteaga, "Overview of epidermal growth factor receptor biology and its role as a therapeutic target in human neoplasia." *Semin. Oncol.* (2002) 3-9, 29(5 Suppl 14).
Arteaga et al., "Overview of rationale and clinical trials with signal transduction inhibitors in lung cancer." *Semin. Oncol.* (2002) 15-26, 29(1; Suppl. 4).
Arteaga, "Epidermal growth factor receptor dependence in human tumors: more than just expression?" *Oncologist* (2002) 31-39, 7(Suppl. 4).
Ashley et al., "Monoclonal antibodies to growth factors and growth factor receptors: their diagnostic and therapeutic potential in brain tumors." *Journal of neuro-oncology* (1997) 259-273, 35(3).
Atlas et al., "Growth regulation of human renal carcinoma cells: role of transforming growth factor alpha." *Cancer Res.* (1992) 3335-3339, 52(12).
Aujame et al., "High affinity human antibodies by phage display." *Human antibodies* (1997) 155-168, 8(4).
Austin et al, "Endocytosis and sorting of ErbB2 and the site of action of cancer therapeutics trastuzumab and geldanamycin." *Mol. Biol. Cell* (2004) 5268-5282, 15(12).
Azzazy et al., "Phage display technology: clinical applications and recent innovations." *Clinical biochemistry* (2002) 425-445, 35(6).
Baerga-Ortiz et al., "Epitope mapping of a monoclonal antibody against human thrombin by H/D-exchange mass spectrometry reveals selection of a diverse sequence in a highly conserved protein." *Protein science* (2002) 1300-1308, 11(6).
Bailey et al., "Evaluation of epidermal growth factor receptor (EGFR) as a predictive marker in patients with non-small-cell lung cancer (NSCLC) receiving first- line gefitinib combined with platinum-based chemotherapy" *Journal of Clinical Oncology, 2004 ASCO Annual Meeting Proceedings (Post-Meeting Edition)* (2004) Abstract 7013, 22(14S; Jul. 15 Supplement).
Balaban et al., "The effect of ionizing radiation on signal transduction: antibodies to EGF receptor sensitize A431 cells to radiation." *Biochimica et biophysica acta* (1996) 147-156, 1314(1-2).
Baly et al., "Development and characterization of a rhuMAb HER2 antibody ADCC assay for clinical evaluation of cytotoxic potency." *Proceedings of the American Association for Cancer Research* (1997) 27-28 (Abstract 181), 38.
Bandyopadhyay et al., "Physical interaction between epidermal growth factor receptor and DNA-dependent protein kinase in mammalian cells." *Journal of Biological Chemistry* (1998) 1568-1573, 273(3).
Barendswaard et al., "Rapid and specific targeting of monoclonal antibody A33 to a colon cancer xenograft in nude mice." *Int. J. Oncol.* (1998) 45-53, 12(1).
Barnette et al:, "Association of the anti-inflammatory activity of phosphodiesterase 4 (PDE4) inhibitors with either inhibition of PDE4 catalytic activity or competition for [3H]rolipram binding." *Biochemical pharmacology* (1996) 949-956, 51(7).
Baselga et al., "Phase I study of AEE788, a novel multitargeted inhibitor of ErbB and VEGF receptor family tyrosine kinases (A pharmacokinetic (PK)-pharmacodynamic (PD) study to identify the optimal therapeutic dose regimen)." *J. Clinical Oncology* (2005) Abstract 3028, 23.
Baselga et al., "Cetuximab (C225) plus cisplatin/carboplatin is active in patients (pts) with recurrent/metastatic squamous cell carcinoma of the head and neck (SCCHN) progressing on a same dose and schedule platinum-based regimen" *Proceedings of the American Society of Clinical Oncology* (2002) Abstract 900, 21.
Baselga et al., "Antitumor activity of paclitaxel in combination with anti-growth factor receptor monoclonal antibodies in breast cancer xenografts." *Proceedings of the American Association for Cancer Research* (1994) 380 (Abstract 2262), 35.
Baselga, "Combining the Anti-EGFR Agent Gefitinib With Chemotherapy in Non-Small-Cell Lung Cancer: How Do We Go From Intact to Impact?" *Journal of Clinical Oncology* (2004) 759-761, 22(5).
Baselga et al., "Phase I safety, pharmacokinetic, and pharmacodynamic trial of ZD1839, a selective oral epidermal growth factor receptor tyrosine kinase inhibitor, in patients with five selected solid tumor types." *J. Clin. Oncol.* (2002) 4292-4302, 20(21).
Baselga et al., "Mechanism of action of trastuzumab and scientific update." *Semin. Oncol.* (2001) 4-11;28(5; Suppl. 16).
Baselga, "Targeting the epidermal growth factor receptor: a clinical reality." *J. Clin. Oncol.* (2001) 41S-44S, 19(18; Supplement).
Baselga, "The EGFR as a target for anticancer therapy—focus on cetuximab." *Eur. J. Cancer* (2001) S16-22, 37 Suppl. 4.
Baselga, "Clinical trials of Herceptin(R) (trastuzumab)." *Eur. J. Cancer* (2001) 18-24, 37 Suppl 1.
Baselga, "Herceptin alone or in combination with chemotherapy in the treatment of HER2-postive metastatic breast cancer: pivotal trials." *Oncology* (2001) 14-21, 61(Suppl. 2) .
Baselga et al., "Mechanism of action of anti-HER2 monoclonal antibodies." *Ann Oncol .* (2001) S35-41, 12(Suppl. 1).
Baselga et al., "Phase I studies of anti-epidermal growth factor receptor chimeric antibody C225 alone and in combination with cisplatin." *J. Clin. Oncol.* (2000) 904-914, 18(4).
Baselga et al., "Continuous Administration of ZD1839 (Iressa), a Novel Oral Epidermal Growth Factor Receptor Tyrosine Kinase Inhibitor (EGFR-TKI), in Patients with Five Selected Tumor Types: Evidence of Activity and Good Tolerability (Abstract 686)" *Proceedings of the American Society of Clinical Oncology* (2000) 177a, 19.
Baselga et al., "ZD1839 ('Iressa') as an anticancer agent." *Drugs* (2000) 33-40; discussion 41-2, 60(Suppl. 1).
Baselga et al., "Recombinant humanized anti-HER2 antibody (Herceptin) enhances the antitumor activity of paclitaxel and doxorubicin against HER2/neu overexpressing human breast cancer xenografts." *Cancer Res.* (1998) 2825-2831, 58(13).
Baselga et al., "Phase II study of weekly intravenous recombinant humanized anti-p185HER2 monoclonal antibody in patients with HER2/neu-overexpressing metastatic breast cancer." *J. Clin. Oncol.* (1996) 737-744, 14(3).

(56) References Cited

OTHER PUBLICATIONS

Baselga et al., "Receptor blockade with monoclonal antibodies as anti-cancer therapy." *Pharmacology & Therapeutics* (1994) 127-154, 64(1).
Baselga et al., "Phase II multicenter study of the antiepidermal growth factor receptor monoclonal antibody cetuximab in combination with platinum-based chemotherapy in patients with platinum-refractory metastatic and/or recurrent squamous cell carcinoma of the head and neck." *J. Clin. Oncol.* (2005) 5568-5577, 23(24).
Baselga et al., "Phase II and tumor pharmacodynamic study of gefitinib in patients with advanced breast cancer." *J. Clin. Oncol.* (2005) 5323-5333, 23(23).
Baselga et al., "Phase II study of efficacy, safety, and pharmacokinetics of trastuzumab monotherapy administered on a 3-weekly schedule." *J. Clin. Oncol.* (2005) 2162-2171, 23(10).
Baselga, "Why the epidermal growth factor receptor? The rationale for cancer therapy." *Oncologist* (2002) 2-8, 7(Suppl. 4).
Beckmann et al., "Expression analyses of epidermal growth factor receptor and HER-2/neu: no advantage of prediction of recurrence or survival in breast cancer patients." *Oncology* (1996) 441-447, 53(6).
Beers et al., "Immunotoxins with increased activity against epidermal growth factor receptor vIII-expressing cells produced by antibody phage display." *Clin. Cancer Res.* (2000) 2835-2843, 6(7).
Behr et al., "Radioimmunotherapy of small volume disease of colorectal cancer metastatic to the liver: preclinical evaluation in comparison to standard chemotherapy and initial results of a phase I clinical study." *Clin. Cancer Res.* (1999) 3232s-3242s, 5(10; Supplement).
Bell et al., "Inherited susceptibility to lung cancer may be associated with the T790M drug resistance mutation in EGFR." *Nature Genetics* (2005) 1315-1316, 37(12).
Bell et al., "Epidermal growth factor receptor mutations and gene amplification in non-small-cell lung cancer: molecular analysis of the Ideal/intact gefitinib trials." *J. Clin. Oncol.* (2005) 8081-8092, 23(31).
Bender et al.,"Immunotherapy of human glioma xenografts with unlabeled, 131I-, or 125I-labeled monoclonal antibody 425 to epidermal growth factor receptor." *Cancer Res.* (1992) 121-126, 52(1).
Benichou et al., "Random fragment libraries using yeast expression plasmid." *Methods Mol. Biol.* (1996) 241-255, 66.
Bequinot et al., "Down-regulation of the epidermal growth factor receptor in KB cells is due to receptor internalization and subsequent degradation in lysosomes" *Chemical Abstract* (1984) 1592k, p. 141, 101.
Berkers et al., "The effects of receptor density and cell shape on epidermal growth factor binding." *Journal of Receptor Research* (1992) 71-100, 12(1).
Bertics et al., "Alteration of epidermal growth factor receptor activity by mutation of its primary carboxyl-terminal site of tyrosine self-phosphorylation." *Journal of Biological Chemistry* (1988) 3610-3617, 263(8).
Bertics et al., "Self-phosphorylation enhances the protein-tyrosine kinase activity of the epidermal growth factor receptor." *Journal of Biological Chemistry* (1985) 14642-14647, 260(27).
Bhattacharya-Chatterjee et al., "The anti-idiotype vaccines for immunotherapy." *Current opinion in molecular therapeutics* (2001) 63-69, 3(1).
Bianco et al., "Antitumor activity of combined treatment of human cancer cells with ionizing readiation and anti-epidermal growth factor receptor monoclonal antibody C225 plus type I protein kinase A antisense oligonucleotide." *Clin. Cancer Res.* (2000) 4343-4350, 6(11).
Bianco et al., "Loss of PTEN/MMAC1/TEP in EGF receptor-expressing tumor cells counteracts the antitumor action of EGFR tyrosine kinase inhibitors." *Oncogene* (2003) 2812-2822, 22(18).
Bier et al., "Clinical trial with escalating doses of the antiepidermal growth factor receptor humanized monoclonal antibody EMD 72 000 in patients with advanced squamous cell carcinoma of the larynx and hypopharynx." *Cancer chemotherapy and pharmacology* (2001) 519-524, 47(6).
Bier et al., "Anti-(epidermal growth factor) receptor monoclonal antibodies for the induction of antibody-dependent cell-mediated cytotoxicity against squamous cell carcinoma lines of the head and neck." *Cancer Immunol. Immunother.* (1998) 167-173, 46(3).
Bier et al., "Dose-dependent access of murine anti-epidermal growth factor receptor monoclonal antibody to tumor cells in patients with advanced laryngeal and hypopharyngeal carcinoma." *European archives of oto-rhino-larvngology : official journal of the European Federation of Oto-Rhino-Laryngoloqical Societies (EUFOS) : affiliated with the German Society for Oto-Rhino-Laryngology—Head and Neck Surgery* (1995) 433-439, 252(7).
Biernat et al., "Predominant expression of mutant EGFR (EGFRvIII) is rare in primary glioblastomas." *Brain Pathology (Zurich, Switzerland)* (2004) 131-136, 14(2).
Bigner et al., "Characterization of the epidermal growth factor receptor in human glioma cell lines and xenografts." *Cancer Res.* (1990) 8017-8022, 50(24).
Bindon et al., "Importance of antigen specificity for complement-mediated lysis by monoclonal antibodies." *European Journal of Immunology* (1988) 1507-1514, 18(10).
Biscardi et al., "c-Src, receptor tyrosine kinases, and human cancer." *Advances in Cancer Research* (1999) 61-119, 76.
Bishop, "The molecular genetics of cancer." *Science* (1987) 305-311, 235(4786).
Bishop et al., "Differential sensitivity of cancer cells to inhibitors of the epidermal growth factor receptor family." *Oncogene* (2002) 119-127, 21(1).
Blagosklonny et al., "Why Iressa failed: toward novel use of kinase inhibitors (outlook)." *Cancer Biology & Therapy* (2003) 137-140, 2(2).
Bleeker et al., "Dual mode of action of a human anti-epidermal growth factor receptor monoclonal antibody for cancer therapy." *Journal of immunology (Baltimore, Md : 1950)* (2004) 4699-4707, 173(7).
Blume-Jensen et al., "Oncogenic kinase signalling." *Nature* (2001) 355-365, 411(6835).
Boder et al., "Phage Display and Its Applications" *Methods Enzymol.* Chapter 25 "Yeast surface display for directed evolution of protein expression, affinity, and stability" (2000) 430-444, 328.
Boder et al., "Directed evolution of antibody fragments with monovalent femtomolar antigen-binding affinity." *Proceedings of the National Academy of Sciences of the United States of America* (2000) 10701-10705, 97(20).
Boder et al., "Yeast surface display for screening combinatorial polypeptide libraries." *Nat. Biotechnol.* (1997) 553-557, 15(6).
Bogan et al:, "Anatomy of hot spots in protein interfaces." *J. Mol. Biol.* (1998) 1-9, 280(1).
Boger, "Design, synthesis, and evaluation of DNA minor groove binding agents: the duocarmycins" *Pure & Appl. Chem.* (1994) 837-844, 66(4).
Boghaert et al., "Antibody-targeted chemotherapy with the calicheamicin conjugate hu3S193-N-acetyl gamma calicheamicin dimethyl hydrazide targets Lewisy and eliminates Lewisy-positive human carcinoma cells and xenografts." *Clin. Cancer Res.* (2004) 4538-4549, 10(13).
Bonner et al., "Cetuximab improves locoregional control and survival of locoregionally advanced head and neck cancer: independent review of mature data with a median follow-up of 45 months" *Presented at the Annual AACR-NCI-EORTC International Conference on Molecular Targets and Cancer Therapeutics: Discovery, Biology, and Clinical Applications; Nov. 14-18, 2005. Philadelphia, Pa.* (2011) Abstract B106.
Bonner et al., "Cetuximab prolongs survival in patients with locoregionally advanced squamous cell carcinoma of head and neck (A phase III study of high dose radiation therapy with or without cetuximab)" *Journal of Clinical Oncology, 2004 ASCO Annual Meeting Proceedings (Post-Meeting Edition)* (2004) Abstract 5507, 22(14S; Jul. 15 Supplement).
Bonner et al., "Enhanced apoptosis with combination C225/radiation treatment serves as the impetus for clinical investigation in head and neck cancers" *Proceedings of the Annual Meeting of the American Society of Clinical Oncology* (2000) 4a (Abstract 5F), 10.

(56) References Cited

OTHER PUBLICATIONS

Bonner et al., "Continued response following treatment with IMC-C225 an EGFr MoAb combined with RT in advancedhead and neck malignancies." *J. Clin. Oncol.* (2000) 47S-53S, 18(21; Supplement).

Bonner et al., "Radiotherapy plus cetuximab for squamous-cell carcinoma of the head and neck." *N. Engl. J. Med.* (2006) 567-578, 354(6).

De Bono et al., "The ErbB receptor family: a therapeutic target for cancer." *Trends in molecular medicine* (2002) S19-26, 8(4; Supplement).

Boonstra et al., "The epidermal growth factor." *Cell biology international* (1995) 413-430, 19(5).

Bos et al., "Phase I studies of anti-epidermal growth factor receptor chimeric monoclonal antibody C225 in patients with EGFR overexpressing tumors" *American Society of Clinical Oncology* (1966) 443 (Abstract 1381), 15.

Bos et al., "PD153035, a tyrosine kinase inhibitor, prevents epidermal growth factor receptor activation and inhibits growth of cancer cells in a receptor number-dependent manner." *Clin. Cancer Res.* (1997) 2099-2106, 3(11).

Boschelli, "Small molecule inhibitors of receptor tyrosine kinases" *Drugs of the Future* (1999) 515-537, 24(5).

Boyer et al., "Relative cytotoxic activity of immunotoxins reactive with different epitopes on the extracellular domain of the c-erbB-2 (HER-2/neu) gene product p185." *Int. J. Cancer* (1999) 525-531, 82(4).

Brady et al., "Malignant astrocytomas treated with iodine-125 labeled monoclonal antibody 425 against epidermal growth factor receptor: a phase II trial." *Int. J. Radiat. Oncol. Biol. Phys.* (1992) 225-230, 22(1).

Brock et al., "Current perspectives in gliomas." *Medical oncology (Northwood, London, England)* (1997) 103-120, 14(2).

Brown et al., "Antibodies vol. 1: A practical approach" *Murine Monoclonal Antibodies. Antibodies vol. 1. A Practical Approach. D. Catty. Oxford England, IRL Press* (1988) 81-104.

Brown et al., "Antiepidermal growth factor receptor antibodies augment cytotoxicity of chemotherapeutic agents on squamous cell carcinoma cell lines." *Otolaryngology—Head and Neck Surgery : Official Journal of American Academy of Otolaryngology-Head and Neck Surgery* (2000) 75-83, 122(1).

Brüggemann et al., "The immunogenicity of chimeric antibodies." *The Journal of Experimental Medicine* (1989) 2153-2157, 170(6).

Bruns et al., "Blockade of the epidermal growth factor receptor signaling by a novel tyrosine kniase inhibitor leads to apoptosis of endothelial cells and therapy of human pancreatic carcinoma." *Cancer Res.* (2000) 2926-2935, 60(11).

Bruns et al., "Epidermal growth factor receptor blockade with C225 plus gemcitabine results in regression of human pancreatic carcinoma growing orthotopically in nude mice by antiangiogenic mechanisms." *Clin. Cancer Res.* (2000) 1936-1948, 6(5).

Bucci et al., "EGF-R expression in ductal breast cancer: proliferation and prognostic implications." *Anticancer research* (1997) 769-774, 17(1B).

Bucholtz, "Radiolabeled antibody therapy." *Seminars in oncology nursing* (1987) 67-73, 3(1).

Buchsbaum et al., "Experimental radioimmunotherapy." *Medical physics* (1993) 551-567, 20(2; Part 2).

Budillon et al., "ZD1839, An Epidermal Growth Factor Receptor Tyrosine Kinase Inhibitor, Upgregulates P27KIP1 Inducing G1 Arrest and Enhancing the Antitumor Effect of Interferon" *Proceedings of the Annual Meeting of the American Association for Cancer Research* (2000) 773 (Abstract 4910), 41.

Burgess et al., "Murine epidermal growth factor: heterogeneity on high resolution ion-exchange chromatography." *EMBO J.* (1983) 2065-2069, 2(11).

Burgess, "EGFR family: structure physiology signalling and therapeutic targets." *Growth Factors* (2008) 263-274, 26(5).

Burris et al., "Phase I safety, pharmacokinetics, and clinical activity study of lapatinib (GW572016), a reversible dual inhibitor of epidermal growth factor receptor tyrosine kinases, in heavily pretreated patients with metastatic carcinomas." *J. Clin. Oncol.* (2005) 5305-5313, 23(23).

Burstein et al., "A phase II, open-label, multicenter study of lapatinib in two cohorts of patients with advanced or metastatic breast cancer who have progressed while receiving Trastuzumab-containing regimens." *Annals of Oncology* (2004) 27 (Abstract 1040), 15(Suppl. 3).

Burstein et al., "Trastuzumab and vinorelbine as first-line therapy for HER2-overexpressing metastatic breast cancer: multicenter phase II trial with clinical outcomes, analysis of serum tumor markers as predictive factors, and cardiac surveillance algorithm." *J. Clin. Oncol.* (2003) 2889-2895, 21(15).

Burtness et al., "Phase III trial comparing cisplatin (C) +placebo to C +anti-epidermal growth factor antibody (EGF-R) C225 in patients (pts) with metastatic/recurrent head & neck cancer (HNC) (Abstract 901)" *Proceedings of the American Society of Clinical Oncology* (2002) 226a, 21.

Burtness et al., "Phase III randomized trial of cisplatin plus placebo compared with cisplatin plus cetuximab in metastatic/recurrent head and neck cancer: an Eastern Cooperative Oncology Group study." *J. Clin. Oncol.* (2005) 8646-8654, 23(34).

Busam et al., "Cutaneous side-effects in cancer patients treated with the antiepidermal growth factor receptor antibody C225." *The British journal of dermatology* (2001) 1169-1176, 144(6).

Buss et al., "Altered epidermal growth factor (EGF)-stimulated protein kinase activity in variant A431 cells with altered growth responses to EGF." *Proceedings of the National Academy of Sciences of the United States of America* (1982) 2574-2578, 79(8).

Cadena et al., "Receptor protein tyrosine kinases." *In: Protein Phosphorylation* (Chapter 9) (Editor: Marks: Publisher: VCH Publishers, Inc., New York, NY). (1996) 265-284.

Cadena et al., "The intracellular tyrosine kinase domain of the epidermal growth factor receptor undergoes a conformational change upon autophosphorylation." *Journal of Biological Chemistry* (1994) 260-265, 269(1).

Cai et al., "Quantitative PET of EGFR expression in xenograft-bearing mice using 64Cu-labeled cetuximab, a chimeric anti-EGFR monoclonal antibody." *European Journal of Nuclear Medicine and Molecular Imaging* (2007) 850-858, 34(6).

Caldas et al., "Humanization of the anti-CD18 antibody 6.7: an unexpected effect of a framework residue in binding to antigen." *Mol. Immunol.* (2003) 941-952, 39(15).

Callaghan et al., "A complete description of the EGF-receptor exon structure: implication in oncogenic activation and domain evolution." *Oncogene* (1993) 2939-2948, 8(11).

Campos-González et al., "Immunodetection of the ligand-activated receptor for epidermal growth factor." *Growth Factors* (1991) 305-316, 4(4).

Cappuzzo et al., "Increased HER2 gene copy number is associated with response to gefitinib therapy in epidermal growth factor receptor-positive non-small-cell lung cancer patients." *J. Clin. Oncol.* (2005) 5007-5018, 23(22).

Cappuzzo et al., "Epidermal growth factor receptor gene and protein and gefitinib sensitivity in non-small-cell lung cancer." *J. Natl. Cancer Inst.* (2005) 643-655, 97(9).

Carlin et al., "S6 is the human receptor for epidermal growth factor (EGF)" *Cell Genet.* (1982) 256, 32.

Carlin et al., "Identity of human epidermal growth factor (EGF) receptor with glycoprotein SA-7: evidence for differential phosphorylation of the two components of the EGF receptor from A431 cells." *Proceedings of the National Academy of Sciences of the United States of America* (1982) 5026-5030, 79(16).

Carpenter, "Receptors for epidermal growth factor and other polypeptide mitogens." *Annual Review of Biochemistry* (1987) 881-914, 56.

Carpenter, "Properties of the receptor for epidermal growth factor." *Cell* (1984) 357-358, 37(2).

Carteni et al., "Panitumumab a novel drug in cancer treatment." *Ann Oncol.* (2007)vi16-21, 18 Suppl 6.

Carter, "Identification and validation of cell surface antigens for antibody targeting in oncology" *Endocrine-Related Cancer* (2004) 659-687, 11(4).

(56) References Cited

OTHER PUBLICATIONS

Carter, "Improving the efficacy of antibody-based cancer therapies." *Nature Rev. Cancer* (2001) 118-129, 1(2).

Carter et al., "Humanization of an anti-p185HER2 antibody for human cancer therapy." *Proceedings of the National Academy of Sciences of the United States of America* (1992) 4285-4289, 89(10).

Carter et al., "Tissue-specific transformation by oncogenic mutants of epidermal growth factor receptor." *Critical reviews in oncogenesis* (1994) 389-428, 5(4).

Cartron et al., "Therapeutic activity of humanized anti-CD20 monoclonal antibody and polymorphism in IgG Fc receptor FcγRIIIa gene." *Blood* (2002) 754-758, 99(3).

Casado et al., "A phase I/IIA pharmacokinetic (PK) and serial skin and tumor pharmacodynamic (PD) study of the EGFR irreversible tyrosine kinase inhibitor EKB-569 in combination with 5-fluorouracil (5FU), leucovorin (LV) and irinotecan (CPT-11) (FOLFIRI regimen) in patients (pts) with advanced colorectal cancer (ACC). " *Journal of Clinical Oncology* (2004) 255s (Abstract 3543), 22.

Casset et al., "A peptide mimetic of an anti-CD4 monoclonal antibody by rational design." *Biochem. Biophys. Res. Commun.* (2003) 198-205, 307(1).

Catimel et al., "Purification and characterization of a novel restricted antigen expressed by normal and transformed human colonic epithelium." *Journal of Biological Chemistry* (1996) 25664-25670, 271(41).

Chaffanet et al., "EGF receptor amplification and expression in human brain tumours." *Eur. J. Cancer* (1992) 11-17, 28(1).

Chakravarti et al., "Insulin-like growth factor receptor I mediates resistance to anti-epidermal growth factor receptor therapy in primary human glioblastoma cells through continued activation of phosphoinositide 3-kinase signaling." *Cancer Res.* (2002) 200-207, 62(1).

Chan et al., "EGFR Tyrosine Kinase Inhibition Decreases Epithelial Proliferation in DCIS of the Breast, Whereas C-ERBB2 Blockade, Does Not" *Proceedings of the Annual Meeting of the American Association for Cancer Research* (2000) 482 (Abstract 3074), 41.

Chang et al., "Ligand-induced internalization of the epidermal growth factor receptor is mediated by multiple endocytic codes analogous to the tyrosine motif found in constitutively internalized receptors." *Journal of Biological Chemistry* (1993) 19312-19320, 268(26).

Chantry, "The kinase domain and membrane localization determine intracellular interactions between epidermal growth factor receptors." *Journal of Biological Chemistry* (1995) 3069-3073, 270(7).

Chau et al., "The association between EGFR variant III, HPV, p16, c-MET, EGFR gene copy number and response to EGFR inhibitors in patients with recurrent or metastatic squamous cell carcinoma of the head and neck." *Head & neck oncology* (20.11) 11, 3.

Chen et al., "Mice mutant for Egfr and Shp2 have defective cardiac semilunar valvulogenesis." *Nature Genetics* (2000) 296-299, 24(3).

Cherk et al., "Lack of correlation of hypoxic cell fraction and angiogenesis with glucose metabolic rate in non-small cell lung cancer assessed by 18F-Fluoromisonidazole and 18F-FDG PET." *J. Nucl. Med.* (2006) 1921-1926, 47(12).

Chien et al., "Significant structural and functional change of an antigen-binding site by a distant amino acid substitution: proposl of a structural mechanism." *Proceedings of the National Academy of Sciences of the United States of America* (1989) 5532-5536, 86(14).

Ching et al., "Expression of mRNA for epidermal growth factor, transforming growth factor-alpha and their receptor in human prostate tissue and cell lines." *Molecular and cellular biochemistry* (1993) 151-158, 126(2).

Chinkers et al., "Rapid induction of morphological changes in human carcinoma cells A-431 by epidermal growth factors." *The Journal of Cell Biology* (1979) 260-265, 83(1).

Chong et al., "Phase I trial of 131I-huA33 in patients with advanced colorectal carcinoma." *Clin. Cancer Res.* (2005) 4818-4826, 11(13).

Chopra, "11In-Labeled CHX-A-DTPA conjugated monoclonal antibody (mAb) 806 targeting the epidermal growth factor receptor deletion variant de2-7 (EGFRvIII)" *Molecular Imaging and Contrast Agent Database (MICAD) [Internet]. Bethesda(MD): National Center for Biotechnology Information (US)* (2010) 1-5.

Chopra, "125I-Labeled monoclonal antibody (mAb) 806 targeting the epidermal growth factor receptor deletion variant de2-7 (EGFRvIII)." *Molecular Imaging and Contrast Agent Database (MICAD) [Internet]. Bethesda(MD): National Center for Biotechnology Information (US)* (2010) 1-4.

Chopra, "111In-Labeled chimeric monoclonal antibody, ch806, targeting the epidermal growth factor receptor deletion variant de2-7 (EGFRvIII)." *Molecular Imaging and Contrast Agent Database (MICAD) [Internet]. Bethesda(MD): National Center for Biotechnology Information (US)* (2010) 1-5.

Chopra, "124I-Labeled residulizing ligand IMP-R4 conjugated chimeric monoclonal antibody ch806 targeting the epidermal growth factor receptor deletion variant de2-7(EGFRv111)." *Molecular Imaging and Contrast Agent Database (MICAD) [Internet]. Bethesda(MD): National Center for Biotechnology Information (US)* (2010) 1-5.

Christensen et al., "High levels of HER-2 expression alter the ability of epidermal growth factor receptor (EGFR) family tyrosine kinase inhibitors to inhibit EGFR phosphorylation in vivo." *Clin. Cancer Res.* (2001) 4230-4238, 7(12).

Christensen et al., "Immunohistorchemical detection of epidermal growth factor receptor in laryngeal squamous cell carcinomas." *Acta otolaryngol* (1992) 734-738, 112(4).

Christmann et al., "Epitope mapping and affinity purification of monospecific antibodies by *Escherichia coli* cell surface display of gene-derived random peptide libraries." *J. lmmunol. Methods* (2001) 163-173, 257(1-2).

Chu et al., "Receptor dimerization is not a factor in the signalling activity of a transforming variant epidermal growth factor receptor (EGFRvIII)." *Biochem. J.* (1997) 855-861, 324 ( Pt 3).

Chung et al., "Increased eprodermal growth factor receptor gene copy number is associated with poor prognosis in head and neck squamous cell carcinomas." *Journal of Clinical Oncology* (2006) 4170-4176, 24(25).

Chung et al., "Cetuximab shows activity in colorectal cancer patients with tumors that do not express the epidermal growth factor receptor by immunohistochemistry." *J. Clin. Oncol.* (2008) 1803-1810, 23(9).

Ciardiello et al., "Potentiation of cytotoxic drugs activity in human cancer cells by ZD-1839 (IRESSA), and EGFR-selective tyrosine kinase inhibitor." *Proceedings of the American Association for Cancer Research* (2000) 482 (Abstract 3075), 41.

Ciardiello et al., "Epidermal growth factor receptor (EGFR) as a target in cancer therapy: understanding the role of receptor expression and other molecular determinants that could influence the response to anti-EGFR drugs." *Eur. J. Cancer* (2003) 1348-1354, 39(10).

Ciardiello et al., "A novel approach in the treatment of cancer: targeting the epidermal growth factor receptor." *Clin. Cancer Res.* (2001) 2958-2970, 7(10).

Ciardiello et al., "Inhibition of growth factor production and angiogenesis in human cancer cells by ZD1839 (Iressa), a selective epidermal growth factor receptor tyrosine kinase inhibitor." *Clin. Cancer Res.* (2001) 1459-1465, 7(5).

Ciardiello et al., "Antiangiogenic and antitumor activity of anti-epidermal growth factor receptor C225 monoclonal antibody in combination with vascular endothelial growth factor antisense oligonucleotide in human GEO colon cancer cells." *Clin. Cancer Res.*(2000) 3739-3747, 6(9).

Ciardiello et al., "Antitumor effect and potentiation of cytotoxic drugs activity in human cancer cells by ZD-1839 (Iressa), an epidermal growth factor receptor-selective tyrosine kinase inhibitor." *Clin. Cancer Res.* (2000) 2053-2063, 6(5).

Ciardiello, "Epidermal growth factor receptor tyrosine kinase inhibitors as anticancer agents." *Drugs* (2000) 25-32; discussion 41-2, 60(Suppl. 1).

Ciardiello et al., "Antitumor activity of sequential treatment with topotecan and anti-epidermal growth factor receptor monoclonal antibody C225." *Clin. Cancer Res.* (1999) 909-916, 5(4).

(56) References Cited

OTHER PUBLICATIONS

Ciardiello et al., "Cooperative inhibition of renal cancer growth by anti-epidermal growth factor receptor antibody and protein kinase a antisense oligonucleotide." *J. Natl. Cancer Inst.* (1998) 1087-1094, 90(14).

Ciardiello et al., "Antitumor activity of combined blockade of epidermal growth factor receptor and protein kinase A." *J. Natl. Cancer Inst.* (1996) 1770-1776, 88(23).

Ciardiello et al., "Cooperative antiproliferative effects of 8-chlorocyclic AMP and 528 anti-epidermal growth factor receptor monoclonal antibody on human cancer cells." *Clin. Cancer Res.* (1995) 161-167, 1(2).

Ciesielski et al., "Oncogenic epidermal growth factor receptor mutants with tandem duplication: gene structure and effects on receptor function." *Oncogene* (2000) 810-820, 19(6).

Clark, "Antibody humanization: a case of the 'Emperors new clothes'?" *Immunology today* (2000) 397-402, 21(8).

Clarke et al., "Therapeutic efficacy of anti-Lewis (y) humanized 3S 193 radioimmunotherapy in a breast cancer model: enhanced activity when combined with Taxol chemotherapy" *Clin. Cancer Res.* (2000) 3621-3628, 6.

Clarke et al., "Mutant epidermal growth factor receptor enhances induction of vascular endothelial growth factor by hypoxia and insulin-like growth factor-1 via a PI3 kinase dependent pathway." *British Journal of Cancer* (2001) 1322-1329, 84(10).

Clarke et al., "In vivo biodistribution of a humanized anti-Lewis Y monoclonal antibody (hu3S193) in MCF-7 xenografted BALB/c nude mice." *Cancer Res.* (2000) 4804-4811, 60(17).

Clayton et al., "Unligated epidermal growth factor receptor forms higher order oligomers within microclusters on A431 cells that are sensitive to tyrosine kinase inhibitor binding." *Biochemistry* (2007) 4589-4597, 46(15).

Clynes et al., "Inhibitory Fc receptors modulate in vivo cytotoxicity against tumor targets." *Nature Med.* (2000) 443-446, 6(4).

Co et al., "Humanized antibodies for therapy." *Nature* (1991) 501-502, 351(6326).

Cobleigh et al., "Multinational study of the efficacy and safety of humanized anti-HER2 monoclonal antibody in women who have HER2-overexpressing metastatic breast cancer that has progressed after chemotherapy for metastatic disease." *J. Clin. Oncol.* (1999) 2639-2648, 17(9).

Cochran et al., "Domain-level antibody epitope mapping through yeast surface display of epidermal growth factor receptor fragments." *J. Immunol. Methods* (2004) 147-158, 287(1-2).

Cohen et al., "Phase II study of ZD1839 (Iressa) in recurrent or metastatic squamous cell carcinoma of the head and neck (SCCHN)." *Proceedings of the American Society of Clinical Oncology* (2002) 225a (Abstract 899), 21.

Cohen et al., "Safety profile of the monoclonal antibody (MoAb) IMC-C255, an anti-epidermal growth factor receptor (EGFR) used in the treatment of EGFR-positive tumors." *Proceedings of the American Society of Clinical Oncology* (2000) 474a (Abstract 1862), 19.

Cohen et al., "United States Food and Drug Administration Drug Approval summary: Gefitinib (ZD1839; Iressa) tablets." *Clin. Cancer Res.* (2004) 1212-1218, 10(4).

Cohen et al., "Epidermal growth factor-receptor-protein kinase interactions. Co-purification of receptor and epidermal growth factor-enhanced phosphorylation activity." *Journal of Biological Chemistry* (1980) 4834-4842, 255(10).

Cokgor et al., "Phase I trial results of iodine-131-labeled antitenascin monoclonal antibody 8106 treatment of patients with newly diagnosed malignant gliomas." *J. Clin. Oncol.* (2000) 3862-3872, 18(22).

Colapinto et al., "Comparative localization of murine monoclonal antibody Me1-14 F(ab')2 fragment and whole IgG2a in human glioma xenografts." *Cancer Res.* (1988) 5701-5707, 48(20).

Collins, "Gene amplification in human gliomas." *Glia* (1995) 289-296, 15(3).

Collins, "Amplified genes in human gliomas." *Seminars in cancer biology* (1993) 27-32, 4(1).

Cortez et al., "Influence of size, surface, cell line, and kinetic properties on the specific binding of A33 antigen-targeted multilayered particles and capsules to colorectal cancer cells." *ACS nano* (2007) 93-102, 1(2).

Cortez et al., "Targeting and Uptake of Multilayered Particles to Colorectal Cancer Cells" *Advanced Materials* (2006) 1998-2003, 18.

Corti et al., "Idiotope determining regions of a mouse monoclonal antibody and its humanized versions. Identification of framework residues that affect idiotype expression." *J. Mol. Biol.* (1994) 53-60, 235(1).

Cowley et al., "Increased EGF receptors on human squamous carcinoma cell lines." *British Journal of Cancer* (1986) 223-229, 53(2).

Cragg et al., "Signaling antibodies in cancer therapy." *Curr. Opin. Immunol.* (1999) 541-547, 11(5).

Crawford et al., "ABX-EGF in combination with paclitaxel and carboplatin for advanced non-small cell lung cancer (NSCLC)" *Journal of Clinical Oncology, 2004 ASCO Annual Meeting Proceedings (Post-Meeting Edition)* (2004) 7083, 22(14S).

Crombet et al., "Use of the anti-EGFR antibody h-R3 in combination with radiotherapy in the treatment of advanced head and neck cancer (Abstract 53)" *Proceedings of the American Society of Clinical Oncology* (2002) 14a, 21.

Crombet et al., "Phase I clinical evaluation of a neutralizing monoclonal antibody against epidermal growth factor receptor in advanced brain tumor patients: preliminary study." *Hybridoma* (2001) 131-136, 20(2).

Crombet et al., "Use of the humanized anti-epidermal growth factor-receptor monoclorial antibody h-R3 in combination with-radiotherapy in the treatment of locally advanced head and neck cancer patients." *J. Clin. Oncol.* (2004) 1646-1654, 22(9).

Cunningham et al., "High-resolution epitope mapping of hGH-receptor interactions by alanine-sdanning mutagenesis." *Science* (1989) 1081-1085, 244(4908).

Cunningham et al., "Cetuximab monotherapy and cetuximab plus irinotecan in irinotecan-refractory metastatic colorectal cancer." *N. Engl. J. Med.* (2004) 337-345, 251(4).

Cvrljevic et al., "Activation of Src induces mitochondrial localisation of de2-7EGFR (EGFRvIII) in glioma cells: implications for-glucose metabolism." *Journal of cell science* (2011) 2938-2950, 124(Part 17).

Dadparvar et al., "Indium-111-labeled anti-EGFr-425 scintigraphy in the detection of malignant gliomas." *Cancer* (1994) 884-889, 73(3; Supplement).

Daley et al.; "Transformation of an interleukin 3-dependent hernatopoietic cell line by the chronic myelogenous leukemia-specific P210bcr/abl protein." *Proceedings of the National Academy of Sciences of the United States of America* (1988) 9312-9316, 85(23).

Damjanov et al., "Immunohistochemical localization of the epidermal growth factor receptor in normal human tissues." *Laboratory investigation; a journal of technical methods and pathology* (1986) 588-592, 55(5).

Damle, "Antibody-drug conjugates ace the tolerability test." *Nat. Biotechnol.* (2008) 884-885, 26(8).

Damstrup et al., "In vitro invasion of small-cell lung cancer cell lines correlates with expression of epidermal growth factor receptor." *British Journal of Cancer* (1998) 631-640, 78(5).

Damstrup et al., "Epidermal growth factor receptor mutation type III transfected into a small lung cancer cell line is predominantly localized at the cell surface and enhances the malignant phenotype." *Int. J. Cancer* (2002) 7-14, 97(1).

Daugherty et al., "Polymerase chain reaction facilitates the cloning, CDR-grafting, and rapid-expression of a murine monoclonal antibody directed against the CD18 component of leukocyte integrins." *Nucleic acids research* (1991) 2471-2476, 19(9).

Davies et al., "Genetic analysis of epidermal growth factor action: assignment of human epidermal growth factor receptor gene to chromosome 7." *Proceedings of the National Academy of Sciences of the United States of America* (1980) 4188-4192, 77(7).

Davies et al., "Specificity and mechanism of action of some commonly used protein kinase inhibitors." *Biochem. J.* (2000) 95-105, 351(Part 1).

Davis et al., "Transgenic mice as a source of fully human antibodies for the treatment of cancer." *Cancer Metastasis Rev.* (1999) 421-425, 18(4).

(56) References Cited

OTHER PUBLICATIONS

Dawson et al., "A phase II trial of gefitinib (Iressa, ZD1839) in stage IV and recurrent renal cell carcinoma." *Clin. Cancer Res.* (2004) 7812-7819, 10(23).
Dazzi et al., "Expression of epidermal growth factor receptor (EGF-R) in non-small cell lung cancer. Use of archival tissue and correlation of EGF-R with histology, tumour size, node status and survival." *British Journal of Cancer* (1989) 746-749, 59(5).
Dechant et al., "Effect of combinations of EGF-R antibodies on complement-dependent tumor cell lysis" *Journal of Clinical Oncology* (2008) 14005, 26(15S).
Decker, "Transmembrane signaling by epidermal growth factor receptors lacking autophosphorylation sites." *Journal of Biological Chemistry* (1993) 9176-9179, 268(13).
Decker, "Aspects of the metabolism of the epidermal growth factor receptor in A431 human epidermoid carcinoma cells." *Mol. Cell Biol.* (1984) 571-575, 4(4).
Deen et al., "Brain Tumor Working Group Report on the 9th International Conference on Brain Tumor Research and Therapy. Organ System Program, National Cancer Institute." *Journal of neuro-oncology* (1993) 243-272, 16(3).
Dehm et al., "SRC gene expression in human cancer: the role of transcriptional activation." *Biochemistry and cell biology* (2004) 263-274, 82(2).
Denardo et al., "Strategies for developing effective radioimmunotherapy for solid tumors." *Clin. Cancer Res.* (1999) 3219s-3223s, 5(10; Supplement).
Denardo et al., "A new era for radiolabeled antibodies in cancer?" *Curr. Opin.Immunol.* (1999) 563-569, 11(5).
Dewitt et al., "Quantitative analysis of the EGF receptor autocrine system reveals cryptic regulation of cell response by ligand capture." *Journal of cell science* (2001) 2301-2313, 114(Part 12).
Dicosimo et al., "Schedule-dependent effects of the epidermal growth factor receptor (EGFR) tyrosine kinase inhibitor gefitinib in combination with the mammalian target of rapamycin (mTOR) inhibitor everolimus (RAD001)." *Proceedings of the American Society of Clinical Oncology* (2004) 213s (Abstract 3074).
Diedrich et al., "Distribution of epidermal growth factor receptor gene amplification in brain tumours and correlation to prognosis." *Journal of Neurology* (1995) 683-688, 242(10).
Van Dijk et al., "Human antibodies as next generation therapeutics." *Current opinion in chemical biology* (2001) 368-374, 5(4).
Discafani et al., "Irreversible inhibition of epidermal growth factor receptor tyrosine kinase with in vivo activity by N-[4-[(3-bromophenyl)amino]-6-quinazolinyl]-2-butynamide (CL-387,785)." *Biochemical pharmacology* (1999) 917-925, 57(8).
Dittadi et al., "Epidermal growth factor receptor in lung malignancies. Comparison between cancer and normal tissue." *British Journal of Cancer* (1991) 741-744, 64(4).
Domagala et al., "Stoichiometry, kinetic and binding analysis of the interaction between epidermal growth factor (EGF) and the extracellular domain of the EGF receptor." *Growth Factors* (2000) 11-29, 18(1).
Van Doorn et al., "Follicular and epidermal alterations in patients treated with ZD1839 (Iressa), an inhibitor of the epidermal growth factor receptor." *The British journal of dermatology* (2002) 598-601, 147(3).
Doronina et al., "Enhanced Activity of Monomethylauristatin F through Monoclonal Antibody Delivery: Effects of Linker Technology on Efficacy and Toxicity" *Bioconjugate chemistry* (2006) 114-124, 17(1).
Downward et al., "Close similarity of epidermal growth factor receptor and v-erb-B oncogene protein sequences." *Nature* (1984) 521-527, 307(5951).
Eberhard et al., "Mutations in the epidermal growth factor receptor and in KRAS are predictive and prognostic indicators in patients with non-small-cell lung cancer treated with chemotherapy alone and in combination with erlotinib." *J. Clin. Oncol.* (2005) 5900-5909, 23(25).
Egloff et al., "Targeting epidermal growth factor receptor and SRC pathways in head and neck cancer." *Semin. Oncol.* (2008) 286-297, 35(3).
Ekstrand et al., "Altered subcellular location of an activated and tumour-associated epidermal growth factor receptor." *Oncogene* (1995) 1455-1460, 10(7).
Ekstrand et al., "Functional characterization of an EGF receptor with a truncated extracellular domain expressed in glioblastomas with EGFR gene amplification." *Oncogene* (1994) 2313-2320, 9(8).
Ekstrand et al., "Amplified and rearranged epidermal growth factor receptor genes in human glioblastomas reveal deletions of sequences encoding portions of the N- and/or C-terminal tails." *Proceedings of the National Academy of Sciences of the United States of America* (1992) 4309-4313, 89(10).
Elleman et al., "Identification of a determinant of epidermal growth factor receptor ligand-binding specificity using a truncated, high-affinity form of the ectodomain." *Biochemistry* (2001) 8930-8939, 40(30).
Eller et al., "Activity of anti-epidermal growth factor receptor monoclonal antibody C225 against glioblastoma multiforme." *Neurosurgery* (2002) 1005-13; discussion 1013-4, 51(4).
Ellgaard et al., "Quality control in the endoplasmic reticulum." *Nat. Rev. Mol. Cell. Biol.* (2003) 181-191, 4(3).
Ellis et al., "Preclinical analysis of the analinoquinazoline AG1478, a specific small molecule inhibitor of EGF receptor tyrosine kinase." *Biochemical pharmacology* (2006) 1422-1434, 71(10).
Ennis, "Monoclonal Anti-EGF Receptor Antibodies Inhibit the Growth of Malignant and Nonmalignant Human Mammary Epithelial Cells." *J. Cell Biochem.* (1989) 104 (Abstract E207)(Suppl. 13B).
Ennis et al., "The EGF receptor system as a target for antitumor therapy." *Cancer investigation* (1991) 553-562, 9(5).
Ennis et al., "Anti-epidermal growth factor receptor antibodies inhibit the autocrine-stimulated growth of MDA-468 human breast cancer cells." *Molecular endocrinology (Baltimore, Md.)* (1989) 1830-1838, 3(11).
Epenetos et al., "Long term survival of patients with advanced ovarian cancer treated with intraperitoneal, radioimmunotherapy." *International journal of gynecological cancer : official journal of the International Gynecological Cancer Society* (2000) 44-46, 10(Suppl. 1).
Epenetos et al., "Antibody guided irradiation of brain glioma by arterial infusion of radioactive monoclonal antibody against epidermal growth factor receptor and blood group A antigen." *British medical journal (Clinical research ed.)* (1985) 1463-1466, 290(6480).
Erickson, "Antibody-Maytansinoid Conjugates are Activated in Targeted Cancer Cells by Lysosomal Degradation and Linker-Dependent Intracellular Processing" *Cancer Research* (2006) 4426-4433, 66(8).
Eriksen et al., "The EGFRvIII variant in squamous cell carcinomas of the head and neck: Expression and correlation with clinico-pathological parameters in 675 patients from the randpmised DAHANCA 6/7 study." *ECCO 15—34th ESMO Multidisciplinary Congress (Berlin)* (2009) 472 (Abstract P-8507).
Ezekiel et al., "Phase I trial of chimerized anti-epidermal growth factor receptor (Anti-EGFr) antibody in combination with either once-daily or twice-daily irradiation for locally advanced head and neck malignancies." *Proceedings of the American Society of Clinical Oncology* (1999) 388a (Abstract 1501), 18.
Fan et al., "Blockade of epidermal growth factor receptor by anti-EGFR monoclonal antibody 225 causes GI arrest of A431 cells with induction of p27KIPI" *Proceedings of the American Association for Cancer Research* (1996) 10 (Abstract #69), 37.
Fan et al., "Therapeutic application of anti-growth factor receptor antibodies." *Current opinion in oncology* (1998) 67-73, 10(1).
Fan et al., "Antibody-induced epidermal growth factor receptor dimerization mediates inhibition of autocrine proliferation of A431 squamous carcinoma cells." *Journal of Biological Chemistry* (1994) 27595-27602, 269(44).
Fan et al., "Blockade of epidermal growth factor receptor function by bivalent and monovalent fragments of 225 anti-epidermal growth factor receptor monoclonal antibodies." *Cancer Res.* (1993) 4322-4328, 53(18).

(56) References Cited

OTHER PUBLICATIONS

Fantl et al., "Signalling by receptor tyrosine kinases." *Annual review of biochemistry* (1993) 453-481, 62.
Farrugia et al., "A possible role for metallic ions in the carbohydrate cluster recognition displayed by a Lewis Y specific antibody." *PLoS ONE* (2009) e7777, 4(11).
Feldhaus et al., "Flow-cytometric isolation of human antibodies from a nonimmune Saccharomyces cerevisiae surface display library." *Nat. Biotechnol.* (2003) 163-170, 21(2).
Feldkamp et al., "Expression of activated epidermal growth factor receptors, Ras-guanosine triphosphate, and mitogen-activated protein kinase in human glioblastoma multiforme specimens." *Neurosurgery* (1999) 1442-1453, 45(6).
Fendly et al., "Characterization of murine monoclonal antibodies reactive to either the human epidermal growth factor receptor or HER2/neu gene product." *Cancer Res.* (1990) 1550-1558, 50(5).
Fenstermaker et al., "Deletion and tandem duplication of exons 2-7 in the epidermal growth factor receptor gene of a human malignant glioma." *Oncogene* (2000) 4542-4548, 19(39).
Ferguson, "Structure-based view of epidermal growth factor receptor regulation." *Annual review of biophysics* (2008) 353-373, 37.
Fernandes et al., "Glycosylation-induced conformational modification positively regulates receptor-receptor association: a study with an aberrant epidermal growth factor receptor (EGFRvIII/DeltaEGFR) expressed in cancer cells." *Journal of Biological Chemistry* (2001) 5375-5383, 276(7).
Ferrara et al., "Discovery and development of bevacizumab, an anti-VEGF antibody for treating cancer." *Nature reviews. Drug discovery* (2004) 391-400, 3(5).
Ferry et al., "Intermittent Oral ZD1839 (Iressa), a Novel Epidermal Growth Factor Receptor Tyrosine Kinase Inhibitor (EGFR-TKI), Show Evidence of Good Tolerability and Activity: Final Results from a Phase I Study (Abstract 5E)" *Proceedings of the American Society of Clinical Oncology* (2000) 3a, 19.
Figlin et al., "ABX-EGF, a fully human anti-epidermal growth factor receptor (EGFR) monoclonal antibody (mAb) in patients with advanced cancer: phase 1 clinical results (Abstract 35)" *Proceedings of the American Society of Clinical Oncology* (2002) 10a, 21.
Filmus et al., "Epidermal growth factor receptor gene-amplified MDA-468 breast cancer cell line and its nonamplified variants." *Mol. Cell Biol.* (1987) 251-257, 7(1).
Filmus et al., "Amplified, overexpressed and rearranged epidermal growth factor receptor gene in a human astrocytoma cell line." *Biochem. Biophys. Res. Commun.* (1985) 207-215, 131(1).
Filmus et al., "MDA-468, a human breast cancer cell line with a high number of epidermal growth factor (EGF) receptors, has an amplified EGF receptor gene and is growth inhibited by EGF." *Biochem. Biophys. Res. Commun.* (1985) 898-905, 128(2).
Finkler et al., "Phase 2 Evaluation of OSI-774, a Potent Oral Antagonist of the EGFR-TK in Patients with Advanced Ovarian Carcinoma." *Proceedings of the American Society of Clinical Oncology* (2001) 208a (Abstract 831), 20.
Di Fiore et al., "Overexpression of the human EGF receptor confers an EGF-dependent transformed phenotype to NIH 3T3 cells." *Cell* (1987) 1063-1070, 51(6).
Fischer-Colbrie et al., "EGFR and steroid receptors in ovarian carcinoma: comparison with prognostic parameters and outcome of patients." *Anticancer research* (1997) 613-619, 17(1B).
Fisher et al., "Induction and apoptotic regression of lung adenocarcinomas by regulation of a K-Ras transgene in the presence and absence of tumor suppressor genes." *Genes Dev.* (2001) 3249-3262, 15(24).
Flynn et al., "Campath-1H monoclonal antibody therapy." *Current opinion in oncology* (2000) 574-581, 12(6).
Fong et al., "Epidermal growth factor receptor monoclonal antibody inhibits constitutive receptor phosphorylation, reduces autonomous growth, and sensitizes androgen-independent prostatic carcinoma cells to tumor necrosis factor α." *Cancer Res.* (1992). 5887-5892, 52(21).
Foo et al:, "Functional imaging of intratumoral hypoxia." *Molecular imaging and biology : MIB : the official publication of the Academy of Molecular Imaging* (2004) 291-305, 6(5).
Forastiere et al., "Head and neck cancer." *N. Engl. J. Med.* (2001)1890-1900, 345(26).
Ford et al., "Pharmacogenomic approaches for identifying markers predictive of tumor response to Cetuximab (Erbitux)" *Proc. Amer. Assoc. Cancer Res.* (2004) Abstract 2032, 45.
Ford et al., "Targeting epidermal growth factor receptor in head and neck cancer." *Head & neck* (2003) 67-73, 25(1).
Fornier et al., "Trastuzumab in combination with chemotherapy for the treatment of metastatic breast cancer." *Semin. Oncol.* (2000) 38-45; discussion 92-100, 27(6; Suppl. 11).
Foulon et al., "Positively charged templates for labeling internalizing antibodies: comparison of N-succinimidyl 5-iodo-3-pyridinecarboxylate and the D-amino acid peptide KRYRR." *Nucl. Med. Biol.* (2001)769-777, 28(7).
Fowler et al., "A mutation in the epidermal growth factor receptor in waved-2 mice has a profound effect on receptor biochemistry that results in impaired lactation." *Proceedings of the National Academy of Sciences of the United States of America* (1995) 1465-1469, 92(5).
Fox et al., "Tumour angiogenesis." *The Journal of pathology* (1996) 232-237, 179(3).
Fraker et al., "Protein and cell membrane iodinations with a sparingly soluble chloroamide, 1,3,4,6-tetrachloro-3a,6a-diphrenylglycoluril." *Biochem. Biophys. Res. Commun.* (1978) 849-857, 80(4).
Frame, "Newest findings on the oldest oncogene; how activated src does it." *Journal of cell science* (2004) 989-998, 117(Part 7).
Francisco, "cAC10-vcMMAE, an anti-CD30-monomethyl auristatin E conjugate with potent and selective antitumor activity" *Blood* (2003) 1458-1465, 102(4).
Frank et al., "SPOT synthesis. Epitope analysis with arrays of synthetic peptides prepared on cellulose membranes." *Methods Mol. Biol.* (1996) 149-169, 66.
Franklin et al., "Association between activation of ErbB pathway genes and survival following gefitinib treatment in advanced BAC (SWOG 0126)." *Proceedings of the Annual Meeting of the American Society of Clinical Oncology* (2004) 620s (Abstract 7015), 22.
Frederick et al., "Analysis of genomic rearrangements associated with EGRFvIII expression suggests involvement of Alu repeat elements." *Neuro-oncology* (2000) 159-163, 2(3).
Frederick et al., "Diversity, and frequency of epidermal growth factor receptor mutations in human glioblastomas." *Cancer Res.* (2000) 1383-1387, 60(5).
Friedman et al., "Temozolomide and treatment of malignant glioma." *Clin. Cancer Res.* (2000) 2585-2597, 6(7).
Friedman et al., "Glioblastoma multiforme and the epidermal growth factor receptor." *N. Engl. J. Med.* (2005) 1997-1999, 353(19).
Friedman et al., "Synergistic down-regulation of receptor tyrosine kinases by combinations of mAbs: implications for cancer immunotherapy." *Proceedings of the National Academy of Sciences of the United States of America* (2005) 1915-1920, 102(6).
Friess et al., "Combination treatment with erlotinib and pertuzumab against human tumor xenografts is superior to monotherapy." *Clin. Cancer Res.* (2005) 5300-5309, 11(14).
Fry, "Site-directed irreversible inhibitors of the erbB family of receptor tyrosine kinases as novel chemotherapeutic agents for cancer." *Anti-cancer drug design* (2000) 3-16, 15(1).
Fry, "Inhibition of the epidermal growth factor receptor family of tyrosine kinases as an approach to cancer chemotherapy: progression from reversible to irreversible inhibitors." *Pharmacology & therapeutics* (1999) 207-218, 82(2-3).
Fry et al., "Specific, irreversible inactivation of the epidermal growth factor receptor and erbB2, by a new class of tyrosine kinase inhibitor." *Proceedings of the National Academy of the Sciences of the United States of America* (1998) 12022-12027, 95(20).
Fry et al., "Biochemical and antiproliferative properties of 4-[ar(alk)ylamino]pyridopyrimidines, a new chemical class of potent and specific epidermal growth factor receptor tyrosine kinase inhibitor." *Biochemical pharmacology* (1997) 877-887, 54(8).
Fry et al., "A specific inhibitor of the epidermal growth factor receptor tyrosine kinase." *Science* (1997) 1093-11095, 265(5175).

(56) References Cited

OTHER PUBLICATIONS

Fujino et al., "A comparison of epidermal growth factor receptor levels and other prognostic parameters in non-small cell lung cancer." *Eur. J. Cancer* (1996) 2070-2074, 32A(12).
Fukai et al., "Antitumor activity of cetuximab against malignant glioma cells overekpressing EGFR deletion mutant variant III." *Cancer science* (2008) 2062-2069, 99(10).
Fukuoka et al., "Final results from a phase II trial of ZD1839 ('Iressa') for patients with advanced non-small cell lung carcinoma (Ideal 1)." *Proceedings of the American Society of Clinical Oncology* (2002) 298a (Abstract 1188), 21.
Fukuoka et al., "Multi-institutional randomized phase II trial of gefitinib for previously treated patients with advanced non-small-cell lung cancer."*J. Clin. Oncol.* (2003) 2237-2246, 21(12).
Gamou et al., "Glycosylation of the epidermal growth factor receptor and its relationship to membrane transport and ligand binding." *Journal of biochemistry* (1988) 388-396, 104(3).
Gan et al., "Targeting a unique EGFR epitope with monoclonal antibody 806 activates NF-kappaB and initiates tumour vascular normalization." *Journal of cellular and molecular medicine* (2009) 3993-4001, 13(9B).
Gan et al., "The EGFRvIII variant in glioblatoma multiforme." *Journal of clinical neuroscience : official journal of the Neurosurgical Society of Australasia* (2009) 748-754, 16(6).
Gan et al., "The epidermal growth factor receptor (EGFR) tyrosine kinase inhibitor AG1478 increases the formation of inactive untethered EGFR dimers. Implications for combination therapy with monoclonal antibody 806." *Journal of Biological Chemistry* (2007) 2840-2850, 282(5).
Garinchesa et al., "Organ-specific expression of the colon dancer antigen A33, a cell surface target for antibody-based therapy." *Int. J. Oncol.* (1996) 465-471, 9(3).
Garrett et al., "Antibodies-specifically targeting a locally misfolded region of tumor associated EGFR." *Proceedings of the National Academy of Sciences of the United States of America* (2009) 5082-5087, 106(13).
Ge et al., "Evidence of high incidence of EGFRvIII expression and coexpression with EGFR in human invasive breast cancer by laser capture microdissection and immunohistochemical analysis." *Int. J. Cancer* (2002) 357-361, 98(3).
George et al., "Differential effects of anti-beta2-glycoprotein I antibodies on endothelial cells and on the manifestations of experimental antiphospholipid syndrome." (1998) 900-906, 97(9).
Giaccone et al., "Combination therapy with ZD1839 (Iressa), an orally active, selective, epidermal growth factor receptor tyrosine kinase inhibitor (EGFR-TKI), gemcitabine and cisplatin, in patients with advanced solid tumors: promising preliminary results on tolerability, efficacy, and pharmacokinetics." *Clinical Cancer Research* (2001) 3765s (Abstract 553), 7.
Gibson et al., "Randomized phase III trial results of panitumumab, a fully human anti-epidermal growth factor receptor monoclonal antibody, in metastatic colorectal cancer." *Clin. Colorectal Cancer* (2006) 29-31, 6(1).
Gill et al., "Relationship between production of epidermal growth factor receptors, gene amplification, and chromosome 7 translocation in variant A431 cells." *Somatic cell and molecular genetics* (1985) 309-318, 11(4).
Gill et al., "New targeted therapies in gastrointestinal cancers." *Current treatment options in oncology* (2003) 393-403, 4(5).
Giusti et al., "Somatic diversification of S107 from an antiphosphocholine to an anti-DNA autoantibody is due to a single base change in its heavy chain variable region." *Proceedings of the National Academy of Sciences of the United States of America* (1987) 2926-2930, 84(9).
Glennie et al., "Clinical trials of antibody therapy." *Immunology today* (2000) 403-410, 21(8).
Glennie et al., "Renaissance of cancer therapeutic antibodies." *Drug discovery today* (2003) 503-510, 8(11).
Goldberg, "Cetuximab." *Nature reviews. Drug discovery* (2005) S10-1(Suppl. 10).
Goldenberg et al., "Imaging of human tumor xenografts with an indium-111-labeled anti-epidermal growth factor receptor monoclonal antibody." *J. Natl. Cancer Inst.* (1989) 1616-1625, 81(21).
Goldenberg, "Advancing role of radiolabeled antibodies in the therapy of cancer." *Cancer Immunol. Immunother.* (2003) 281-296, 52(5).
Goldenberg, "Targeting therapy of cancer with radiolabeled anitbodies," *J. Nucl. Med.* (2002) 693-713, 43(5).
Goldman et al., "Epidermal growth factor stimulates vascular endothelial growth factor production by human malignant glioma cells: a model of glioblastoma multiforme pathophysiology." *Mol. Biol. Cell* (1993) 121-133, 4(1).
Goldman et al., "Heterodimerization of the erbB-1 and erbB-2 receptors in human breast carcinoma cells: a mechanism for receptor transregulation." *Biochemistry* (1990) 11024-11028, 29(50).
Gonzalez, "Epidermal growth factor-based cancer vaccine for non-small-cell lung cancer therapy" *Annals of Oncology* (2003) 461-466, 14(3).
Gorgoulis et al., "Molecular and immunohistochemical evaluation of epidermal growth factor receptor and c-erb-B-2 gene product in transitional cell carcinomas of the urinary bladder: a study in Greek patients." *Modern pathology : an official journal of the United States and Canadian Academy of Pathology, Inc* (1995) 758-764, 8(7).
Gorre et al., "Clinical resistance to STI-571 cancer therapy caused by BCR-ABL gene mutation or amplification." *Science* (2001) 876-880, 293(5531).
Goss et al., "Final results of the dose escalation phase of a phase I pharmacokinetics (PK), pharmacodynamic (PD), and biological activity study of ZD1839." *Proceedings of the American Society of Clinical Oncology* (2001) 85a (Abstract 335), 20.
Graeven et al., "Phase I study of the humanised anti-EGFR monoclonal antibody matuzumab (EMD 72000) combined with gemcitabine in advanced pancreatic cancer." *British Journal of Cancer* (2006) 1293-1299, 94(9).
Grandal et al., "EGFRvIII escapes down-regulation due to impaired internalization and sorting to lysosomes." *Carcinogenesis* (2007) 1408-1417, 28(7).
Grandis et al., "Elevated levels of transforming growth factor alpha and epidermal growth factor receptor messenger RNA are early markers of carcinogenesis in head and neck cancer." *Cancer Res.* (1993) 3579-3584, 53(15).
Grandis et al., "Levels of TGF-alpha and EGFR protein in head and neck squamous cell carcinoma and patient survival." *J. Natl. Cancer Inst.* (1998),824-832, 90(11).
Graness et al., "Protein-tyrosine-phosphatase-mediated epidermal growth factor (EGF) receptor transinactivation and EGF receptor-independent stimulation of mitogen-activated protein kinase by bradykinin in A431 cells." *Biochem. J.* (2000) 441-447, 347(Part 2).
Graus-Porta et al., "Single-chain antibody-mediated intracellular retention of ErbB-2 impairs Neu differentiation factor and epidermal growth factor signaling." *Mol. Cell Biol.*(1995) 1182-1191, 15(3).
Green et al., "Monoclonal antibody therapy for solid tumors." *Cancer Treat Rev.* (2000) 269-286, 26(4).
Greenspan et al., "Defining epitopes: It's not as easy as it seems." *Nat. Biotechnol.* (1999) 936-937, 17(10).
Groner et al., "Therapeutic antibodies." *Current molecular medicine* (2004) 539-547, 4(5).
Grunwald et al., "Development of the epidermal growth factor receptor inhibitor OSI-774" *Seminars in Oncology* (2003) 23-31, 30(3; Suppl. 6).
Gschwind et al., "The discovery of receptor tyrosine kinases: targets for cancer therapy." *Nature Rev. Cancer* (2004) 361-370, 4(5).
Gullick, "Type I growth factor receptors: current status and future work." *Biochemical Society symposium* (1998) 193-198, 63.
Gullick, "A new model for the interaction of EGF-like ligands with their receptors: the new one-two." *Eur. J. Cancer* (1994) 2186, 30A(14).
Gullick, "Growth factors, growth factor receptors and neoplasia." *Human & experimental toxicology* (1991) 398-400, 10(6).
Gullick, "Prevalence of aberrant expression of the epidermal growth factor receptor in human cancers." *British medical bulletin* (1991) 87-98, 47(1).

(56) References Cited

OTHER PUBLICATIONS

Gulliford et at., "Intensification of growth factor receptor signalling by phorbol treatment of ligand-primed cells implies a dimer-stabilizing effect of protein kinase C-dependent dependent juxtamembrane domain phosphorylation." *Cellular signalling* (1999) 245-252, 11(4).
Gunnett et al., "Phase II study of antiepidermal growth factor receptor (EGFR) antibody C225 alone in patients (pts) with metastatic renal carcinoma (RCC)." *Annual Meeting of the American Society of Clinical Oncology* (1999) 340a (Abstract 1309), 18.
Günther et al., "The secreted form of the epidermal growth factor receptor. Characterization and crystallization of the receptor-ligand complex." *Journal of Biological Chemistry* (1990) 22082-22085; 265(36).
Gupta et al., "Development of an EGFRvIII specific recombinant antibody." *BMC biotechnology* (2010) 72, 10.
Güssow et al., "Humanization of monoclonal antibodies." *Methods in Enzymology* (1991) 99-121, 203.
Haas-Kogan et al., "Epidermal growth factor receptor, protein kinase B/Akt, and glioma response to erlotinib." *J. Natl. Cancer Inst.* (2005) 880-887, 97(12).
Haber et al., "Molecular targeted therapy of lung cancer: EGFR mutations and response to EGFR inhibitors." *Cold Spring Harbor symposia on quantitative biology* (2005) 419-426, 70.
Hackel et al., "Epidermal growth factor receptors: critical mediators of multiple receptor pathways." *Current opinion in cell biology* (1999) 184-189, 11(2).
Haigler et al., "Visualization by fluorescence of the binding and internalization of epidermal growth factor in human carcinoma cells A-431." *Proceedings of the National Academy of Sciences of the United States of America* (1978) 3317-3321, 75(7).
Halatsch et al., "Marked inhibition of glioblastoma target cell tumorigenicity in vitro by retrovirus-mediated transfer of a hairpin ribozyme against deletion-mutant epidermal growth factor receptor messenger RNA." *J. Neurosurg.* (2000) 297-305, 92(2).
Halatsch et al., "Epidermal growth factor receptor inhibition for the treatment of glioblastoma multiforme and other malignant brain tumours." *Cancer Treat Rev.* (2006).74-89, 32(2).
Halatsch et al., "Inverse correlation of epidermal growth factor receptor messenger RNA induction and suppression of anchorage-independent growth by OSI-774, an epidermal growth factor receptor tyrosine kinase inhibitor, in glioblastoma multiforme cell lines." *J. Neurosurg.* (2004).523-533, 100(3).
Haley et al., "The human EGF receptor gene: structure of the 110 kb locus and identification of sequences regulating its transcription." *Oncogene research* (1987) 375-396, 1(4).
Haley, "Regulation of epidermal growth factor receptor expression and activation: a brief review." *Symposia of the Society for Experimental Biology* (1990) 21-37, 44.
Hambek et al:, "Tumor Necrosis Factor α Sensitizes Low Epidermal Growth Factor Receptor (EGFR)—expressed Carcinomas for Anti-EGFR Therapy." *Cancer Res.* (2001) 1045-1049, 61.
Hamblett et al., "Effects of drug loading on the antitumor activity of a monoclonal antibody drug conjugate." *Clin. Cancer Res.* (2004) 7063-7070, 10(20).
Han et al., "Predictive and prognostic impact of epidermal growth factor receptor mutation in non-small-cell lung cancer patients treated with gefitinib." *J. Clin. Oncol.*(2005) 2493-2501, 23(11).
Han et al., "Tyrphostin AG 1478 preferentially inhibits human glioma cells expressing truncated rather than wild-type epidermal growth factor receptors." *Cancer Res.* (1996) 3859-3861, 56(17).
Hanahan et al., "The hallmarks of cancer." *Cell* (2000) 57-70, 100(1).
Hanks et al., "The protein kinase family: conserved features and deduced phylogeny of the catalytic domains." *Science* (1988) 42-52, 241(4861).
Hanna et al., "Phase II trial of cetuximab in patients with previously treated non-small-cell lung cancer." *Journal of Clinical Oncology* (2006) 5253-5258, 24(33).

Harari et al., "Combining radiation with molecular blockade of the EGF receptor in cancer therapy." *Proceedings of the American Association for Cancer Research* (1999) 3747s (Abstract 88), 5.
Harari et al., "Molecular mechanisms underlying ErbB2/HER2 action in breast cancer." *Oncogene* (2000) 6102-6114, 19(53).
Harari, "Epidermal growth factor receptor inhibition strategies in oncology." *Endocrine-related cancer* (2004) 689-708, 11(4).
Harari et al., "Head and neck cancer as a clinical model for molecular targeting of therapy: combining EGFR blockade with radiation." *Int. J. Radiat. Oncol. Biol. Phys.* (2001) 427-433, 49(2).
Harries et al., "The development and clinical use of trastuzumab (Herceptin)." *Endocrine-related cancer* (2002) 75-85, 9(2).
Harris et al., "The Role of ERBB2 Extracellular Domain in Predicting Response to Chemotherapy in Breast Cancer Patients." *Proceedings of the Annual Meeting of the American Society of Clinical Oncology* (1996) 108 (Abstract 96), 15.
Harris et al., "Epidermal Growth Factor Receptor: A Marker of Early Relapse in Breast Cancer and Tumor Stage Progression in Bladder Cancer; Interactions with neu." *In: The Molecular Diagnostics-of Human Cancer (Editors: Furth and Greaves; Publisher: Cold Spring Harbor, NY: Cold Spring Harbor Laboratory).* (1989) 353-357.
Harris et al., "Therapeutic antibodies—the coming of age." *Trends in biotechnology* (1993) 42-44, 11(2).
Hatanpaa et al., "Epidermal growth factor receptor in glioma: signal transduction, neuropathology, imaging, and radioresistance." *Neoplasia* (2010) 675-684, 12(9).
Hayman et al., "Cell transformation by the epidermal growth factor receptor and v-erbB." *Cancer cells* (Cold Spring Harbor, N.Y.: 1989) (1991) 302-307, 3(8).
He et al., "Inhibition of human squamous cell carcinoma growth in vivo by epidermal growth factor receptor antisense RNA transcribed from the U6 promoter." *J. Natl. Cancer Inst.* (1998) 1080-1087, 90(14).
Heath et al., "The human A33 antigen is a transmembrane glycoprotein and a novel member of the immunoglobulin superfamily." *Proceedings of the National Academy of Sciences of the United States of America* (1997) 469-474, 94(2).
Hecht et al., "ABX-EGF monotherapy in patients (pts) with metastatic colorectal cancer (mCRC) (An updated analysis)." *Proceedings of the American Society of Clinical Oncology* (2004) 247s (AbStract 3511), 23.
Heimberger et al., "The natural history of EGFR and EGFRvIII in glioblastoma patients." *Journal of translational medicine* (2005) 38, 3.
Heimberger et al., "Prognostic effect of epidermal growth factor receptor and EGFRvIII in glioblastoma multiforme patients." *Clin. Cancer Res.* (2005) 1462-1466, 11(4).
Heimberger et al.; "Epidermal growth factor receptor VIII peptide vaccination is efficacious against established intracerebral tumors." *Clin. Cancer Res.* (2003)4247-4254, 4254, 9(11).
Heimberger et al., "Brain tumors in mice are susceptible to blockade of epidermal growth factor receptor (EGFR) with the oral, specific, EGFR-tyrosine kinase inhibitor ZD1839 (iressa)." *Clin. Cancer Res.* (2002) 3496-3502, 8(11).
Helin et al., "Internalization and down-regulation of the human epidermal growth factor receptor are regulated by the carboxyl-terminal tyrosines." *Journal of Biological Chemistry* (1991) 8363-8368, 266(13).
Helin et al., "The biological activity of the human epidermal growth factor receptor is positively regulated by its C-terminal tyrosines." *Oncogene* (1991) 825-832, 6(5).
Hendler et al., "Human squamous cell lung cancers express increased epidermal growth factor receptors." *J. Clin. Invest.* (1984) 647-651, 74(2).
Henn et al., "Polysomy of chromosome 7 is correlated with overexpression of the erbB oncogene in human glioblastoma cell lines." *Human genetics* (1986) 104-106, 74(1).
Henry et al., "A prostate-specific membrane antigen-targeted monoclonal antibody-chemotherapeutic conjugate designed for the treatment of prostate cancer." *Cancer Res.* (2004) 7995-8001, 64(21).
Hens et al., "Anti-EGFRvIII monoclonal antibody armed with 177Lu: in vivo comparison of macrocyclic and acyclic ligands." *Nucl. Med. Biol.* (2010) 741-750, 37(7).

(56) References Cited

OTHER PUBLICATIONS

Hens et al., "Labeling internalizing anti-epidermal growth factor receptor variant III monoclonal antibody with (177)Lu: in vitro comparison of acyclic and macrocyclic ligands." *Nucl. Med. Biol.* (2009) 117-128, 36(2).
Herbertson et al., "Phase I biodistribution and pharmacokinetic study of Lewis Y-targeting immunoconjugate CMD-193 in patients with advanced epithelial cancers." *Clin. Cancer Res.* (2009) 6709-6715, 15(21).
Herbst et al., "Regulation of postendocytic trafficking of the epidermal growth factor receptor through endosomal retention." *Journal of Biological Chemistry* (1994) 12865-12873, 269(17).
Herbst, "Dose-comparative monotherapy trials of ZD1839 in previously treated non-small small cell lung cancer patients" *Seminars in Oncology* (2003) 30-38, 30(1).
Herbst et al., "IMC-C225, an anti-epidermal growth factor receptor monoclonal antibody, for treatment of head and neck cancer." *Expert opinion on biological therapy* (2001) 719-732, 1(4).
Herbst et al., "Phase II multicenter study of the epidermal growth factor receptor antibody cetuximab and cisplatin for recurrent and refractory squamous cell carcinoma of the head and neck." *J. Clin. Oncol.* (2005) 5578-5587, 23(24).
Herbst et al., "Phase I/II trial evaluating the anti-vascular endothelial growth factor monoclonal antibody bevacizumab in combination with the HER-1/epidermal growth factor receptor tyrosine kinase inhibitor erlotinib for patients with recurrent non-small-cell lung cancer." *J. Clin. Oncol.* (2005) 2544-2555, 23(11).
Herbst, "Erlotinib (Tarceva): An update on the clinical trial program" *Seminars in Oncology* (2003) 34-46, 30(3H).
Herbst et al., "IMC-C225, an anti-epidermal growth factor receptor monoclonal antibody for treatment of head and neck cancer." *Semin. Oncol.* (2002) 18-30, 29(5; Suppl. 14).
Herbst et al., "Selective oral epidermal growth factor receptor tyrosine kinase inhibitor ZD1839 is generally well-tolerated and has activity in non-small-cell lung cancer and other solid tumors: results of a phase I trial." *J. Clin. Oncol.* (2002) 3815-3825, 20(18).
Herbst, "Targeted therapy in non-small-cell lung cancer." *Oncology (Williston Park, N.Y.)* (2002) 19-24, 16(9; Suppl. 9).
Herbst et al., "Monoclonal antibodies to target epidermal growth factor receptor-positive tumors: a new paradigm for cancer therapy." *Cancer* (2002) 1593-1611, 94(5).
Herbst et al., "Epidermal growth factor receptors as a target for cancer treatment: the emerging role of IMC-C225 in the treatment of lung and head and neck cancers." *Semin. Oncol.* (2002) 27-36, 29(1 Suppl 4).
Hertler et al., "Immunotoxins: a clinical review of their use in the treatment of malignancies." *J. Clin. Oncol.* (1989) 1932-1942, 7(12).
Van Der Heyden et al., "Identification of an intracellular domain of the EGF receptor required for high-affinity binding of EGF." *FEBS letters* (1997) 265-268, 410(2-3).
Hidalgo et al., "Phase 1 trial of EKB-569, an irreversible inhibitor of the epidermal growth factor receptor (EGFR), in patients with advanced solid tumors." *Proceedings of the American Society of Clinical Oncology* (2002) 17a (Abstract 65), 21.
Hidalgo et al., "Phase I and pharmacologic study of OSI-774, an epidermal growth factor receptor tyrosine kinase inhibitor, in patients with advanced solid malignancies." *J. Clin. Oncol.* (2001) 3267-3279, 19(13).
Hirata et al., "ZD1839 (Iressa) induces antiangiogenic effects through inhibition of epidermal growth factor receptor tyrosine kinase." *Cancer Res.* (2002) 2554-2560, 62(9).
Hird et al., "Immunotherapy with Monoclonal Antibodies." *In: Genes and Cancer (Chapter 17) (Editor: Carry; Publisher: John Wiley & Sons, Ltd).* (1990) 183-189.
Hirsch et al., "Increased epidermal growth factor receptor gene copy number detected by fluorescence in situ hybridization associates with increased sensitivity to gefitinib in patients with bronchioloalveolar carcinoma subtypes: a Southwest Oncology Group Study." *J. Clin. Oncol.* (2005) 6838-6845, 23(28).
Hirsch et al., "Epidermal growth factor receptor in non-small-cell lung carcinomas: correlation between gene copy number and protein expression and impact on prognosis." *J. Clin. Oncol.* (2003)3798-3807, 21(20).
Hoffman et al., "Phase I Trials of CDR-Grafted Humanized Monoclonal Antibody Hu3S193 in Patients with Lewis-Y Expressing Solid Tumors." *Proc. Am. Soc. Clin. Oncol.*(2001) Abstract 2634, 20.
Hoffmann et al., "Antitumor activity of anti-epidermal growth factor receptor monoclonal antibodies and cisplatin in ten human head and neck squamous cell carcinoma lines." *Anticancer research* (1997) 4419-4425, 17(6D).
Holbro et al., "The ErbB receptors and their role in cancer progression." *Exp. Cell Res.* (2003) 99-110, 284(1).
Holbrook et al., "Thermodynamic mixing of molecular states of the epidermal growth factor receptor modulates macroscopic ligand binding affinity." *Biochem. J.* (2000) 99-108, 352(Part 1).
Holland, "Glioblastoma multiforme: the terminator." *Proceedings of the National Academy of Sciences of the United States of America* (2000) 6242-6244, 97(12).
Holland et al., "A constitutively active epidermal growth factor receptor cooperates with disruption of G1 cell-cycle arrest pathways to induce glioma-like lesions in mice." *Genes Dev.* (1998) 3675-3685, 12(23).
Hollstein et al., "Amplification of epidermal growth factor receptor gene but no evidence of ras mutations in primary human esophageal cancers." *Cancer Res.* (1988) 5119-5123, 48(18).
Holm et al., "Functional mapping and single chain construction of the anti-cytokeratin 8 monoclonal antibody TS1." *Mol. Immunol.* (2007) 1075-1084, 44(6).
Holmes et al., "Structural consequences of humanizing an antibody." *Journal of immunology* (1997) 2192-2201, 158(5).
Honegger et al., "Biological activities of EGF-receptor mutants with individually altered autophosphorylation sites." *EMBO J.* (1988) 3045-3052, 7(10).
Hong et al., "Efficacy and Safety of the Anti-Epidermal Growth Factor Antibody (EGFR) IMC-225, in Combination with Cisplatin in Patients with Recurrent Squamous Cell Carcinoma of the Head and Neck (SCCHN) Refractory to Cisplatin Containing Chemotherapy." *Proceedings of the American Society of Clinical Oncology* (2001) 224a (Abstract 895), 20.
Hortobagyi, "Overview of Treatment Results With Trastuzumab (Herceptin) in Metastatic Breast Cancer." *Seminars in Oncology* (2001) 43-47, 28(6; Suppl. 18).
Hosoi et al., "Exogenous ATP and other nucleoside phosphates modulate epidermal growth factor receptors of A-431 epidermoid carcinoma cells." *Proceedings of the National Academy of Sciences of the United States of America* (1989) 4510-4514, 86(12).
Huang et al., "Phosphotyrosine signaling analysis of site-specific mutations on EGFRvIII identifies determinants governing glioblastoma cell growth." *Molecular bioSystems* (2010) 1227-1237, 6(7).
Huang et al., "Uncovering therapeutic targets for glioblastoma: a system biology approach." *Cell cycle (Georgetown, Tex.)* (2007)2750-2754, 6(22).
Huang et al., "Quantitative analysis of EGFRvIII cellular signaling networks reveals a combinatorial therapeutic strategy for glioblastoma." *Proceedings of the National Academy of Sciences of the United States of America* (2007) 12867-12872, 104(31).
Huang et al., "Epidermal growth factor receptor blockade with C225 modulates proliferation, apoptosis, and radiosensitivity in squamous cell carcinomas of the head and neck." *Cancer Res.* (1999) 1935-1940, 59(8).
Huang et al., "Epidermal growth factor receptor inhibition in cancer therapy: biology, rationale and preliminary clinical results." *Investigational new drugs* (1999) 259-269, 17(3).
Huang et al, "Modulation of radiation response and tumor-induced angiogenesis after epidermal growth factor receptor inhibition by ZD1839 (Iressa)." *Cancer Res.* (2002) 4300-4306, 62(15).
Huang et al., "Dual-agent molecular targeting of the epidermal growth factor receptor (EGFR): combining anti-EGFR antibody with tyrosine kinase inhibitor." *Cancer Res.* (2004) 5355-5362, 64(15).

(56) References Cited

OTHER PUBLICATIONS

Hubbard et al., "Protein tyrosine kinase structure and function." *Annual review of biochemistry* (2000) 373-398, 69.
Hubbard, "EGF receptor inhibition: attacks on multiple fronts." *Cancer Cell* (2005) 287-288, 7(4).
Huber et al., "Trimodal cancer treatment: beneficial effects of combined antiangiogenesis, radiation, and chemotherapy." *Cancer Res.* (2005) 3643-3655, 65(9).
Hudson et al., "Engineered antibodies." *Nature Med.* (2003) 129-134, 9(1).
Humphrey et al., "Deletion-mutant epidermal growth factor receptor in human gliomas: effects of type II mutation on receptor function." *Biochem. Biophys. Res. Commun.* (1991) 1413-1420, 178(3).
Humphrey et al., "Amplification and expression of the epidermal growth factor receptor gene in human glioma xenografts." *Cancer Res.* (1988) 2231-2238, 48(8).
Humphreys et al., "Therapeutic antibody production technologies: molecules, applications, expression and purification." *Current opinion in drug discovery & development* (2001) 172-185, 4(2).
Hunts et al., "Hyperproduction and gene amplification of the epidermal growth factor receptor in squamous cell carcinomas." *Japanese journal of cancer research : Gann* (1985) 663-666, 76(8).
Hurtt et al., "Amplification of epidermal growth factor receptor gene in gliomas: histopathology and prognosis." *Journal of neuropathology and experimental neurology* (1992) 84-90, 51(1).
Hurwitz et al., "Bevacizumab plus irinotecan, fluorouracil, and leucovorin for metastatic colorectal cancer." *N. Engl. J. Med.* (2004) 2335-2342, 350(23).
Hynes et al., "ERBB receptors and cancer: the complexity of targeted inhibitors." *Nature Rev. Cancer* (2005) 341-354, 5(5).
Illidge et al., "Antibody therapy of lymphoma." *Expert opinion on pharmacotherapy* (2001) 953-961, 2(6).
Inoue et al., "Paclitaxel enhances the effects of the anti-epidermal growth factor receptor monoclonal antibody ImClone C225 in mice with metastatic human bladder transitional cell carcinoma." *Clin. Cancer Res.* (2000) 4874-4884, 6(12).
Ishida et al., "[The expression technology of chimeric and humanized antibodies]." *Nippon rinsho. Japanese journal of clinical medicine* (2002) 439-444, 60(3). English translation of Japanese document.
Ishitoya et al., "Gene amplification and overexpression of EGF receptor in squamous cell carcinomas of the head and neck." *British Journal of Cancer* (1989) 559-562, 59(4).
Ishizawar et al., "c-Src and cooperating partners in human cancer." *Cancer Cell* (2004) 209-214, 6(3).
Italiano, "Targeting the epidermal growth factor receptor in colorectal cancer: advances and controversies." *Oncology* (2006) 161-167,10(3).
Iznaga-Escobar et al., "Technetium-99m-antiepidermal growth factor-receptor antibody in patients with tumors of epithelial origin: part II. Pharmacokinetics and clearances." *J. Nucl. Med.* (1998) 1918-1927, 39(11).
Jamnongjit et al., "Epidermal growth factor receptor signaling is required for normal ovarian steroidogenesis and oocyte maturation." *Proceedings of the National Academy of Sciences of the United States of America* (2005) 16257-16262, 102(45).
Janmaat et al., "Response to epidermal growth factor receptor inhibitors in non-small cell lung cancer cells: limited antiproliferative effects and absence of apoptosis associated with persistent activity of extracellular signal-regulated kinase or Akt kinase pathways." *Clin. Cancer Res.* (2003) 2316-2326, 9(6).
Jänne et al., "Epidermal growth factor receptor mutations in non-small-cell lung cancer: implications for treatment and tumor biology." *J. Clin. Oncol.* (2005) 3227-3234, 23(14).
Jaros et al., "Prognostic implications of p53 protein, epidermal growth factor receptor, and Ki-67 labelling in brain tumours." *British Journal of Cancer* (1992) 373-385, 66(2).
Jay et al., "Chemical sysnthesis of a biologically active gene for human immune interferon-gamma. Prosepect for site-specific mutageneisis and structure-function studies." *Journal of Biological Chemistry* (1984) 6311-6317, 259(10).
Ji et al., "EGFR targeted therapy: view from biological standpoint." *Cell cycle (Georgetown, Tex.)* (2006) 2072-2076, 5(18).
Ji et al., "The impact of human EGFR kinase domain mutations on lung tumorigenesis and in vivo sensitivity to EGFR-targeted therapies." *Cancer Cell* (2006) 485-495, 9(6).
Ji et al., "Epidermal growth factor receptor variant III mutations in lung tumorigenesis and sensitivity to tyrosine kinase inhibitors." *Proceedings of the National Academy of Sciences of the United States of America* (2006) 7817-7822, 103(20).
Jiang et al., "A novel peptide isolated from a phage display peptide library with trastuzumab can mimic antigen epitope of HER-2." *Journal of Biological Chemistry* (2005) 4656-4662, 280(6).
Jiang et al., "Growth suppression of human hepatocellular carcinoma xenografts by a monoclonal antibody CH12 directed to epidermal growth factor receptor variant III." (2011) 5913-5920, 286(7).
Johns, "Targeting the Transition State" *Science's STKE* (2004) tw259, 2004(242).
Johns et al., "A Novel Antibody Directed to the Epidermal Growth Factor Receptor (EGFR) Displays Additive and Synergistic Anti-tumour Activity when used in Combination with Standard EGFR Therapeutics." *The Proceedings of the 15th Annual Lorne Cancer Conference, Lorne, Victoria, Australia.* (2003) Abstract P212.
Johns et al., "A Novel Antibody Directed to the Epidermal Growth Factor Receptor (EGFR) Displays Additive and Synergistic Anti-Tumor Activity When Used in Combination with Standard EGFR Therapeutics." *Proceedings of the International Symposium sponsored by the Cancer Research Institute, New York, U.S.A.*(2002) Abstract P-08.
Johns et al., "Biological Properties of the Glioma Associated Delta 2-7 Epidermal Growth Factor Receptor." *The 11th International Conference on Second Messengers and Phosphoprtiens, Melbourne, Australia* (2001) Abstract P183.
Johns et al., "Annual Branch Report 1998 ("Pre-clinical evaluation of antibodies directed to the de2-7 epidermal growth factor receptors")" *Ludwig Institute for Cancer Research* (2000) 118-119.
Johns et al., "A Novel Antibody Directed to the Epidermal Growth Factor Receptor (EGFR) Displays Additive and Synergistic Anti-tumor Activity when Used in Combination with Standard EGFR therapeutics (Abstract 2877)" *Proceedings of the American Association of Cancer Research* (2002) 580, 43.
Johns et al., "The antitumor monoclonal antibody 806 recognizes a high-mannose form of the EGF receptor that reaches the cell surface when cells over-express the receptor" *FASEB J.* (2005) 1-18, 19(3).
Johns et al., "MAb 806 enhances the efficacy of ionizing radiation in glioma xenografts expressing the de2-7 epidermal growth factor receptor." *Int. J. Radiat. Oncol. Biol. Phys.* (2010) 572-578, 78(2).
Jones et al:, "A quantitative protein interaction network for the ErbB receptors using protein microarrays." *Nature* (2006) 168-174, 439(7073).
De Jong et al., "Expression of growth factors, growth-inhibiting factors, and their receptors in invasive breast cancer. II: Correlations with proliferation and angiogenesis." *The Journal of pathology* (1998) 53-57, 184(1).
Jorgensen et al., "Immunoconjugates: A Therapy Whose Time Has Come?" *Preclinica* (2004) 1-4, 2.
Jorissen et al., "Characterization of a comparative model of the extracellular domain of the epidermal growth factor receptor." *Protein science* (2000) 310-324, 9(2).
Jost et al., "The EGF receptor—an essential regulator of multiple epidermal functions." *European journal of dermatology : EJD* (2000) 505-510, 10(7).
Jung et al., "Local immunotherapy of glioma patients with a combination of 2 bispecific antibody fragments and resting autologous lymphocytes: evidence for in situ t-cell activation and therapeutic efficacy." *Int. J. Cancer* (2001) 225-230, 91(2).
Jutten et al., "Binding of cetuximab to the EGFRvIII deletion mutant and its biological consequences in malignant glioma cells." *Radiotherapy and oncology* (2009) 393-398, 92(3).
Kalofonos et al., "Antibody guided diagnosis and therapy of brain gliomas using radiolabeled monoclonal antibodies against epidermal growth factor receptor and placental alkaline phosphatase." *J. Nucl. Med.* (1989) 1636-1645, 30(10).

(56) References Cited

OTHER PUBLICATIONS

Kamat et al., "Enhanced EGFR inhibition and distinct epitope recognition by EGFR antagonistic mAbs C225 and 425." *Cancer biology & therapy* (2008) 726-733, 7(5).
Kamb et al., "A cell cycle regulator potentially involved in genesis of many tumor types." *Science* (1994) 436-440, 264(5157).
Kaminski et al., "Iodine-131-anti-B1 radioimmunotherapy for B-cell lymphoma." *J. Clin Oncol.* (1996) 1974-1981, 14(7).
Karnes et al., "Inhibition of epidermal growth factor receptor kinase induces protease-dependent apoptosis in human colon cancer cells." *Gastroenterology* (1998) 930-939, 114(5).
Karnes et al., "Autonomous proliferation of colon cancer cells that coexpress transforming growth factor alpha and its receptor. Variable effects of receptor-blocking antibody." *Gastroenterology* (1992) 474-485, 102(2).
Karpel-Massler et al., "Therapeutic inhibition of the epidermal growth factor receptor in high-grade gliomas: where do we stand?" *Molecular cancer research : MCR* (2009) 1000-1012, 7(7).
Kashmiri et al., "Development of a minimally immunogenic variant of humanized anti-carcinoma monoclonal antibody CC49." *Crit. Rev. Oncol. Hematol.* (2001) 3-16, 38(1).
Kasprzyk et al., "Therapy of an animal model of hunian gastric cancer using a combination of anti-erbB-2 monoclonal antibodies." *Cancer Res.* (1992) 2771-2776, 52(10).
Katzel et al., "Recent advances of novel targeted therapy in non-small cell lung cancer." *Journal of hematology & oncology* (2009) 2, 2.
Kawagoe et al., "Immunohistochemical demonstration of epidermal growth factor (EGF) receptors in normal human placental villi." *Placenta* (1990) 7-15, 11(1).
Kawamoto et al., "Relation of epidermal growth factor receptor concentration to growth of human epidermoid carcinoma A431 cells." *Journal of Biological Chemistry* (1984).7761-7766, 259(12).
Kawamoto et al., "Growth stimulation of A431 cells by epidermal growth factor: identification of high-affinity receptors for epidermal growth factor by an anti-receptor monoclonal antibody." *Proceedings of the National Academy of Sciences of the United States of America* (1983) 1337-1341, 80(5).
Ke et al., "Differential expression of epidermal growth factor receptor in human head and neck cancers." *Head & neck* (1998) 320-327, 20(4).
Kelly et al., "ZD1839 ('IRESSA'), an oral EGFR-TKI (epidermal growth factor receptor tyrosine kinase inhibitor): Pharmacokinetic results of a phase I study in patients with advanced cancer." *Proceedings of the Annual Meeting of the American Association for Cancer Research* (2000) 612-613 (Abstract 3896), 41.
Kelly et al., "Therapeutic efficacy of 177Lu-CHX-A-DTPA-hu3S193 radioimmunotherapy in prostate cancer is enhanced by EGFR inhibition or docetaxel chemotherapy." *The Prostate* (2009) 92-104, 69(1).
Khazaeli et al., "Low Immunogenicity of a Chimeric Monoclonal Antibody (MoAb), IMC-C225, Used to Treat Epidermal Growth Factor Receptor-Positive Tumors." *Proceedings of the American Society of Clinical Oncology* (2000) 207a (Abstract 808), 19.
Khazaeli et al., "Human immune response to monoclonal antibodies." *Journal of immunotherapy with emphasis on tumor immunology : official journal of the Society for Biological Therapy* (1994) 42-52, 15(1).
Khazaeli et al., "Pharmacokinetics and immune response of 131I-chimeric mouse/human B72.3 (human gamma 4) monoclonal antibody in humans." *Cancer Res.* (1991) 5461-5466, 51(20).
Khazaie et al., "EGF receptor in neoplasia and metastasis." *Cancer Metastasis Rev.* (1993) 255-274, 12(3-4).
Kies et al., "Final report of the efficacy and safety of the anti-epidermal growth factor antibody Erbitux (IMC-C225), in combination with cisplatin in patients with recurrent squamous cell carcinoma of the head and neck (SCCHN) refractory to cisplatin containing chemotherapy." *Proceedings of the American Society of Clinical Oncology* (2002) 232a (Abstract 925), 21.
Kikkawa et al., "[Immunohistochemical and histopathological study of expression of epidermal growth factor receptors in gastric cancer]." *Nippon Geka Gakkai zasshi* (1993) 1231-1238, 94(12). Abstract in English of Japanese Document.
Kil et al., "A leucine-based determinant in the epidermal growth factor receptor juxtamembrane domain is required for the efficient transport of ligand-receptor complexes to lysosomes." *Journal of Biological Chemistry* (1999) 3141-3150, 274(5).
Kim et al., "A phase II study of Erbitux (IMC-225), an epidermal growth factor receptor (EGFR) blocking antibody, in combination with docetaxel in chemotherapy refractory/resistant patients with advanced non-small cell lung cancer (NSCLC) (Abstract 1168)" *Proceedings of the American Society of Clinical Oncology* (2011) 293a, 21.
Kim et al., "Epidermal growth factor receptor biology (IMC-C225)." *Current opinion in oncology* (2001) 506-513, 13(6).
Kim et al., "Regulation of epidermal growth factor receptor internalization by G protein-coupled coupled receptors." *Biochemistry* (2003) 2887-2894, 42(10).
King et al., "Preparation and preclinical evaluation of humanised A33 immunoconjugates for radioimmunotherapy." *British Journal of Cancer* (1995) 1364-1372, 72(6).
Kiyota et al., "Expression of a truncated epidermal growth factor receptor in oral squamous cell carcinomas." *Cancer Letters* (2000) 9-15, 161(1).
Kiyota et al., "Anti-epidermal growth factor receptor monoclonal antibody 225 upregulates p27(KIP1) and p15(INK4B) and induces G1 arrest in oral squamous carcinoma cell lines." *Oncology* (2002) 92-98, 63(1).
Klapper et al., "Tumor-inhibitory antibodies to HER-2/ErbB-2 may act by recruiting c-Cbl and enhancing ubiquitination of HER-2." *Cancer Res .* (2000) 3384-3388, 60(13).
Klapper et al., "Biochemical and clinical implications of the ErbB/HER signaling network of growth factor receptors." *Advances in cancer research* (2000) 25-79, 77.
Klijn et al., "The prognostic value of epidermal growth factor receptor (EGF-R) in primary breast cancer: results of a 10 year follow-up study." *Breast cancer research and treatment* (1994) 73-83, 29(1).
Klijn et al.; "The clinical significance of epidermal growth factor receptor (EGF-R) in human breast cancer: a review on 5232 patients." *Endocrine reviews* (1992) 3-17, 13(1).
Klingbeil et al., "Analysis of substrate recognition determinants in a synthetic peptide containing the Tyr 1173 autophosphorylation site of the epidermal growth factor receptor." *Archives of biochemistry and biophysics* (1995) 745-750, 316(2).
Klingler-Hoffmann et al., "Inhibition of phosphatidylinositol 3-kinase signaling negates the growth advantage imparted by a mutant epidermal growth factor receptor on human glioblastoma cells." *Int. J. Cancer* (2003) 331-339, 105(3).
Klohs et al., "Inhibitors of tyrosine kinase." *Current opinion in oncology* (1997) 562-568, 9(6).
Knecht et al., "Carcinornas unresponsive to either cisplatinum or anti-EGFR therapy can be growth inhibited by combination therapy of both agents." *Anticancer research* (2003) 2577-2583, 23(3B).
Knutson et al., "Rapid, reversible internalization of cell surface insulin receptors. Correlation with insulin-induced down-regulation." *Journal of Biological Chemistry* (1983) 12139-12142, 258(20).
Kobayashi et al., "An alternative inhibitor overcomes resistance caused by a mutation of the epidermal growth factor receptor." *Cancer Res.* (2005) 7096-7101, 65(16).
Kobayashi et al., "EGFR mutation and resistance of non-small-cell lung cancer to gefitinib." *N. Engl. J. Med.* (2005) 786-792, 352(8).
Kondo et al., "Mapping of the human gene for epidermal growth factor receptor (EGFR) on the p13 leads to q22 region of chromosome 7." *Cytogenet. Cell Genet.* (1983) 14, 35(1).
Kopetz, "Synergistic effects of combination therapy with anti-EGFR and anti-Src therapy in vitro in colon cancer" *Gastrointestinal Cancers Symposium* (2007) Abstract 406.
Koprivica et al., "EGFR activation mediates inhibition of axon regeneration by myelin and chondroitin sulfate proteoglycans." *Science* (2005) 106-110, 310(5745).
Korshunov et al., "Prognostic value of tumour associated antigen immunoreactivity and apoptosis in cerebral glioblastomas: an analysis of 168 cases." *Journal of clinical pathology* (1999) 574-580, 52(8).

(56) References Cited

OTHER PUBLICATIONS

Kosaka et al., "Mutations of the epidermal growth factor receptor gene in lung cancer: biological and clinical implications." *Cancer Res.* (2004) 8919-8923, 64(24).
Kramer et al., "Regulation of daily locomotor activity and sleep by hypothalamic EGF receptor signaling." *Science* (2001) 2511-2515, 294(5551).
Kris et al., "A phase II trial of ZD1839 ('Iressa') in advanced non-small cell lung cancer (NSCLC) patients who had failed platinum- and docetaxel-based regimens (Ideal 2)." *Proceedings of the American Society of Clinical Oncology* (2002) 292a (Abstract 1166), 21.
Kris et al., "Objective regressions in non-small-cell lung cancer patients treated in phase I trials of oral ZD1839 (Iressa), a selective tyrosine kinase inhibitor that blocks the epidermal growth factor receptor (EGFR) (Abstract 233)" *Lung Cancer* (2000) 72, 29.
Krug et al., "Targeting Lewis Y (Le(y)) in small cell lung cancer with a humanized monoclonal antibody, hu3S193: a pilot trial testing two dose levels." *Journal of thoracic oncology : official publication of the International Association for the Study of Lung Cancer* (2007) 947-952, 2(10).
Kuan et al., "EGF mutant receptor vIII as a molecular target in cancer therapy." *Endocrine-related cancer* (2001) 83-96, 8(2).
Kuan et al., "Increased binding affinity enhances targeting of glioma xenografts by EGFRvIII-specific scFv." *Int. J. Cancer* (2000) 962-969, 88(6).
Kuan et al., "EGFRvIII as a promising target for antibody-based brain tumor therapy." *Brain tumor pathology* (2000) 71-78, 17(2).
Kuan et al., "125I-labeled anti-epidermal growth factor receptor-vIII single-chain Fv exhibits specific and high-level targeting of glioma xenografts." *Clin. Cancer Res.* (1999) 1539-1549, 5(6).
Kubo et al., "Three-dimensional magnetic resonance microscopy of pulmonary solitary tumors in transgenic mice." *Magnetic resonance in medicine : official journal of the Society of Magnetic Resonance in Medicine / Society of Magnetic Resonance in Medicine* (2006) 698-703, 56(3).
Kumar et al., "Regulation of phosphorylation of the c-erbB-2/HER2 gene product by a monoclonal antibody and serum growth factor(s) in human mammary carcinoma cells." *Mol. Cell Biol.* (1991) 979-986, 11(2).
Kunkel et al., "Inhibition of the epidermal growth factor receptor tyrosine kinase by PD153035 in human A431 tumors in athymic nude mice." *Investigational new drugs* (1996) 295-302, 13(4).
Kurpad et al., "Tumor antigens in astrocytic gliomas." *Glia* (1995) 244-256, 15(3).
Kwak et al., "Irreversible inhibitors of the EGF receptor may circumvent acquired resistance to gefitinib." *Proceedings of the National Academy of Sciences of the United States of America* (2005) 7665-7670, 102(21).
Kwok et al., "Cell cycle dependence of epidermal growth factor induced radiosensitization." *Int. J. Radiat. Oncol. Biol. Phys.* (1992) 525-527, 22(3).
Kwok et al., "Differences in EGF related radiosensitisation of human squamous carcinoma cells with high and low numbers of EGF receptors." *British Journal of Cancer* (1991) 251-254, 64(2).
Lackmann et al., "Eph, a protein family coming of age: more confusion, insight, or complexity?" *Science signaling* (2008) re2, 1(15).
Lacouture, "Mechanisms of cutaneous toxicities to EGFR inhibitors." *Nature Rev. Cancer* (2006) 803-812, 6(10).
Laderoute et al., "Epidermal growth factor modifies cell cycle control in A431 human squamous carcinoma cells damaged by ionizing radiation." *Cancer Res.* (1994) 1407-1411, 54(6).
Lakowicz, "Principles of Fluorescence Spectroscopy" *Principles of fluorescence spectroscopy. 2nd edit, Kluwer Academic/Plenum, New York* (1999) Table of Contents.
Lal et al., "Mutant epidermal growth factor receptor up-regulates molecular effectors of tumor invasion." *Cancer Res.* (2002) 3335-3339, 62(12).
Lammering et al., "Radiosensitization of malignant glioma cells through overexpression of dominant-negative epidermal growth factor receptor." *Clin. Cancer. Res.* (2001) 682-690, 7(3).

Lammering et al., "Inhibition of the type III epidermal growth factor receptor variant mutant receptor by dominant-negative EGFR-CD533 enhances malignant glioma cell radiosensitivity." *Clin. Cancer Res.* (2004) 6732-6743, 10(19).
Lammering et al., "EGFRvIII-mediated radioresistance through a strong cytoprotective response." *Oncogene* (2003) 5545-5553, 22(36).
Lammerts Van Bueren et al., "The antibody zalutumumab inhibits epidermal growth factor receptor signaling by limiting intra- and intermolecular flexibility." *Proceedings of the National Academy of Sciences of the United States of America* (2008) 6109-6114, 105(16).
Lammerts Van Bueren et al., "Effect of target dynamics on pharmacokinetics of a novel therapeutic antibody against the epidermal growth factor receptor: implications for the mechanisms of action." *Cancer Res.* (2006) 7630-7638, 66(15).
Landry et al., "Antibody recognition of a conformational epitope in a peptide antigen: Fv-peptide complex of an antibody fragment specific for the mutant EGF receptor, EGFRvIII." *J. Mol. Biol.* (2001) 883-893, 308(5).
Langedijk et al., "Antigenic structure of the central conserved region of protein G of bovine respiratory syncytial virus." *Journal of virology* (1997) 4055-4061, 71(5).
Lango et al., "Targeting growth factor receptors: integration of novel therapeutics in the management of head and neck cancer." *Current opinion in oncology* (2001) 168-175, 13(3).
Lanzetti et al., "The Eps8 protein coordinates EGF receptor signalling through Rac and trafficking through Rab5." *Nature* (2000) 374-377, 408(6810).
Lapthorn et al., "Cystine nooses and protein specificity." *Nature structural biology* (1995) 266-268, 2(4).
Larysz et al., "Epidermal growth factor receptor gene expression in high grade gliomas?" *Folia neuropathologica / Association of Polish Neuropathologists and Medical Research Centre, Polish Academy of Sciences* (2011) 28-38, 49(1).
Lassman et al., "Response of glioblastomas to EGFR kinase inhibitors." *N. Engl. J.Med.* (2006) 525-6; author reply 525-6, 354(5).
Lautrette et al., "Angiotensin II and EGF receptor cross-talk in chronic kidney diseases: a new therapeutic approach." *Nature Med.* (2005) 867-874, 11(8).
Lawrentschuk et al., "Assessing regional hypoxia in human renal tumours using 18F-fluoromisonidazole positron emission tomography." *BJU international* (2005) 540-546, 96(4).
Lax et al., "Epidermal growth factor (EGF) induces oligomerization of soluble, extracellular, ligand-binding domain of EGF receptor. A low resolution projection structure of the ligand-binding domain." *Journal of Biological Chemistry* (1991) 13828-13833, 266(21).
Lax et al., "Noncontiguous regions in the extracellular domain of EGF receptor define ligand-binding specificity." *Cell regulation* (1991) 337-345, 2(5).
Lax et al., "Functional analysis of the ligand binding site of EGF-receptor utilizing chimeric chicken/human receptor molecules." *EMBO J.* (1989) 421-427, 8(2).
Leahy et al., "A mammalian expression vector for expression and purification of secreted proteins for structural studies." *Protein Expr. Purif.* (2000) 500-506, 20(3).
Learn et al., "Resistance to tyrosine kinase inhibition by mutant epidermal growth factor receptor variant III contributes to the neoplastic phenotype of glioblastoma multiforme." *Clin. Cancer Res.* (2004) 3216-3224, 10(9).
Lee et al., "ImmunoPET detection of xenografts expressing de2-7 EGFR using Iodine-124 labelled ch806 via residualising ligand IMPR4" *J. Nucl. Med.* (2006) 429P, 47(5,Suppl. 1).
Lee et al., "Immuno-PET of human colon xenograft—bearing BALB/c nude mice using 124I-CDR-grafted humanized A33 monoclonal antibody." *J. Nucl. Med.* (2001) 764-769,42(5).
Lee et al., "Immuno-PET quantitation of de2-7 epidermal growth factor receptor expression in glioma using 124I-IMP-R4-labeled antibody ch806." *J. Nucl. Med.* (2010) 967-972, 51(6).
Lee et al., "Enhanced efficacy of radioimmunotherapy with 90Y-CHX-A-DTPA-hu3S193 by inhibition of epidermal growth factor receptor (EGFR) signaling with EGFR tyrosine kinase inhibitor AG1478." *Clin. Cancer Res.* (2005) 7080s-7086s, 11.

(56) References Cited

OTHER PUBLICATIONS

Lee et al., "Immuno-PET for tumor targeting." *J. Nucl. Med.* (2003) 1282-1283, 44(8).
Lee et al., "Therapeutic efficacy of antiglioma mesenchymal extracellular matrix 131I-radiolabeled murine monoclonal antibody in a human glioma xenograft model." *Cancer Res.* (1988) 559-566, 48(3).
Legge, "Computational Design of Humanized Antibodies against the Epidermal Growth Factor Receptor (PhD Thesis)" *Submitted in total fulfillment of the requirements of the degree of Doctor of Philosophy. University of Melbourne.* (2003) 1-278.
Lei et al., "Enhancement of chemosensitivity and programmed cell death by tyrosine kinase inhibitors correlates with EGFR expression in non-small cell lung cancer cells." *Anticancer research* (1999) 221-228, 19.
Lenferink et al., "Blockade of the epidermal growth factor receptor tyrosine kinase suppresses tumorigenesis in MMTV/Neu + MMTV/TGF-alpha bigenic mice." *Proceedings of the National Academy of Sciences of the United States of America* (2000) 9609-9614, 97(17).
Lenz et al., "Consistent Response to Treatment with Cetuximab Monotherapy in Patients with Metastatic Colorectal Cancer." *Journal of Clinical Oncology, 2005 ASCO Annual Meeting Proceedings* (2005) Abstract 3536, 23(16S; Part I of II: Jun. 1 Supplement).
Lenz et al., "Multicenter phase II and translational study of cetuximab in metastatic colorectal carcinoma refractory to irinotecan, oxaliplatin, and fluoropyrimidines." *Journal of Clinical Oncology* (2006) 4914-4921, 24(30).
Leon et al., "Genetic aberrations in human brain tumors." *Neurosurgery* (1994) 708-722, 34(4).
Leu et al., "Functional implication of the interaction between EGF receptor and c-Src." *Frontiers in bioscience : a journal and virtual library* (2003) s28-38, 8.
Levitzki et al., "Tyrosine kinase inhibition: an approach to drug development." *Science* (1995) 1782-1788, 267(5205).
Lewis Phillips et al., "Targeting HER2-Positive Breast Cancer with Trastuzumab-DM1, an Antibody-Cytotoxic Drug Conjugate" *Cancer Research* (2008) 9280-9290, 68(22).
Li et al., "Mutant epidermal growth factor receptor displays increased signaling through the phosphatidylinositol-3 kinase/AKT pathway and promotes radioresistance in cells of astrocytic origin." *Oncogene* (2004) 4594-4602, 23(26).
Li et al., "Resistance to small molecule inhibitors of epidermal growth factor receptor in malignant gliomas." *Cancer Res.* (2003) 7443-7450, 63(21).
Li et al., "Therapeutic anti-EGFR antibody 806 generates responses in murine de novo EGFR mutant-dependent lung carcinomas." *J. Clin. Invest.* (2007) 346-352, 117(2).
Li et al., "EGF receptor variant III as a target antigen for tumor immunotherapy. " *Expert Review of Vaccines* (2008) 977-985, 7(7).
Li et al., "Structural basis for EGF receptor inhibition by the therapeutic antibody IMC-11F8" *Structure* (2008)—216-227, 16(2).
Li et al., "Structural basis for inhibition of the epidermal growth factor receptor by cetuximab." *Cancer Cell* (2005) 301-311, 7(4).
Libermann et al., "Amplification, enhanced expression and possible rearrangement of EGF receptor gene in primary human brain tumours of glial origin." *Nature* (1985) 144-147, 313(5998).
Libermann et al., "Expression of epidermal growth factor receptors in human brain tumors." *Cancer Res.* (1984) 753-760, 44(2).
Lichtner et al., "Signaling-inactive epidermal growth factor receptor/ligand complexes in intact carcinoma cells by quinazoline tyrosine kinase inhibitors." *Cancer Res.* (2001) 5790-5795, 61(15).
Lin et al., "Expression cloning of human EGF receptor complementary DNA: gene amplification and three related messenger RNA products in A431 cells." *Science* (1984) 843-848, 224(4651).
Lindmo et al., "Determination of the immunoreactive fraction of radiolabeled monoclonal antibodies by linear extrapolation to binding at infinite antigen excess." *J. Immunol. Methods* (1984) 77-89, 72(1).

Lipton et al., "Elevated Serum HER-2/neu Level Predicts Decreased Response to Hormone Therapy in Metastatic Breast Cancer." *Proceedings of the American Society of Clinical Oncology* (2000) 71a (Abstract 274), 19.
Little et al., "Of mice and men: hybridoma and recombinant antibodies." *Immunology Today* (2000) 364-370, 21(8).
Liu et al., "Epidermal growth factor receptor activation: an upstream signal for transition of quiesbent astrocytes into reactive astrocytes after neural injury:" *The Journal of neuroscience : the official journal of the Society for Neuroscience* (2006) 7532-7540, 26(28).
Liu et al., "Clinical significance of EGFR amplification and the aberrant EGFRvIII transcript in conventionally treated astrocytic gliomas." *Journal of Molecular Medicine (Berlin, Germany)*(2005) 917-926, 83(11).
Liu et al., "The effect of epidermal growth factor receptor variant III on glioma cell migration by stimulating ERK phosphorylation through the focal adhesion kinase signaling pathway." *Archives of Biochemistry and Biophysics* (2010) 89-95, 502(2).
Liu et al., "Engineering therapeutic monoclonal antibodies." *Immunological Reviews* (2008) 9-27, 222.
Liu et al., "Generation of anti-idiotype antibodies for application in clinical immunotherapy laboratory analyses." *Hybridoma and Hybridomics* (2003) 219-228, 22(4).
Livneh et al., "Reconstitution of human epidermal growth factor receptors and its deletion mutants in cultured hamster cells." *Journal of Biological Chemistry* (1986) 12490-12497, 261(27).
Lo, "EGFR-targeted therapy in malignant glioma: novel aspects and mechanisms of drug resistance." *Current Molecular Pharmacology* (2010) 37-52, 3(1).
Lobuglio et al., "Mouse/human chimeric monoclonal antibody in man: kinetics and immune response." *Proceedings of the National Academy of Sciences of the United States of America* (1989) 4220-4224, 86(11).
Loew et al., "The epidermal growth factor receptor as a therapeutic target in glioblastoma multiforme and other malignant neoplasms." *Anti-Cancer Agents in Medicinal Chemistry* (2009) 703-715, 9(6).
Lofts et al., "c-erbB2 amplification and overexpression in human tumors." *In: Genes, Oncogenes, and Hormones: Advances in Cellular and Molecular Biology of Breast Cancer (Editors: Dickson and Lippman; Publisher: Kluwer Academic, Boston, MA).* (2011) 161-179.
Di Lorenzo et al., "Expression of epidermal growth factor receptor correlates with disease relapse and progression to androgen-independence in human prostate cancer." *Clin. Cancer Res.* (2002) 3438-3444, 8(11).
Lorimer et al., "Activation of extracellular-regulated kinases by normal and mutant EGF receptors." *Biochimica et Biophysica Acta* (2001) 1-9, 1538(1).
Lorimer et al., "Recombinant immunotoxins specific for a mutant epidermal growth factor receptor: targeting with a single chain antibody variable domain isolated by phage display." *Proceedings of the National Academy of Sciences of the United States of America* (1996) 14815-14820, 93(25).
Lorimer et al., "Immunotoxins that target an oncogenic mutant epidermal growth factor receptor expressed in human tumors." *Clin. Cancer Res.* (1995) 859-864, 1(8).
Lorimer, "Mutant epidermal growth factor receptors as targets for cancer therapy." *Current Cancer Drug Targets* (2002) 91-102, 2(2).
Lorusso et al., "Improvements in quality of life and disease-related symptoms in phase I trials of the selective oral epidermal growth factor receptor tyrosine kinase inhibitor ZD1839 in non-small cell lung cancer and other solid tumors:" *Clin. Cancer Res.* (2003) 2040-2048, 9(6).
Lu et al., "Fyn and SRC are effectors of oncogenic epidermal growth factor receptor signaling in glioblastoma patients." *Cancer Res.* (2009) 6889-6898, 69(17).
Ludwig Institute for Cancer Research, "Annual Branch Report 2005" *Ludwig Institute for Cancer Research* (2005) 1-7.
Ludwig Institute for Cancer Research, "Annual Research Report 2002-2003" *Ludwig Institute for Cancer Research* (2003) 1-7.
Ludwig Institute for Cancer Research, "Clinical Trial Confirms Novel EGFR Antibody Targets Tumours But Not Normal Titsues" *Ludwig Institute for Cancer Research* (2010).

(56) References Cited

OTHER PUBLICATIONS

Ludwig Institute for Cancer Research, "Annual Research Highlights Report 2006" *Ludwig Institute for Cancer Research* (2006) 1-56.
Ludwig Institute for Cancer Research, "Annual Research Highlights Report 2005" *Ludwig Institute for Cancer Research* (2005) 3.
Ludwig Institute for Cancer Research, "Annual Research Report 2004" *Ludwig institute for Cancer Research* (2004) 7, 12, 79, 83-84, 98, 204 and 240.
Ludwig Institute for Cancer Research, "Annual Research Report 2002" *Ludwig Institute for Cancer Research* (2002) 8, 84-86 and 99-100.
Ludwig Institute for Cancer Research, "Annual Research Report 2003" *Ludwig Institute for Cancer Research* (2003) 81-83, 93 and 152.
Ludwig Institute for Cancer Research, "Annual Report 1999-2000" *Ludwig Institute for Cancer Research* (2000) 1-13.
Lui et al., "EGFR—mediated cell cycle regulation." *Anticancer Research* (2002) 1-11, 22(1A).
Lund et al., "Phosphorylation of the epidermal growth factor receptor at threonine 654 inhibits ligand-induced internalization and down-regulation." *Journal of Biological Chemistry* (1990) 20517-20523, 265(33).
Luwor et al., "A Soluble Form of the Epidermal Growth Factor Receptor (EGFR) Specific Tyrosine Kinase Inhibitor AG1478 Enhances the Efficacy of Chemotherapy." *Proceedings of the American Association for Cancer Research* (2002) 784 (Abstract 3885), 43.
Luwor et al., "The 806 Antibody Inhibits the Growth of Tumor Xenografts Expressing either the de2-7 or Amplified Epidermal Growth Factor Receptor (EGFR) but not Wild-Type EGFR." *Austin and Repatriation Medical Centre Research Week* (2001) Abstract 46.
Luwor et al., "The 806 Antibody Inhibits the Growth of Tumor Xenografts Expressing either the de2-7 or Amplified Epidermal Growth Factor Receptor (EGFR) but not Wild-Type EGFR." *Proceedings of the 13th Annual Lorne Cancer Conference, Lorne, Victoria, Australia* (2001) Abstract 208.
Luwor et al., "Monoclonal Antibody 806 Inhibits the Growth of Tumor Xenografts Expressing either the de2-7 or Amplified Epidermal Growth Factor Receptor (EGFR) but not Wild-Type EGFR." *Austin and Repatriation Medical Centre Research Week* (2000) Poster Presentation (Abstract 88).
Luwor et al., "Monoclonal Antibody 806 Inhibits the Growth of Tumor Xenografts Expressing either the de2-7 or Amplified Epidermal Growth Factor Receptor (EGFR) but not Wild-Type EGFR." *Austin and Repatriation Medical Centre Research Week* (2000) Abstract 88.
Luwor, "The Monoclonal Antibody 806 and tyrosine Kinase inhibitor AG1478: Novel epidermal growth factor receptor therapeutics (PhD Thesis)" *Submitted in Total Fulfilment of the Requirements for the Degree of Doctor of Philosophy, University of Melbourne.* (2003) 1-331.
Luwor et al., "The tumor-specific de2-7 epidermal growth factor receptor (EGFR) promotes cells survival and heterodimerizes with the wild-type EGFR." *Oncogene* (2004) 6095-6104, 23(36).
Lyall et al., "EGF induces receptor down-regulation with no receptor recycling in KB Cells" *Chemical Abstracts* (1985) 56832q, 102(7).
Lydon et al., "A potent protein-tytonsine kinase inhibitor which selectively blocks proliferation of epidermal growth factor receptor-expressing tumor cells in vitro and in vivo." *Int. J. Cancer* (1998) 154-163, 76(1).
Lynch et al., "A phase II trial of cetuximab as therapy for recurrent non-small cell lung cancer (NSCLC)." *Proceedings of the American Society of Clinical Oncology* (2004) 637s (Abstract 7084), 23.
Lynch et al., "Therapeutic potential of ABX-EGF: a fully human anti-epidermal growth factor receptor monoclonal antibody for cancer treatment." *Semin. Oncol.* (2002) 47-50, 29(1 Suppl 4).
Lynch et al., "Activating mutations in the epidermal growth factor receptor underlying responsiveness of non-small-cell lung cancer to gefitinib." *N. Engl. J. Med.* (2004) 2129-2139, 350(21).
Maccallum et al., "Antibody-antigen interactions: contact analysis and binding site topography." *J. Mol. Biol.* (1996) 732-745, 262(5).

Macdiarmid et al., "Sequential treatment of drug-resistant tumors with targeted minicells containing siRNA or a cytotoxic drug." *Nat. Biotechnol:* (2009) 643-651, 27(7).
Mach, "Monoclonal Antibodies." In: *Oxford Textbook of Oncology (Chapter 1.8) (Editors: Peckman et al.; Publisher: Oxford Univ. Press, Oxford).* (1995) 81-103, 1.
Machiels et al., "Zalutumumab plus best supportive care versus best supportive case alone in patients with recurrent or metastatic squamous-cell carcinoma of the head and neck after failure of platinum-based chemotherapy: an open-label, randomised phase 3 trial" *The Lancet Oncology* (2011) 333-343, 12(4).
Maciag, "The human epidermal growth factor receptor-kinase complex" *Trends in Biochemical Sciences* (1982) 197-198, 7.
Maeda et al., "pH-dependent receptor/ligand-dissociation as a determining factor for intracellular sorting of ligands for epidermal growth factor receptors in rat hepatocytes." *Journal of Contrblled Release : Official Journal of the Controlled Release Society* (2002)71-82, 82(1).
Magné et al., "Influence of epidermal growth factor receptor (EGFR), p53 and intrinsic MAP kinase pathway status of tumour cells on the antiproliferative effect of ZD1839 ('Iressa')." *British Journal of Cancer* (2002) 1518-1523, 86(9).
Malden et al., "Selective ampification of the cytoplasmic domain of the epidermal growth factor receptor gene in glioblastoma multiforme." *Cancer Res.* (1988) 2711-2714, 48(10).
Malik et al.; "Safety and efficacy of panitumumab monotherapy in patients with metastatic colorectal cancer (mCRC)" *Journal of Clinical Oncology, 2005 ASCO Annual Meeting Proceedings* (2005) Abstract 3520, 23(16S; Part I of II: Jun. 1 Supplement).
Malik et al., "Pharmacodynamic evaluation of the epidermal growth factor receptor inhibitor OSI-774 in human epidermis of cancer patients." *Clin. Cancer Res.* (2003) 2478-2486, 9(7).
Maloney et al., "IDEC-C2B8 (Rituximab) anti-CD20 monoclonal antibody therapy in patients with relapsed low-grade non-Hodgkin's lymphoma." *Blood* (1997) 2188-2195, 90(6).
Mamot et al., "Epidermal growth factor receptor-targeted immunoliposomes significantly enhance the efficacy of multiple anti-cancer drugs in vivo." *Cancer Res.* (2005) 11631-11638, 65(24).
Mamot et al., "Epidermal growth factor receptor (EGFR)—targeted immunoliposomes mediate specific and efficient drug delivery to EGFR- and EGFRvIII-overexpressing tumor cells." *Cancer Res.* (2003) 3154-3161, 63(12).
Mano et al., "Phase I trial of zalutumumab and irinotecan in metastatic colorectal cancer patients who have failed irinotecan-and cetuximab7-based therapy" *ASCO Meeting* (2009).
Margolis et al., "All autophosphorylation sites of epidermal growth factor (EGGF) receptor and HER2/neu are located in their carboxyl-terminal tails. Identification of a novel site in EGF receptor." *Journal of Biological Chemistry* (1989) 10667-10671, 264(18).
Marie et al., "EGFR tyrosine kinase domain mutations in human gliomas." *Neurology* (2005) 1444-1445, 64(8).
Mariuzza et al., "The structural basis of antigen-antibody recognition." *Annual review of Biophysics and Biophysical Chemistry* (1987) 139-159, 16.
Markowitz et al., "Growth stimulation by coexpression of transforming growth factor-alpha and epidermal growth factor-receptor in normal and adenomatous human colon epithelium." *J. Clin. Invest.* (1990) 356-362, 86(1).
Marks et al., "By-passing immunization: building high affinity human antibodies by chain shuffling." *Bio/technology (Nature Publishing Company)* (1992) 779-783, 10(7).
Martinazzi et al., "Epidermal growth factor receptor immunohistochemistry in different histological types of infiltrating breast carcinoma." *Journal of Clinical Pathology* (1993) 1009-1010, 46(11).
Maruo et al., "Immunohistochemical demonstration of elevated expression of epidermal growth factor receptor in the neoplastic changes of cervical squamous epithelium." *Cancer* (1992) 1182-1187, 69(5).
Masui et al., "Treatment with anti-EGF receptor monoclonal antibody causes regression of DiFi human colorectal carcinoma xenografts." *Proceedings of the American Association for Cancer Research* (1991) 394 (Abstract 2340), 32.

(56) References Cited

OTHER PUBLICATIONS

Masui et al., "Enhanced tumorigenesis of NR6 cells which express non-down-regulating epidermal growth factor receptors." *Cancer Res.* (1991) 6170-6175, 51(22).
Masui et al., "Cytotoxicity against human tumor cells mediated by the conjugate of anti-epidermal growth factor receptor monoclonal antibody to recombinant ricin A chain." *Cancer Res.* (1989) 3482-3488, 49(13).
Masui et al., "Mechanism of antitumor activity in mice for anti-epidermal growth factor receptor monoclonal antibodies with different isotypes." *Cancer Res.* (1986) 5592-5598, 46(11).
Matar et al., "Combined epidermal growth factor receptor targeting with the tyrosine kinase inhibitor gefitinib (ZD1839) and the monoclonal antibody cetuximab (IMC-C225): superiority over single-agent receptor targeting." *Clin. Cancer Res.* (2004) 6487-6501, 10(19).
Mateo et al., "Humanization of a mouse monoclonal antibody that blocks the epidermal growth factor receptor: recovery of antagonistic activity." *Immunotechnology : an International Jobrnal of Immunological Engineering* (1997) 71-81, 3(1).
Matsumoto et al., "Blockade of EGF-R signaling with anti-EGFR monoclonal antibody (Mab) C225 inhibits matrix metalloproteinase-9 (MMP-9) expression and invasion of human transitional cell carcinoma (TCC) in vitro and in vivo." *Proceedings of the American Association for Cancer Research* (1998) 3 (Abstract 565), 39.
Matsuo et al., "ZD1839; a selective epidermal growth factor receptor tyrosine kinase inhibitor, shows antimetastatic activity using a hepatocellular carcinoma model." *Molecular Cancer Therapeutics* (2003) 557-561, 2(6).
Mattoon et al., "The tethered configuration of the EGF receptor extracellular domain exerts only a limited control of receptor function." *Proceedings of the National Academy of Sciences of the United States of America* (2004) 923-928, 101(4).
Maurizi et al., "Prognostic significance of epidermal growth factor receptor in laryngeal squamous cell carcinoma." *British Journal of Cancer* (1996) 1253-1257, 74(8).
Mayes et al., "Biosynthesis of the epidermal growth factor receptor in A431 cells." *EMBO J.* (1984) 531-537, 3(3).
McCafferty et al.; "Phage antibodies: filamentous-phage displaying antibody variable domains." *Nature* (1990) 552-554, 348(6301).
McLeod et al., "In vivo pharmacology and anti-tumour evaluation of the tyrphostin tyrosine kinase inhibitor RG13022." *British Journal of Cancer* (1996) 1714-1718, 74(11).
Mehra et al., "Efficient mapping of protein antigenic determinants." *Proceedings of the National Academy of Sciences of the United States of America* (1986) 7013-7017, 83(18).
Meikrantz et al., "Apoptosis and the cell cycle." *J. Cell Biochem.* (1995) 160-174, 58(2).
Meilhoc et al., "High efficiency transformation of intact yeast cells by electric field pulses." *Bio/technology (Nature Publishing Company)* (1990) 223-227, 8(3).
Mellinghoff et al., "Molecular determinants of the response of glioblastomas to EGFR kinase inhibitors." *N. Engl. J. Med.* (2005) 2012-2024, 353(19).
Mellstedt, "Monoclonal antibodies in human cancer." *Drugs of Today* (2003) 1-16, 39(Suppl.C).
Mendelsohn et al., "A phase I study of chimerized anti-epidermal growth factor receptor (EGFR) monoclonal antibody, C225, in combination with cisplatin (CDDP) in patients (pts) with recurrent head and neck squamous cell carcinoma (SCC)." *Annual Meeting of the American Society of Clinical Oncology* (1999) 389a (Abstract 1502), 18.
Mendelsohn et al., "Antibodies to growth factors and receptors." *In: Biologic Therapy of Cancer (Section 21.6) (Editors: DeVita, et al.; Publisher: JB Lippincott Co.)* (1995) 607-623.
Mendelsohn et al., "Principles of molecular cell biology of cancer: growth factors." *In: Cancer: Principles and Practice of Oncology (Chapter 7) (Editors: DeVita, et al.; Publisher: J.B. Lippincott, Philadelphia).* (1993) 114-133.

Mendelsohn et al., "The Willet F. Whitmore, Jr., Lectureship: blockade of epidermal growth factor receptors as anticancer therapy." *The Journal of Urology* (2001) 1152-1157, 165(4).
Mendelsohn, "The epidermal growth factor receptor as a target for cancer therapy." *Endocrine-Related Cancer* (2001) 3-9, 8(1).
Mendelsohn et al., "The EGF receptor family as targets for cancer therapy." *Oncogene* (2000) 6550-6565, 19(56).
Mendelsohn, "Blockade of receptors for growth factors: an anticancer therapy—the fourth annual Joseph H Burchenal American Association of Cancer Research Clinical Research Award Lecture." *Clin. Cancer Res.* (2000) 747-753, 6(3).
Mendelsohn, "Epidermal growth factor receptor inhibition by a monoclonal antibody as anticancer therapy," *Clin. Cancer Res.* (1997) 2703-2707, 3(12 pt 2).
Mendelsohn et al., "Epidermal growth factor receptor family and chemosensitization." *J. Natl. Cancer Inst.* (1997) 341-343, 89(5).
Mendelsohn et al., *In Cellular and Molecular Bio. of Tumors and Preventative Clinical Applications (New York: Alan R. Liss, Inc.)* (1988) 307-312 (Reference not available).
Mendelsohn et al., "Anti-epidermal growth factor receptor monoclonal antibodies may inhibit A431 tumor cell proliferation by blocking an autocrine pathway." *Transactions of The Association of American Physicians* (1987) 173-178, 100.
Mendelsohn et al., "Epidermal growth factor receptor targeting in cancer." *Semin. Oncol* (2006) 369-385, 33(4).
Mendelsohn et al., "Status of epidermal growth factor receptor antagonists in the biology and treatment of cancer." *J. Clin. Oncol.* (2003) 2787-2799, 21(14).
Mendelsohn, "Targeting the epidermal growth factor receptor for cancer therapy." *J. Clin. Oncol.* (2002) 1S-13S, 20(18 Suppl).
Merlino et al., "Structure and localization of genes encoding aberrant and normal epidermal growth factor receptor RNAs from A431 human carcinoma cells." *Mol. Cell Biol.* (1985) 1722-1734, 5(7).
Messa et al., "EGF, TGF-alpha, and EGF-R in human colorectal adenocarcinoma." *Acta oncologica (Stockholm, Sweden)* (1998) 285-289, 37(3).
Messing et al., "Epidermal growth factor—interactions with normal and malignant urothelium: in vivo and in situ studies." *The Journal of Urology* (1987) 1329-1335, 138(5).
Milano et al., "EGFR-targeting drags in combination with cytotoxic agents: from bench to bedside, a contrasted reality." *British Journal of Cancer* (2008) 1-5, 99(1).
Miller et al., "A Pilot-Trial Demonstrates the Safety of ZD1839 (Iressa), an Oral Epidermal Growth Factor Receptor Tyrosine Kinase Inhibitor (EGFR-TKI), in Combination with Carboplatin (C) and Paclitaxel (P) in Previously Untreated Advanced Non-Small Cell Lung Cancer (NSCLC)." *Proc. Am. Soc. Clin. Oncol.* (2001) Abstract 1301, 20.
Mills et al., "Fully human antibodies to MCAM/MUC18 inhibit tumor growth and metastasis of human melanoma." *Cancer Res.* (2002) 5106-5114, 62(17).
Mineo et al., "Regulated migration of epidermal growth factor receptor from caveolae." *Journal of Biological Chemistry* (1999) 30636-30643, 274(43).
Mischel et al., "Targeted molecular therapy of GBM." *Brain Pathology (Zurich, Switzerland)* (2003) 52-61, 13(1).
Mishima et al., "Expression of a tumor-specific mutant epidermal growth factor receptor mediates glioma cell invasion in vivo" *Proc. Am. Assoc. Cancer Res.* (1999) 519, 40.
Mishima et al., "A peptide derived from the non-receptor-binding region of urokinase plasminogen activator inhibits glioblastoma growth and angiogenesis in vivo in combination with cisplatin." *Proceedings of the National Academy of Sciences of the United States of America* (2000) 8484-8489, 97(15).
Mitra et al., "Passive antibody-mediated immunotherapy for the treatment of malignant gliomas." *Neurosurgery Clinics of North America* (2010) 67-76, 21(1).
Moasser et al., "The tyrosine kinase inhibitor ZD1839 ('Iressa') inhibits HER2-driven signaling and suppresses the growth of HER2-overexpressing tumor cells." *Cancer Res.* (2001) 7184-7188, 61(19).
Modjtahedi et al.; "EGFR blockade by tyrosine kinase inhibitor or monoclonal antibody inhibits growth, directs terminal differentiation

(56) References Cited

OTHER PUBLICATIONS and induces apoptosis in the human squamous cell carcinoma HN5." *Int. J. Oncol.* (1998) 335-342, 13(2).
Modjtahedi et al., "Phase I trial and tumour localisation of the anti-EGFR monoclonal antibody ICR62 in head and neck or lung cancer." *British Journal of Cancer* (1996) 228-235, 73(2).
Modjtahedi et al., "Differentiation or immune destruction: two pathways for therapy of squamous cell carcinomas with antibodies to the epidermal growth factor receptor." *Cancer Res.* (1994) 1695-1701, 54(7).
Modjtahedi et al., "The receptor for EGF and its ligands—expression, prognostic value and target for therapy in cancer (review)." *Int. J. Oncol.* (1994) 277-296, 4(2).
Modjtahedi et al., "Immunotherapy of human tumour xenografts overexpressing the EGF receptor with rat antibodies that block growth factor-receptor interaction." *British Journal of Cancer* (1993) 254-261, 67(2).
Modjtahedi et al., "The human EGF receptor as a target for cancer therapy: six new rat mAbs against the receptor on the breast carcinoma MDA-MB 468." *British Journal of Cancer* (1993) 247-253, 67(2).
Modjtahedi et al., "Targeting of cells expressing wild-type EGFR and type-III mutant EGFR (EGFRvIII) by anti-EGFR MAb ICR62: a two-pronged attack for tumour therapy." *Int. J. Cancer* (2003) 273-280, 105(2).
Moghal et al., "Multiple positive and negative regulators of signaling by the EGF-receptor." *Current Opinion in Cell Biology* (1999) 190-196, 11(2).
Montgomery et al., "Expression of oncogenic epidermal growth factor receptor family kinases induces paclitaxel resistance and alters beta-tubulin isotype expression." *Journal of Biological Chemistry* (2000) 17358-17363, 275(23).
Morales et al., "Humanized versus murine anti-human epidermal growth factor receptor monoclonal antibodies for immunoscintigraphic studies." *Nucl. Med. Biol.* (2000) 199-206, 27(2).
Morea et al., "Antibody structure, prediction and redesign." *Biophysical Chemistry* (1997) 9-16, 68(1-3).
Moriki et al., "Activation of preformed EGF receptor dimers by ligand-induced rotation of the transmembrane domain." *J. Mol. Biol.* (2001) 1011-1026, 311(5).
Moroni et al., "Gene copy number for epidermal growth factor receptor (EGFR) and clinical response to antiEGFR treatment in colorectal cancer: a cohort study." *The Lancet Oncology* (2005) 279-286, 6(5).
Morrison et al., "Recombinant chimeric monoclonal antibodies." *Important Advances in Oncology* (1990) 3-18.
Moscatello et al., "Constitutive activation of phosphatidylinositol-3-kinase by a naturally occurring mutant epidermal growth factor receptor." *Journal of Biological Chemistry* (1998) 200-206, 273(1).
Moscatello et al., "A naturally occurring mutant human epidermal growth factor receptor as a target for peptide vaccine immunotherapy of tumors." *Cancer Res.* (1997) 1419-1424, 57(8).
Moscatello et al., "Transformational and altered signal transduction by a naturally occurring mutant EGF receptor." *Oncogene* (1996) 85-96, 13(1).
Moscatello et al., "Frequent expression of a mutant epidermal growth factor receptor in multiple human tumors." *Cancer Res.* (1995) 5536-5539, 55(23).
Motoyama et al., "The efficacy of ErbB receptor-targeted anticancer therapeutics is influenced by the availability of epidermal growth factor-related peptides." *Cancer Res.* (2002) 3151-3158, 62(11).
Moulder et al., "Epidermal growth factor receptor (HER1) tyrosine kinase inhibitor ZD1839 (Iressa) inhibits HER2/neu (erbB2)—overexpressing breast cancer cells in vitro and in vivo." *Cancer Res.* (2001) 8887-8895, 61(24).
Moyer et al., "Induction of apoptosis and cell cycle arrest by CP-358,774, an inhibitor of epidermal growth factor receptor tyrosine kinase." *Cancer Res.* (1997) 4838-4848, 57(21).

Murthy et al., "Binding of an antagonistic monoclonal antibody to an intact and fragmented EGF-receptor polypeptide." *Archives of biochemistry and biophysics* (1987) 549-560, 252(2).
Muthuswamy et al., "Controlled dimerization of ErbB receptors provides evidence for differential signaling by homo- and heterodimers." *Mol. Cell Biol.* (1999) 6845-6857, 19(10).
Nagane et al., "Human glioblastoma xenografts overexpressing a tumor-specific mutant epidermal growth factor receptor sensitized to cisplatin by the AG1478 tyrosine kinase inhibitor." *J. Neurosurg.* (2001) 472-479, 95(3).
Nagane et al., "Aberrant receptor signaling in human malignant gliomas: mechanisms and therapeutic implications." *Cancer Letters* (2001) S17-S21, 162 Suppl.
Nagane et al., "Drug resistance of human glioblastoma cells conferred by a tumor-specific mutant epidermal growth factor receptor through modulation of Bcl-XL and caspase-3-like proteases." *Proceedings of the National Academy of Sciences of the United States of America* (1998) 5724-5729, 95(10).
Nair et al., "Crystal structure of an antibody bound to an immunodominant peptide epitope: novel features in peptide-antibody recognition." *Journal of Immunology (Bethesda, MD : 1950)* (2000) 6949-6955, 165(12).
Nakagawa et al., "A Phase I Intermittent Dose-Escalation Trial of ZD1939 (Iressa) in Japanese Patients with Solid malignant tumours." *Proceedings of the American Society of Clinical Oncology* (2000) 183 (Abstract 711), 19.
Naramura et al., "Therapeutic potential of chimeric and murine anti-(epidermal growth factor receptor) antibodies in a metastasis model for human melanoma." *Cancer Immunol. Immunother.* (1993) 343-349, 37(5).
Narita et al., "Mutant epidermal growth factor receptor signaling down-regulates p27 through activation of the phosphatidylinositol 3-kinase/Akt pathway in glioblastomas." *Cancer Res.* (2002) 6764-6769, 62(22).
Natale et al., "ZD1839 (Iressa): what's in it for the patient?" *Oncologist* (2002) 25-30, 7(Suppl. 4).
Neal et al., "The epidermal growth factor receptor and the prognosis of bladder cancer." *Cancer* (1990) 1619-1625, 65(7).
Neal et al., "Epidermal-growth-factor receptors in human bladder cancer: comparison of invasive and superficial tumours." *Lancet* (1985) 366-368, 1(8425).
Negri et al., "In vitro and in vivo stability and anti-tumour efficacy of an anti-EGFR/anti-CD3 F(ab')2 bispecific monoclonal antibody." *British Journal of Cancer* (1995) 928-933, 72(4).
Nice et al., "Instrumental biosensors: new perspectives for the analysis of biomolecular interactions." *BioEssays : news and reviews in molecular, cellular and developmental biology* (1999) 339-352, 21(4).
Nicholson et al., "EGFR and cancer prognosis." *Eur. J. Cancer* (2001) S9-15, 37 Suppl 4.
Niikura et al., "Expression of epidermal growth factor-related proteins and epidermal growth factor receptor in common epithelial ovarian tumors." *International journal of gynecological pathology : official journal of the International Society of Gynecological Pathologists* (1997) 60-68, 16(1).
Nishikawa et al., "Immunohistochemical analysis of the mutant epidermal growth factor, ΔEGFR, in glioblastoma." *Brain tumor pathology* (2004) 53-56, 21(2).
Noonberg et al., "Tyrosine kinase inhibitors targeted to the epidermal growth factor receptor subfamily: role as anticancer agents." *Drugs* (2000) 753-767, 59(4).
Normanno et al., "Cooperative inhibitory effect of ZD1839 (Iressa) in combination with trastuzumab (Herceptin) on human breast cancer cell growth." *Ann Oncol.* (2002) 65-72, 13(1).
Normanno et al., "Growth inhibition of human colon carcinoma cells by combinations of anti-epidermal growth factor-related growth factor antisense oligonucleotides." *Clin. Cancer Res.* (1996) 601-609, 2(3).
Normanno et al., "Epidermal growth factor receptor (EGFR) signaling in cancer." *Gene* (2006) 2-16, 366(1).
Norton et al., "Overall survival (OS) advantage to simultaneous chemotherapy (CRx) plus the humanized anti-HER2 monoclonal antibody Herceptin (H) in HER2- overexpressing (HER2+) meta-

(56) References Cited

OTHER PUBLICATIONS static breast cancer (MBC)." *Proceedings of the American Society of Clinical Oncology* (1999) 127a (Abstract 483), 18.
O-Charoenrat et al., "Overexpression of epidermal growth factor receptor in human head and neck squamous carcinoma cell lines correlates with matrix metalloproteinase-9 expression and in vitro invasion." *Int. J. Cancer* (2000) 307-317, 86(3).
O-Charoenrat et al., "Vascular endothelial growth factor family members are differentially regulated by c-erbB signaling in head and neck squamous carcinoma cells." *Clinical & experimental metastasis* (2000) 155-161, 18(2).
O-Charoenrat et al., "The role of c-erbB receptors and ligands in head and neck squamous cell carcinoma." *Oral oncology* (2002) 627-640, 38(7).
Ochiai et al., "EGFRvIII-targeted immunotoxin induces antitumor immunity that is inhibited in the absence of CD4+ and CD8+ T cells." *Cancer Immunol. Immunother.*(2008) 115-121, 57(1).
Oflazoglu et al., "Potent Anticarcinoma Activity of the Humanized Anti-CD70 Antibody h1F6 Conjugated to the Tubulin Inhibitor Auristatin via an Uncleavable Linker" *Clinical Cancer. Research* (2008) 6171-6180, 14(19).
Ohman et al., "A new antibody recognizing the vIII mutation of human epidermal growth factor receptor." *Tumour biology : the journal of the International Society for Oncodevelopmental Biology and Medicine* (2002)61-69, 23(2).
Okamoto et al., "Expression of constitutively activated EGFRvIII in non-small cell lung cancer." *Cancer Science* (2003) 50-56, 94(1).
Olayioye et al., "The ErbB signaling network: receptor heterodimerization in development and cancer." *EMBO J.* (2000) 3159-3167, 19(13).
Olayioye et al., "ErbB-1 and ErbB-2 acquire distinct signaling properties dependent upon their dimerization partner.", *Mol. Cell Biol.* (1998) 5042-5051, 18(9).
Old, "Immunotherapy for cancer." *Sci. Am.* (1996) 136-143, 275(3).
Olson et al., "Transmodulation of epidermal growth factor binding by platelet-derived growth factor and 12-O-tetradecanoylphorbol-13-acetate is not sodium-dependent in Balb/c/3T3 cells." *Journal of Biological Chemistry* (1990) 1847-1851, 265(4).
Omidfar et al., "Production of a novel camel single-domain antibody specific for the type III mutant EGFR." *Tumor biology : the journal of the International Society for Oncodevelopmental Biology and Medicine* (2004) 296-305, 25(5-6).
Omidfar et al., "Production and characterization of a new antibody specific for the mutant EGF receptor, EGFRvIII, in Camelus bactrianus." *Tumour biology : the journal of the International Society for Oncodevelopmental Biology and Medicine* (2004) 179-187, 25(4).
Opresko et al., "Endocytosis and lysosomal targeting of epidermal growth factor receptors are mediated by distinct sequences independent of the tyrosine kinase domain." *Journal of Biological Chemistry* (1995) 4325-4333, 270(9).
Orntoft et al., "Clinical aspects of altered glycosylation of glycoproteins in cancer." *Electrophoresis* (1999) 362-371, 20(2).
Osband et al., "Problems in the investigational study and clinical use of cancer immunotherapy." *Immunology today* (1990) 193-195, 11(6).
Ostermann et al., "Effective Immunoconjugate Therapy in Cancer Models Targeting a Serine Protease of Tumor Fibroblasts" *Clinical Cancer Research* (2008) 4584-4592, 14(14).
Overdijk et al., "Role of ADCC in the in vivo antitumor effects of zalutumumab, a human anti-EGF receptor antibody" *ASCO Meeting* (2010).
Overholser et al., "Epidermal growth factor receptor blockade by antibody IMC-C225 inhibits growth of a human pancreatic carcinoma xenograft in nude mice." *Cancer* (2000) 74-82, 89(1).
Owens et al., "The genetic engineering of monoclonal antibodies." *J. Immunol. Methods* (1994) 149-165, 168(2).
Ozanne et al., "Over-expression of the EGF receptor is a hallmark of squamous cell carcinomas." *The Journal of Pathology* (1986) 9-14, 149(1).
Ozawa et al., "Prognostic significance of epidermal growth factor receptor in esophageal squamous cell carcinomas." *Cancer* (1989) 2169-2173, 63(11).
Padlan et al., "Identification of specificity-determining residues in antibodies." *FASEB J.*(1995) 133-139, 9(1).
Padlan, "Anatomy of the antibody molecule." *Mol. Immunol.* (1994) 169-217, 31(3).
Padlan, "A possible procedure for reducing the immunogenicity of antibody variable domains while preserving their ligand-binding properties." *Mol. Immunol.* (1991) 489-498, 28(4-5).
Padlan, "On the nature of antibody combining sites: unusual structural features that may confer on these sites an enhanced capacity for binding ligands." *Proteins* (1990) 112-124, 7(2).
Paez et.al., "EGFR mutations in lung cancer: correlation with clinical response to gefitinib therapy." *Science* (2004) 1497-1500, 304.
Paganelli et al., "Antibody-guided three-step therapy for high grade glioma with yttrium-90 biotin." *European Journal of Nuclear Medicine* (1999) 348-357, 26(4).
Pai et al., "The use of immunotoxins for cancer therapy." *Eur. J. Cancer* (1993) 1606-1609, 29A(11).
Pai et al., "Prostaglandin E2 transactivates EGF receptor: a novel mechanism for promoting colon cancer growth and gastrointestinal hypertrophy." *Nature Med.* (2002) 289-293, 8(3).
Pao et al., "Epidermal growth factor receptor mutations, small-molecule kinase inhibitors, and non-small-cell lung cancer: current knowledge and future directions." *J. Clin. Oncol.* (2005) 2556-2568, 23(11).
Pao et al., "Acquired resistance of lung adenocarcinomas to gefitinib or erlotinib is associated with a second mutation in the EGFR kinase domain." *PLoS Medicine* (2005) e73, 2(3).
Pao et al., "KRAS mutations and primary resistance of lung adenocarcinomas to gefitinib or erlotinib." *PLoS Medicine* (2005) e17, 2(1).
Pao et al., "EGF receptor gene mutations are common in lung cancers from 'never smokers' and are associated with sensitivity of tumors to gefitinib and erlotinib." *Proceedings of the National Academy of Sciences of the United States of America* (2004) 13306-13311, 101(36).
Park et al., "A review of the benefit-risk profile of gefitinib in Asian patients with advanced non-small-cell lung cancer." *Current Medical Research and Opinion* (2006) 561-573, 22(3).
Parker et al., "Preferential activation of the epidermal growth factor receptor in human colon carcinoma liver metastases in nude mice." *The Journal of Histochemistry and Cytochemistry : Official Journal of the Histochemistry Society* (1998) 595-602, 46(5).
De Pascalis et al., "Grafting of 'abbreviated' complementarity-determining regions containing specificity-determining residues essential for ligand contact to engineer a less immunogenic humanized monoclonal antibody." *Journal of immunology (Baltimore, Md : 1950)* (2002) 3076-3084, 169(6).
Pastan, "Targeted-therapy of cancer with recombinant immunotoxins." *Biochimica et Biophysica Acta* (1997) C1-6, 1333(2).
Patel et al., "Monoclonal antibody cetuximab binds to and down-regulates constitutively activated epidermal growth factor receptor vIII on the cell surface." *Anticancer research* (2007) 3355-3366, 27.
Pavelic et al., "Evidence for a role of EGF receptor in the progression of human lung carcinoma." *Anticancer Research* (1993) 1133-1137, 13(4).
Pawson et al., "SH2 and SH3 domains." *Current Biology* (1993) 434-442, 3(7).
Pawson, "Protein modules and signalling networks." *Nature* (1995) 573-580, 373.
Pedersen et al., "The type III epidermal growth factor receptor mutation. Biological significance and potential target for anti-cancer therapy." *Ann Oncol.* (2001) 745-760, 12(6).
Pedersen et al., "Analysis of the epidermal growth factor receptor specific transcriptome: effect of receptor expression level and an activating mutation." *J. Cell Biochem.* (2005) 412-427, 96(2).
Pedersen et al., "[Mutations in the epidermal growth factor receptor: structure and biological function in human tumors]." *Ugeskrift for laeger* (2006) 2354-2361, 168(24).

(56) References Cited

OTHER PUBLICATIONS

Pegram et al., "Antibody dependent cell-mediated cytotoxicity in breast cancer patients in Phase III clinical trials of a humanized anti-HER2 antibody." *Proceedings of the Annual Meeting of the American Association for Cancer Research* (1997) 602 (Abstract 4044), 39.

Pegram et al., "Inhibitory effects of combinations of HER-2/neu antibody and chemotherapeutic agents used for treatment of human breast cancers." *Oncogene* (1999) 2241-2251, 18(13).

Pegram et al., "Phase II study of receptor-enhanced chemosensitivity using recombinant humanized anti-p185HER2/neu monoclonal antibody plus cisplatin in patients with HER2/neu-overexpressing metastatic breast cancer refractory to cherhotherapy treatment." *J. Clin. Oncol.* (1998) 2659-2671, 16(8).

Pegram et al., "The effect of HER-2/neu overexpression on chemotherapeutic drug sensitivity in human breast and ovarian cancer cells." *Oncogene* (1997) 537-547, 15(5).

Pegram et al., "Rational combinations of trastuzumab with chemotherapeutic drugs used in the treatment of breast cancer." *J. Natl. Cancer Inst.* (2004) 739-749, 96(10).

Pelloski et al., "Epidermal growth factor receptor variant III status defines clinically distinct subtypes of glioblastoma." *Journal of Clinical Oncology* (2007) 2288-2294, 25(16).

Peng et al., "Anti-epidermal growth factor receptor monoclonal antibody 225 up-regulates p27KIP1 and induces G1 arrest in prostatic cancer cell line DU145." *Cancer Res.* (1996) 3666-3669, 56(16).

Perera et al., "Internalisation and Trafficking of the Monoclonal Antibody 806 Reactive Epidermal Growth Factor Receptor." *Austin Health Research Week, Austin Hospital, Melbourne, Australia* (2003) Abstract 112.

Perera et al., "The Influence of Epidermal Growth Factor Receptor (EGFR) Number and Activation on the Efficacy of Antibodies Directed to the Receptor." *Proceedings of the 14th Annual Lorne Cancer Conference, Lorne, Victoria, Australia* (2002) Abstract 216.

Perera et al., "Requirement for the yon Hippel-Lindau tumor suppressor gene for functional epidermal growth factor receptor blockade by monoclonal antibody C225 in renal cell carcinoma." *Clin. Cancer Res.* (2000) 1518-1523, 6(4).

Perera, "Therapeutic Efficacy and Intracellular Trafficking of Anti-Epidermal Growth Factor Receptor Antibodies (PhD Thesis)" *Submitted in Total Fulfilment of the Requirements for the Degree of Doctor of Philosophy, University of Melbourne*. (2004) 1-239.

Perera et al., "Internalization, intracellular trafficking, and biodistribution of monoclonal antibody 806: a novel anti-epidermal growth factor receptor antibody." *Neoplasia* (2007) 1099-1110, 9(12).

Perez-Soler et al., "A phase II trial of-the epidermal growth factor receptor (EGFR) tyrosine kinase inhibitor OSI-774, following platinum-based chemotherapy in patients (pts) with advanced EGFR-expressing, non-small cell lung cancer (NSCLC)." *Proceedings of the American Society of Clinical Oncology* (2001) 310a (Abstract 1235), 20.

Perez-Soler et al., "Tumor Studies in Patients With Head & Neck Cancer Treated With Humanized Anti-Epidermal Growth Factor (EGFR) Monoclonal Antibody C225 in Combination With Cisplatin." *Proceedings of the American Society of Clinical Oncology* (1998) 393a (Abstract 1514), 17.

Perez-Soler et al., "Tumor epidermal growth factor receptor studies in patients with non-small-cell lung cancer or head and neck cancer treated with monoclonal antibody RG 83852." *J. Clin. Oncol.*(1994) 730-739, 12(4).

Pérez-Soler, "HER1/EGFR targeting: refining the strategy." *Oncologist* (2004) 58-67, 9(1).

Perl et al., "Conditional gene expression in the respiratory epithelium of the mouse." *Transgenic research* (2002) 21-29, 11(1).

Perrotte et al., "Anti-epidermal growth factor receptor antibody C225 inhibits angiogenesis in human transitional cell carcinoma growing orthotopically in nude mice." *Clin. Cancer Res.* (1999) 257-265, 5(2).

Petit et al., "Neutralizing antibodies against epidermal growth factor and ErbB-2/neu tyrosine kinases down-regulate vascular endothelial growth factor production by tumor cells in vitro and in vivo: angiogenic implications for signal transduction therapy of solid tumors." *The American Journal of Pathology* (1997) 1523-1530, 151(6).

Petrides et al., "Modulation of pro-epiderrnal growth factor, pro-transforming growth factor alpha and epidermal growth factor receptorgene expression in human renal carcinomas." *Cancer Res.* (1990) 3934-3939, 50(13).

Pfister et al., "A phase I trial of the epidermal growth factor receptor (EGFR)-directed bispecific antibody (BsAB) MDX-447 in patients with solid tumors." *Proceedings of the American Society of Clinical Oncology* (1999) 433a (Abstract 1667), 18.

Pfosser et al., "Role of target antigen in bispecific-antibody-mediated killing of human glioblastoma cells: a pre-clinical study." *Int. J. Cancer* (1999) 612-616, 80(4).

Pfreundschuh et al., "Serological analysis of cell surface antigens of malignant human brain tumors." *Proceedings of the National Academy of Sciences of the United States of America* (1978) 5122-5126, 75(10).

Pietras et al., "Monoclonal antibody to HER-2/neureceptor modulates repair of radiation-induced DNA damage and enhances radiosensitivity of human breast cancer cells overexpressing this oncogene." *Cancer Res.* (1999) 1347-1355, 59(6).

Pietras et al., "Remission of human breast cancer xenografts on therapy with humanized monoclonal antibody to HER-2 receptor and DNA-reactive drugs." *Oncogene*(1998) 2235-2249, 17(17).

Pillay et al., "The plasticity of oncogene addiction: implications for targeted therapies directed to receptor tyrosine kinases." *Neoplasia* (2009) 448-458, 11(5).

Politi et al:, "Lung adenocarcinomas induced in mice by mutant EGF receptors found in human lung cancers respond to a tyrosine kinase inhibitor or to down-regulation of the receptors." *Genes Dev.* (2006) 1496-1510, 20(11).

Pontén et al., "Long term culture of normal and neoplastic human glia." *Acta pathologica et microbiologica Scandinavica* (1968) 465-486, 74(4).

Power et al., "Construction, expression and characterisation of a single-chain diabody derived from a humanised anti-Lewis Y cancer targeting antibody using a heat-inducible bacterial secretion vector." *Cancer Immunol. Immunother.* (2001) 241-250, 50(5).

Power et al., "Noncovalent scFv multimers of tumor-targeting anti-Lewis(y) hu3S193 humanized antibody." *Protein Science: a Publication of the Protein Society* (2003) 734-747, 12(4).

Prados et al., "Biology and treatment of malignant glioma." *Semin. Oncol.* (2000) 1-10, 27(3; Suppl. 6).

Prenzel et al., "The epidermal growth factor receptor family as a central element for cellular signal transduction and diversification." *Endocrine-Related Cancer* (2001) 11-31, 8(1).

Press et al., "Inhibition of catabolism of radiolabeled antibodies by tumor cells using lysosomotropic amines and carboxylic ionophores." *Cancer Res.* (1990) 1243-1250, 50(4).

Press et al., "Ricin A-chain containing immunotoxins directed against different epitopes on the CD2 molecule differ in their ability to kill normal and malignant T cells." *Journal of immunology (Baltimore, Md : 1950)* (1988) 4410-4417, 141(12).

Presta et al., "Humanization of an anti-vascular endothelial growth factor monoclonal antibody for the therapy of solid tumors and other disorders." *Cancer Res.* (1997) 4593-4599, 57(20).

Presta et al., "Humanization of an antibody directed against IgE." *Journal of immunology (Baltimore, Md : 1950)* (1993) 2623-2632, 151(5).

Presta, "Molecular engineering and design of therapeutic antibodies." *Curr. Opin. Immunol.* (2008) 460-470, 20(4).

Presta, "Engineering of therapeutic antibodies to minimize immunogenicity and optimize function." *Advanced drug delivery reviews* (2006) 640-656, 58(5-6).

Prewett et al., "Mouse-human chimeric anti-epidermal growth factor receptor antibody C225 inhibits the growth of human renal cell carcinoma xenografts in nude mice." *Clin. Cancer Res.* (1998) 2957-2966, 4(12).

(56) References Cited

OTHER PUBLICATIONS

Prewett et al., "The biologic effects of C225, a chimeric monoclonal antibody to the EGFR, on human prostate carcinoma." *Journal of Immunotherapy with Emphasis on Tumor Immunology : Official Journal of the Society for Biological Therapy* (1996) 419-427, 19(6).
Prewett et al., "Anti-tumor and cell cycle responses in KB cells treated with a chimeric anti-EGFR monoclonal antibody in combination with cisplatin." *Int. J. Oncol.* (1996) 217-224, 9(2).
Prewett et al., "Enhanced antitumor activity of anti-epidermal growth factor receptor monocolonal antibody IMC-C225 in combination with irinotecan (CPT-11) against human colorectal tumor xenografts." *Clin. Cancer Res.* (2002) 994-1003, 8(5).
Prigent et al., "Enhanced tumorigenic behavior of glioblastoma cells expressing a truncated epidermal growth factor receptor is mediated through the Ras-Shc-Grb2 pathway." *Journal of Biological Chemistry* (1996) 25639-25645, 271(41).
Prigent et al., "The type 1 (EGFR-related) family of growth factor receptors and their ligands." *Progress in Growth Factor Research* (1992) 1-24, 4(1).
Privalsky et al., "The membrane glycoprotein encoded by the retroviral oncogene v-erb-B is structurally related to tyrosine-specific protein kinases." *Proceedings of the National Academy of Sciences of the United States of America* (1984) 704-707, 81(3).
Pruss et al., "Variants of 3T3 cells lacking mitogenic response to epidermal growth factor." *Proceedings of the National Academy of Sciences of the United States of America* (1977) 3918-3921, 74(9).
Pütz et al., "Functional fine-mapping and molecular modeling of a conserved loop epitope of the measles virus hernagglutinin protein." *Eur. J. Biochem.* (2003) 1515-1527, 270(7).
Raben et al., "C225 anti-EGFR antibody potentiates radiation (RT) and chemotherapy (CT) cytotoxicity in human non-small cell lung cancer (NSCLC) cells in vitro and in vivo." *Proceedings of the American Society of Clinical Oncology* (2001) 257a (Abstract 1026), 20.
Raben et al., "Treatment of human intracranial gliomas with chimeric monoclonal antibody against the epidermal growth factor receptor increases survival of nude mice when treated concurrently with irradiation." *Proceedings of the American Association for Cancer Research* (1999) 184 (Abstract 1224), 40
Raben et al., "ZD1839, a selective epidermal growth factor receptor tyrosine kinase inhibitor, alone and in combination with radiation and chemotherapy as a new therapeutic strategy in non-small cell lung cancer." *Semin. Oncol.* (2002) 37-46, 29(1; Suppl. 4).
Radinsky et al., "Level and function of epidermal growth factor receptor predict the metastatic potential of human colon carcinoma cells." *Clin. Cancer Res.* (1995) 19-31, 1(1).
Raizer, "HER1/EGFR tyrosine kinase inhibitors for the treatment of glioblastoma multiforme." *Journal of Neuro-Oncology* (2005) 77-86, 74(1).
Rakowicz-Szulczynska et al., "Epidermal growth factor (EGF) and monoclonal antibody to cell surface EGF receptor bind to the same chromatin receptor." *Archives of Biochemistry and Biophysics* (1989) 456-464, 268(2).
Ramnarain et al., "Differential gene expression analysis reveals generation of an autocrine loop by a mutant epidermal growth factor receptor in glioma cells." *Cancer Res.* (2006) 867-874, 66(2).
Ramos et al., "Treatment of high-grade glioma patients with the humanized anti-epidermal growth factor receptor (EGFR) antibody h-R3: report from a phase I/II trial." *Cancer biology & therapy* (2006) 375-379, 5(4).
Ramos-Suzarte et al., "99mTc-labeled antihuman epidermal growth factor receptor antibody in patients with tumors of epithelial origin: Part III. Clinical trials safety and diagnostic efficacy." *J. Nucl. Med.* (1999) 768-775, 40(5).
Ramsland et al., "Structural convergence antibody binding of carbohydrate determinants in Lewis Y tumor antigens." *J. Mol. Biol.* (2004) 809-818, 340(4).
Ranson, "ZD1839 (Iressa): for more than just non-small cell lung cancer." *Oncologist* (2002) 16-24, 7(Suppl. 4).

Rao et al., "Radiosensitization of human breast cancer cells by a novel ErbB family receptor tyrosine kinase inhibitor." *Int. J. Radiat. Oncol. Biol. Phys.* (2000) 1519-1528, 48(5).
Raymond et al., "General method for plasmid construction using homologous recombination." *BioTechniques* (1999) 134-8, 140-1, 26(1).
Rayzman et al., "Monoclonal antibodies for cancer therapy." *Cancer Forum* (2002) 104-108, 26(2).
Reardon et al., "Recent advances in the treatment of malignant astrocytoma." *Journal of Clinical Oncology* (2006) 1253-1265, 24(8).
Reed, "Dysregulation of apoptosis in cancer." *J. Clin. Oncol.* (1999) 2941-2953, 17(9).
Reese et al., "Effects of the 4D5 antibody on HER2/neu heterodimerization with other class I receptors in human breast cancer cells." *Proceedings of the Annual Meeting of the American Association for Cancer Research* (1996) 51 (Abstract 353), 37.
Van Regenmortel et al., "Comparative immunological methods." *Methods in Enzymology* (1993) 130-140, 224.
Reilly et al., "A comparison of EGF and MAb 528 labeled with 111In for imaging human breast cancer." *J. Nucl. Med.* (2000) 903-911, 41(5).
Reiss et al., "Activation of the autocrine transforming growth factor alpha pathway in human squamous carcinoma cells." *Cancer Res.* (1991) 6254-6262, 51(23; Part 1).
Reist et al., "Astatine-211 labeling of internalizing anti-EGFRvIII monoclonal antibody using N-succinimidyl 5-[211At]astato-3-pyridinecarboxylate." *Nucl. Med. Biol.* (1999) 405-411, 26(4).
Reist et al., "In vitro and in vivo behavior of radiolabeled chimeric anti-EGFRvIII monoclonal antibody: comparison with its murine parent." *Nucl. Med. Biol.* (1997) 639-647, 24(7).
Reist et al., "Radioiodination of internalizing monoclonal antibodies using N- succinimidyl 5-iodo-3-pyridinecarboxylate." *Cancer Res.* (1996) 4970-4977, 56(21).
Reiter et al., "Comparative genomic sequence analysis and isolation of human and mouse alternative EGFR transcripts encoding truncated receptor isoforms." *Genomics* (2001) 1-20, 71(1).
Rettig et al., "Immunogenetics of human cell surface differentiation." *Annual review of immunology* (1989) 481-511, 7.
Reynolds et al., "Human transforming growth factors induce tyrosine phosphorylation of EGF receptors." *Nature* (1981) 259-262, 292(5820).
Ribas et al., "Systemic delivery of siRNA via targeted nanoparticles in patients with cancer: Results from a first-in-class phase I clinical trial" *J. Clin. Oncol.* (2010) Abstract 3022, 38(15S).
Riemer et al., "Mimotope vaccines: epitope mimics induce anticancer antibodies." *Immunology letters* (2007) 1-5, 113(1).
Riemer et al., "Vaccination with cetuximab mimotopes and biological properties of induced anti-epidermal growth factor receptor antibodies." *J. Natl. Cancer Inst.* (2005) 1663-1670, 97(22).
Riemer et al., "Matching of trastuzumab (Herceptin) epitope mimics onto the surface of Her-2/neu—a new method of epitope definition." *Mol. Immunol.* (2005) 1121-1124, 42(9).
Riese et al., "Specificity within the EGF family/ErbB receptor family signaling network." *BioEssays : news and reviews in molecular, cellular and developmental biology* (1998) 41-48, 20(1).
Rieske et al., "A comparative study of epidermal growth factor receptor (EGFR) and MDM2 gene amplicification and protein immunoreactivity in human glioblastomas." *Polish Journal of Pathology : Official Journal of the Polish Society of Pathologists* (1998) 145-149, 49(3).
Rinehart et al., "A phase 1 clinical and pharmacokinetic study of oral CI-1033, a pan-erbB tyrosine kinase inhibitor in patients with advanced solid tumors." *Proceedings of the American Society of Clinical Oncology* (2002) 11a (Abstract 41), 21.
Ringerike et al., "High-affinity binding of epidermal growth factor (EGF) to EGF receptor is disrupted by overexpression of mutant dynamin (K44A)." *Journal of Biological Chemistry* (1998) 16639-16642, 273(27).
Ritter et al., "Serological analysis of human anti-human antibody responses in colon cancer patients treated with repeated doses of humanized monoclonal antibody A33." *Cancer Res.* (2001) 6851-6859, 61(18).

(56) References Cited

OTHER PUBLICATIONS

Riva et al., "Role of nuclear medicine in the treatment of malignant gliomas: the locoregional radioimmunotherapy approach." *European Journal of Nuclear Medicine* (2000) 601-609, 27(5).

Rivera et al., "Current situation of Panitumumab, Matuzumab, Nimotuzumab and Zalutumumab." *Acta oncologica (Stockholm, Sweden)* (2008) 9-19, 47(1).

Ro et al., "Amplified and overexpressed epidermal growth factor receptor gene in uncultured primary human breast carcinoma." *Cancer Res.* (1988) 161-164, 48(1).

Robert et al., "Phase I study of anti—epidermal growth factor receptor antibody cetuximab in combination with radiation therapy in patients with advanced head and neck cancer." *J. Clin. Oncol.* (2001) 3234-3243, 19(13).

Rocha-Lima et al., "EGFR targeting of solid tumors." *Cancer control : journal of the Moffitt Cancer Center* (2007) 295-304, 14(3).

Rodeck et al., "Monoclonal antibody 425 inhibits growth stimulation of carcinoma cells by exogenous EGF and tumor-derived EGF/TGF-alpha." *J. Cell Biochem.* (1990) 69-79, 44(2).

Rodeck et al., "Interactions between growth factor receptors and corresponding monoclonal antibodies in human tumors." *J. Cell Biochem.* (1987) 315-320, 35(4).

Rodeck et al., "Tumor growth modulation by a monoclonal antibody to the epidermal growth factor receptor: immunologically mediated and effector cell-independent effects." *Cancer Res.* (1987) 3692-3696, 47(14).

Roepstorff et al., "Sequestration of epidermal growth factor receptors in non-caveolar lipid rafts inhibits ligand binding." *Journal of Biological Chemistry* (2002) 18954-18960, 277(21).

Roguska et al., "A comparison of two murine monoclonal antibodies humanized by CDR-grafting and variable domain resurfacing." *Protein Engineering* (1996) 895-904, 9(10).

Roguska et al., "Humanization of murine monoclonal antibodies through variable domain resurfacing." *Proceedings of the National Academy of Sciences of the United States of America* (1994) 969-973, 91(3).

Rosell et al., "Randomized phase II study of cetuximab in combination with cisplatin (C) and vinorelbine (V) vs. CV alone in the first-line treatment of patients (pts) with epidermal growth factor receptor (EGFR)—expressing advanced non- small-cell lung cancer (NSCLC)" *Journal of Clinical Oncology, 2004 ASCO Annual Meeting Proceedings (Post-Meeting Edition)* (2004) Abstract 7012, 22(14S; Jul. 15 Supplement).

Rosell et al., "Randomized phase II study of cetuximab in combination with cisplatin (C) and vinorelbine (V) vs. CV alone in the first-line treatment of patients (pts) with epiderinal growth factor receptor (EGFR)—expressing advanced non-small-cell lung cancer (NSCLC)." *Proceedings of the American Society of Clinical Oncology* (2004) 620s (Abstract 7012), 23.

Rosenberg et al., "Erbitux (IMC-225) plus weekly irinotecan (CPT-11), fluorouricil (5FU) and leucovorin (LV) in colorectal cancer (CRC) that expresses the epidermal growth factor receptor (EGFR)." *Proceedings of the American Society of Clinical Oncology* (2002) 135a (Abstract 536), 21.

Ross et al., "Anticancer antibodies." *American Journal of Clinical Pathology* (2003) 472-485, 119(4).

Rothacker, "Ligand binding induces a conformational change in the untethered epidermal growth factor receptor" *Ludwig Institute for Cancer Research* (2010).

Rougier et al., "Cetuximab +FOLFIRI as first-line treatment for metastatic colorectal CA." *Proceedings of the Annual Meeting of the American Society of Clinical Oncology* (2004) 248s (Abstract 3513), 22.

Rowinsky et al., "Safety, pharmacokinetics, and activity of ABX-EGF, a fully human anti-epidermal growth factor receptor monoclonal antibody in patients with metastatic renal cell cancer." *J. Clin. Oncol.* (2004) 3003-3015, 22(15).

Rubin et al., "Monclonal Antibody (MoAb) IMC-C225, an Anti-Epidermal Growth Factor Receptor (EGFr), for Patients (Pts) with EGRr-Positive Tumors Refractory to or in Relapse from Previous Therapeutic Regimens" *Proc. Am. Soc. Clin. Oncol.* (2000) Abstract 1860, 19.

Rubin et al., "Monoclonal antibody (MoAb) IMC-C225, an anti-epidermal growth factor receptor (EGFR), for patients with EGFR-positive tumors refractory to or in relapse from previous therapeutic regimens." *Proceedings of the American Society of Clinical Oncology* (2000) 474a (Abstract 1860), 193.

Rubin Grandis et al., "Inhibition of epidermal growth factor receptor gene expression and function decreases proliferation of head and neck squamous carcinoma but not normal mucosal epithelial cells." *Oncogene* (1997) 409-416, 15(4).

Rubin Grandis et al., "Quantitative immunohistochemical analysis of transforming growth factor-alpha and epidermal growth factor receptor in patients with squamous cell carcinoma of the head and neck." *Cancer* (1996) 1284-1292, 78(6).

Rubio et al., "Cetuximab in combination with oxaliplatin/5-fluorouracil (5-FU)/folinic acid (FA) (FOLFOX-4) in the first-line treatment of patients with epidermal growth factor receptor (EGFR)—expressing metastatic colorectal cancer: An international phase II study." *Journal of Clinical Oncology, 2005 ASCO Annual Meeting Proceedings* (2005) Abstract 3535, 23(16S; Part I of II: Jun. 1 Supplement).

Rusch et al., "Overexpression of the epidermal growth factor receptor and its ligand transforming growth factor alpha is frequent in resectable non-small cell lung cancer but does not predict tumor progression." *Clin. Cancer Res.* (1997) 515-522, 3(4).

Rusnak et al., "The effects of the novel EGFR/ErbB-2tyrosine kinase inhibitor, GW2016, on the growth of human normal and transformed cell lines." *Proceedings of the American Association for Cancer Research* (2001) 803 (Abstract 4309), 42.

Rusnak et al., "The effects of the novel, reversible epidermal growth factor receptor/ErbB-2 tyrosine kinase inhibitor, GW2016, on the growth of human normal and tumor-derived cell lines in vitro and in vivo." *Molecular cancer therapeutics* (2001) 85-94, 1(2).

Safa et al., "Adjuvant immunotherapy for melanoma and colorectal cancers." *Semin. Oncol.* (2001) 68-92, 28(1).

Saikali et al., "Expression of nine tumour antigens in a series of human glioblastoma multiforme: interest of EGFRvIII, IL-13Ralpha2, gp100 and TRP-2 for immunotherapy." *Journal of Neuro-Oncology* (2007) 139-148, 81(2).

Sainsbury et al., "Epidermal-growth-factor receptor status as predictor of early recurrence of and death from breast cancer." *Lancet* (1987) 1398-1402, 1(8547).

Sainsbury et al., "Presence of epidermal growth factor receptor as an indicator of poor prognosis in patients with breast cancer." *Journal of Clinical Pathology* (1985) 1225-1228, 38(11).

Sako et al., "Single-molecule imaging of EGFR signalling on the surface of living cells." *Nature Cell Biology* (2000) 168-172, 2(3).

Sakurada et al., "Epidermal growth factor receptor tyrosine kinase inhibitors in lung cancer: impact of primary or secondary mutations." *Clinical lung cancer* (2006) S138-44, 7(Suppl. 4).

Salazar et al., "Dose-dependent inhibition of the EGFR and signalling pathways with the anti-EGFR monoclonal antibody (MAb) EMD 72000 administered every three weeks (q3w). A phase I pharmacokinetic/pharmacodynamic (PK/PD) study to define the optimal biological dose (OBD)." *Proceedings of the American Society of Clinical Oncology* (2004) 127s (Abstract 2002), 22.

Saleh et al., "Combined modality therapy of A431 human epidermoid cancer using anti-EGFr antibody C225 and radiation." *Cancer Biotherapy & Radiopharmaceuticals* (1999) 451-463, 14(6).

Salomon et al., "Epidermal growth factor-related peptides and their receptors in human malignancies." *Crit. Rev. Oncol. Hematol.* (1995) 183-232, 19(3).

Saltz et al., "Interim Report of Randomized Phase II Trial of Cetuximab/Bevacizumab/Irinotecan (CBI) versus Cetuximab/Bevacizumab (CB) in Irinotecan-Refractory Colorectal Cancer" *Proceedings of the American Society of Clinical Oncology* (2006) Abstract 169b.

Saltz et al., "The presence and intensity of the cetuximab-induced acne-like rash predicts increased survival in studies across multiple malignancies" *Proc. Am. Soc. Clin. Oncol.* (2003) Abstract 817, 22.

(56) References Cited

OTHER PUBLICATIONS

Saltz et al., "Single agent IMC-C225 (Erbitux[TM]) has activity in CPT-11 refractory colorectal cancer that expresses the epidermal growth factor receptor (EGFR)." *Proceedings of the American Society of Clinical Oncology* (2002) 127a (Abstract 504), 21.
Saltz et al., "Cetuximab (IMC-225) plus irinotecan (CPT-11) is active in CPT-11- refractory colorectal cancer (CRC) that expresses epidermal growth factor receptor (EGFR)." *Proceedings of the American Society of Clinical Oncology* (2001) 3a (Abstract 7), 20.
Saltz et al., "Phase II trial of cetuximab in patients with refractory colorectal cancer that expresses the epidermal growth factor receptor." *J. Clin. Oncol*.(2004) 1201-1208, 22(7).
Sampson et al., "An EGFRvIII specific peptide vaccine generates antitumor immunity through a humoral pathway." *Neuro-oncology* (1999) S103 (Abstract 135).
Sampson et al., "Tumor-specific immunotherapy targeting the EGFRvIII mutation in patients with malignant glioma." *Seminars in immunology* (2008) 267-275, 20(5).
Sanderson et al., "In vivo drug-linker stability of an anti-CD30 dipeptide-linked auristatin immunoconjugate." *Clin. Cancer Res.* (2005) 843-852, 11(2; Part 1).
Sandler, "Nondermatologic adverse events associated with anti-EGFR therapy." *Oncology* (Williston Park, N.Y.) (2006) 35-40, 20(5 Suppl 2).
De Santes et al., "Radiolabeled antibody targeting of the HER-2/neu oncoprotein." *Cancer Res.* (1992) 1916-1923, 52(7).
Santon et al., "Effects of epidermal growth factor receptor concentration on tumorigenicity of A431 cells in nude mice." *Cancer Res.* (1986) 4701-4705, 46(9).
Sartor, "Biological modifiers as potential radiosensitizers: targeting the epidermal growth factor receptor family." *Semin. Oncol.* (2000) 15-20; discussion 92-100, 27(6 Suppl. 11).
Sartor, "Mechanisms of disease: Radiosensitization by epidermal growth factor receptor inhibitors." *Nature Clinical Practice. Oncology* (2004) 80-87, 1(2).
Sarup et al., "Characterization of an anti-p185HER2 monoclonal antibody that stimulates receptor function and inhibits tumor cell growth." *Growth Regulation* (1991) 72-82, 1(2).
Sato et al., "Derivation and assay of biological effects of monoclonal antibodies to epidermal growth factor receptors." *Methods in Enzymology* (1987) 63-81, 146.
Sato et al., "Biological effects in vitro of monoclonal antibodies to human epidermal growth factor receptors." *Molecular biology & medicine* (1983) 511-529, 1(5).
Sauter et al., "Patterns of epidermal growth factor receptor amplification in malignant gliomas." *The American Journal of Pathology* (1996) 1047-1053, 148(4).
Scher et al., "Changing pattern of expression of the epidermal growth factor receptor and transforming growth factor alpha in the progression of prostatic neoplasms." *Clin. Cancer Res.* (1995) 545-550, 1(5).
Schlegel et al., "Amplification of the epidermal-growth-factor-receptor gene correlates with different growth behaviour in human glioblastoma." *Int. J. Cancer* (1994) 72-77, 56(1).
Schlessinger, "Cell signaling by receptor tyrosine kinases." *Cell* (2000) 211-225, 103(2).
Schlessinger, "Common and distinct elements in cellular signaling via EGF and FGF receptors." *Science* (2004) 1506-1507, 306(5701).
Schmidt et al., "Suppression of metastasis formation by a recombinant single chain antibody-toxin targeted to full-length and oncogenic variant EGF receptors." *Oncogene* (1999) 1711-1721, 18(9).
Schmidt et al:, "Expression of an oncogenic mutant EGE receptor markedly increases the sensitivity of cells to an EGF-receptor-specific antibody-toxin." *Int. J. Cancer* (1998) 878-884, 75(6).
Schmidt et al., "Epidermal growth factor receptor signaling intensity determines intracellular protein interactions, ubiquitination, and internalization." *Proceedings of the National Academy of Sciences of the United States of America* (2003) 6505-6510, 100(11).

Schmidt-Ullrich et al., "Radiation-induced proliferation of the human A431 squamous carcinoma cells is dependent on EGFR tyrosine phosphorylation." *Oncogene* (1997) 1191-1197, 15(10).
Schmiedel et al.; "Matuzumab binding to EGFR prevents the conformational rearrangement required for dimerization." *Cancer Cell* (2008) 365-373, 13(4).
Schmitz et al., "Interaction of antibodies with ErbB receptor extracellular regions" *Experimental Cell Research* (2009) 659-670, 315(4).
Schnürch et al., "Growth inhibition of xenotransplanted human carcinomas by a monoclonal antibody directed against the epidermal growth factor receptor." *Eur. J. Cancer* (1994) 491-496, 30A(4).
Schwechheimer et al., "EGFR gene amplification—rearrangement in human glioblastomas." *Int. J. Cancer* (1995) 145-148, 62(2).
Scott, "Structural Biology and Molecular Imaging in Cancer Therapeutics" *Bosch Institute Annual Scientific Meeting* (Sydney, Australia) (2010).
Scott, "Pathway Specific Therapeutics: from Cancer Biology to Targeted Therapy" *Garvan Signalling Symposium* (Melbourne, Australia) (2010).
Scott, "Targeting a Novel EGFR Epitope on Cancer Cells" *Ludwig Institute for Cancer Reasearch* (2010) Abstract 014.
Scott, "Antibody Therapeutics" *Ludwig Institute Colon Cancer Initiative Symposium* (Baltimore, MD, United States) (2010).
Scott, "Development of a humanised antibody against a novel epitope of EGFR" *2010 Australasian Vaccines & Immunotherapy Development [AVID] Meeting* (Melbourne, Australia) (2010).
Scott, "Development of a novel anti-EGFR humanised antibody—the complex path from Academia to Industry" *Lowy Symposium* (Sydney, Australia) (2010).
Scott, "Novel Antibodies that bind to a conformational epitope of EGFR" *IBC 20th Annual Antibody Engineering Conference* (San Diego, CA, United States) (2009).
Scott, "Targeting a Novel EGFR Epitope on Cancer Cells" *LICR Translational Oncology Conference* (Melbourne, Australia) (2009).
Scott, "Cell Surface Targets for Therapy" *LICR Brain Cancer Initiative Meeting* (Rockville, MD, United States) (2009).
Scott, "Targeting a Novel EGFR Epitope on Cancer Cells" *Keystone Symposia: Antibodies as Drugs: Targeted Cancer Therapies* (Whistler British Columbia, Canada) (2009).
Scott, "Therapy of EGFR Expressing Cancers with a Novel Tumour Specific Antibody" *AHMRC Congress* (Brisbane, Qld, Australia) (2008).
Scott, "Understanding the Biology of Targeted Therapies in Cancer" *University of Melbourne/Royal Melbourne Hospital/Western Hospital Consortium Seminar* (Melbourne, Australia) (2008).
Scott, "The biology of EGFR in normal and diseased tissues" *Australian Lung Cancer Conference* (Surfers Paradise, Qld, Australia) (2008).
Scott, "Recombinant Antibody Therapy of Cancer—The LICR Antibody Program" *A\* Star Agency for Science, Technology and Research, ICMB* (Singapore) (2008).
Scott, "Epidermal Growth Factor Receptor Targeting for Cancer Therapy" *3rd Barossa Meeting—Signalling Systems* (Barossa Valley, South Australia) (2007).
Scott, "Cell Surface and Intracellular targets for antibody directed cancer therapeutics" *City of Hope Cancer Center* (Los Angeles, CA, United States) (2007).
Scott, "Of Mice and Man—The Role of Growth Factor Receptors in Cancer" *Austin Hospital Division of Medicine Grand Round* (Melbourne, Australia) (2007).
Scott, "Targeting the Epidermal Growth Factor Receptor for Antibody Therapy of Solid Tumours" *Third International AntibOZ Conference* ( Heron Island, Queensland, Australia) (2007).
Scott, "Targeting a Tumour Specific Epitope of the Epidermal Growth Factor Receptor" *2007 Keystone Symposium: Antibodies as Drugs: From Basic Biology to the Clinic* (Alberta, Canada) (2007).
Scott, "Targeting the Epidermal Growth Factor Receptor for Antibody Therapy of Solid Tumours" *17th Annual IBC Antibody Engineering Conference* (San Diego, CA, United States) (2006).
Scott, "EGFR Targeted Therapeutics" *ComBio 2006* (Brisbane, Australia) (2006).

(56) References Cited

OTHER PUBLICATIONS

Scott, "Implications of Antibody:Receptor Binding Structure and Signalling on Tumour Growth" *Discovery Science & Biotechnology Conference (Melbourne, Australia)* (2006).
Scott, "Targeting the Epidermal Growth Factor Receptor for Antibody Therapy of Solid Tumours" *EGFR Cascade Meeting (San Diego, CA, United States)* (2006).
Scott, "Implications of Antibody:Receptor Binding Structure and Signalling on Tumour Growth" *Monash University—Department of Biochemistry & Molecular Biology (Melbourne, Australia)* (2005).
Scott, "Receptor Based Targets for Antibody Therapy of Solid Tumours" *The Second China International Symposium on Antibody Engineering: Current Status and Future Perspective of Antibody Therapeutics (Beijing, China)* (2005).
Scott, "Novel Antibody that Inhibits EGFR Activation"*Fifth International Congress on Monoclonal Antibodies in Cancer (Quebec City, Canada)* (2005).
Scott, "Growth Factors and their implications in head and neck cancer" *Garnett Passe Scientific Meeting: Frontiers in Otorhinolaryngology 2004 (Noosa, Queensland, Australia)* (2004).
Scott, "Recombinant Antibodies for Immune and Cell Signalling Based Therapeutics" *AntibOZ 2 Conference (Heron Island, Queensland, Australia)* (2004).
Scott, "Targeted Cancer Therapeutics—the Role of Signalling and Immune Effector Mechanisms" *Royal North Shore Hospital Scientific Forum (Sydney, NSW, Australia)* (2003).
Scott, "Targeted Therapeutics—the Role of Signalling and Immune Effector Mechanism" *Centre for Immunology and Cancer Research, University of Queensland (Brisbane, Queensland, Australia)* (2003).
Scott, "Targetted Therapeutics—the Role of Signalling and Immune Effector Mechanisms" *Peter MacCallum Cancer Immunology Program Seminar (Melbourne, Australia)* (2003).
Scott, "Comparison of Phase I Trials of Anti-Epidermal Growth Factor Receptor (EGFR) Monoclonal Antibodies (Mabs) 528 and 225 Labelled With 1-131 and In-111" *J. Nucl. Med.* (1993) 213P, 34(5).
Scott, "Molecular Targets for Cancer Therapeutics" *Baker Institute Seminar (Melbourne, Australia)* (2002).
Scott, "Molecular Targets for Cancer Therapeutics" *Cambridge University Seminar (United Kingdom)* (2002).
Scott, "Molecular Targets for Cancer Therapeutics" *Monash University Seminar (Melbourne, Australia)* (2002).
Scott et al., "Specific targeting, biodistribution, and lack of immunogenicity of chimeric anti-GD3 monoclonal antibody KM871 in patients with metastatic melanoma: results of a phase I trial." *J. Clin. Oncol.* (2001) 3976-3987, 19(19).
Scott et al., "Construction, production, and characterization of humanized anti-Lewis Y monoclonal antibody 3S193 for targeted immunotherapy of solid tumors." *Cancer Res.* (2000) 3254-3261, 60(12).
Scott et al., "Antibody-based immunological therapies." *Curr. Opin. Immunol.* (1997) 717-722, 9(5).
Scott et al., "Clinical promise of tumour immunology." *Lancet* (1997) SII19-22, 349(Suppl. 2).
Scott et al., "Tumor imaging and therapy." *Radiologic clinics of North America* (1993) 859-879, 31(4).
Scott et al., "A Phase I single dose escalation trial of ch806 in patients with advanced tumors expressing the 806 antigen. " *Journal of Clinical Oncology, 2006 ASCO Annual Meeting Proceedings Part I.* (2006) 13028, 24(18S (Jun. 20 Supplement)).
Scott et al., "A phase I biodistribution and pharmacokinetic trial of humanized monoclonal antibody Hu3s193 in patients with advanced epithelial cancers that express the Lewis-Y antigen." *Clin. Cancer Res.* (2007) 3286-3292, 13(11).
Scott et al., "A phase I trial of humanized monoclonal antibody A33 in patients with colorectal carcinoma: biodistribution, pharmacokinetics, and quantitative tumor uptake." *Clin. Cancer Res.* (2005) 4810-4817, 11(13).
Scott et al., "Immunological effects of chimeric anti-GD3 monoclonal antibody KM871 in patients with metastatic melanoma." *Cancer immunity : a journal of the Academy of Cancer Immunology* (2005) 3, 5.
Scott et al., "A Phase I dose-escalation study of sibrotuzumab in patients with advanced or metastatic fibroblast activation protein-positive cancer." *Clin. Cancer Res.* (2003) 1639-1647, 9(5).
Sellers et al., "Apoptcisis and cancer drug targeting." *J. Clin. Invest.* (1999) 1655-1661, 104(12).
Senter, "Potent antibody drug conjugates for cancer therapy" *Current Opinion in Chemical Biology* (2009) 235-244, 13(3).
Senzer et al., "Phase 2 Evaluation of OSI-774, a Potent Oral Antagonist of the EGFR-TK in Patients with Advanced Squamous Cell Carcinoma of the Head and Neck." *Proceedings of the American Society of Clinical Oncology* (2001) 2a (Abstract 6), 20.
Sepp-Lorenzino et al., "Farnesyl:protein transferase inhibitors (FTIs) block tyrosine kinase signal transduction and act in concert with an anti-EGR receptor antibody to inhibit cancer cell growth." *Proceedings of the Annual Meeting of the American Association for Cancer Research* (1996) 421-422 (Abstract 2877), 37.
Sharafinski et al., "Epidermal growth factor receptor targeted therapy of squamous cell carcinoma of the head and neck." *Head & Neck* (2010) 1412-1421, 32(10).
She et al., "The Bad protein integrates survival signaling by EGFR/MAPK and PI3K/Akt kinase pathways in PTEN-deficient tumor cells." *Cancer Cell* (2005) 287-297, 8(4).
Shepherd et al., "Unraveling the mystery of prognostic and predictive factors in epidermal growth factor receptor therapy." *Journal of Clinical Oncology* (2006) 1219-20; author reply 12201, 24(7).
Sherrill et al., "Activation of epidermal growth factor receptor by epidermal growth factor." *Biochemistry* (1996) 5705-5718, 35(18).
Shibata et al., "Enhancing effects of epidermal growth factor on human squamous cell carcinoma motility and matrix degradation but not growth." *Tumour biology : the Journal of the International Society for Oncodevelopmental Biology and Medicine* (1996) 168-175; 17(3).
Shigematsu et al., "Somatic mutations of epidermal growth factor receptor signaling pathway in lung cancers." *Int. J. Cancer* (2006) 257-262, 118(2).
Shigematsu et al., "Clinical and biological features associated with epidermal growth factor receptor gene mutations in lung cancers." *J. Natl. Cancer Inst.* (2005) 339-346, 97(5).
Shimizu et al., "Detection of epidermal growth factor receptor gene amplification in human squamous cell carcinomas using fluorescence in situ hybridization." *Japanese Journal of Cancer Research : Gann* (1994) 567-571, 85(6).
Shimizu et al., "Genetics of cell surface receptors for bioactive polypeptides: binding of epidermal growth factor is associated with the presence of human chromosome 7 in human-mouse cell hybrids." *Proceedings of the National Academy of Sciences of the United States of America* (1980) 3600-3604, 77(6).
Shin et al., "Epidermal growth factor receptor-targeted therapy with C225 and cisplatin in patients with head and neck cancer." *Clin. Cancer Res.* (2001) 1204-1213, 7(5).
Shin et al., "Dysregulation of epidermal growth factor receptor expression in premalignant lesions during head and neck tumorigenesis." *Cancer Res.* (1994) 3153-3159, 54(12).
Shinkawa et al., "The absence of fucose but not the presence of galactose or bisecting N-acetylglucosamine of human IgG1 complex-type oligosaccharides shows the critical role of enhancing antibody-dependent cellular cytotoxicity." *Journal of Biological Chemistry* (2003) 3466-3473, 278(5).
Shinojima et al., "Prognostic value of epidermal growth factor receptor in patients with glioblastoma multiforme." *Cancer Res.* (2003) 6962-6970, 63(20).
Shintani, "Gefitinib ('Iressa', ZD1839), an epidermal growth factor receptor tyrosine kinase inhibitor, up-regulates p27KIP1 and induces G1 arrest in oral squamous cell carcinoma cell lines" *Oral oncology* (2004) 43-51, 40(1).
Shintani et al., "Intragenic mutation analysis of the human epidermal growth factor receptor (EGFR) gene in malignant human oral keratinocytes." *Cancer Res.* (1999) 4142-4147, 59(16).

(56) References Cited

OTHER PUBLICATIONS

Shusta et al., "Directed evolution of a stable scaffold for T-cell receptor engineering." *Nat. Biotechnol.* (2000) 754-759, 18(7).
Shusta et al., "Yeast polypeptide fusion surface display levels predict thermal stability and soluble secretion efficiency." *J. Mol. Biol.* (1999) 949-956, 292(5).
Sibilia et al., "The EGF receptor provides an essential survival signal for SOS—dependent dependent skin tumor development." *Cell* (2000) 211-220, 102(2).
Siegel-Lakhai et al., "Current knowledge and future directions of the selective epidermal growth factor receptor inhibitors erlotinib (Tarceva) and gefitinib (Iressa)." *Oncologist* (2005) 579-589, 10(8).
Silver et al., "Erbb is linked to the alpha-globin locus on mouse chromosome 11." *Mol. Cell Biol.* (1985) 1784-1786, 5(7).
Sirotnak et al., "Potentiation of cytotoxic agents against human tumors in mice by ZD1839 (Iressa), an inhibitor of EGFR tyrosine kinase, does not require high levels of expression of EGFR:" *Proceedings of the Annual Meeting of the American Association for Cancer Research* (2000) 482 (Abstract 3076), 41.
Sirotnak et al., "Efficacy of cytotoxic agents against human tumor xenografts is markedly enhanced by coadministration of ZD1839 (Iressa), an inhibitor of EGFR tyrosine kinase." *Clin. Cancer Res.* (2000)4885-4892, 6(12).
Sivasubramanian et al., "Structural model of the mAb 806-EGFR complex using computational docking followed by computational and experimental mutagenesis." *Structure* (2006) 401-414, 14(3).
Skov et al., "Interaction of platinum drugs with clinically relevant x-ray doses in mammalian cells: a comparison of cisplatin, carboplatin, iproplatin, and tetraplatin." *Int. J. Radiat. Oncol. Biol. Phys.* (1991) 221-225, 20(2).
Slamon, "Use of Chemotherapy Plus a Monoclonal Antibody Against HER2 for Metastatic Breast Cancer That Overexpresses HER2" *The New England Journal of Medicine* (2001) 783-792, 344(11).
Slamon et al., "Addition of Herceptin (Humanized anti-HER2 antibody) to first line chemotherapy for HER2 overexpressing metastatic breast cancer (HER2+/MBC) markedly increases anticancer activity: a randomized, multinational controlled phase III trial." *Proceedings of the Annual Meeting of the American Society of Clinical Oncology* (1998) 98a (Abstract 377), 17.
Slamon et al., "Studies of the HER-2/neu proto-oncogene in human breast and ovarian cancer." *Science* (1989) 707-712, 244(4905).
Slichenmyer et al., "Anticancer therapy targeting the erbB family of receptor tyrosine kinases." *Semin. Oncol.* (2001) 67-79, 28(5; Suppl. 16).
Slieker et al., "Synthesis of epidermal growth factor receptor in human A431 cells. Glycosylation-dependent acquisition of ligand binding activity occurs post-translationally in the endoplasmic reticulum." *Journal of Biological Chemistry* (1986) 15233-15241, 261(32).
Slieker et al., "Post-translational processing of the epidermal growth factor receptor. Glycosylation-dependent acquisition of ligand-binding capacity." *Journal of Biological Chemistry* (1985) 687-690, 260(2).
Sliwkowski et al., "Nonclinical studies addressing the mechanism of action of trastuzumab (Herceptin)." *Semin. Oncol.* (1999) 60-70, 26(4 Suppl 12).
Smith et al., "PTEN mutation, EGFR amplification, and outcome in patients with anaplastic astrocytoma and glioblastoma multiforme." *J. Natl. Cancer Inst.* (2001) 1246-1256, 93(16).
Snyder et al., "Overview of monoclonal antibodies and small molecules targeting the epidermal growth factor receptor pathway in colorectal cancer." *Clin. Colorectal Cancer* (2005) S71-80, 5(Suppl. 2).
Sobol et al., "Epidermal growth factor receptor expression in human lung carcinomas defined by a monoclonal antibody." *J. Natl. Cancer Inst.* (1987) 403-407, 79(3).
Soderquist et al., "Glycosylation of the epidermal growth factor receptor in A-431 cells. The contribution of carbohydrate to receptor function." *Journal of Biological Chemistry* (1984) 12586-12594, 259(20).
Solbach et al., "Antitumor effect of MAb EMD 55900 depends on EGF-R expression and histopathology." *Neoplasia* (2002) 237-242, 4(3).
Solomon et al., "EGFR blockade with ZD1839 ('Iressa') potentiates the antitumor effects of single and multiple fractions of ionizing radiation in human A431 squamous cell carcinoma." *Int. J. Radiat. Oncol. Biol. Phys.* (2003) 713-723, 55(3).
Solomon et al., "Rash from EGFR inhibitors: opportunities and challenges for palliation." *Current oncology reports* (2008) 304-308, 10(4).
Sonabend et al., "Targeting epidermal growth factor receptor variant III: a novel strategy for the therapy of malignant glioma." *Expert Review of Anticancer Therapy* (2007) S45-50, 7(12; Supplement).
Sørensen et al., "Injury-induced innate immune response in human skin mediated by transactivation of the epidermal growth factor receptor." *J. Clin. Invest.* (2006) 1878-1885, 116(7).
Sorscher, "EGFR mutations and sensitivity to gefitinib." *N. Engl. J. Med.* (2004) 1260-1261, 351(12).
Soulieres, "Multicenter Phase II Study of Erlotinib, an Oral Epidermal Growth Factor Receptor Tyrosine Kinase Inhibitor, in Patients With Recurrent or Metastatic Squamous Cell Cancer of the Head and Neck" *Journal of Clinical Oncology* (2004) 77-85, 22(1).
Spurr et al., "Mapping of cellular oncogenes; erb B on chromosome 7" *Cytogenet. Cell Genet.* (1984) 590, 37.
Spurr et al., "Chromosomal localisation of the human homologues to the Oncogenes erbA and B." *EMBO J.* (1984) 159-163, 3(1).
Sridhar et al., "Inhibitors of epidermal-growth-factor receptors: a review of clinical research with a focus on non-small-cell lung cancer." *The Lancet Oncology* (2003) 397-406, 4(7).
Stabin et al., "OLINDA/EXM: the second-generation personal computer software for internal dose assessment in nuclear medicine." *J. Nucl. Med.* (2005) 1023-1027, 46(6).
Stancovski et al., "Mechanistic aspects of the opposing effects of monoclonal antibodies to the ERBB2 receptor on tumor growth." *Proceedings of the National Academy of Sciences of the United States of America* (1991) 8691-8695, 88(19).
Steffens et al., "Targeting of renal cell carcinoma with iodine-131-labeled chimeric monoclonal antibody G250." *J. Clin. Oncol.* (1997) 1529-1537, 15(4).
Stockert et al., "Generation and characterization of mouse monoclonal antibodies to mutant human EGFR and expression of mutant human EGFR in normal and tumor tissue" *Ludwig Institute for Cancer Research* (1997) 212-213.
Stockert et al., "Generation and characterization of monoclonal antibodies to mutant and amplieifed epidermal growth factor receptor" *Ludwig Institute for Cancer Research* (1995) 212-213.
Stockhausen et al.; "Maintenance of EGFR and EGFRvIII expressions in an in vivo and in vitro model of human glioblastoma multiforme." *Exp. Cell Res.* (2011) 1513-1526, 317(11).
Stragliotto et al., "Multiple infusions of anti-epidermal growth factor receptor (EGFR) monoclonal antibody (EMD 55,900) in patients with recurrent malignant gliomas." *Eur. J. Cancer* (1996) 636-640, 32A(4).
Studnicka et al., "Human-engineered monoclonal antibodies retain full specific binding activity by preserving non-CDR complementarity-modulating residues." *Protein Engineering* (1994) 805-814, 7(6).
Sugawa et al., "Function of aberrant EGFR in malignant gliomas." *Brain Tumor Pathology* (1998) 53-57, 15(1).
Sugimura et al., "[Immunohistochemical study on the expression of epidermal growth factor receptor (EGF-R) in invasive cervical cancer of the uterus]." *Nippon Sanka Fujinka Gakkai zasshi* (1992) 689-694, 44(6).
Sunada et al., "Monoclonal antibody against epidermal growth factor receptor is internalized without stimulating receptor phosphorylation." *Proceedings of the National Academy of Sciences of the United States of America* (1986) 3825-3829, 83(11).
Sutherland et al., "Lysosomal trafficking and cysteine protease metabolism confer target-specific cytotoxicity by peptide-linked anti-CD30-auristatin conjugates." *Journal of Biological Chemistry* (2006) 10540-10547, 281(15).
Suwa et al., "Epidermal growth factor receptor-dependent cytotoxic effect of anti-EGFR antibody-ribonuclease conjugate on human cancer cells." *Anticancer Research* (1999) 4161-4165, 19(5B).

(56) References Cited

OTHER PUBLICATIONS

Swaisland et al., "Pharmacokinetics and tolerability of the orally active selective epidermal growth factor receptor tyrosine kinase inhibitor ZD1839 in healthy volunteers." Clinical pharmacokinetics (2001) 297-306, 40(4).

Tabernero et al., "An international phase II study of cetuximab in combination with oxaliplatin/5-fluorouracil (5-FU)/folinic acid (FA) (FOLFOX-4) in the first-line treatment of patients with metastatic colorectal cancer (CRC) expressing epidermal growth factor receptor (EGFR)." *Proceedings of the American Society of Clinical Oncology* (2004) 248s (Abstract 3512), 23.

Tabernero et al., "A phase I PK and serial tumor and skin pharmacodynamic (PD) study of weekly (q1w), every 2-week (q2w) or every 3-week (q3w) 1-hour (h) infusion EMD72000, a humanized monoclonal anti-epidermal growth factor receptor (EGFR) antibody, in patients (pt) with advanced tumors." *Proceedings of the American Society of Clinical Oncology* (2003) 192 (Abstract 770), 22.

Taetle et al., "Effects of anti-epidermal growth factor (EGF) receptor antibodies and an anti-EGF receptor recombinant-ricin A chain immunoconjugate on growth of huirian cell" *Chemical Abstracts* (1988) 184218a, 109(21).

Taetle et al., "Effects of anti-epidermal growth factor (EGF) receptor antibodies and an anti-EGF receptor recombinant-ricin A chain immunoconjugate on growth of human cells." *J. Natl. Cancer Inst.* (1988) 1053-1059, 80(13).

Tahtis et al., "Biodistribution properties of (111)indium-labeled C-functionalized trans-cyclohexyl diethylenetriaminepentaacetic acid humanized 3S193 diabody and F(ab')(2) constructs in a breast carcinoma xenograft model." *Clin. Cancer Res.* (2001) 1061-1072, 7(4).

Tai et al., "Co-overexpression of fibroblast growth factor 3 and epidermal growth factor receptor is correlated with the development of nonsmall cell lung carcinoma." *Cancer* (20066) 146-155, 106(1).

Takahashi et al., "Radioimmunodetection of human glioma xenografts by monoclonal antibody to epidermal growth factor receptor." *Cancer Res.* (1987) 3847-3850, 47(14).

Takasu et al., "Antibody-based therapy for brain tumor." *Nippon rinsho. Japanese journal of clinical medicine* (2005) 563-568, 63(Suppl. 9).

Takasu et al., "Radioimmunoscintigraphy of intracranial glioma xenograft with a technetium-99m-labeled mouse monoclonal antibody specifically recognizing type III mutant epidermal growth factor receptor." *Journal of neuro-oncology* (2003) 247-256, 63(3).

Tan et al., "Pharmacokinetics of cetuximab after administration of escalating single dosing and weekly fixed dosing in patients with solid tumors." *Clin. Cancer Res.* (2006) 65176522, 12(21).

Tang et al., "Epidermal growth factor receptor vIII enhances tumorigenicity in human breast cancer." *Cancer Res.* (2000) 3081-3087, 60(11).

Tang et al., "The autocrine loop of TGF-alpha/EGFR and brain tumors." *Journal of neuro-oncology* (1997) 303-314, 35(3).

Tang et al., "Phase II study of ispinesib in recurrent or metastatic squamous cell carcinoma of the head and neck." *Investigational new drugs* (2008) 257-264, 26(3).

Tannock, "Treatment of cancer with radiation and drugs." *J. Clin. Oncol.* (1996) 3156-3174, 14(12).

Tanswell et al., "Population pharmacokinetics of antifibroblast activation protein monoclonal antibody F19 in cancer patients." *British journal of clinical pharmacology* (2001) 177-180, 51(2).

Tateishi et al., "Prognostic influence of the co-expression of epidermal growth factor receptor and c-erbB-2 protein in human lung adenocarcinoma." *Surgical oncology* (1994) 109-113, 3(2).

Temam et al., "Epidermal growth factor receptor copy number alterations correlate with poor clinical outcome in patients with head and neck squamous cancer." *Journal of Clinical Oncology* (2007) 2164-2170, 25(16).

Temming et al., "Evaluation of RGD-targeted albumin carriers for specific delivery of auristatin E to tumor blood vessels." *Bioconjugate chemistry* (2006) 1385-1394, 17(6).

Teramoto et al., "Inhibitory effect of anti-epidermal growth factor receptor antibody on a human gastric cancer." *Cancer* (1996) 1639-1645, 77(8 Suppl).

Tewes et al., "Results of a phase I trial of the humanized anti epidermal growth factor receptor (EGFR) monoclonal antibody EMD 72000 in patients with EGFR expressing solid tumors." *Proceedings of the American Society of Clinical Oncology* (2002) 95a (Abstract 378), 21.

Thaung et al., "Novel ENU-induced eye mutations in the mouse: models for human eye disease." *Human molecular genetics* (2002) 755-767, 11(7).

Thomas et al., "Pharmacokinetic and pharmacodynamic properties of EGFR inhibitors under clinical investigation." *Cancer Treat Rev.* (2004) 255-268, 30(3).

Thompson et al., "The EGF receptor: structure, regulation and potential role in malignancy." *Cancer surveys* (1985) 767-788, 4(4).

Tice et al., "Mechanism of biological synergy between cellular Src and epidermal growth factor receptor." *Proceedings of the National Academy of Sciences of the United States of America* (1999) 1415-1420, 96(4).

Tietze et al., "Novel analogues of CC-1065 and the duocarmycins for the use in targeted tumour therapies." *Anti-cancer agents in medicinal chemistry* (2009) 304-325, 9(3).

Tochon-Danguy et al., "Imaging and quantitation of the hypoxic cell fraction of viable tumor in an animal model of intracerebral high grade glioma using [18F]fluoromisonidazole (FMISO)." *Nucl. Med. Biol.* (2002) 191-197, 29(2).

Todd et al., "Epidermal growth factor receptor (EGFR) biology and human oral cancer." *Histology and histopathology* (1999) 491-500, 14(2).

Toi et al., "Epidermal growth factor receptor expression as a prognostic indicator in breast cancer." *Eur. J. Cancer* (1991) 977-980, 27(8).

Tokuda et al., "In vitro and in vivo anti-tumour effects of a humanised monoclonal antibody against c-erbB-2 product." *British Journal of Cancer* (1996) 1362-1365, 73(11).

Tokumo et al., "The relationship between epidermal growth factor receptor mutations and clinicopathologic features in non-small cell lung cancers." *Clin. Cancer Res.* (2005) 1167-1173, 11(3).

Torres et al., "Phase I/II clinical trial of the humanized anti-EGF-r monoclonal antibody h-R3 labelled with 99mTc in patients with tumour of epithelial origin." *Nuclear medicine communications* (2005) 1049-1057, 26(12).

Toth et al., "Analysis of EGFR gene amplification, protein overexpression and tyrosine kinase domain mutation in recurrent glioblastoma." *Pathology oncology research : POR* (2009) 225-229, 15(2).

Toyooka et al., "EGFR mutation and response of lung cancer to gefitinib." *N. Engl. J. Med.* (2005) 2136, 352(20).

Trail et al., "Monoclonal antibody drug conjugates in the treatment of cancer." *Curr. Opin. Immunol.* (1999) 584-588, 11(5).

Tran et al., "CAML is required for efficient EGF receptor recycling." *Developmental cell* (2003) 245-256, 5(2).

Traxler et al., "AEE788: a dual family epidermal growth factor receptor/ErbB2 and vascular endothelial growth factor receptor tyrosine kinase inhibitor with antitumor and antiagiogenic activity." *Cancer Res.* (2004) 4931-4941, 64(14).

Trigo et al., "Cetuximab monotherapy is active in patients (pts) with platinum-refractory recurrent/metastatic squamous cell carcinoma of the head and neck (SCCHN) (Results of a phase II study)." *Proceedings of the American Society of Clinical Oncology* (2004) 488s (Abstract 5502), 22.

Trummell et al., "The biological effects of anti-epidermal growth factor receptor and ionizing radiation in human head and neck tumor cell lines." *Proceedings of the American Association for Cancer Research* (1999) 144 (Abstract 958), 40.

Tsao et al., "Erlotinib in lung cancer—molecular and clinical predictors of outcome." *N. Engl. J. Med.* (2005) 133-144, 353(2).

Tsuchihashi et al., "Responsiveness to cetuximab without mutations in EGFR." *N. Engl. J. Med.* (2005) 208-209, 353(2).

Tsugu et al., "Localization of aberrant messenger RNA of epidermal growth factor receptor (EGFR) in malignant glioma." *Anticancer research* (1997) 2225-2232, 17(3C).

(56) References Cited

OTHER PUBLICATIONS

Türkeri et al., "Impact of the expression of epidermal growth factor, transforming growth factor alpha, and epidermal growth factor receptor on the prognosis of superficial bladder cancer." *Urology* (1998) 645-649, 51(4).
Turner et al., "EGF receptor signaling enhances in vivo invasiveness of DU-145 human prostate carcinoma cells." *Clinical & experimental metastasis* (1996) 409-418, 14(4).
Tzahar et al., "Bivalence of EGF-like ligands drives the ErbB signaling network." *EMBO J.* (1997) 4938-4950, 16(16).
Uegaki et al., "Clinicopathological significance of epidermal growth factor and its receptor in human pancreatic cancer." *Anticancer research* (1997) 3841-3847, 17(5B).
Uemura et at., "Internal image anti-idiotype antibodies related to renal-cell carcinoma-associated antigen G250." *Int. J. Cancer* (1994) 609-614, 56(4).
Ullrich et al., "Signal transduction by receptors with tyrosine kinase activity." *Cell* (1990) 203-212, 61(2).
Ushiro et al., "Identification of phosphotyrosine as a product of epidermal growth factor-activated protein kinase in A-431 cell membranes." *Journal of Biological Chemistry* (1980) 8363-8365, 255(18).
Vagin et al., "Spherically averaged phased translation function and its application to the search for molecules and fragments in electron-density maps." *Acta Crystallogr. D. Biol. Crystallogr.* (2001) 1451-1456, 57(pt 10).
Vaidyanathan et al., "Improved xenograft targeting of tumor-specific anti-epidermal growth factor receptor variant III antibody labeled using N-succinimidyl 4-guanidinomethyl-3-iodobenzoate." *Nucl. Med. Biol.* (2002) 1-11, 29(1)
Vajdos et al., "Comprehensive functional maps of the antigen-binding site of an anti-ErbB2 antibody obtained with shotgun scanning mutagenesis." *J. Mol. Biol.* (2002) 415-428, 320(2).
Vanhoefer et al., "Phase I study of the humanized antiepidermal growth factor receptor monoclonal antibody EMD72000 in patients with advanced solid tumors that express the epidermal growth factor receptor." *J. Clin. Oncol.* (2004) 175-184, 22(1).
Veale et al., "The relationship of quantitative epidermal growth factor receptor expression in non-small cell lung cancer to long term survival." *British Journal of Cancer* (1993) 162-165, 68(1).
Veale et al., "Epidermal growth factor receptors in non-small cell lung cancer." *British Journal of Cancer* (1987) 513-516, 55(5).
Velu et al., "Epidermal-growth-factor-dependent transformation by a human EGF receptor proto-oncogene." *Science* (1987) 1408-1410, 238(4832).
Venter et al., "Overexpression of the c-erbB-2 oncoprotein in human breast carcinomas: immunohistological assessment correlates with gene amplification." *Lancet* (1987) 69-72, 2(8550).
Verbeek et al., "Overexpression of EGFR and c-erbB2 causes enhanced cell migration in human breast cancer cells and NIH3T3 fibroblasts." *FEBS letters* (1998) 145-150, 425(1).
Vermorken et al., "Cetuximab (Erbitux®) in recurrent/metastatic (R&M) squamous cell carcinoma of the head and neck (SCCHN) refractory to first-line platinum- based therapies" *Journal of Clinical Oncology, 2005 ASCO Annual Meeting Proceedings* (2005) Abstract 5505, 23(16S; Part I of II: Jun. 1, Supplement).
Vermorken et al., "Platinum-based chemotherapy plus cetuximab in head and neck cancer." *N. Engl. J. Med.* (2008) 1116-1127, 359(11).
Verveer et al., "Quantitative imaging of lateral ErbB1 receptor signal propagation in the plasma membrane." *Science* (2000) 1567-1570, 290(5496).
Viana-Pereira et al., "Analysis of EGFR overexpression, EGFR gene amplification and the EGFRvIII mutation in Portuguese high-grade gliomas." *Anticancer research* (2008) 913-920, 28(2A).
Van De Vijver et al., "Ligand-induced activation of A431 cell epidermal growth factor receptors occurs primarily by an autocrine pathway that acts upon receptors on the surface rather than intracellularly." *Journal of Biological Chemistry* (1991) 7503-7508, 266(12).

Viloria-Petit et al., "Acquired resistance to the antitumor effect of epidermal growth factor receptor-blocking antibodies in vivo: a role for altered tumor angiogenesis." *Cancer Res.* (2001) 5090-5101, 61(13).
Vincent et al., "Anticancer efficacy of the irreversible EGFr tyrosine kinase inhibitor PD 0169414 against human tumor xenografts." *Cancer chemotherapy and pharmacology* (2000) 231-238, 45(3).
Vitali et al., "Monoclonal Antibody 806 Inhibits the Growth of Subcutaneous and Intracranial Tumor Xenografts Expressing either the de2-7 or Amplified Epidermal Growth Factor Receptor (EGFR) but not Wild-Type EGFR." *Proceedings of the 14th Annual Lorne Cancer Conference, Lorne, Victoria, Australia* (2002) Abstract 221.
Vitali et al., "Monoclonal Antibody 806 Inhibits the Growth of Subcutaneous and Intracranial Tumor Xenografts Expressing either the de 2-7 or Amplified Epidermal Growth Factor Receptor (EGFR) but not Wild-Type EGFR." *Proceedings of the 14th Annual Lorne Cancer Conference, Lorne, Victoria, Australia* (2002) Poster Presentation (Abstract 221).
Voelzke et al., "Targeting the epidermal growth factor receptor in high-grade astrocytomas." *Current treatment options in oncology* (2008) 23-31, 9(1).
Vogel et al., "First-Line Herceptin® Monotherapy in Metastatic Breast Cancer" *Oncology* (2001) 37-41, 61(Suppl. 2).
Vogel et al., "Efficacy and safety of trastuzumab as a single agent in first-line treatment of HER2-overexpressing metastatic breast cancer." *J. Clin. Oncol.* (2002) 719-726, 20(3).
Vogt et al., "Relationships linking amplification level to gene overexpression in gliomas." *PLoS ONE* (2010) e14249, 5(12).
Volm et al., "Prognostic value of ERBB-1, VEGF, cyclin A, FOS, JUN and MYC in patients with squamous cell lung carcinomas." *British Journal of Cancer* (1998) 663-669, 77(4).
Wakeling et al., "Specific inhibition of epidermal growth factor receptor tyrosine kinase by 4-anilinoquinazolines." *Breast cancer research and treatment* (1996) 67-73, 38(1).
Wakeling, "Epidermal growth factor receptor tyrosine kinase inhibitors." *Current opinion in pharmacology* (2002) 382-387, 2(4).
Wakeling et al., "Human EGFR, a candidate gene for the Silver-Russell syndrome, is biallelically expressed in a wide range of fetal tissues." *European journal of human genetics : EJHG* (1998) 158-164, 6(2).
Waksal, "Role of an anti-epidermal growth factor receptor in treating cancer." *Cancer Metastasis Rev.* (1999) 427-436, 18(4).
Waldmann, "Monoclonal antibodies in diagnosis and therapy." *Science* (1991) 1657-1662, 252(5013).
Walewski et al., "Rituximab (Mabthera, Rituxan) in patients with recurrent indolent lymphoma: evaluation of safety and efficacy in a multicenter study." *Medical oncology (Northwood, London, England)* (2001) 141-148, 18(2).
Walker et al., "Activation of the Ras/mitogen-activated protein kinase pathway by kinase-defective epidermal growth factor receptors results in cell survival but not proliferation." *Mol. Cell Biol.* (1998) 7192-7204, 18(12).
Walker et al., "Biochemical characterization of mutant EGF receptors expressed in the hemopoietic cell line BaF/3." *Growth Factors* (1998) 53-67, 16(1).
Walker et al., "Reconstitution of the high affinity epidermal growth factor receptor on cell-free membranes after transmodulation by platelet-derived growth factor." *Journal of Biological Chemistry* (1991) 2746-2752, 266(5).
Walker et al., "Expression of epidermal growth factor receptor mRNA and protein in primary breast carcinomas." *Breast cancer research and treatment* (1999) 167-176, 53(2).
Walton et al., "Analysis of deletions of the carboxyl terminus of the epidermal growth factor receptor reveals self-phosphorylation at tyrosine 992 and enhahced in vivo tyrosine phosphorylation of cell substrates." *Journal of Biological Chemistry* (1990) 1750-1754, 265(3).
Wang et al., "Immunohistochemical localization of c-erbB-2 protein and epidermal growth factor receptor in normal surface epithelium, surface inclusion cysts, and common epithelial tumours of the ovary." *Virchows Archiv. A. Pathological anatomy and histopathology* (1992):393-400, 421(5).

(56) References Cited

OTHER PUBLICATIONS

Wang et al., "Epidermal growth factor receptor vIII enhances tumorigenicity and resistance to 5-fluorouracil in human hepatocellular carcinoma." *Cancer Letters* (2009) 30-38, 279(1).
Wang et al., "Epidermal growth factor receptor is a cellular receptor for human cytomegalovirus." *Nature* (2003) 456-461, 424(6947).
Wang et al., "Endocytosis deficiency of epidermal growth factor (EGF) receptor-ErbB2 heterodimers in response to EGF stimulation." *Mol. Biol. Cell* (1999) 1621-1636, 10(5).
Wargalla et al., "Rate of internalization of an immunotoxin correlates with cytotoxic activity against human tumor cells." *Proceedings of the National Academy of Sciences of the United States of America* (1989) 5146-5150, 86(13).
Waterfield et al., "A monoclonal antibody to the human epidermal growth factor receptor." *J. Cell Biochem.* (1982) 149-161, 20(2).
Waterman et al., "Molecular mechanisms underlying endocytosis and sorting of ErbB receptor tyrosine kinases." *FEBS letters* (2001) 142-152, 490(3).
Waterman et al., "Alternative intracellular routing of ErbB receptors may determine signaling potency." *Journal of Biological Chemistry* (1998) 13819-13827, 273(22).
Waugh et al., "Epidermal growth factor receptor activation is localized within low-buoyant density, non-caveolar membrane domains." *Biochem. J.* (1999) 591-597, 337(Part 3).
Webster et al., "Engineering antibody affinity and specificity." *International journal of cancer* (1988) 13-16, 3.
Wedegaertner et al., "Effect of carboxyl terminal truncation on the tyrosine kinase activity of the epidermal growth factor receptor." *Archives of biochemistry and biophysics* (1992) 273-280, 292(1).
Wedegaertner et al., "Activation of the purified protein tyrosine kinase domain of the epidermal growth factor receptor." *Journal of Biological Chemistry* (1989) 11346-11353, 264(19).
Weiner, "An overview of monoclonal antibody therapy of cancer." *Semin. Oncol.* (1999) 41-50, 26(4 Suppl 12).
Weiss et al., "Rapid mapping of protein functional epitopes by combinatorial alanine scanning." *Proceedings of the National Academy of Sciences of the United States of America* (2000) 8950-8954, 97(16).
Wells, "EGF receptor." *The international journal of biochemistry & cell biology* (1999) 637-643, 31(6).
Wells et al., "Ligand-induced transformation by a noninternalizing epidermal growth factor receptor." *Science* (1990) 962-964, 247(4945).
Welt et al., "Phase I study of humanized A33 (huA33) antibody in patients with advanced colorectal cancer." *Proceedings of the Annual Meeting of the American Society of Clinical Oncology* (1997) 436a (Abstract 1563), 16.
Welt et al., "Phase I/II study of iodine 125-labeled monoclonal antibody A33 in patients with advanced colon cancer." *J. Clin. Oncol.* (1996) 1787-1797, 14(6).
Welt et al., "I/II study of iodine 131-labeled monoclonal antibody A33 in patients with advanced colon cancer." *J. Clin. Oncol.* (1994) 1561-1571, 12(8).
Welt et al., "Antibody targeting in metastatic colon cancer: a phase I study of monoclonal antibody F19 against a cell-surface protein of reactive tumor stromal fibroblasts." *J. Clin. Oncol.* (1994) 1193-1203, 12(6).
Welt et al., "Quantitative analysis of antibody localization in human metastatic colon cancer: a phase I study of monoclonal antibody A33." *J. Clin. Oncol.* (1990) 1894-1906, 8(11).
Welt et al., "Phase I study of anticolon cancer humanized antibody A33." *Clin. Cancer Res.* (2003) 1338-1346, 9(4).
Welt et al., "Preliminary report of a phase I study of combination chemotherapy and humanized A33 antibody immunotherapy in patients with advanced colorectal cancer." *Clin. Cancer Res.* (2003) 1347-1353, 9(4).
Wen et al., "Potentiation of antitumor activity of PG-TXL with anti-EGFR monoclonal antibody C225 in MDA-MB-468 human breast cancer xenograft." *Proceedings of the American Association for Cancer Research* (2000) 323 (Abstract 2052), 51.

Weppler et al., "Expression of EGFR variant vIII promotes both radiation resistance and hypoxia tolerance." *Radiotherapy and oncology* (2007) 333-339, 83(3).
Wersäall et al., "Intratumoral infusion of the monoclonal antibody, mAb 425, against the epidermal-growth-factor receptor in patients with advanced malignant glioma." *Cancer Immunol. Immunother.* (1997) 157-164, 44(3).
Westwood et al., "Adoptive transfer of T cells modified with a humanized chimeric receptor gene inhibits growth of Lewis-Y-expressing tumors in mice." *Proceedings of the National Academy of Sciences of the United States of America* (2005) 19051-19056, 102(52).
Wheeler et al., "Mechanisms of acquired resistance to cetuximab: role of HER (ErbB) family members." *Oncogene* (2008) 3944-3956, 27(28).
Wheeler et al., "Epidermal growth factor receptor variant III mediates head and neck cancer cell invasion via STAT3 activation." *Oncogene* (2010) 5135-5145, 29(37).
Whitson et al., "Functional effects of glycosylation at Asn-579 of the epidermal growth factor receptor." *Biochemistry* (2005) 14920-14931, 44(45).
Wikstrand et al., "Antibodies and molecular immunology: immunohistochemistry and antigens of diagnostic significance" *In: Russell and Rubinstein's Pathology of Tumors of the Nervous System* (Chapter 8) (Editors: Bigner, et al.; Publishers: Arnold and Oxford University Press, Inc., New York, NY). (1998) 251-304.
Wikstrand et al., "Monoclonal antibody therapy of human gliomas: current status and future approaches." *Cancer Metastasis Rev.* (1999) 451-464, 18(4).
Wikstrand et al., "Investigation of a synthetic peptide as immunogen for a variant epidermal growth factor receptor associated with gliomas." *Journal of neuroimmunology* (1993) 165-173, 46(1-2).
Wikstrand et al., "Comparative localization of glioma-reactive monoclonal antibodies in vivo in an athymic mouse human glioma xenograft model." *Journal of neuroimmunoloay* (1987) 37-56, 15(1).
Wikstrand et al., "Production and characterization of two human glioma xenograft-localizing monoclonal antibodies." *Cancer Res.* (1986) 5933-5940, 46(11).
Wiley et al., "The role of tyrosine kinase activity in endocytosis, compartmentation, and down-regulation of the epidermal growth factor receptor." *Journal of Biological Chemistry* (1991) 11083-11094; 266(17).
Wiley, "Trafficking of the ErbB receptors and its infuence on signaling ." *Exp. Cell Res.* (2003) 78-88, 284(1).
Willett et al., "Direct evidence that the VEGF-specific antibody bevacizumab has antivascular effects in human rectal cancer" *Nature Med.* (2004) 145-147, 10(2).
Williams et al., "Combination of ZD1839 ('Iressa'), an EGFR tyrosine kinase inhibitor, and radiotherapy increases antitumour efficacy in a human colon cancer xenograft model." *Proceedings of the American Association for Cancer Research* (2001) 715 (Abstract 3840), 42.
Williams et al., "ZD1839 ('Iressa'), a specific oral epidermal growth factor receptor-tyrosine kinase inhibitor, potentiates radiotherapy in a human colorectal cancer xenograft model." *British Journal of Cancer* (2002) 1157-1161, 86(7).
Winer et al., "New Combinations with Herceptin® in Metastatic Breast Cancer." *Oncology* (2001) 50-57, 61(Suppl. 2).
Winkler et al., "Epidermal growth factor and transforming growth factor alpha bind differently to the epidermal growth factor receptor." *Biochemistry* (1989) 6373-6378, 28(15).
Winter et al., "Man-made antibodies." *Nature* (1991) 293-299, 349(6307).
Wollman et al., "Effect of epidermal growth factor on the growth and radiation sensitivity of human breast cancer cells in vitro." *Int. J. Radiat. Oncol. Biol. Phys.* (1994) 91-98, 30(1).
Woltjer et al., "Direct identification of residues of the epidermal growth factor receptor in close proximity to the amino terminus of bound epidermal growth factor." *Proceedings of the National Academy of Sciences of the United States of America* (1992) 7801-7805, 89(16).
Wong et al., "Increased expression of the epidermal growth factor receptor gene in malignant gliomas is invariably associated with gene

(56) References Cited

OTHER PUBLICATIONS amplification." *Proceedings of the National Academy of Sciences of the United States of America* (1987) 6899-6903, 84(19).
Wood et al., "A unique structure for epidermal growth factor receptor bound to GW572016 (Lapatinib): relationships among protein conformation, inhibitor off-rate, and receptor activity in tumor cells." *Cancer Res.* (2004) 6652-6659, 64(18).
Woodburn et al., "ZD1839 ('Iressa') A Selective Epidermal Growth Factor Receptor Tyrosine Kinase Inhibitor (EGFR-TKI): Inhibition of CFOS MRNA, an Intermediate Marker of EGFR Activation Correlates With Tumor Growth Inhibition." *Proceedings of the Annual Meeting of the American Association for Cancer Research* (2000) 402 (Abstract 2552), 41.
Woodburn et al., "ZD1839, an epidermal growth factor tyrosine kinase inhibitor selected for clinical development." *Proceedings of the Annual Meeting of the American Association for Cancer Research* (1997) 633 (Abstract 4251), 38.
Woodburn, "The epidermal growth factor receptor and its inhibition in cancer therapy." *Pharmacology & therapeutics* (1999) 241-250, 82(2-3).
Wu et al., "Human epidermal growth factor (EGF) receptor sequence recognized by EGF competitive monoclonal antibodies. Evidence for the localization of the EGF-binding site." *Journal of Biological Chemistry* (1989) 17469-17475, 264(29).
Wu et al., "Targeted delivery of methotrexate to epidermal growth factor receptor-positive brain tumors by means of cetuximab (IMC-C225) dendrimer bioconjugates." *Molecular cancer therapeutics* (2006) 52-59, 5(1).
Wu et at, "Humanization of a murine monoclonal antibody by simultaneous optimization of framework and CDR residues." *J. Mol. Biol.* (1999) 151-162, 294(1).
Wu et al., "Apoptosis induced by an anti-epidermal growth factor receptor monoclonal antibody in a human colorectal carcinoma cell line and its delay by insulin." *J. Clin. Invest.* (1995) 1897-1905, 95(4).
Xie et al., "In vitro invasiveness of DU-145 human prostate carcinoma cells is modulated by EGF receptor-mediated signals." *Clinical & experimental metastasis* (1995) 407-419, 13(6).
Xiong et al., "Cetuximab, a monoclonal antibody targeting the epidermal growth factor receptor, in combination with gemcitabine for advanced pancreatic cancer: a multicenter phase II Trial." *J. Clin. Oncol.* (2004) 2610-2616, 22(13).
Xu et al., "Antibody-induced growth inhibition is mediated through immunochemically and functionally distinct epitopes on the extracellular domain of the c-erbB-2 (HER-2/neu) gene product p185." *Int. J. Cancer* (1993) 401-408, 53(3).
Xu et al., "Characterization of epidermal growth factor receptor gene expression in malignant and normal human cell lines." *Proceedings of the National Academy of Sciences of the United States of America* (1984) 7308-7312, 81(23).
Xu et al., "Human epidermal growth factor receptor cDNA is homologous to a variety of RNAs overproduced in A431 carcinoma cells." *Nature* (1984) 806-810, 309(5971).
Yamanaka et al., "Coexpression of epidermal growth factor receptor and ligands in human pancreatic cancer is associated with enhanced tumor aggressiveness." *Anticancer research* (1993) 565-569, 13(3).
Yamazaki et al., "Inhibition of tumor growth by ribozyme-mediated suppression of aberrant epidermal growth factor receptor gene expression." *J. Natl. Cancer Inst.* (1998) 581-587, 90(8).
Yang et al., "Therapeutic potential of ABX-EGF, a fully, human anti-EGF receptor monoclonal antibody, for cancer treatment." *Proceedings of the American Society of Clinical Oncology* (2000) 48a (Abstract 183), 19.
Yang et al., "Modification of Gemcitabine-Induced Radiosesitization by the Nitroxide Tempol." *Proceedings of the American Society of Clinical Oncology* (1999) 457a (Abstract 1765), 18.
Yang et al., "ModificationGenistein, a tyrosine kinase inhibitor, reduces EGF-induced EGF receptor internalization and degradation in human hepatoma HepG2 cells." *Biochem. Biophys. Res. Commun.* (1996) 309-317, 224(2).

Yang et al., "Identification and characterization of Ch806 mimotopes." *Cancer Immunology, Immunotherapy* (2010) 1481-1487, 59(10).
Yang et al., "Molecular targeting and treatment of EGFRvIII-positive gliomas using boronated monoclonal antibody L8A4." *Clin. Cancer Res.* (2006) 3792-3802, 12(12).
Yang et al., "Development of a syngeneic rat brain tumor model expressing EGFRvIII and its use for molecular targeting studies with monoclonal antibody L8A4." *Clin. Cancer Res.* (2005) 341-350, 11(1).
Yang et al., "Development of ABX-EGF, a fully human anti-EGF receptor monoclonal antibody, for cancer therapy." *Crit. Rev. Oncol. Hematol.* (2001) 17-23, 38(1).
Yang et al., "Eradication of established tumors by a fully human monoclonal antibody to the epidermal growth factor receptor without concomitant chemotherapy." *Cancer Res.* (1999) 1236-1243, 59(6).
Yao et al., "Enhanced expression of c-myc and epidermal growth factor receptor (C-erbB-1) genes in primary human renal cancer." *Cancer Res.* (1988) 6753-6757, 48(23).
Yarden et al., "Self-phosphorylation of epidermal growth factor receptor: evidence for a model of intermolecular allosteric activation." *Biochemistry* (1987) 1434-1442, 26(5).
Ye et al., "Augmentation of a humanized anti-HER2 mAb 4D5 induced growth inhibition by a human-mouse chimeric anti-EGF receptor mAb C225." *Oncogene* (1999) 731-738, 18(3).
Yeatman, "A renaissance for SRC." *Nature Rev. Cancer* (2004) 470-480, 4(6).
Yip et al., "Identification of epitope-regions recognized by tumor inhibitory and stimulatory anti-ErbB-2 monoclonal antibodies: implications for vaccine design." *Journal of immunology (Baltimore, Md : 1950)* (2001) 5271-5278, 166(8).
Yip et al., "Structural analysis of the ErbB-2 receptor using monoclonal antibodies: Implications for receptor signalling." *Int. J. Cancer* (2003) 303-309, 104(3).
Ymer et al., "Glioma Specific Extracellular Missense Mutations in the First Cysteine Rich Region of Epidermal Growth Factor Receptor (EGFR) Initiate Ligand Independent Activation" *Cancers* (2011) 2032-2049, 3.
Yoshida et al., "Studies of the expression of epidermal growth factor receptor in human renal cell carcinoma: a comparison of immunohistochemical method versus ligand binding assay." *Oncology* (1997) 220-225, 54(3).
Yoshida et al., "EGF and TGF-alpha, the ligands of hyperproduced EGFR in human esophageal carcinoma cells, act as autocrine growth factors." *Int. J. Cancer* (1990) 131-135, 45(1).
Yoshimoto et al., "Development of a real-time RT-PCR assay for detecting EGFRvIII in glioblastoma samples." *Clin. Cancer Res.* (2008) 488-493, 14(2).
Yoshitake et al., "Conjugation of Glucose Oxidase from Aspergillus niger and Rabbit Antibodies Using N-Hydroxysuccinimide Ester of N-(4-Carboxycyclohexylmethyl)- Maleimide" *Eur. J. Biochem.* (1979) 395-399, 101(2).
Yu et al., "Co-expression of EGFRvIII with ErbB-2 enhances tumorigenesis: EGFRvIII mediated constitutively activated and sustained signaling pathways, whereas EGF-induced a transient effect on EGFR-mediated signaling pathways." *Cancer biology & therapy* (2008) 1818-1828, 7(11).
Yu et al., "The biosynthetic gene cluster of the maytansinoid antitumor agent ansamitocin from Actinosynnema pretiosum." *Proceedings of the National Academy of Sciences of the United States of America* (2002) 7968-7973, 99(12).
Yu et al., "Ligand-independent dimer formation of epidermal growth factor receptor (EGFR) is a step separable from ligand-induced EGFR signaling." *Mol. Biol. Cell* (2002) 2547-2557, 13(7).
Zalutsky, "Growth factor receptors as molecular targets for cancer diagnosis and therapy." *The quarterly journal of nuclear medicine : official publication of the Italian Association of Nuclear Medicine (AIMN) [and] the International Association of Radiopharmacology(IAR)* (1997) 71-77, 41(2).
Zarcone et al., "Epidermal growth factor receptor expression: is it the same in normal and malignant endometria?" *Clinical and experimental obstetrics & gynecology* (1995) 298-300, 22(4).

(56) References Cited

OTHER PUBLICATIONS

Zhang et al., "Therapeutic monoclonal antibodies for the ErbB family of receptor tyrosine kinases." *Cancer biology & therapy* (2003) S122-6, 2(4; Suppl. 1).
Zhang et al., "Novel approaches to treatment of advanced colorectal cancer with anti-EGFR monoclonal antibodies." *Annals of medicine* (2006) 545-551, 38(8).
Zhen et al., "Characterization of glycosylation sites of the epidermal growth factor receptor." *Biochemistry* (2003) 5478-5492, 42(18).
Zhu et al., "Epidermal growth factor receptor: association of extracellular domain negatively regulates intracellular kinase activation in the absence of ligand." *Growth Factors* (2003) 15-30, 21(1).
Zhu et al., "EGFR tyrosine kinase inhibitor AG1478 inhibits cell proliferation and arrests cell cycle in nasopharyngeal carcinoma cells." *Cancer Letters* (2001) 27-32, 169(1).
Zinner et al., "A phase I clinical and biomarker study of the novel pan-erbB tyrosine kinase inhibitor, CI-1033, in patients with solid tumors." *Clinical Cancer Research* (2001) 3767s (Abstract 566), 7.
Aboud-Pirak, Hurwitz, Bellot, Schlessinger and Sela, *Proc. Natl. Acad. Sci. USA* (1989)3778-3781, 86.
Aboud-Pirak, Hurwitz, Pirak, Bellot, Schlessinger and Sela, *J. Natl. Cancer Inst.* (1988) 1605-1611, 80.
Arteaga and Baselga, *Cancer Cell* (2004) 525-531, 5.
Avital et al. *Cancer* (2000) 1692-1698, 89(8).
Baselga and Arteaga, *J. Clin. Oncol.* (2005) 2445-2459, 23.
Baselga, J. *Science* (2006) 1175-1178, 312.
Baselga, Norton, Masui, Pandiella, Coplan, Miller and Mendelsohn, "Antitumor effects of doxorubicin in combination with anti-epidermal growth factor receptor monoclonal antibodies." *J. Natl. Cancer Inst (Bethesda)* (1993) 1327-1333, 85.
Baselga, Pfister, Cooper, Cohen, Burtness, Bos, D'Andrea, Seidman, Norton, Gunnett, Falcey, Anderson, Waksal and Mendelsohn, "Phase I studies of anti-epidermal growth factor receptor chimeric antibody C225 alone and in combination with cisplatin. " *J. Clin. Oncol.* (2000) 904-914, 18.
Batra, Castelino-Prabhu and Wikstrand, "Epidermal growth factor ligand independent, unregulated, cell-transforming potential of a naturally occurring human mutant EGFRvIII gene." *Cell Growth Differ.* (1995) 1251-1259, 6.
Behr et al. *Cancer* (2002) 1373-1381, 94(4 Suppl.).
Bernier, J. *Expert. Rev Anticancer Ther.* (206) 1539-1552, 6.
Bird et al. *Science* (1988) 423-426, 242.
Bouyain, Longo, Li, Ferguson and Leahy, *Proc. Natl. Acad. Sci. USA* (2005) 15024-15029, 102.
Burgess, A. W. H. S. Cho, C. Eigenbrot, K. M. Ferguson, T. P. Garrett, D. J. Leahy, M. A. Lemmon, M. X. Sliwkowski, C. W. Ward and S. Yokoyama, *Mol. Cell* (2003)541-552, 12.
Chao, Cochran and Wittrup, *J. Mol. Biol.* (2004) 539-550, 342.
Chao, Ginger, "Characterizing and engineering antibodies against the epidermal growth factor receptor." *Submission to the Department of Chemical Engineering in partial fulfillment of the requirements for the degree of Doctor of Philosophy in Chemical Engineering at the Massachusetts Institute of Technology* (Feb. 2008).
Cho, H. S. and D. J. Leahy, *Science* (2002) 1330-1333, 297.
Cho, H. S. K. Mason, K. X. Ramyar, A. M. Stanley, S. B. Gabelli, D. W. Denney, Jr. and D. J. Leahy, "Structure of the extracellular region of HER2 alone and in complex with the Herceptin Fab." *Nature* (2003) 756-760, 421.
Clayton, Walker, Orchard, Henderson, Fuchs, Rothacker, Nice and Burgess, *J. Biol. Chem.* (2005) 30392-30399, 280.
Davies et al. "Affinity improvement of single antibody VH domains: residues in all three hypervariable regions affect antigen binding." *Immunotechnology* (1996) 169-179, 2(3).
De Larco, J. E. And G. J. Todaro, *J. Cell. Physiol.* (1978) 335-342, 94.
De Larco, J. E. R. Reynolds, K. Carlberg, C. Engle and G. J. Todaro, *J. Biol. Chem.* (1980) 3685-3690, 255.
Divgi, C. R. S. Welt, M. Kris, F. X. Real, S. D. Yeh, R. Gralla, B. Merchant, S. Schweighart, M. Unger and S. M. Larson, "Phase I and imaging trial of indium 11-labeled anti-epidermal factor receptor monoclonal antibody 225 in patients with squamous growth cell lung carcinoma." *J. Natl. Cancer Inst.* (1991) 97-104, 83.
Ekstrand, James, Cavenee, Seliger, Pettersson and Collins, *Cancer Res.* (1991) 2164-2172, 51.
Emsley and Cowtan, *Acta crystallographica* (2004) 2126-2132, 60.
Faillot, Magdélenat, Mady, Stasiecki, Fohanno, Gropp, Poisson and Delattre, "A phase I study of an anti-epidermal growth factor receptor monoclonal antibody for the treatment of malignant gliomas." *Neurosurgery* (1996) 478-483, 39.
Fairlie, Uboldi, De Souza, Hemmings, Nicola and Baca, *Protein Expression and Purification* (2002) 171-178, 26.
Fan, Baselga, Masui and Mendelsohn, "Antitumor effect of antiepidermal growth factor receptor monoclonal antibodies plus cis-diamminedichloroplatinum on well established A431 cell xenografts." *Cancer Res.* (1993) 4637-4642, 53.
Ferguson, K. M. M. B. Berger, J. M. Mendrola, H. S. Cho, D. J. Leahy and M. A. Lemmon, *Mol. Cell* (2003) 507-517, 11.
Foulon et al. *Cancer Res.* (2000) 4453-4460, 60(16).
Gadella, T. W. J and T. M. Jovin, *Journal of Cell Biology* (1995) 1543-1558, 129.
Garcia De Palazzo, I. G. Adams, P. Sundareshan, A. Wong, J. Testa, D. Bigner and L. Weiner, "Expression of mutated epidermal growth factor receptor by non-small cell lung carcinomas." *Cancer Res.* (1993) 3217-3220, 53.
Garrett, McKern, Lou, Elleman, Adams, Lovrecz, Kofler, Jorissen, Nice, Burgess and Ward, *Mol. Cell* (2003) 495-505, 11.
Garrett, T. P. N. M. McKern, M. Lou, T. C. Elleman, T. E. Adams, G. O. Lovrecz, H. J. Zhu, F. Walker, M. J. Frenkel, P. A. Hoyne, R. N. Jorissen, E. C. Nice, A. W. Burgess and C. W. Ward, *Cell* (2002) 763-773, 110.
Gill, G. N. T. Kawamoto, C. Cochet, A. Le, J. D. Sato, H. Masui, C. McLeod and J. Mendelsohn, *J. Biol. Chem.* (1984) 7755-7760, 259.
Gold et al. *Crit. Rev. Oncol. Hematol.* (2001) 147-154, 39(1-2).
Goldenberg, D.M. *Crit. Rev. Oncol. Hematol.* (2001) 195-201, 39(1-2).
Goldstein, Prewett, Zuklys, Rockwell and Mendelsohn, "Biological efficacy of a chimeric antibody to the epidermal growth factor receptor in a human tumor xenograft model." *Clin. Cancer Res.* (1995) 1311-1318, 1(11).
Hills, D. G. Rowlinson-Busza and W. J. Gullick, "Specific targeting of a mutant, activated EGF receptor found in glioblastoma using a monoclonal antibody." *Int. J. Cancer* (1995) 537-543, 63.
Hogg, P.J. *Trends Biochem. Sci.* (1003) 210-214, 28.
Holbro and Hynes, *Annu. Rev. Pharmacol. Toxicol.* (2004) 195-217, 44.
Holliger et al. *PNAS* (1993) 6444-6448, 90.
Holt et al. "Domain Antibodies: Proteins for Therapy." *Trends in Biotechnology* (2003) 484-490, 21(11).
Hooft, Vriend, Sander and Abola, *Nature* (1996) 272, 381.
Huang et al. *Clin. Cancer Res.* (2000) 2166-2174, 6(6).
Huang, Nagane and Klingbeil, "The enhanced tumorigenic activity of a mutant epidermal growth factor receptor common in human cancers is mediated by threshold levels of constitutive tyrosine phosphorylation and unattenuated signaling." *J. Biol. Chem.* (1997) 2927-2935, 272.
Humphrey, P. A. A. J. Wong, B. Vogelstein, M. R. Zalutsky, G. N. Fuller, G. E. Archer, H. S. Friedman, M. M. Kwatra, S. H. Bigner and D. D. Bigner, "Anti-synthetic peptide antibody reacting at the fusion junction of deletion-mutant epidermal growth factor receptors in human glioblastoma." *Proc. Natl. Acad. Sci. USA* (1990) 4207-4211, 87.
Huston et al. *PNAS* (1988) 5879-5883, 85.
Johns, Mellman, Cartwright, Ritter, Old, Burgess and Scott, "The anti-tumor monoclonal antibody 806 recognizes a high-mannose form of the EGF receptor that reaches the cell surface when cells over-express the receptor." *FASEB J.* (2005) 780-782, 19(7).
Johns, Perera, Vernes, Vitali, Cao, Cavenee, Scott and Furnari, "The efficacy of EGFR-specific antibodies against glioma xenografts is influenced by receptor levels, activation status and heterodimerization." *Clin. Cancer Res.* (2007) 1911-1925, 13(6).
Johns, T. G. E. Stockert, G. Ritter, A. A. Jungbluth, H. J. Huang, W. K Cavenee, F. E. Smyth, C. M. Hall, N. Watson, E. C. Nice, W. J. Gullick, L. J. Old, A. W. Burgess and A. M. Scott, "Novel monoclonal

(56) References Cited

OTHER PUBLICATIONS antibody specific for the DE2-7 Epidermal Growth Factor Receptor (EGFR) that also recognizes the EGFR expressed in cells containing amplification of the EGFR gene." *Int. J. Cancer* (2002) 398-408, 98.
Johns, T. G. R. B. Luwor, C. Murone, F. Walker, J. Weinstock, A. A. Vitali, R. M. Perera, A. A. Jungbluth, E. Stockert, L. J. Old, E. C. Nice, A. W. Burgess and A. M. Scott, "Anti-tumor efficacy of cytotoxic drugs and the monoclonal antibody 806 is enhanced by the epidermal growth factor receptor (EGFR) inhibitor AG1478. " *Proc. Natl. Acad. Sci. USA* (2003) 15871-15876, 100.
Johns, T.G. T.E. Adams, J.R. Cochran, N.E. Hall, P.A. Hoyne, M.J. Olsen, Y.S. Kim, J. Rothacker, E.C. Nice, F. Walker, G. Ritter, A.A. Jungbluth,L.J. Old, C.W. Ward, A.W. Burgess, K.D. Wittrup and A.M. Scott, "Identification of the Epitope for the EGFR-Specific Monoclonal Antibody 806 Reveals that it Preferentially Recognizes an Untethered Form of the Receptor." *J. Biol. Chem.* (2004) 30375-30384, 279(29).
Jorissen, R. N. F. Walker, N. Pouliot, T. P. Garrett, C. W. Ward and A. W. Burgess,"Epidermal growth factor receptor: mechanisms of activation and signalling." *Exp. Cell Res.* (2003) 31-53, 284.
Jungbluth, A. A. E. Stockert, H. J. Huang, V. P. Collins, K. Coplan, K. Iversen, D. Kolb, T. J. Johns, A. M. Scott, W. J. Gullick, G. Ritter, L. Cohen, M. J. Scanlan, W. K. Cavanee and L. J. Old, "A Monoclonal Antibody Recognizing Human Cancers with Amplification/Over-Expression of the Human Epidermal Growth Factor Receptor." *Proc. Natl. Acad. Sci. USA* (2003) 639-644, 100.
Kim et al. *Int. J. Cancer* (2002) 542-547, 97(4).
Laskowski, Macarthur, Moss and Thornton, *J. Appl. Cryst.* (1993) 283-291, 26.
Luwor, R. B. T. G. Johns, C. Murone, H. J. Huang, W. K. Cavenee, G. Ritter, L. J. Old, A. W. Burgess and A. M. Scott, "Monoclonal Antibody 806 Inhibits the Growth of Tumor Xenografts Expressing Either the DE2-7 or Amplified Epidermal Growth Factor Receptor (EGFR) but not Wild-Type EGFR." *Cancer Res.*(2001) 5355-5361, 61.
MacDonald, Chisholm and Habib, *Br. J. Cancer* (1990) 579-584, 62.
Masui, Kawamoto, Sato, Wolf, Sato and Mendelsohn, "Growth inhibition of human tumor cells in athymic mice by anti-epidermal growth factor receptor monoclonal antibodies." *Cancer Res.* (1984) 1002-1007, 44.
McIntosh et al. *Cancer Biother. Radiopharm.* (1997) 287-294, 12(4).
Mellinghoff, Cloughesy and Mischel, *Clin. Cancer Res.* (2007) 378-381, 13.
Mickey, Stone, Wunderli, Mickey, Vollmer and Paulson, *Cancer Res.* (1977) 4049-4058, 37.
Milas et al. *Clin. Cancer Res.* (2000) 701-708, 6(2).
Mishima, K. T. G. Johns, R. B. Luwor, A. M. Scott, E. Stockert, A. A. Jungbluth X. D. JI P. Suvarna J. R. Voland, L. J. Old, H. J. Huang and W. K. Cavenee, "Growth Suppression of Intracranial Xenografted Gliboblatomas Overexpressing Mutant Epidermal Growth Factor Receptors by Systemic Administration of Monoclonal Antibody (mAb) 806, a Novel Antibody Directed to the Receptor." *Cancer Res.* (2001) 5349-5354, 61.
Modjtahedi et al. *Cell Biophys.* (1993) 129-146, 22(1-3).
Murshudov, Vagin and Dodson, *Actacrystallographica* (1997) 240-255, 53.
Nagane, Coufal, Lin, Bogler, Cavenee and Huang, "A common mutant epidermal growth factor receptor confers enhanced tumorigenicity on human glioblastoma cells by increasing proliferation and reducing apoptosis." *Cancer Res.* (1996) 5079-5086, 56.
Neidhardt, Bloch and Smith, *Journal of Bacteriology* (1974) 736-747, 119.
Nishikawa, R. X. D. Ji, R. C. Harmon, C. S. Lazar, G. N. Gill, W. K. Cavenee and H. J. Huang, "A mutant epidermal growth factor receptor common in human glioma confers enhanced tumorigenicity." *Proc. Natl. Acad. Sci. USA* (1994) 7727-7731, 91.
Ogiso, H. R. Ishitani, O. Nureki, S. Fukai, M. Yamanaka, J. H. Kim, K. Saito, A. Sakamoto, M. Inoue, M. Shirouzu and S. Yokoyama, *Cell* (2002) 775-787, 110.

Okamoto, Yoshikawa, Obata, Shibuya, Aoki, Yoshida and Takahashi, "Monoclonal antibody against the fusion junction of a deletion-mutant epidermal growth factor receptor." *Br. J. Cancer* (1996) 1366-1372, 73.
Olapade-Olaopa, Moscatello, Mackay, Horsburgh, Sandhu, Terry, Wong and Habib, "Evidence for the differential expression of a variant EGF receptor protein in human prostate cancer." *Br. J. Cancer* (2000) 186-194, 82.
Otwinowski and Minor, "Processing of X-ray diffraction data collected in oscillation mode." *Methods in Enzymology* (1997) 307-326, 276.
Palacios, Henson, Steinmetz and McKeam, *Nature* (1984) 126-131, 309.
Panousis, C. V.M. Rayzman, T.G. Johns, C. Renner, Z. Liu, G. Cartwright, F.T. Lee, D. Wang, H. Gan, D. Cao, A. Kypridis, F.E. Smyth, M.W. Brechbiel, A.W. Burgess, L.J. Old and A.M. Scott, "Engineering and characterisation of chimeric monoclonal antibody 806 (ch806) for targeted immunotherapy of tumours expressing de2-7 EGFR or amplified EGFR." *British Journal of Cancer* (2005) 1069-1077, 92(6).
Perera, Narita, Furnari, Gan, Murone, Ahlkvist, Luwor, Burgess, Stockert and Jungbluth, "A novel EGFR antibody that displays synergistic anti-tumor activity when combined with conventional EGFR therapeutics." *Clin. Cancer Res.* (2005) 6390-6399, 11.
Power and Hudson, *J. Immunol. Methods* (2000) 193-204, 242.
Reist, Archer, Kurpad, Wikstrand, Vaidyanathan, Willingham, Moscatello, Wong, Bigner and Zalutsky, "Tumor-specific anti-epidermal growth factor receptor variant in monoclonal antibodies: use of the tyramine-cellobiose radio iodination method enhances cellular retention and uptake in tumor xenografts." *Cancer Res.* (1995) 4375-4382, 55.
Reist, Archer, Wikstrand, Bigner and Zalutsky, "Improved targeting of an anti-epidermal growth factor receptor variant III monoclonal antibody in tumor xenografts after labeling using N-succinimidyl 5-iodo-3-pyridinecarboxylate." *Cancer Res.* (1997) 1510-1515, 57.
Sampson, Crotty, Lee, Archer, Ashley, Wikstrand, Hale, Small, Dranoff, Friedman, Friedman and Bigner, "Unarmed, tumor-specific monoclonal antibody effectively treats brain tumors." *Proc. Natl. Acad. Sci. USA* (2000).7503-7508, 97.
Schlessinger, J. *Cell* (2002) 669-672, 110.
Schneebaum et al. *World J. Surg.* (2001) 1495-1498, 25(12).
Scott, Lee, Tebbutt, Herbertson, Gill, Liu, Skrinos, Murone, Saunder and Chappell, "A Phase I clinical trial with monoclonal antibody ch806 targeting transitional state and mutant epidermal growth factor receptors." *Proc. Natl. Acad. Sci. USA* (2007) 4071-4076, 104(10).
Seymour, L. "Novel anti-cancer agents in development : exciting prospects and new challenges." *Cancer Treat Rev.* (1999) 301-312, 25.
Sizeland and Burgess, *Mol. Biol. Cell* (1992) 1235-1243, 3.
Sizeland and Burgess, *Mol. Cell Bio.* (1991) 4005-4014, 11.
Sok, Coppelli, Thomas, Lango, Xi, Hunt, Freilino, Graner, Wikstrand, Bigner, Gooding, Furnari and Grandis, *Clin. Cancer Res.* (2006) 5064-5073, 12.
Stamos, J. M.X. Sliwkowski and C. Eigenbrot, *J. Biol. Chem.* (2002) 46265-46272, 277.
Stein et al. *Cancer* (2002) 51-61, 94(1).
Sturgis, Sacks, Masui, Mendelsohn and Schantz, "Effects of antiepidermal growth factor receptor antibody 528 on the proliferation and differentiation of head and neck cancer." *Otolaryngol. Head Neck Surg.*(1994).633-643, 111.
Sugawa, Ekstrand, James and Collins, "Identical splicing of aberrant epidermal growth factor receptor transcripts from amplified re-arranged genes in human glioblastomas." *Proc. Natl. Acad. Sci. USA* (1990) 8602-8606, 87.
Todaro, G.J. J.E. Delarco and S. Cohen, *Nature* (1976) 26-31, 264.
Ullrich, A. L. Coussens, J. S. Hayflick, T. J. Dull, A. Gray, A.W. Tam, J. Lee, Y. Yarden, T. A. Libermann and J. Schlessinger, *Nature* (1984) 418-425, 309.
Vagin and Teplyakov, *J. Appl. Cryst.* (1997) 1022-1025, 30.
Van De Loosdrecht, Beelen, Ossenkoppele, Broekhoven and Langenhuijsen, *J. Immunol. Methods* (1994) 311-320, 174.

(56) References Cited

OTHER PUBLICATIONS

Van Den Eynde and Scott, *Tumor Antigens. In : P. J. Delves and I. M. Roitt (eds.) Encyclopedia of Immunology, Second Edition (London: Academic Press)* (1998) 2424-2431.

Voldborg, Damstrup, Spang-Thomsen and Poulsen, "Epidermal growth factor receptor (EGFR) and EGFR mutations, function and possible role in clinical trials." Ann. Oncol. (1997) 1197-1206, 8.

Wade, Hojo, Biochem, Kawasaki, Johns, Catimel, Rothacker and Nice, *Anal. Biochem*.(2006) 315-317, 348.

Walker, Orchard, Jorissen, Hall, Zhang, Hoyne, Adams, Johns, Ward and Garrett, "CR1/CR2 Interactions Modulate the Functions of the Cell Surface Epidermal Growth Factor Receptor." *J. Biol. Chem.* (2004) 22387-22398, 279.

Ward et al. *Nature* (1989) 544-546, 341.

Wikstrand, C. J. C. J. Reist, G. E. Archer, M. R. Zalutsky and D. D. Bigner,"The class in variant of the epidermal growth factor receptor (EGFRvIII): characterization and utilization as an immunotherapeutic target." *J. Neurovirol.* (1998) 148-158, 4.

Wikstrand, C. J. L. P. Hale, S. K. Batra, M. L. Hill, P. A. Humphrey, S. N. Kurpad, R. E. McLendon, D. Moscatello, C. N. Pegram and C. J. Reist "Monoclonal antibodies against EGFRvin are tumor specific and react with breast and lung carcinomas and malignant gliomas." *Cancer Res.* (1995) 3140-3148, 55.

Wikstrand, McLendon, Friedman and Bigner, "Cell surface localization and density of the tumor-associated variant of the epidermal growth factor receptor, EGFRvIII." *Cancer Res.* (1997) 4130-4140, 57.

Wong, A. J. J. M. Ruppert, S. H. Bigner, C. H. Grzeschik, P. A. Humphrey, D. S. Bigner and B. Vogelstein, "Structural alterations of the epidermal growth factor receptor gene in human gliomas." *Proc. Natl. Acad. Sci. USA* (1992) 2965-2969, 89.

Yamazaki, Fukui and Ueyama, "Amplification of the structurally and functionally altered epidermal growth factor receptor gene (c-erbB) in human brain tumors." *Mol. Cell Biol.* (1988) 1816-1820, 8.

Yamazaki, H. Y. Ohba, N. Tamaoki and M. Shibuya, "A deletion mutation within the ligand binding domain is responsible for activation of epidermal growth factor receptor gene in human brain tumors." *Jpn. J. Cancer Res.* (1990) 773-779, 81.

Yarden and Schlessinger, *Biochemistry* (1987) 1443-1451, 26.

Yarden, Y. and M. X. Sliwkowski, *Nat. Rev. Mol. Cell Biol.* (2001) 127-137, 2.

Yen, L. N. Benlimame, Z. R. Nie, D. Xiao, T. Wang, A. E. Al Moustafa, H. Esumi, J. Milanini, N. E. Hynes, G. Pages and M. A. Alaoui-Jamali, *Mol. Biol. Cell*, (2002) 4029-4044, 13(11).

Ymer, Tucker, Sanderson, Hapel, Campbell and Young, *Nature* (1985) 255-258, 19-25(317).

Zhang, Gureasko, Shen, Cole and Kuriyan, *Cell*, (2006) 1137-1149, 125.

\* cited by examiner

FIGURE 1

Light Chain
CDR1-806  23HSSQDINSNIG
CDR1-175  23HSSQDISSNIG
CDR2-806  49YHGTNLDD
CDR2-175  49YHGTNLED
CDR3-806  89VQYAQFPWT
CDR3-175  89VQYGQFPWT Heavy Chain
CDR1-806  31SDFAWN
CDR1-175  31SDYAWN
CDR2-806  51YISYSGNTRYNPSLKS
CDR2-175  51YISYSANTRYNPSLKS
CDR3-806  97VTAGRGFPY
CDR3-175  97ATAGRGFPY First residue number is given.
Underline indicates the residues which contact EGFR287-302

SEQUENCE LISTING

```
<160> NUMBER OF SEQ ID NOS: 14

<210> SEQ ID NO 1
<211> LENGTH: 11
<212> TYPE: PRT
<213> ORGANISM: Mus musculus

<400> SEQUENCE: 1

His Ser Ser Gln Asp Ile Ser Ser Asn Ile Gly
1               5                   10

<210> SEQ ID NO 2
<211> LENGTH: 8
<212> TYPE: PRT
<213> ORGANISM: Mus musculus

<400> SEQUENCE: 2

Tyr His Gly Thr Asn Leu Glu Asp
1               5

<210> SEQ ID NO 3
<211> LENGTH: 9
<212> TYPE: PRT
<213> ORGANISM: Mus musculus

<400> SEQUENCE: 3

Val Gln Tyr Gly Gln Phe Pro Trp Thr
1               5

<210> SEQ ID NO 4
<211> LENGTH: 6
<212> TYPE: PRT
<213> ORGANISM: Mus musculus

<400> SEQUENCE: 4

Ser Asp Tyr Ala Trp Asn
1               5

<210> SEQ ID NO 5
<211> LENGTH: 16
<212> TYPE: PRT
<213> ORGANISM: Mus musculus

<400> SEQUENCE: 5

Tyr Ile Ser Tyr Ser Ala Asn Thr Arg Tyr Asn Pro Ser Leu Lys Ser
1               5                   10                  15

<210> SEQ ID NO 6
<211> LENGTH: 9
```

-continued

```
<212> TYPE: PRT
<213> ORGANISM: Mus musculus

<400> SEQUENCE: 6

Ala Thr Ala Gly Arg Gly Phe Pro Tyr
1               5

<210> SEQ ID NO 7
<211> LENGTH: 11
<212> TYPE: PRT
<213> ORGANISM: Mus musculus

<400> SEQUENCE: 7

His Ser Ser Gln Asp Ile Asn Ser Asn Ile Gly
1               5                   10

<210> SEQ ID NO 8
<211> LENGTH: 8
<212> TYPE: PRT
<213> ORGANISM: Mus musculus

<400> SEQUENCE: 8

Tyr His Gly Thr Asn Leu Asp Asp
1               5

<210> SEQ ID NO 9
<211> LENGTH: 9
<212> TYPE: PRT
<213> ORGANISM: Mus musculus

<400> SEQUENCE: 9

Val Gln Tyr Ala Gln Phe Pro Trp Thr
1               5

<210> SEQ ID NO 10
<211> LENGTH: 6
<212> TYPE: PRT
<213> ORGANISM: Mus musculus

<400> SEQUENCE: 10

Ser Asp Phe Ala Trp Asn
1               5

<210> SEQ ID NO 11
<211> LENGTH: 16
<212> TYPE: PRT
<213> ORGANISM: Mus musculus

<400> SEQUENCE: 11

Tyr Ile Ser Tyr Ser Gly Asn Thr Arg Tyr Asn Pro Ser Leu Lys Ser
1               5                   10                  15

<210> SEQ ID NO 12
<211> LENGTH: 9
<212> TYPE: PRT
<213> ORGANISM: Mus musculus

<400> SEQUENCE: 12

Val Thr Ala Gly Arg Gly Phe Pro Tyr
1               5

<210> SEQ ID NO 13
<211> LENGTH: 13
<212> TYPE: PRT
<213> ORGANISM: Artificial Sequence
```

```
<220> FEATURE:
<223> OTHER INFORMATION: synthetic junctional peptide

<400> SEQUENCE: 13

Leu Glu Glu Lys Lys Gly Asn Tyr Val Val Thr Asp His
 1               5                  10

<210> SEQ ID NO 14
<211> LENGTH: 16
<212> TYPE: PRT
<213> ORGANISM: Artificial Sequence
<220> FEATURE:
<223> OTHER INFORMATION: synthetic peptide

<400> SEQUENCE: 14

Cys Gly Ala Asp Ser Tyr Glu Met Glu Glu Asp Gly Val Arg Lys Cys
 1               5                  10                  15
```

MONOCLONAL ANTIBODY 175 TARGETING THE EGF RECEPTOR AND DERIVATIVES AND USES THEREOF

This application is a 371 national phase application of International Application No. PCT/US2008/009771, filed on Aug. 14, 2008, which claims priority to U.S. Provisional Application 60/964,692, filed on Aug. 14, 2007.

FIELD OF THE INVENTION

The present invention relates to antibodies, particularly antibody 175, and fragments thereof, which bind to the EGF receptor, particularly to amplified or overexpressed epidermal growth factor receptor (EGFR) and to the de2-7 EGFR truncation of the EGFR. These antibodies are useful in the diagnosis and treatment of cancer. The antibodies of the present invention may also be used in therapy in combination with chemotherapeutics or anti-cancer agents and/or with other antibodies or fragments thereof.

BACKGROUND OF THE INVENTION

The treatment of proliferative disease, particularly cancer, by chemotherapeutic means often relies upon exploiting differences in target proliferating cells and other normal cells in the human or animal body. For example, many chemical agents are designed to be taken up by rapidly replicating DNA so that the process of DNA replication and cell division is disrupted. Another approach is to identify antigens on the surface of tumor cells or other abnormal cells which are not normally expressed in developed human tissue, such as tumor antigens or embryonic antigens. Such antigens can be targeted with binding proteins such as antibodies which can block or neutralize the antigen. In addition, the binding proteins, including antibodies and fragments thereof, may deliver a toxic agent or other substance which is capable of directly or indirectly activating a toxic agent at the site of a tumor.

The EGFR is an attractive target for tumor-targeted antibody therapy because it is overexpressed in many types of epithelial tumors (Voldborg, B. R., et al. (1997) Ann Oncol 8:1197-206; den Eynde, B. and Scott, A. M. (1998) Tumor Antigens. In: P. J. Delves and I. M. Roitt (eds.), Encyclopedia of Immunology, Second Edition, pp. 2424-31. London: Academic Press). Moreover, expression of the EGFR is associated with poor prognosis in a number of tumor types including stomach, colon, urinary bladder, breast, prostate, endometrium, kidney and brain (e.g., glioma). Consequently, a number of EGFR antibodies have been reported in the literature with several undergoing clinical evaluation (Baselga, J., et al. (2000) J Clin Oncol. 18: 904; Faillot, T., et al. (1996) Neurosurgery 39: 478-83; Seymour, L. (1999) Cancer Treat Rev 25: 301-12). Results from studies using EGFR mAbs in patients with head and neck cancer, squamous cell lung cancer, brain gliomas and malignant astrocytomas have been encouraging. The anti-tumor activity of most EGFR antibodies is enhanced by their ability to block ligand binding (Sturgis, E. M., et al. (1994) Otolaryngol Head Neck Surg 111: 633-43; Goldstein, N. I., et al. (1995) Clin Cancer Res 1: 1311-8). Such antibodies may mediate their efficacy through both modulation of cellular proliferation and antibody dependent immune functions (e.g. complement activation). The use of these antibodies, however, may be limited by uptake in organs that have high endogenous levels of EGFR such as the liver and skin (Baselga, J., et al. (2000) J Clin Oncol. 18: 904; Faillot, T., et al. (1996) Neurosurgery 39: 478-83).

A significant proportion of tumors containing amplifications of the EGFR gene (i.e., multiple copies of the EGFR gene) also co-express a truncated version of the receptor (Wikstrand, C. J., et al. (1998) J Neurovirol 4: 148-58) known as de2-7 EGFR, ΔEGFR, or Δ2-7 (terms used interchangeably herein) (Olapade-Olaopa, E. O., et al. (2000) Br J Cancer 82: 186-94). The rearrangement seen in the de2-7 EGFR results in an in-frame mature mRNA lacking 801 nucleotides spanning exons 2-7 (Wong, A. J., et al. (1992) Proc Natl Acad Sci USA 89: 2965-9; Yamazaki, H., et al. (1990) Jpn J Cancer Res 81: 773-9; Yamazaki, H., et al. (1998) Mol Cell Biol 8: 1816-20; Sugawa, N., et al. (1990) Proc Natl Acad Sci USA 87: 8602-6). The corresponding EGFR protein has a 267 amino acid deletion comprising residues 6-273 of the extracellular domain and a novel glycine residue at the fusion junction (Sugawa, N., et al. (1990) Proc Natl Acad Sci USA 87: 8602-6). This deletion, together with the insertion of a glycine residue, produces a unique junctional peptide at the deletion interface. The de2-7 EGFR has been reported in a number of tumor types including glioma, breast, lung, ovarian and prostate (Wikstrand, C. J., et al. (1997) Cancer Res. 57: 4130-40; Olapade-Olaopa, E. O., et al. (2000) Br J Cancer 82: 186-94; Wikstrand, C. J., et al. (1995) Cancer Res 55: 3140-8; Garcia de Palazzo, I. E., et al. (1993) Cancer Res 53: 3217-20). While this truncated receptor does not bind ligand, it possesses low constitutive activity and imparts a significant growth advantage to glioma cells grown as tumor xenografts in nude mice (Nishikawa, R., et al. (1994) Proc Natl Acad Sci USA 91: 7727-31, 1994) and is able to transform NIH3T3 cells and MCF-7 cells (Batra, S. K., et al. (1995) Cell Growth Differ 6: 1251-9). The cellular mechanisms utilized by the de2-7 EGFR in glioma cells are not fully defined but are reported to include a decrease in apoptosis and a small enhancement of proliferation (Nagane, M., et al. (1996) Cancer Res 56: 5079-86).

As expression of this truncated receptor is restricted to tumor cells it represents a highly specific target for antibody therapy. Accordingly, a number of laboratories have reported the generation of both polyclonal and monoclonal antibodies specific to the unique peptide of de2-7 EGFR (Wikstrand, C. J., et al (1998) J Neurovirol 4: 148-58; Humphrey, P. A., et al (1990) Proc Natl Acad Sci USA 87: 4207-11; Okamoto, S., et al (1996) Br J Cancer 73: 1366-72; Hills, D., et al (1995) Int J Cancer 63: 537-43). A series of mouse mAbs, isolated following immunization with the unique de2-7 peptide, all showed selectivity and specificity for the truncated receptor and targeted de2-7 EGFR positive xenografts grown in nude mice (Wikstrand, C. J., et al (1995) Cancer Res 55: 3140-8; Reist, C. J., et al (1997) Cancer Res 57: 1510-5; Reist, C. J., et al (1995) Cancer Res 55: 4375-82).

However, one potential shortcoming of de2-7 EGFR antibodies is that only a proportion of tumors exhibiting amplification of the EGFR gene also express the de 2-7 EGFR. Therefore, de2-7 EGFR specific antibodies would be expected to be useful in only a percentage of EGFR positive tumors. Thus, while the extant evidence of activity of EGFR antibodies is encouraging, the observed limitations on range of applicability and efficacy reflected above remain. Accordingly, it would be desirable to have antibodies and like agents that demonstrate efficacy with a broad range of tumors, and it is toward the achievement of that objective that the present invention is directed. In addition, antibodies which do not target normal tissues and EGFR in the absence of amplification, overexpression, or mutation, would be particularly useful. One such antibody, monoclonal antibody mAb806, has been previously described in WO02092771 and WO05081854. Additional such antibodies are needed and would be desirable.

The citation of references herein shall not be construed as an admission that such is prior art to the present invention.

SUMMARY OF THE INVENTION

The antibodies of the present invention, antibody 175 and fragments thereof or monomers, recombinant, or hybrid antibodies derived therefrom, recognize an EGFR epitope which is found in tumorigenic, hyperproliferative or abnormal cells and is not detectable in normal or wild type cells. The antibodies of the present invention are further exemplified by the antibody mAb 175 described herein.

This invention describes an antibody targeting the same EGF receptor epitope as the previously described monoclonal antibody (mAb) 806 (described in WO02092771 and WO05081854). The complementary determining regions (CDRs), the most important amino acids for antigen binding, of mAb 175 are highly homologous to the 806 antibody, with only a few amino acid differences.

The binding of an antibody to its target antigen is mediated through the complementarity-determining regions (CDRs) of its heavy and light chains, there being three CDR regions CDR1, CDR2, and CDR3. Accordingly, antibodies based on the CDR regions of the heavy or light chain, and preferably both, of mAb175 will be useful antibodies for diagnostic and therapeutic applications, including in vivo therapy. Antibodies which are based on the CDRs of the mAb 175 antibody identified will be useful for targeting tumors with amplified EGFR regardless of their de2-7 EGFR status. As mAb 175 does not bind significantly to normal, wild type receptor, there would be no significant uptake in normal tissue, a limitation of EGFR antibodies currently being developed.

The sequences of monoclonal antibody 175, targeting the EGF-receptor, have been determined and the CDR regions of the antibody have the amino acid sequences set out in FIG. 1. The CDRs for each of the light chain and the heavy chain are provided herein. The Ab175 light chain CDRs correspond to CDR1 (SEQ ID NO: 1), CDR2 (SEQ ID NO: 2) and CDR3 (SEQ ID NO: 3). The Ab175 heavy chain CDRs correspond to CDR1 (SEQ ID NO: 4), CDR2 (SEQ ID NO: 5) and CDR3 (SEQ ID NO: 6).

Similar to antibody 806, the 175 antibodies of the invention also recognize amplified wild type EGFR and the de2-7 EGFR, yet bind to an epitope distinct from the unique junctional peptide of the de2-7 EGFR mutation (junctional peptide LEEKKGNYVVTDH (SEQ ID NO:13). MAb 175 binds to the surface of A431 cells, which have an amplification of the EGFR gene but do not express the de2-7 EGFR. Importantly, mAb 175, like mAb 806, does not bind significantly to normal tissues such as liver and skin, which express levels of endogenous, wild type (wt) EGFR, but wherein EGFR is not aberrantly expressed or amplified.

While having very similar characteristics as mAb 806 with regard to the epitope binding, immunohistochemical staining etc., mAb 175 does show a higher potency than mAb 806 in treating human glioma xenografts expressing the de2-7 EGF-receptor.

In one aspect, the present invention provides an antibody capable of binding an antigen wherein said antibody comprises a polypeptide binding domain comprising an amino acid sequence substantially as set out in the CDRs of the light chain of Ab175, comprising CDR1, CDR2, and/or CDR3, including as set out in SEQ ID NOs: 1-3. In a further aspect, the present invention provides an antibody capable of binding an antigen wherein said antibody comprises a polypeptide binding domain comprising an amino acid sequence substantially as set out in the CDRs of the heavy chain of Ab175, comprising CDR1, CDR2, and/or CDR3, including as set out in SEQ ID NOs: 4-6. Thus, the invention contemplates recombinant, humanized, chimeric, veneered, or other such antibodies, or antibody peptides, including domain peptides comprising the CDRs of the heavy and/or light chain of Ab175. Such antibodies may comprise the sequences as set out in SEQ ID NOS: 1-3 for light chain, and SEQ ID NOs: 4-6 for heavy chain. In a preferred embodiment, the binding domains are carried by a human antibody framework.

In further aspects, the invention provides an isolated nucleic acid which comprises a sequence encoding an antibody as defined above, and methods of preparing antibodies of the invention which comprise expressing said nucleic acids under conditions to bring about expression of said binding member, and recovering the binding member.

Yet a further aspect of the invention are compositions of such antibodies with additional antibodies, such as antibodies which bind to EGFR, preferably inhibiting ligand binding thereto. Such compositions can be "one pot" cocktails, kits, and so forth, preferably formulated for ease of administration.

Antibodies or fragments thereof according to the invention may be used in a method of treatment or diagnosis of the human or animal body, such as a method of treatment of a tumor in a human patient which comprises administering to said patient an effective amount of an antibody of the invention.

The present invention also relates to a recombinant DNA molecule or cloned gene, or a degenerate variant thereof, which encodes an antibody of the present invention; preferably a nucleic acid molecule, in particular a recombinant DNA molecule or cloned gene, encoding the antibody VH CDR 1, 2, and/or 3 domains shown in FIG. 1 (SEQ ID NOs: 4-6). In another embodiment, the present invention also relates to a recombinant DNA molecule or cloned gene, or a degenerate variant thereof, preferably a nucleic acid molecule, in particular a recombinant DNA molecule or cloned gene, encoding the antibody VL CDR 1, 2, and/or 3 domains shown in FIG. 1 (SEQ ID NOs: 1-3).

In a further embodiment of the invention, the full DNA sequence of the recombinant DNA molecule or cloned gene encoding the sequences provided herein may be operatively linked to an expression control sequence which may be introduced into an appropriate host. The invention accordingly extends to unicellular hosts transformed with the cloned gene or recombinant DNA molecule comprising a DNA sequence encoding the present VH and/or VL CDRs, or portions thereof, of the antibody, and more particularly, a DNA sequence encoding the VH and/or VL CDRs set forth above and in FIG. 1 and in SEQ ID NOs: 1, 2, 3, 4, 5 and/or 6.

The present invention naturally contemplates several means for preparation of the antibodies and active fragments thereof, including as illustrated herein known recombinant techniques, and the invention is accordingly intended to cover such synthetic or chimeric antibody preparations within its scope. The isolation of the nucleic acid and amino acid sequences disclosed herein facilitates the reproduction of the antibody of the present invention by such recombinant techniques, and accordingly, the invention extends to expression vectors prepared for expression in host systems by recombinant DNA techniques, and to the resulting transformed hosts.

The present invention provides drugs or other entities, including antibodies such as anti-idiotype antibodies, that are capable of binding to the antibody thereby modulating, inhibiting or potentiating the antibody activity. Such anti-idiotype antibodies would be useful in the development of drugs that would specifically bind the antibodies such as mAb175 or its epitope or that would potentiate its activity.

The diagnostic utility of the present invention extends to the use of the antibodies of the present invention in assays to characterize tumors or cellular samples or to screen for tumors or cancer, including in vitro and in vivo diagnostic assays. In an immunoassay, a control quantity of the antibodies, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached.

Antibodies of the invention may carry a detectable or functional label. The specific binding members may carry a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{121}I$, $^{124}I$, $^{125}I$, $^{131}I$, $^{111}In$, $^{211}At$, $^{198}Au$, $^{67}Cu$, $^{225}Ac$, $^{213}Bi$, $^{99}Tc$ and $^{186}Re$. When radioactive labels are used, known currently available counting procedures may be utilized to identify and quantitate the antibodies. In the instance where the label is an enzyme, detection may be accomplished by any of the presently utilized colorimetric, spectrophotometric, fluorospectrophotometric, amperometric or gasometric techniques known in the art.

The radiolabelled antibodies and fragments thereof, are useful in in vitro diagnostics techniques and in in vivo radioimaging techniques. In a further aspect of the invention, radiolabelled antibodies and fragments thereof, particularly radioimmunoconjugates, are useful in radioimmunotherapy, particularly as radiolabelled antibodies for cancer therapy. In a still further aspect, the radiolabelled antibodies and fragments thereof, are useful in radioimmuno-guided surgery techniques, wherein they can identify and indicate the presence and/or location of cancer cells, precancerous cells, tumor cells, and hyperproliferative cells, prior to, during or following surgery to remove such cells.

Immunoconjugates or antibody fusion proteins of the present invention, wherein the antibodies and fragments thereof, of the present invention are conjugated or attached to other molecules or agents further include, but are not limited to binding members conjugated to a chemical ablation agent, toxin, immunomodulator, cytokine, cytotoxic agent, chemotherapeutic agent or drug.

The present invention includes an assay system which may be prepared in the form of a test kit for the quantitative analysis of the extent of the presence of, for instance, amplified EGFR or de2-7EGFR. The system or test kit may comprise a labeled component prepared by one of the radioactive and/or enzymatic techniques discussed herein, coupling a label to the antibody, and one or more additional immunochemical reagents, at least one of which is a free or immobilized components to be determined or their binding partner(s).

In a further embodiment, the present invention relates to certain therapeutic methods which would be based upon the activity of the antibody, or active fragments thereof, or upon agents or other drugs determined to possess the same activity. A first therapeutic method is associated with the prevention or treatment of cancer, including but not limited to head and neck, breast, prostate and glioma.

In particular, the antibodies of the present invention, and in a particular embodiment the 175 antibody whose CDR domain region sequences are presented in FIG. 1 and in SEQ ID NOS: 1-6 herein, or active fragments thereof, and chimeric (bispecific) or synthetic antibodies derived therefrom can be prepared in pharmaceutical compositions, including a suitable vehicle, carrier or diluent, for administration in instances wherein therapy is appropriate, such as to treat cancer. Such pharmaceutical compositions may also include methods of modulating the half-life of the antibodies or fragments by methods known in the art, such as pegylation. Such pharmaceutical compositions may further comprise additional antibodies or therapeutic agents.

Thus, a composition of the present invention may be administered alone or in combination with other treatments, therapeutics or agents, either simultaneously or sequentially dependent upon the condition to be treated. In addition, the present invention contemplates and includes compositions comprising the antibody or fragment thereof, herein described and other agents or therapeutics such as anti-cancer agents or therapeutics, anti-EGFR agents or antibodies, or immune modulators. More generally these anti-cancer agents may be tyrosine kinase inhibitors or phosphorylation cascade inhibitors, post-translational modulators, cell growth or division inhibitors (e.g. anti-miotics), PDGFR inhibitors or signal transduction inhibitors. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. Thus, these agents may be anti-EGFR specific agents, such as AG1478, or may be more general anti-cancer and anti-neoplastic agents, non limiting examples including doxorubicin, carboplatin and cisplatin. In addition, the composition may be administered with immune modulators, such as interleukins, tumor necrosis factor (TNF) or other growth factors, cytokines or hormones such as dexamethasone which stimulate the immune response and reduction or elimination of cancer cells or tumors. The composition may also be administered with, or may include combinations along with other anti-EGFR antibodies, including but not limited to the anti-EGFR antibodies mAb806; antibody 528; 225; SC-03; 108 (ATCC HB9764) U.S. Pat. No. 6,217,866; 14E1 (U.S. Pat. No. 5,942,602); DH8.3; L8A4; Y10; HuMAX-EGFr (Genmab/Medarex); ICR62; and ABX-EGF (Abgenix).

The present invention also includes antibodies and fragments thereof, which are covalently attached to or otherwise associated with other molecules or agents. These other molecules or agents include, but are not limited to, molecules (including antibodies or antibody fragments) with distinct recognition characteristics, toxins, ligands, and chemotherapeutic agents.

Other objects and advantages will become apparent to those skilled in the art from a review of the ensuing detailed description, which proceeds with reference to the following illustrative drawings, and the attendant claims.

DETAILED DESCRIPTION

Figure 2:
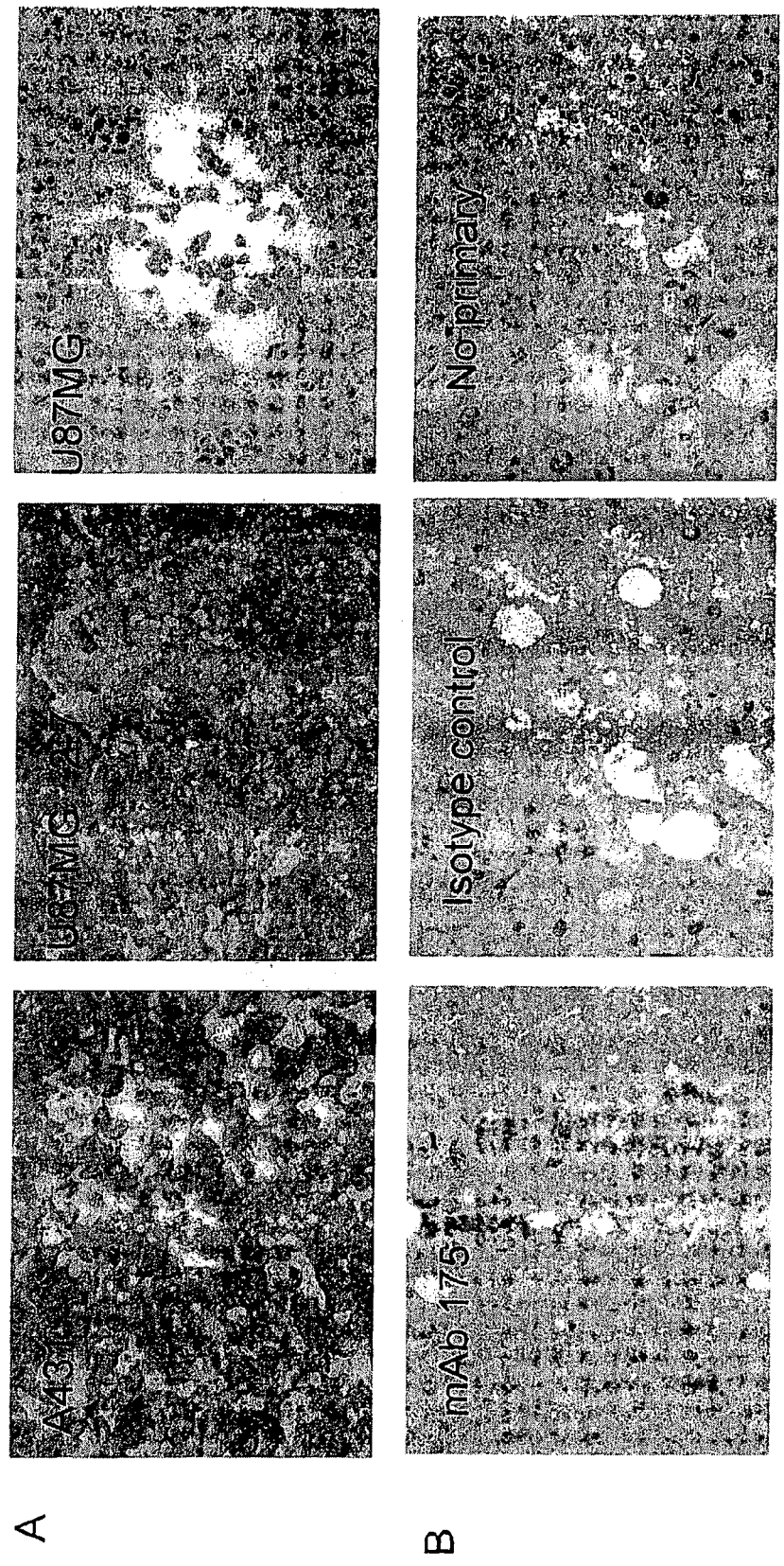
FIG. 2: Immunohistochemical staining of cell lines and normal human liver with mAb175. A: Biotinylated mAb175 was used to stain sections prepared from blocks containing A431 cells (over-express the wtEGFR), U87MG.Δ2-7 cells (express the Δ2-7 EGFR) and U87MG cells (express the wtEGFR at modest levels). B; Staining of normal human liver (400×) with mAb175 (left panel), isotype control (centre panel) and secondary antibody control (right panel). No specific sinusoidal or hepatocyte staining was observed.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A. Terminology

The term "aberrant expression" in its various grammatical forms may mean and include any heightened or altered expression or overexpression of a protein in a tissue, e.g. an increase in the amount of a protein, caused by any means including enhanced expression or translation, modulation of the promoter or a regulator of the protein, amplification of a gene for a protein, or enhanced half-life or stability, such that more of the protein exists or can be detected at any one time, in contrast to a non-overexpressed state. Aberrant expression includes and contemplates any scenario or alteration wherein the protein expression or post-translational modification machinery in a cell is taxed or otherwise disrupted due to enhanced expression or increased levels or amounts of a protein, including wherein an altered protein, as in mutated protein or variant due to sequence alteration, deletion or insertion, or altered folding is expressed.

It is important to appreciate that the term "aberrant expression" has been specifically chosen herein to encompass the state where abnormal (usually increased) quantities/levels of the protein are present, irrespective of the efficient cause of that abnormal quantity or level. Thus, abnormal quantities of protein may result from overexpression of the protein in the absence of gene amplification, which is the case e.g. in many cellular/tissue samples taken from the head and neck of subjects with cancer, while other samples exhibit abnormal protein levels attributable to gene amplification.

In this latter connection, certain of the work of the inventors that is presented herein to illustrate the invention includes the analysis of samples certain of which exhibit abnormal protein levels resulting from amplification of EFGR. This therefore accounts for the presentation herein of experimental findings where reference is made to amplification and for the use of the terms "amplification/amplified" and the like in describing abnormal levels of EFGR. However, it is the observation of abnormal quantities or levels of the protein that defines the environment or circumstance where clinical intervention as by resort to the binding members of the invention is contemplated, and for this reason, the present specification considers that the term "aberrant expression" more broadly captures the causal environment that yields the corresponding abnormality in EFGR levels.

Accordingly, while the terms "overexpression" and "amplification" in their various grammatical forms are understood to have distinct technical meanings, they are to be considered equivalent to each other, insofar as they represent the state where abnormal EFGR protein levels are present in the context of the present invention. Consequently, the term "aberrant expression" has been chosen as it is believed to subsume the terms "overexpression" and "amplification" within its scope for the purposes herein, so that all terms may be considered equivalent to each other as used herein.

The term "antibody" describes an immunoglobulin whether natural or partly or wholly synthetically produced. The term also covers any polypeptide or protein having a binding domain which is, or is homologous to, an antibody binding domain. CDR grafted antibodies are also contemplated by this term.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) multivalent antibody fragments (scFv dimers, trimers and/or tetramers (Power and Hudson, J. Immunol. Methods 242: 193-204 9 (2000))(ix) bispecific single chain Fv dimers (PCT/US92/09965) and (x) "diabodies", multivalent or multispecific fragments constructed by gene fusion (WO94/13804; P. Holliger et al Proc. Natl. Acad. Sci. USA 90 6444-6448, (1993)).

An "antibody combining site" is that structural portion of an antibody molecule comprised of light chain or heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Antibodies may also be bispecific, wherein one binding domain of the antibody is a specific binding member of the invention, and the other binding domain has a different specificity, e.g. to recruit an effector function or the like. Bispecific antibodies of the present invention include wherein one binding domain of the antibody is a specific binding member of the present invention, including a fragment thereof, and the other binding domain is a distinct antibody or fragment thereof, including that of a distinct anti-EGFR antibody, for instance antibody 528 (U.S. Pat. No. 4,943,533), the chimeric and humanized 225 antibody (U.S. Pat. No. 4,943,533 and WO/9640210), an anti-de2-7 antibody such as DH8.3 (Hills, D. et al (1995) Int. J. Cancer 63(4):537-543), antibody L8A4 and Y10 (Reist, C J et al (1995) Cancer Res. 55(19):4375-4382; Foulon C F et al. (2000) Cancer Res. 60(16):4453-4460), ICR62 (Modjtahedi H et al (1993) Cell Biophys. January-June; 22(1-3):129-46; Modjtahedi et al (2002) P.A.A.C.R. 55(14):3140-3148, or the antibody of Wikstrand et al (Wikstrand C. et al (1995) Cancer Res. 55(14):3140-3148. The other binding domain may be an antibody that recognizes or targets a particular cell type, as in a neural or glial cell-specific antibody. In the bispecific antibodies of the present invention the one binding domain of the antibody of the invention may be combined with other binding domains or molecules which recognize particular cell receptors and/or modulate cells in a particular fashion, as for instance an immune modulator (e.g., interleukin(s)), a growth modulator or cytokine (e.g. tumor necrosis factor (TNF), and particularly, the TNF bispecific modality demonstrated in U.S. Ser. No. 60/355,838 filed Feb. 13, 2002 incorporated herein in its entirety) or a toxin (e.g., ricin) or anti-mitotic or apoptotic agent or factor.

Fab and F(ab')$_2$ portions of antibody molecules may be prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may also contain an antibody molecule having a plurality of antibody combining sites, each immunospecific for a different antigen; e.g., a bispecific (chimeric) monoclonal antibody.

The term "antigen binding domain" describes the part of an antibody which comprises the area which specifically binds to and is complementary to part or all of an antigen. Where an antigen is large, an antibody may bind to a particular part of the antigen only, which part is termed an epitope. An antigen binding domain may be provided by one or more antibody variable domains. Preferably, an antigen binding domain comprises an antibody light chain variable region (VL) and an antibody heavy chain variable region (VH).

"Post-translational modification" may encompass any one of or combination of modification(s), including covalent modification, which a protein undergoes after translation is complete and after being released from the ribosome or on the nascent polypeptide cotranslationally. Post-translational modification includes but is not limited to phosphorylation, myristylation, ubiquitination, glycosylation, coenzyme attachment, methylation and acetylation. Post-translational modification can modulate or influence the activity of a protein, its intracellular or extracellular destination, its stability or half-life, and/or its recognition by ligands, receptors or other proteins Post-translational modification can occur in cell organelles, in the nucleus or cytoplasm or extracellularly.

The term "specific" may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

The term "comprise" is generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention referred to above, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which antibodies of the invention, or nucleic acid encoding such antibodies or CDRs thereof will be, in accordance with the present invention. Antibodies and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practiced in vitro or in vivo. Antibodies and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Antibodies may be glycosylated, either naturally or by systems of heterologous eukaryotic cells, or they may be (for example if produced by expression in a prokaryotic cell) unglycosylated.

Also, as used herein, the terms "glycosylation" and "glycosylated" includes and encompasses the post-translational modification of proteins, termed glycoproteins, by addition of oligosaccharides. Oligosaccharides are added at glycosylation sites in glycoproteins, particularly including N-linked oligosaccharides and O-linked oligosaccharides. N-linked oligosaccharides are added to an Asn residue, particularly wherein the Asn residue is in the sequence N-X-S/T, where X cannot be Pro or Asp, and are the most common ones found in glycoproteins. In the biosynthesis of N-linked glycoproteins, a high mannose type oligosaccharide (generally comprised of dolichol, N-Acetylglucosamine, mannose and glucose is first formed in the endoplasmic reticulum (ER). The high mannose type glycoproteins are then transported from the ER to the Golgi, where further processing and modification of the oligosaccharides occurs. O-linked oligosaccharides are added to the hydroxyl group of Ser or Thr residues. In O-linked oligosaccharides, N-Acetylglucosamine is first transferred to the Ser or Thr residue by N-Acetylglucosaminyltransferase in the ER. The protein then moves to the Golgi where further modification and chain elongation occurs. O-linked modifications can occur with the simple addition of the OG1cNAc monosaccharide alone at those Ser or Thr sites which can also under different conditions be phosphorylated rather than glycosylated.

As used herein, "pg" means picogram, "ng" means nanogram, "ug" or "µg" mean microgram, "mg" means milligram, "ul" or "µl" mean microliter, "ml" means milliliter, "l" means liter.

Figures 1, 6:
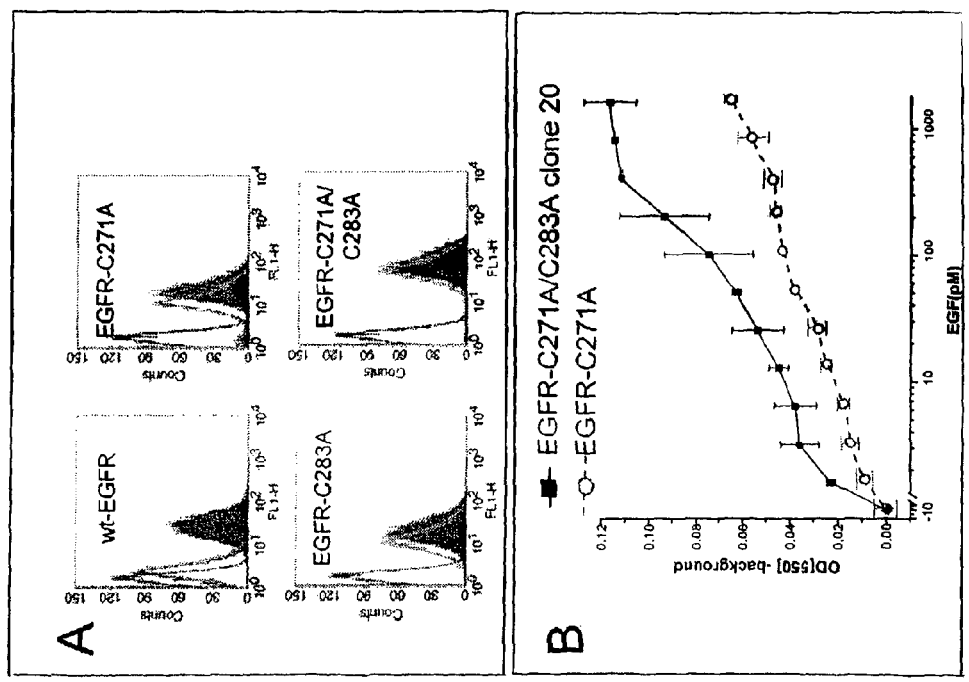
FIG. 1: Alignment of amino acid sequences for CDR's from mAb806 and mAb175. Sequence differences between the two antibodies are bolded.
FIG. 6: Influence of the 271-283 cystine bond on mAb806 binding to the EGFR. A: Cells transfected with wtEGFR, EGFR-C271A, EGFR-C283A or the C271A/C283A mutant were stained with mAb528 (solid pink histogram), mAb806 (blue line) or only the secondary antibody (purple) and then analyzed by FACS. The gain was set up using a class-matched irrelevant antibody.
B: BaF3 cells expressing the EGFR-C271A or C271/283A EGFR were examined for their response to EGF in an MTT assay as described in Methods. $EC_{50}$s were derived using the Bolzman fit of the data points. Data represent mean and sd of triplicate measurements C: BaF3 cells expressing the wt or the EGFR-C271A/C283A were IL-3 and serum starved, then exposed to EGF or vehicle control. Whole cell lyates were separated by SDS-PAGE and immunoblotted with anti-phosphotyrosine antibody (top panel) or anti-EGFR antibody (bottom panel). D: BaF3 cells expressing the wt (left panel) or the C271A/C283A (right panel) EGFR were stimulated with increasing concentrations of EGF in the presence of no antibody (open symbols), mAb 528 (grey circles) or mAb806 (black triangles), both at 10 μg/ml. Data are expressed as mean and sd of triplicate measurements.
Figures 2, 6:
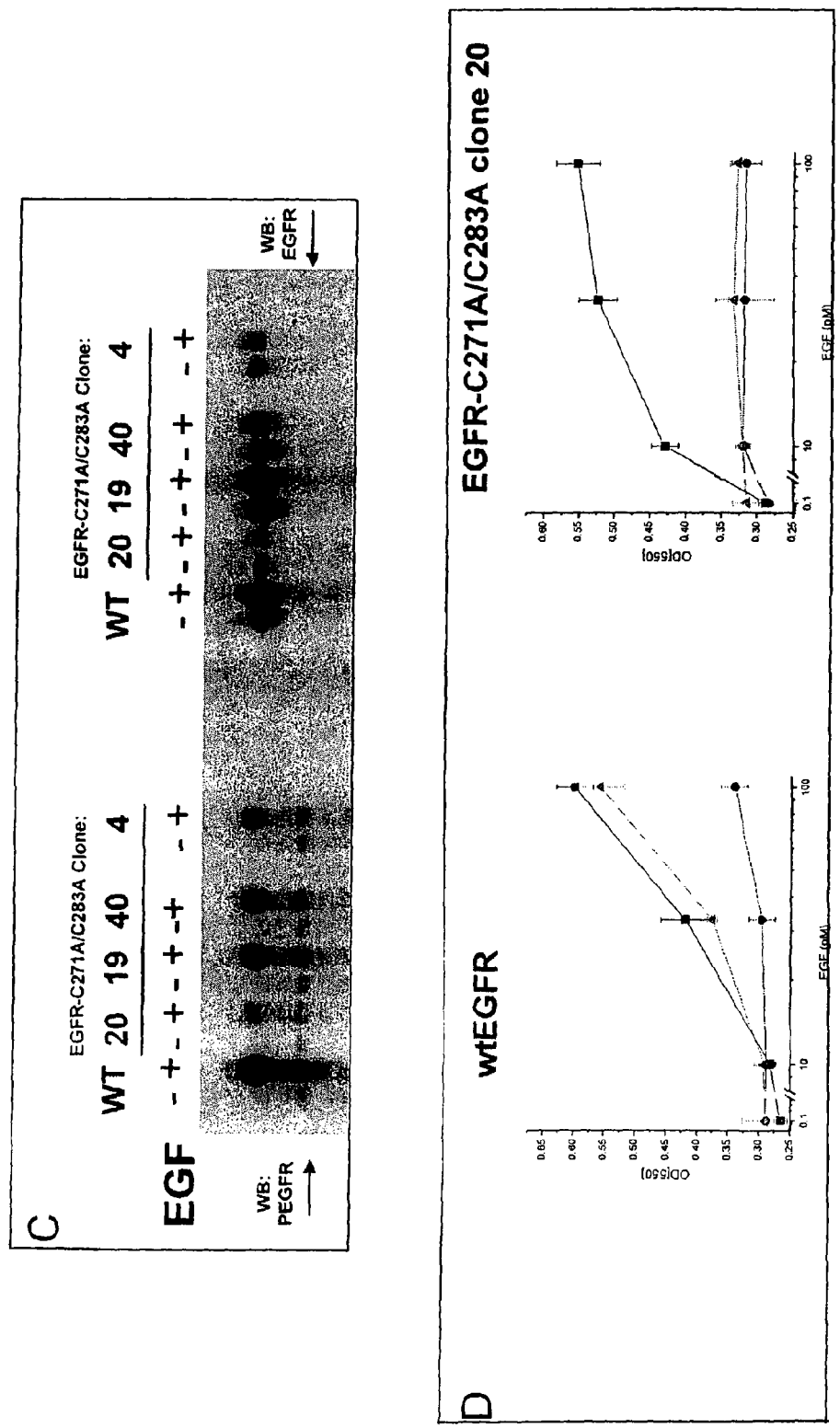

The terms "antibody 175", "175 antibody", "mAb175", and any variants not specifically listed, may be used herein interchangeably, and as used throughout the present application and claims refer to proteinaceous material including single or multiple proteins, and extends to those proteins having the amino acid sequence data described herein and presented in FIG. 1 and having or comprising the amino acid sequences as set out in SEQ ID NOs: 1, 2, 3, 4, 5, and/or 6 and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "antibody 175", "175 antibody" and "mAb175" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

TABLE OF CORRESPONDENCE

SYMBOL

| 1-Letter | 3-Letter | AMINO ACID |
|---|---|---|
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides. Primers are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication.

This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding antibodies of the invention which code for e.g. an antibody having a variable region domain having or comprising the same amino acid sequence as SEQ ID NO: 1, 2, 3, 4, 5, or 6, but which are degenerate to SEQ ID NO: 1, 2, 3, 4, 5, or 6. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in nucleic acid sequences encoding the antibody domains set out herein such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:
Amino Acids with Nonpolar R Groups
Alanine, Valine, Leucine, Isoleucine, Proline, Phenylalanine, Tryptophan, Methionine
Amino Acids with Uncharged Polar R Groups
Glycine, Serine, Threonine, Cysteine, Tyrosine, Asparagine, Glutamine
Amino Acids with Charged Polar R Groups (Negatively Charged at Ph 6.0)
Aspartic acid, Glutamic acid
Basic Amino Acids (Positively Charged at pH 6.0)
Lysine, Arginine, Histidine (at pH 6.0)
Another grouping may be those amino acids with phenyl groups:
Phenylalanine, Tryptophan, Tyrosine
Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, preferably by at least 50 percent, preferably by at least 70 percent, preferably by at least 80 percent, preferably by at least 90%, a clinically significant change in the growth or progression or mitotic activity of a target cellular mass, group of cancer cells or tumor, or other feature of pathology. For example, the degree of EGFR activation or activity or amount or number of EGFR positive cells, particularly of antibody or binding member reactive or positive cells may be reduced.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

B. Detailed Disclosure.

The present invention provides a novel antibody 175 or fragment thereof, including immunogenic fragments, which recognizes an EGFR epitope, particularly the EGFR peptide ($_{287}$CGADSYEMEEDGVRKC$_{302}$(SEQ ID NO: 14)), which is exposed in tumorigenic, hyperproliferative or abnormal cells wherein the epitope is enhanced, revealed, or evident and not detectable in normal or wild type cells. In a particular but non-limiting embodiment, the antibody recognizes an EGFR epitope which is enhanced or evident upon simple carbohydrate modification or early glycosylation and is reduced or not evident in the presence of complex carbohydrate modification or glycosylation. The antibody or fragment thereof does not bind to or recognize normal or wild type cells containing normal or wild type EGFR epitope in the absence of overexpression, amplification, or a tumorigenic event.

In a particular aspect of the invention and as stated above, the present inventors have discovered the novel monoclonal antibody 175, which specifically recognize amplified wild type EGFR and the de2-7 EGFR, yet bind to an epitope distinct from the unique junctional peptide of the de2-7 EGFR mutation. Additionally, while mAb 175 does not recognize the normal, wild type EGFR expressed on the cell surface of glioma cells, it does bind to the extracellular domain of the EGFR immobilized on the surface of ELISA plates, indicating a conformational epitope with a polypeptide aspect. Importantly, mAb 175 did not bind significantly to normal tissues such as liver and skin, which express levels of endogenous wt EGFR that are higher than in most other normal tissues, but wherein EGFR is not overexpressed or amplified. Thus, mAb175 demonstrates novel and useful specificity, recognizing de2-7 EGFR and amplified EGFR, while not recognizing normal, wild type EGFR or the unique junctional peptide which is characteristic of de2-7 EGFR. In a preferred aspect the antibody 175 of the present invention comprises the VH and VL CDR domain amino acid sequences depicted in FIG. 1 and in SEQ ID NOs: 1, 2, 3, 4, 5, and 6.

In another aspect, the invention provides an antibody capable of competing with the 175 antibody, under conditions in which at least 10% of an antibody having the VH and VL sequences of the 175 antibody is blocked from binding to de2-7EGFR by competition with such an antibody in an ELISA assay. As set forth above, anti-idiotype antibodies are contemplated herein.

Diagnostic and Therapeutic Uses

The unique specificity of the 175 antibodies or fragments thereof, of the present invention, provides diagnostic and therapeutic uses to identify, characterize, target and treat, reduce or eliminate a number of tumorigenic cell types and tumor types, for example head and neck, breast, lung, bladder or prostate tumors and glioma, without the problems associated with normal tissue uptake that may be seen with previously known EGFR antibodies. Thus, cells overexpressing EGFR (e.g. by amplification or expression of a mutant or variant EGFR), particularly those demonstrating aberrant post-translational modification may be recognized, isolated, characterized, targeted and treated or eliminated utilizing the 175 antibody(ies) or fragments thereof of the present invention.

The antibodies of the present invention can thus specifically categorize the nature of EGFR tumors or tumorigenic cells, by staining or otherwise recognizing those tumors or cells wherein EGFR overexpression, particularly amplification and/or EGFR mutation, particularly de2-7EGFR, is present. Further, the 175 antibodies of the present invention demonstrate significant in vivo anti-tumor activity against tumors containing amplified EGFR and against de2-7 EGFR positive xenografts. In a further aspect of the invention, there is provided a method of treatment of a tumor, a cancerous condition, a precancerous condition, and any condition related to or resulting from hyperproliferative cell growth comprising administration of an antibody 175 of the invention.

Antibodies of the present invention are designed to be used in methods of diagnosis and treatment of tumors in human or animal subjects, particularly epithelial tumors. These tumors may be primary or secondary solid tumors of any type including, but not limited to, glioma, breast, lung, prostate, head or neck tumors.

Antibody Generation

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890. Panels of monoclonal antibodies produced against EFGR can be screened for various properties; i.e., isotype, epitope, affinity, etc. Of particular interest are monoclonal antibodies that mimic the activity of EFGR or its subunits. Such monoclonals can be readily identified in specific binding member activity assays. High affinity antibodies are also useful when immunoaffinity purification of native or recombinant specific binding member is possible. A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Methods for producing monoclonal anti-EGFR antibodies are also well-known in the art. See Niman et al., *Proc. Natl. Acad. Sci. USA,* 80:4949-4953 (1983). Typically, the EGFR or a peptide analog is used either alone or conjugated to an immunogenic carrier, as the immunogen in the before described procedure for producing anti-EGFR monoclonal antibodies. The hybridomas are screened for the ability to produce an antibody that immunoreacts with the EGFR present in tumorigenic, abnormal or hyperproliferative cells. Other anti-EGFR antibodies include but are not limited to the HuMAX-EGFr antibody from Genmab/Medarex, the 108 antibody (ATCC HB9764) and U.S. Pat. No. 6,217,866, and antibody 14E1 from Schering A G (U.S. Pat. No. 5,942,602).

Recombinant Antibodies, Chimerics, Bispecifics and Fragments

In general, the CDR regions, comprising amino acid sequences substantially as set out as the CDR regions of SEQ ID NOs: 1, 2, 3, 4, 5, and/or 6 will be carried in a structure which allows for binding of the CDR regions to an tumor antigen. By "substantially as set out" it is meant that that CDR regions of the invention will be either identical or highly homologous to the specified regions of SEQ ID NOs: 1, 2, 3, 4, 5, and/or 6. By "highly homologous" it is contemplated that only a few substitutions, preferably from 1 to 8, preferably from 1 to 5, preferably from 1 to 4, or from 1 to 3 or 1 or 2 substitutions may be made in the CDRs.

The structure for carrying the CDRs of the invention will generally be of an antibody heavy or light chain sequence or substantial portion thereof in which the CDR regions are located at locations corresponding to the CDR region of naturally occurring VH and VL antibody variable domains encoded by rearranged immunoglobulin genes. The structures and locations of immunoglobulin variable domains may be determined by reference to Kabat, E. A. et al, Sequences of Proteins of Immunological Interest. 4th Edition. US Department of Health and Human Services. 1987, and updates thereof, now available on the Internet (http://immuno.bme.nwu.edu)).

Preferably, the amino acid sequence substantially as set out as SEQ ID NO: 4, 5, and 6 are carried as the CDR 1, 2, and 3 in a human heavy chain variable domain or a substantial portion thereof, and the amino acid sequences substantially as set out as SEQ ID NOs: 1, 2, and 3 are carried as the CDRs 1-3 respectively in a human light chain variable domain or a substantial portion thereof.

The variable domains may be derived from any germline or rearranged human variable domain, or may be a synthetic variable domain based on consensus sequences of known human variable domains. The CDR-derived sequences of the invention, as defined in the preceding paragraph, may be introduced into a repertoire of variable domains lacking CDR regions, using recombinant DNA technology. For example, Marks et al (Bio/Technology, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking one or more CDR. Marks et al further describe how this repertoire may be combined with a CDR of a particular antibody. Using analogous techniques, the CDR-derived sequences of the present invention may be shuffled with repertoires of VH or VL domains lacking one or more CDR, and the shuffled complete VH or VL domains combined with a cognate VL or VH domain to provide antibodies of the invention. The repertoire may then be displayed in a suitable host system such as the phage display system of WO92/01047 so that suitable specific binding members may be selected. A repertoire may consist of from anything from $10^4$ individual members upwards, for example from $10^6$ to $10^8$ or $10^{10}$ members. Analogous shuffling or combinatorial techniques are also disclosed by Stemmer (Nature, 1994, 370:389-391), who describes the technique in relation to a β-lactamase gene but observes that the approach may be used for the generation of antibodies.

A further alternative is to generate novel VH or VL regions carrying the CDR-derived sequences of the invention using random mutagenesis of, for example, nucleic acid encoding the mAb175 VH or VL CDRs to generate mutations within the domain(s). Such a technique is described by Gram et al (1992, Proc. Natl. Acad. Sci., USA, 89:3576-3580), who used error-prone PCR. Another method which may be used is to direct mutagenesis to CDR regions of VH or VL genes. Such techniques are disclosed by Barbas et al, (1994, Proc. Natl. Acad. Sci., USA, 91:3809-3813) and Schier et al (1996, J. Mol. Biol. 263:551-567). All the above described techniques are known as such in the art and in themselves do not form part of the present invention. The skilled person will be able to use such techniques to provide specific binding members of the invention using routine methodology in the art.

A substantial portion of an immunoglobulin variable domain will comprise at least the three CDR regions. Additional residues at the N-terminal or C-terminal end of the substantial part of the variable domain may be those not normally associated with naturally occurring variable domain regions. For example, construction of antibodies of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as discussed in more detail below.

Although in a preferred aspect of the invention antibodies comprising one or more binding domains based on sequences substantially set out in SEQ ID NOs: 1, 2, 3, 4, 5, and/or 6 are preferred, single binding domains based on either of these sequences form further aspects of the invention. In the case of the binding domain based on the sequence substantially set out in SEQ ID NO:6, or the domains of SEQ ID NOS: 4-6, such binding domain(s) may be used as targeting agents for tumor antigens since it is known that immunoglobulin VH domains are capable of binding target antigens in a specific manner. In the case of either of the single chain specific binding domains, these domains may be used to screen for complementary domains capable of forming a two-domain specific binding member which has in vivo properties as good as or equal to the mAb175 antibody disclosed herein.

This may be achieved by phage display screening methods using the so-called hierarchical dual combinatorial approach as disclosed in U.S. Pat. No. 5,969,108 in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al, ibid.

Antibodies of the present invention may further comprise antibody constant regions or parts thereof. For example, antibodies based on SEQ ID NOs: 1-3 may be attached at their C-terminal end to antibody light chain constant domains including human Cκ or Cλ chains. Similarly, antibodies based on SEQ ID NOs: 4-6 may be attached at their C-terminal end to all or part of an immunoglobulin heavy chain derived from any antibody isotype, e.g. IgG, IgA, IgE, IgD and IgM and any of the isotype sub-classes, particularly IgG1, IgG2b, and IgG4.

The application of molecular engineering to convert murine mAbs into chimeric mAbs (mouse V-region, human C-region) and humanised reagents where only the mAb complementarity-determining regions (CDR) are of murine origin has been critical to the clinical success of mAb therapy. The engineered mAbs have markedly reduced or absent immunogenicity, increased serum half-life and the human Fc portion of the mAb increases the potential to recruit the immune effectors of complement and cytotoxic cells. Investigations into the biodistribution, pharmacokinetics and any induction of an immune response to clinically administered mAbs requires the development of analyses to discriminate between the pharmaceutical and endogenous proteins.

The antibodies, or any fragments thereof, may also be conjugated or recombinantly fused to any cellular toxin, bacterial or other, e.g. pseudomonas exotoxin, ricin, or diphtheria toxin. The part of the toxin used can be the whole toxin, or any particular domain of the toxin. Such antibody-toxin molecules have successfully been used for targeting and therapy of different kinds of cancers, see e.g. Pastan, Biochim Biophys Acta. 1997 Oct. 24; 1333(2):C1-6; Kreitman et al., N Engl J. Med. 2001 Jul. 26; 345(4):241-7; Schnell et al., Leukemia. 2000 January; 14(1):129-35; Ghetie et al., Mol. Biotechnol. 2001 July; 18(3):251-68.

Bi- and tri-specific multimers can be formed by association of different scFv molecules and have been designed as cross-linking reagents for T-cell recruitment into tumors (immunotherapy), viral retargeting (gene therapy) and as red blood cell agglutination reagents (immunodiagnostics), see e.g. Todorovska et al., J Immunol Methods. 2001 Feb. 1; 248(1-2):47-66; Tomlinson et al., Methods Enzymol. 2000; 326:461-79; McCall et al., J. Immunol. 2001 May 15; 166(10):6112-7. Fully human antibodies can be prepared by immunizing transgenic mice carrying large portions of the human immunoglobulin heavy and light chains. These mice, examples of such mice are the Xenomouse™ (Abgenix, Inc.) (U.S. Pat. Nos. 6,075,181 and 6,150,584), the HuMAb-Mouse™ (Medarex, Inc./GenPharm) (U.S. Pat. No. 5,545,806 and 5569825), the TransChromo Mouse™ (Kirin) and the KM Mouse™ (Medarex/Kirin), are well known within the art. Antibodies can then be prepared by, e.g. standard hybridoma technique or by phage display. These antibodies will then contain only fully human amino acid sequences. Fully human antibodies can also be generated using phage display from human libraries. Phage display may be performed using methods well known to the skilled artisan, as in Hoogenboom et al and Marks et al (Hoogenboom H R and Winter G. (1992) J Mol. Biol. 227(2):381-8; Marks J D et al (1991) J Mol. Biol. 222(3):581-97; and also U.S. Pat. Nos. 5,885,793 and 5,969, 108).

Therapeutic Antibodies and Uses

The in vivo properties, particularly with regard to tumor: blood ratio and rate of clearance, of antibodies of the invention will be at least comparable to mAb175. Following administration to a human or animal subject such a specific binding member will show a peak tumor to blood ratio of >1:1. Preferably at such a ratio the specific binding member will also have a tumor to organ ratio of greater than 1:1, preferably greater than 2:1, more preferably greater than 5:1. Preferably at such a ratio the specific binding member will also have an organ to blood ratio of <1:1 in organs away from the site of the tumor. These ratios exclude organs of catabolism and secretion of the administered specific binding member.

Antibodies of the invention may be labelled with a detectable or functional label. Detectable labels include, but are not limited to, radiolabels such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{121}I$, $^{124}I$, $^{125}I$, $^{131}I$, $^{111}In$, $^{211}At$, $^{198}Au$, $^{67}Cu$, $^{225}Ac$, $^{213}Bi$, $^{99}Tc$ and $^{186}Re$, which may be attached to antibodies of the invention using conventional chemistry known in the art of antibody imaging. Labels also include fluorescent labels and labels used conventionally in the art for MRI-CT imagine. They also include enzyme labels such as horseradish peroxidase. Labels further include chemical moieties such as biotin which may be detected via binding to a specific cognate detectable moiety, e.g. labelled avidin. Functional labels include substances which are designed to be targeted to the site of a tumor to cause destruction of tumor tissue. Such functional labels include cytotoxic drugs such as 5-fluorouracil or ricin and enzymes such as bacterial carboxypeptidase or nitroreductase, which are capable of converting prodrugs into active drugs at the site of a tumor.

The 175 antibodies and/or their subunits may possess certain diagnostic applications and may for example, be utilized for the purpose of detecting and/or measuring conditions such as cancer, precancerous lesions, conditions related to or resulting from hyperproliferative cell growth or the like. The radiolabelled 175 antibodies and fragments thereof, are useful in in vitro diagnostics techniques and in in vivo radioimaging techniques and in radioimmunotherapy. In the instance of in vivo imaging, the antibodies of the present invention may be conjugated to an imaging agent rather than a radioisotope(s), including but not limited to a magnetic resonance image enhancing agent, wherein for instance an antibody molecule is loaded with a large number of paramagnetic ions through chelating groups. Examples of chelating groups include EDTA, porphyrins, polyamines crown ethers and polyoximes. Examples of paramagnetic ions include gadolinium, iron, manganese, rhenium, europium, lanthanium, holmium and ferbium. In a further aspect of the invention, radiolabelled 175 antibodies and fragments thereof, particularly radioimmunoconjugates, are useful in radioimmunotherapy, particularly as radiolabelled antibodies for cancer therapy. In a still further aspect, the radiolabelled 175 antibodies and fragments thereof, are useful in radioimmunoguided surgery techniques, wherein they can identify and indicate the presence and/or location of cancer cells, precancerous cells, tumor cells, and hyperproliferative cells, prior to, during or following surgery to remove such cells. Immunoconjugates or antibody fusion proteins of the present invention, wherein the 175 antibodies and fragments thereof, of the present invention are conjugated or attached to other molecules or agents further include, but are not limited to 175 antibodies conjugated to a chemical ablation agent, toxin, immunomodulator, cytokine, cytotoxic agent, chemotherapeutic agent or drug.

Radioimmunotherapy (RAIT) has entered the clinic and demonstrated efficacy using various antibody immunoconjugates. $^{131}I$ labeled humanized anti-carcinoembryonic antigen (anti-CEA) antibody hMN-14 has been evaluated in colorectal cancer (Behr T M et al (2002) Cancer 94(4Suppl):1373-81) and the same antibody with $^{90}Y$ label has been assessed in medullary thyroid carcinoma (Stein R et al (2002) Cancer 94(1):51-61). Radioimmunotherapy using monoclonal antibodies has also been assessed and reported for non-Hodgkin's lymphoma and pancreatic cancer (Goldenberg D M (2001) Crit. Rev Oncol Hematol 39(1-2):195-201; Gold D V et al (2001) Crit. Rev Oncol Hematol 39 (1-2) 147-54). Radioimmunotherapy methods with particular antibodies are also described in U.S. Pat. Nos. 6,306,393 and 6,331,175. Radioimmunoguided surgery (RIGS) has also entered the clinic and demonstrated efficacy and usefulness, including using anti-CEA antibodies and antibodies directed against tumor-associated antigens (Kim J C et al (2002) Int J Cancer 97(4):542-7; Schneebaum S et al (2001) World J Surg 25(12): 1495-8; Avital S et al (2000) Cancer 89(8):1692-8; McIntosh D G et al (1997) Cancer Biother Radiopharm 12 (4):287-94).

Antibodies of the present invention may be administered to a patient in need of treatment via any suitable route, usually by injection into the bloodstream or CSF, or directly into the site of the tumor. The precise dose will depend upon a number of factors, including whether the antibody is for diagnosis or for treatment, the size and location of the tumor, the precise nature of the antibody (whether whole antibody, fragment, diabody, etc), and the nature of the detectable or functional label attached to the antibody. Where a radionuclide is used for therapy, a suitable maximum single dose is about 45 $mCi/m^2$, to a maximum of about 250 $mCi/m^2$. Preferable dosage is in the range of 15 to 40 mCi, with a further preferred dosage range of 20 to 30 mCi, or 10 to 30 mCi. Such therapy may require bone marrow or stem cell replacement. A typical antibody dose for either tumor imaging or tumor treatment will be in the range of from 0.5 to 40 mg, preferably from 1 to 4 mg of antibody in F(ab')2 form. Naked antibodies are preferable administered in doses of 20 to 1000 mg protein per dose, or 20 to 500 mg protein per dose, or 20 to 100 mg protein per dose. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. These formulations may include a second binding protein, such as the EGFR binding proteins described supra. In an especially preferred form, this second binding protein is a monoclonal antibody such as 528 or 225, discussed infra.

Pharmaceutical and Therapeutic Compositions

Antibodies of the present invention will usually be administered in the form of a pharmaceutical composition, which may comprise at least one component in addition to the specific binding member. Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may be administered alone or in combination with other treatments, therapeutics or agents, either simultaneously or sequentially dependent upon the condition to be treated. In addition, the present invention contemplates and includes compositions comprising the binding member, particularly antibody or fragment thereof, herein described and other agents or therapeutics such as anti-cancer agents or therapeutics, hormones, anti-EGFR agents or antibodies, or immune modulators. More generally these anti-cancer agents may be tyrosine kinase inhibitors or phosphorylation cascade inhibitors, post-translational modulators, cell growth or division inhibitors (e.g. anti-mitotics), or signal transduction inhibitors. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. The composition can be administered in combination (either sequentially (i.e. before or after) or simultaneously) with tyrosine kinase inhibitors (including, but not limited to AG1478 and ZD1839, STI571, OSI-774, SU-6668), doxorubicin, temozolomide, cisplatin, carboplatin, nitrosoureas, procarbazine, vincristine, hydroxyurea, 5-fluoruracil, cytosine arabinoside, cyclophosphamide, epipodophyllotoxin, carmustine, lomustine, and/or other chemotherapeutic agents. Thus, these agents may be anti-EGFR specific agents, or tyrosine kinase inhibitors such as AG 1478, ZD1839, STI571, OSI-774, or SU-6668 or may be more general anti-cancer and anti-neoplastic agents such as doxorubicin, cisplatin, temozolomide, nitrosoureas, procarbazine, vincristine, hydroxyurea, 5-fluoruracil, cytosine arabinoside, cyclophosphamide, epipodophyllotoxin, carmustine, or lomustine. In addition, the composition may be administered with hormones such as dexamethasone, immune modulators, such as interleukins, tumor necrosis factor (TNF) or other growth factors or cytokines which stimulate the immune response and reduction or elimination of cancer cells or tumors. An immune modulator such as TNF may be combined together with a member of the invention in the form of a bispecific antibody recognizing the 806 EGFR epitope as well as binding to TNF receptors. The composition may also be administered with, or may include combinations along with other anti-EGFR antibodies, including but not limited to the anti-EGFR antibodies 528, 225, SC-03, DH8.3, L8A4, Y10, ICR62 and ABX-EGF.

Previously the use of agents such as doxorubicin and cisplatin in conjunction with anti-EGFR antibodies have produced enhanced anti-tumor activity (Fan et al, 1993; Baselga et al, 1993). The combination of doxorubicin and mAb 528 resulted in total eradication of established A431 xenografts, whereas treatment with either agent alone caused only temporary in vivo growth inhibition (Baselga et al, 1993). Likewise, the combination of cisplatin and either mAb 528 or 225 also led to the eradication of well established A431 xenografts, which was not observed when treatment with either agent was used (Fan et al, 1993).

Conventional Radiotherapy

In addition, the present invention contemplates and includes therapeutic compositions for the use of the antibody in combination with conventional radiotherapy. It has been indicated that treatment with antibodies targeting EGF receptors can enhance the effects of conventional radiotherapy (Milas et al., Clin Cancer Res. 2000 February: 6(2):701 8, Huang et al., Clin Cancer Res. 2000 June: 6(6):2166 74).

Combinations of the 175 antibody or fragment thereof and anti-cancer therapeutics are contemplated, particularly anti-EGFR therapeutics, including other anti-EGFR antibodies, demonstrate effective therapy, and particularly synergy, against xenografted tumors. The combination of AG1478 and mAb 175 is such an exemplary combination. AG1478 (4-(3-chloroanilino)-6,7-dimethoxyquinazoline) is a potent and selective inhibitor of the EGF receptor kinase and is particularly described in U.S. Pat. No. 5,457,105, incorporated by reference herein in its entirety (see also, Liu, W. et al (1999) J. Cell Sci. 112:2409; Eguchi, S. et al (1998) J. Biol. Chem. 273:8890; Levitsky, A. and Gazit, A. (1995) Science 267: 1782). Therapeutic synergy of the 175 antibody with other anti-EGFR antibodies, particularly with the 528 anti-EGFR antibody is anticipated and contemplated.

The present invention further contemplates therapeutic compositions useful in practicing the therapeutic methods of this invention. A subject therapeutic composition includes, in admixture, a pharmaceutically acceptable excipient (carrier) and one or more antibody 175 or fragment thereof, as described herein as an active ingredient. In a preferred embodiment, the composition comprises an antigen capable of modulating the specific binding of the present binding member/antibody with a target cell.

The preparation of therapeutic compositions which contain polypeptides, analogs or active fragments as active ingredients is well understood in the art. Typically, such compositions are prepared as injectables, either as liquid solutions or suspensions. However, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient. A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of EFGR binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Diagnostic Assays

The present invention also relates to a variety of diagnostic applications, including methods for detecting the presence of stimuli such as aberrantly expressed EGFR, by reference to their ability to be recognized by the present 175 antibody. Diagnostic applications of the antibody(ies) of the present invention include in vitro and in vivo applications well known and standard to the skilled artisan and based on the present description. Diagnostic assays and kits for in vitro assessment and evaluation of EGFR status, particularly with regard to aberrant expression of EGFR, may be utilized to diagnose, evaluate and monitor patient samples including those known to have or suspected of having cancer, a precancerous condition, a condition related to hyperproliferative cell growth or from a tumor sample. The assessment and evaluation of EGFR status is also useful in determining the suitability of a patient for a clinical trial of a drug or for the administration of a particular chemotherapeutic agent or specific binding member, particularly an antibody, of the present invention, including combinations thereof, versus a different agent or antibody. This type of diagnostic monitoring and assessment is already in practice utilizing antibodies against the HER2 protein in breast cancer (Hercep Test, Dako Corporation), where the assay is also used to evaluate patients for antibody therapy using Herceptin. In vivo applications include imaging of tumors or assessing cancer status of individuals, including radioimaging.

As suggested earlier, the diagnostic method of the present invention comprises examining a cellular sample or medium by means of an assay including an effective amount of an antagonist to an EFGR/protein, such as an anti-EFGR antibody, preferably mAb175 as provided herein. In addition, it is preferable for the anti-EFGR antibody molecules used herein be in the form of Fab, Fab', F(ab')$_2$ or F(v) portions or whole antibody molecules. As previously discussed, patients capable of benefiting from this method include those suffering from cancer, a pre-cancerous lesion, a viral infection, pathologies involving or resulting from hyperproliferative cell growth or other like pathological derangement.

The presence of EGFR in cells can be ascertained by the usual in vitro or in vivo immunological procedures applicable to such determinations. A number of useful procedures are known. The procedures and their application are all familiar to those skilled in the art and accordingly may be utilized within the scope of the present invention. In such procedures the EGFR forms complexes with one or more antibody(ies) or binding partners and one member of the complex is labeled with a detectable label. The fact that a complex has formed and, if desired, the amount thereof, can be determined by known methods applicable to the detection of labels. The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. The EGFR or EGFR antibody 175 can also be labeled with a radioactive element or with an enzyme. The radioactive label can be detected by any of the currently available counting procedures. The preferred isotope may be selected from $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{121}$I, $^{124}$I, $^{125}$I, $^{131}$I, $^{111}$In, $^{211}$At, $^{198}$Au, $^{67}$Cu, $^{225}$Ac, $^{213}$Bi, $^{99}$Tc and $^{186}$Re. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

In a further embodiment of this invention, commercial test kits suitable for use by a medical specialist may be prepared to determine the presence or absence of aberrant expression of EGFR, including but not limited to amplified EGFR and/or an EGFR mutation, in suspected target cells. In accordance with the testing techniques discussed above, one class of such kits will contain at least the labeled EGFR or its binding partner, for instance an antibody specific thereto (antibody 175), and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence or capability of cells for aberrant expression or aberrant forms of EGFR, comprising:

(a) a predetermined amount of at least one labeled immunochemically reactive component obtained by the direct or indirect attachment of the 175 antibody or a specific binding partner thereto, to a detectable label;
(b) other reagents; and
(c) directions for use of said kit.

In accordance with the above, an assay system for screening potential drugs effective to modulate the activity of the EFGR, or the aberrant expression of EGFR, and/or the activity or binding of the antibody (particularly 175 antibody) may be prepared. The receptor or the antibody may be introduced into a test system, and the prospective drug may also be introduced into the resulting cell culture, and the culture thereafter examined to observe any changes in the S-phase activity of the cells, due either to the addition of the prospective drug alone, or due to the effect of added quantities of the known agent(s).

Nucleic Acids

The present invention further provides an isolated nucleic acid encoding an antibody 175 of the present invention. Nucleic acid includes DNA and RNA. In a preferred aspect, the present invention provides a nucleic acid which codes for a polypeptide of the invention as defined above, including a polypeptide as set out in SEQ ID NOs: 1, 2, 3, 4, 5, and/or 6. The present invention also provides constructs in the form of plasmids, vectors, transcription or expression cassettes which comprise at least one polynucleotide as above. The present invention also provides a recombinant host cell which comprises one or more constructs as above. A nucleic acid encoding any antibody 175 as provided itself forms an aspect of the present invention, as does a method of production of the antibody which method comprises expression from encoding nucleic acid therefore. Expression may conveniently be achieved by culturing under appropriate conditions recombinant host cells containing the nucleic acid. Following production by expression a specific binding member may be isolated and/or purified using any suitable technique, then used as appropriate.

Antibodies and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic. Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli. The expression of antibodies and antibody fragments in prokaryotic cells such as E. coli is well established in the art. For a review, see for example Plückthun, A. Bio/Technology 9: 545-551 (1991). Expression in eukaryotic cells in culture is also available to those skilled in the art as an option for production of a specific binding member, see for recent reviews, for example Raff, M. E. (1993) Curr. Opinion Biotech. 4: 573-576; Trill J. J. et al. (1995) Curr. Opinion Biotech 6: 553-560. Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid encoding an antibody as disclosed herein. A still further aspect provides a method comprising introducing such nucleic acid into a host cell. The introduction may employ any available technique. The introduction may be followed by causing or allowing expression from the nucleic acid, e.g. by culturing host cells under conditions for expression of the gene. In one embodiment, the nucleic acid of the invention is integrated into the genome (e.g. chromosome) of the host cell. Integration may be promoted by inclusion of sequences which promote recombination with the genome, in accordance with standard techniques. The present invention also provides a method which comprises using a construct as stated above in an expression system in order to express an antibody or polypeptide as above.

As stated above, the present invention also relates to a recombinant DNA molecule or cloned gene, or a degenerate variant thereof, which encodes an antibody 175 or a fragment thereof, that possesses an amino acid sequence set forth in SEQ ID NOs: 1, 2, 3, 4, 5, and/or 6; preferably a nucleic acid molecule. As is well known in the art, DNA sequences may be expressed by operatively linking them to an expression control sequence in an appropriate expression vector and employing that expression vector to transform an appropriate unicellular host.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products. Considering these and other factors a person skilled in the art will be able to construct a variety of vector/expression control sequence/host combinations that will express the DNA sequences of this invention on fermentation or in large scale animal culture.

Analogs, such as fragments, may be produced, for example, by pepsin digestion of antibody peptide(s) or material. Other analogs, such as muteins, can be produced by standard site-directed mutagenesis of specific binding member coding sequences. Analogs exhibiting antibody 175-like activity such as small molecules, whether functioning as promoters or inhibitors, may be identified by known in vivo and/or in vitro assays. A DNA sequence encoding a 175 antibody can be prepared synthetically rather than cloned. The complete sequence is assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem.*, 259:6311 (1984). Synthetic DNA sequences allow convenient construction of genes which will express specific binding member analogs or "muteins". Alternatively, DNA encoding muteins can be made by site-directed mutagenesis of native specific binding member genes or cDNAs, and muteins can be made directly using conventional polypeptide synthesis. A general method for site-specific incorporation of unnatural amino acids into proteins is described in Christopher J. Noren, Spencer J. Anthony-Cahill, Michael C. Griffith, Peter G. Schultz, *Science*, 244:182-188 (April 1989). This method may be used to create analogs with unnatural amino acids.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLES

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

Summary

The EGFR exists in two well-defined conformers—tethered and untethered. The tethered conformer, which has only been observed in ligand-free (and partly ligated) forms of the receptor, can be induced by a ligand to form the untethered, back-to-back dimer. mAb806 recognizes an epitope on some truncated, overexpressed or activated forms of the EGFR on the cell surface, but it does not recognize the EGFR on normal unstimulated cells. Another related antibody, mAb175, also recognizes this unusual epitope. We have determined the 3D-structures of the $EGFR_{287-302}$ peptide epitope bound to Fabs of antibodies mAb806 and mAb175. In the presence of the antibody, the peptide epitope adopts a conformation very similar to that found in both forms of the receptor. However, binding the mAb806 or mAb175 antibodies to the wtEGFR structure would be prohibited by significant steric clashes of the Fab with the CR1 domain in both the tethered and untethered conformations. Examination of the 3D conformation of the CR1 domain suggested that breaking of a disulfide bond just before the epitope should allow the CR1 domain to open up sufficiently to allow binding of either antibodies. The cystine mutant $EGFR_{C271A/C283A}$ not only binds mAb806 and mAb175, but the stoichiometry is 1:1 (i.e. equivalent to mAb528 which recognizes the EGFR L2 ligand binding domain). Whereas mAb806 fails to inhibit the in vitro growth of cells expressing wild-type EGFR, mAb806 inhibits completely, ligand associated stimulation of BaF/3 cells expressing $EGFR_{C271A/C283A}$. Our results indicate that the mechanisms of binding of antibodies mAb806 and mAb175 requires a form of the EGFR where the epitope is preferentially exposed either during receptor activation or through truncation or overexpression. Consequently, and in contrast to other EGFR antibodies, mAb806 preferentially localizes to the tumor in cancer patients overexpressing the EGFR. The mechanism of action suggests new approaches to the generation of antibodies for detection of tumors and for improving antibody/inhibitor killing of cancer cells with over-expressed, truncated or activated forms of receptors in the EGFR family Significance The EGFR is involved in stimulating the growth of many human tumors. Although inhibitors and antagonists have been used as therapeutic agents, success has been limited, in part by interfering with the EGFR on normal tissues and in part by the limited temporal action of some of the agents, ie Abs have longer action. The antibodies Mab806 and Mab175 recognize an unusual conformation of the receptor, which often occurs on tumor cells, but not normal cells. The three dimensional binding site of these antibodies on the EGFR identifies the unusual conformation which explains their tumor specificity. These antibodies synergize with other anti-EGFR agents to induce profound tumor killing in mice. The initial results in cancer patients using radiolabelled forms of the antibodies confirm the tumor selectivity.

Introduction

Understanding the activation of the EGFR by its family of ligands has been challenging but elegant genetic (1-3), biophysical (4-8) and more recently, crystallographic (9-17) studies have revealed many of the complex series of conformational changes and aggregation events required to activate the EGFR intracellular tyrosine kinase domain (18). Amidst these complexities it is apparent that in solution the EGFR extracellular domain adopts at least two fundamental conformations: an inactive tethered conformation and an active untethered or extended, ligand-bound "back-to-back" dimer. The EGFR was the first growth factor receptor to be associated with cancer (19;20). The EGFR is activated by autocrine ligands (19;21;22) and, in a high proportion of advanced gliomas, the EGFR receptor extracellular domain is truncated (23;24) and consequentially activated. Often the activation of the EGFR is required for the maintenance of the malignant state. Conversely, except for a small number of cells in hair follicles and Brunner's gland, in adult organisms the EGFR is expressed at low levels and is inactive in adult life.

Two major classes of agents have been developed to target the EGFR: tyrosine kinase inhibitors (TKI's) and monoclonal antibodies (mAb's). TKI's such as gefitinib (ZD1839) and erlotinib (OSI-774) competitively bind to the ATP pocket of EGFR to inhibit its activation. In contrast, antibodies against EGFR, such as cetuximab (C225) and panitumumab (ABX-EGFR) competitively inhibit ligand binding and thereby prevent receptor activation. Both classes of the inhibitors and antibodies display significant anti-tumor activity in a range of EGFR-dependant mouse xenograft models (25-29) and both have been approved in select cancers including NSCL, pancreatic, head & neck and colon (30-32). While response rates to these EGFR therapeutics are modest, it is hoped that successful identification of patient sub-sets likely to respond to EGFR blockade will be able to improve on outcomes for the patients. In glioma for example, response to Tarceva appears largely restricted to a sub-set of patients who are double positive for Δ2-7EGFR (also called EGFRvIII), the extracellular truncation of the EGFR commonly expressed in glioma, and PTEN (33). While these therapeutics show promise, their use is restricted by dose limiting toxicities such as skin rash, which results from significant uptake of these agents in normal skin where EGFR expression is significant.

Many gliomas over-express EGFR (23;34), predominantly due to amplification of the EGFR gene. EGFR gene amplification in glioma is also associated with a mutation event that leads to the excision of exons 2-7 (34) and the subsequent expression of a truncated, partially activated Δ2-7 EGFR form of the EGFR (35;36) mentioned above. The Δ2-7 EGFR contains a unique fusion peptide at the N-terminus resulting from the splicing together of exons 1 and 8 and the insertion of an unique glycine. Several monoclonal antibodies directed to this junctional peptide have been described (34) and therefore represent potential therapeutics specific for the Δ2-7 EGFR. We generated a panel of Δ2-7 EGFR specific antibodies using NR6 cells (as variant of 3T3 devoid of endogenous EGFR family member) over-expressing this truncated EGFR. While showing robust binding to the Δ2-7 EGFR, some of these antibodies also bind wtEGFR when over-expressed but not when it was expressed at physiological levels. The best described of these antibodies MAb806 (35;37;38), appears not to bind cells expressing less than $1\times10^5$ EGFR on their surface, but only where higher expression levels lead to a distinct population of mAb806 reactive EGFR (5-10% of the total receptor population) (35, 37, 38).

Subsequent epitope mapping studies have shown that mAb806 binds to a short cysteine loop between amino acids 287-302 on the extracellular domain that is only exposed transiently as the EGFR moves from the tethered to the extended conformation (23,28). Thus, mAb806 reactivity is found only in cells with favorable conditions for receptor untethering, such as the presence of mutations (e.g. Δ2-7 EGFR), over-expression or activation of the receptor. In the case of EGFR over-expression, there appears to be increased untethering as a result of both ligand-independent EGFR activation and changes in glycosylation (39). These conditions are common in tumour cells but are rare in normal tissues, thereby allowing mAb806 to preferentially target tumour cells over normal tissues, such as the liver. Indeed, the results from our recently completed Phase I clinical trial with a chimeric version of mAb806 demonstrates that the epitope targeted by this antibody is not exposed on normal tissue but is accessible on a range of EGFR positive tumors (28;40). In xenografts mAb806 has shown robust anti-tumor activity against U87MG glioma cells expressing the Δ2-7 EGFR, as well as a range of other models that over-express the wtEGFR in absence of the this mutation (28;40). Furthermore, mAb806 shows synergistic anti-tumor activity in animal models when used in combination with other EGFR therapeutics, including EGFR kinase inhibitors (27) and antibodies (41). with unrelated epitopes The EGFR amino acid sequence between cysteine residues 287 and 302 is sufficient for the binding mAb806. However, while the truncation found in the Δ2-7 EGFR clearly exposes this cysteine loop for binding by mAb806, the mechanism of mAb806-wtEGFR binding has only been partially resolved. The crystal structure of the EGFR has been solved for both the full length extracellular domain and EGFR-ECD$_{1-501}$ fragment bound to ligand. Analysis of these structures make it evident that mAb806 could not bind to either the tethered EGFR as observed in the full length ECD structure (13) or to the ligand-bound, untethered, back-to-back dimer seen with the EGFR-ECD$_{1-501}$ (14) or EGFR-ECD$_{1-621}$ (42) constructs. Therefore, we have proposed that mAb806 binds to a partially untethered form of the wtEGFR that exist between the inactive and active states. The inability of mAb806 to bind to the ligated, untethered EGFR was further confirmed by pre-incubating wtEGFR expressing BaF/3 cells with EGF under conditions that prevented receptor internalization. Under these conditions a larger percentage of the EGFR should form ligated back-to-back dimers, thus preventing mAb806 binding; an observation that was clearly confirmed (43). However, the effect of ligand on mAb806 binding in a steady state, such as might occur in cells with a robust EGFR/ligand autocrine loop, is unknown. Interestingly, while binding of mAb806 to cell surface wtEGFR is dependant on the conformation of the receptor, in the immunological sense, the epitope is not conformational as mAb806 is an excellent probe for EGFR in Western blots, i.e. it is capable of recognizing the denatured receptor. Clearly, accessibility to the epitope as determined by EGFR conformation, is the most critical factor with respect to mAb806 binding, not the conformation of the epitope itself. MAb806 also binds to EGFR immobilized on plastic and surface plasmon resonance chips (37).

In this report we also describe the biological activity, specificity and epitope of other antibodies, raised in the same manner as mAb806. In order to understand the unique specificity of these antibodies we determined the 3D structures for the mAb806 peptide epitope (EGFR$_{287-302}$) bound to the Fab fragment of mAb806 and mAb175 and the free Fab fragments. The orientation of EGFR$_{287-302}$ on the receptor and the conformation of this peptide bound to antibody confirmed that mAb806 must bind a specific form of the EGFR and that this form must be folded differently to the wtEGFR observed in either the tethered or extended conformation. Using point mutations we examine the influence of an adjacent cysteine loop (amino acids 271-283) on EGFR structure and mAb806/175 reactivity as this loop appears to severely restrict binding of these antibodies. We report the efficacy of mAb806 and 175 against DU145 xenografts, a prostate cell line that possesses a robust TGF-α/EGFR autocrine stimulation loop, and the binding of radiolabeled-mAb806 to a head and neck cancer patient being treated in a Phase I setting (44).

Results mAb175 Specificity

Preliminary binding studies suggested that mAb175 displayed similar specificity for EGFR as mAb806. In the CDR regions of mAb806 (IgG2b) and maB175 (IgG1), the amino acid sequences are almost identical, with only one amino acid difference in each (FIG. 1). All these differences preserve the charge and size of the side-chains. Clearly, these antibodies have arisen independently.

We conducted a set of immunohistochemistry experiments to analyze the specificity of mAb175 binding. mAb 175 stains sections of A431 xenografts that over-express the EGFR (FIG. 2A) and sections of U87MG.Δ2-7 glioma xenografts that express the Δ2-7EGFR (FIG. 2A). In contrast, mAb175 does not stain U87MG xenograft sections. The U87MG cell line only expresses modest levels of the wild type EGFR (FIG. 2A) and has no detectable EGFR autocrine loop. Most importantly, mAb175 does not bind to normal human liver sections (FIG. 2B). Thus, mAb175 appears to demonstrate the same specificity as mAb806: i.e. it detects over-expressed and truncated human EGFR, but not the wtEGFR expressed at modest levels.

Identification of the mAb175 Epitope

Figure 9:
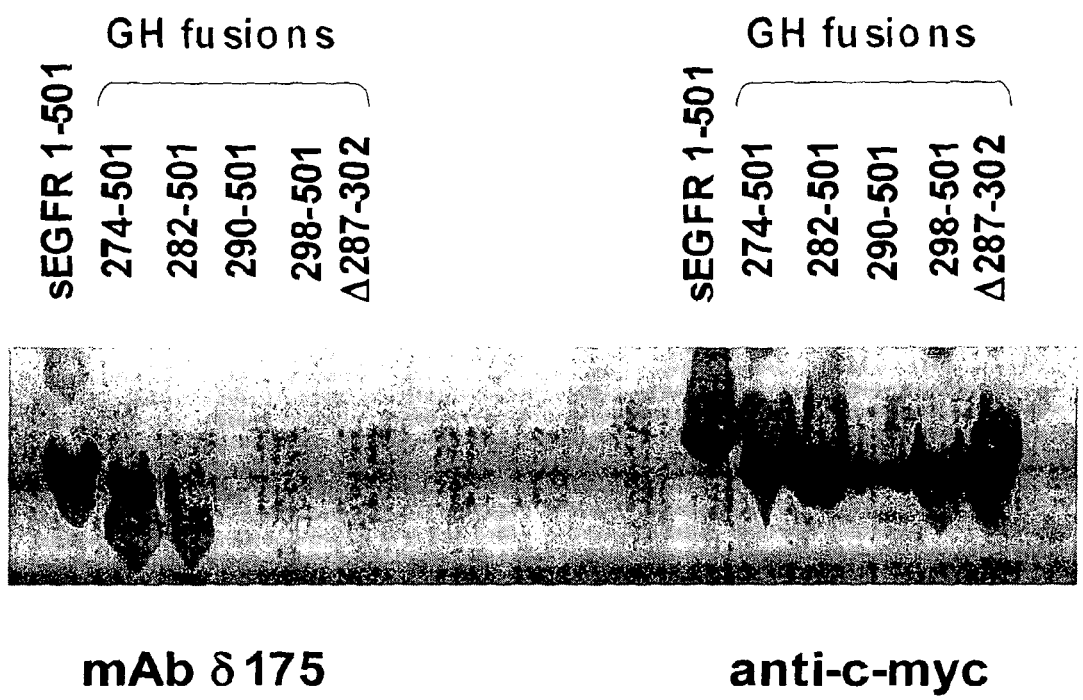
FIG. 9: Reactivity of mAb806 with fragments of the EGFR. Lysates from 293T cells transfected with vectors expressing the soluble 1-501 EGFR fragment or GH/EGFR fragment fusion proteins (GH-274-501, GH-282-501, GH-290-501 and GH-298-501) were resolved by SDS-PAGE, transferred to membrane and immunoblotted with mAb806 (left panel) or the anti-myc antibody 9B11 (right panel).

Since mAb175 also binds the Δ2-7EGFR, in which amino acids 6-273 are deleted, and EGFR$_{1-501}$, the mAb175 epitope must be contained within residues 274-501. When determining the epitope of mAb806, we expressed a series of c-myc-tagged EGFR fragments fused to the carboxy terminus of human GH, all terminating at amino acid 501(45;46). The mAb175 also reacted with both the 274-501 and 282-501 EGFR fragments in Western blots, but did not detect fragments commencing at amino acid 290 or 298 (Supplemental FIG. 9). The presence of all GH-EGFR fusion proteins was confirmed using the c-myc antibody, 9E10 (Supplemental FIG. 9). Therefore, a critical determinant of the mAb175 epitope is located near amino acid 290. Finally, a 274-501 EGFR fragment with the mAb806 epitope deleted (Δ287-302) was also negative for mAb175 binding (FIG. 9), suggesting that this region similarly determined most of the mAb175 binding.

Figure 3:
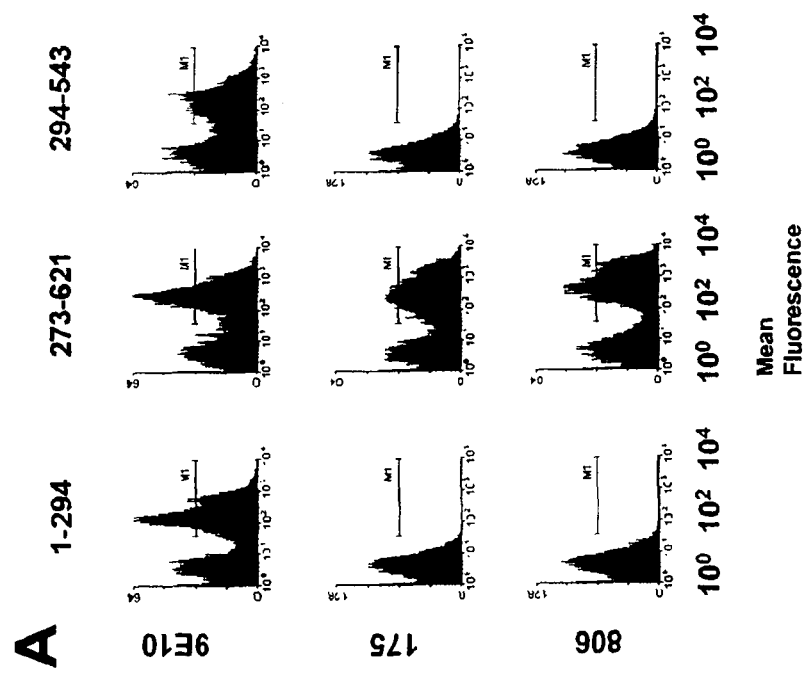
FIG. 3: Reactivity of mAb806 and mAb175 with fragments of the EGFR displayed on yeast. A: Representative flow cytometry histograms depicting the mean fluorescence signal of mAb175 and mAb806 labeling of yeast-displayed EGFR fragments. With yeast display a percentage of cells do not express protein on their surface resulting in 2 histogram peaks. The 9E10 antibody is used as a positive control as all fragments contain a linear C-terminal c-myc tag. B: Summary of antibody binding to various EGFR fragments. C: The EGFR fragments were denatured by heating yeast pellets to 80° C. for 30 min. The c-myc tag was still recognized by the 9E10 anti-myc antibody in all cases, demonstrating that heat treatment does not compromise the yeast surface displayed protein. The conformation sensitive EGFR antibody mAb 225 was used to confirm denaturation.

We used a second approach to characterize the mAb epitope further. Fragments encompassing extracellular domains of the EGFR were expressed on the surface of yeast and tested for mAb175 binding by indirect immunofluorescence using flow cytometry. The mAb175 recognized the yeast fragment 273-621, which corresponds to the extracellular domain of the Δ2-7 EGFR, but not to fragments 1-176, 1-294, 294-543 or 475-621 (FIGS. 3A and 3B). Thus, at least part of the mAb175 epitope must be contained within the region between amino acids 274-294, agreeing with our immunoblotting data using EGFR fragments. Since mAb175 binds to the denatured fragment of the 273-621 (FIG. 3C), the epitope must be linear in nature (Supplemental FIG. 9). It is clear that mAb 806 and mAb175 recognize a similar region and conformation of the EGFR.

Using surface plasmon resonance (BIAcore) we investigated the binding of mAb175 to the EGFR peptide ($_{287}$CGADSYEMEEDGVRKC$_{302}$(SEQ ID NO: 14)). The EGFR$_{287-302}$ was immobilized on the biosensor surface using amine, thiol-disulfide exchange or Pms-Ser coupling chemistries. The latter method immobilizes the peptide exclusively through the N-terminal cysteine (47). mAb175 bound the EGFR$_{287-302}$ in all orientations (Table 1). The affinity of mAb175 for EGFR$_{287-302}$ ranged from 35 nM for Pms-serine coupling to 154 nM for amine coupling. In all cases the binding affinity of mAb175 for EGFR$_{287-302}$ was lower than that obtained for mAb806 (Table 1). We also determined the affinity of mAb175 to two different extracellular fragments of the EGFR. mAb175 bound the 1-501 fragment with an affinity similar to that obtained using the peptide (16 nM versus 35 nM) (Table 1). As expected, the affinity of mAb against the 1-621 full length extracellular domain, which can form the tethered conformation, was much lower (188 nM). Although mAb806 and mAb 175 have similar affinities for EGFR$_{287-302}$, mAb175 appears to display a higher affinity for the extra-cellular domain of the EGFR (Table 1). Clearly, the mAb175 epitope is contained within the EGFR$_{287-302}$ and, like mAb806, the binding affinity to extra-cellular domain of the EGFR is dependent on conformation.

TABLE 1

BIAcore determination of antibody affinities for mAb806 and mAb175 binding to EGFR epitopes

| EGFR Fragment | $K_D$ for mAb175 (nM) | $K_D$ for mAb806 (nM) |
| --- | --- | --- |
| 287-302 (Pms-Ser coupling) | 35 | 16 |
| 287-302 (Thiol coupling) | 143 | 84 |
| 287-302 (Amine coupling) | 154 | 85 |
| 1-501 (Unable to form tether) | 16 | 34 |
| 1-621 (Can form tether) | 188 | 389 |

The panel of mutants of the 273-621 EGFR fragment, expressed on the surface of yeast (45;46), was used to characterize the fine structure of the mAb175 epitope. mAb175 and mAb806 displayed a near identical pattern of reactivity to the mutants (Table 2). Disruption of the 287-302 disulfide bond only had a moderate effect on the epitope reactivity as the antibody bound to all mutants at C287 and to some but not all mutants at C302 (Table 2). Amino acids critical for mAb175 binding include E293, G298, V299, 8300 and C302 (Table 2). mAb175 appeared moderately more sensitive to mutations V299 and D297 but mAb806 also showed reduced binding to some mutations at these sites (Table 2). Again, the mAb175 epitope appears to be essentially the same as the epitope recognized by mAb806.

TABLE 2

Display of EGFR Epitope 287-302 mutations on yeast and the binding scores for mAb806 and mAb175

| EGFR Mutant | mAb806 Binding | mAb175 Binding |
| --- | --- | --- |
| C287A | + | + |
| C287G | + | + |
| C287R | + | + |
| C287S | + | + |
| C287W | + | + |
| C287Y | + | + |
| G288A | ++ | ++ |
| A289K | ++ | ++ |
| D290A | ++ | ++ |
| S291A | ++ | ++ |
| Y292A | ++ | ++ |
| E293A | + | + |
| E293D | + | + |
| E293G | + | + |
| E293K | − | − |
| M294A | ++ | ++ |
| E295A | ++ | ++ |
| E296A | ++ | ++ |
| D297A | ++ | + in contact |
| D297Y | + | + |
| G298A | + | + |
| G298D | − | − |
| G298S | − | − |
| V299A | ++ | + in contact |
| V299D | − | − |
| V299K | ++ | + in contact |
| R300A | ++ | ++ |
| R300C | + | + |
| R300P | − | − |
| K301A | ++ | ++ |
| K301E | + | + |
| C302A | − | − |
| C302F | + | + |
| C302G | − | − |
| C302R | + | + |
| C302S | − | − |
| C302Y | + | + |

Efficacy of mAb175 Against Tumor Xenografts Stimulated by Δ2-7EGFR or an EGFR Autocrine Loop.

We examined the in vivo anti-tumor activity of mAb806 and mAb175 against U87MG.Δ2-7 glioma xenografts. Xenografts were allowed to establish for 6 days before antibody therapy (3 times a week for 2 weeks on days indicated) commenced. At this time the average tumor volume was 100 mm$^3$ (FIG. 4A). mAb175 treatment resulted in a reduction in overall tumor growth rate compared to treatment with vehicle or mAb806 and was highly significant at day 19 post-inoculation (P<0.0001 versus control and P<0.002 versus ma 806), when the control group was sacrificed for ethical reasons. The average tumor volume at this time was 1530, 300 and 100 mm$^3$ for the vehicle, mAb806 and mAb175 treatment groups, respectively (FIG. 4A), confirming mAb175 is anti-tumor activity against xenografts expressing the Δ2-7 EGFR.

Figure 4:
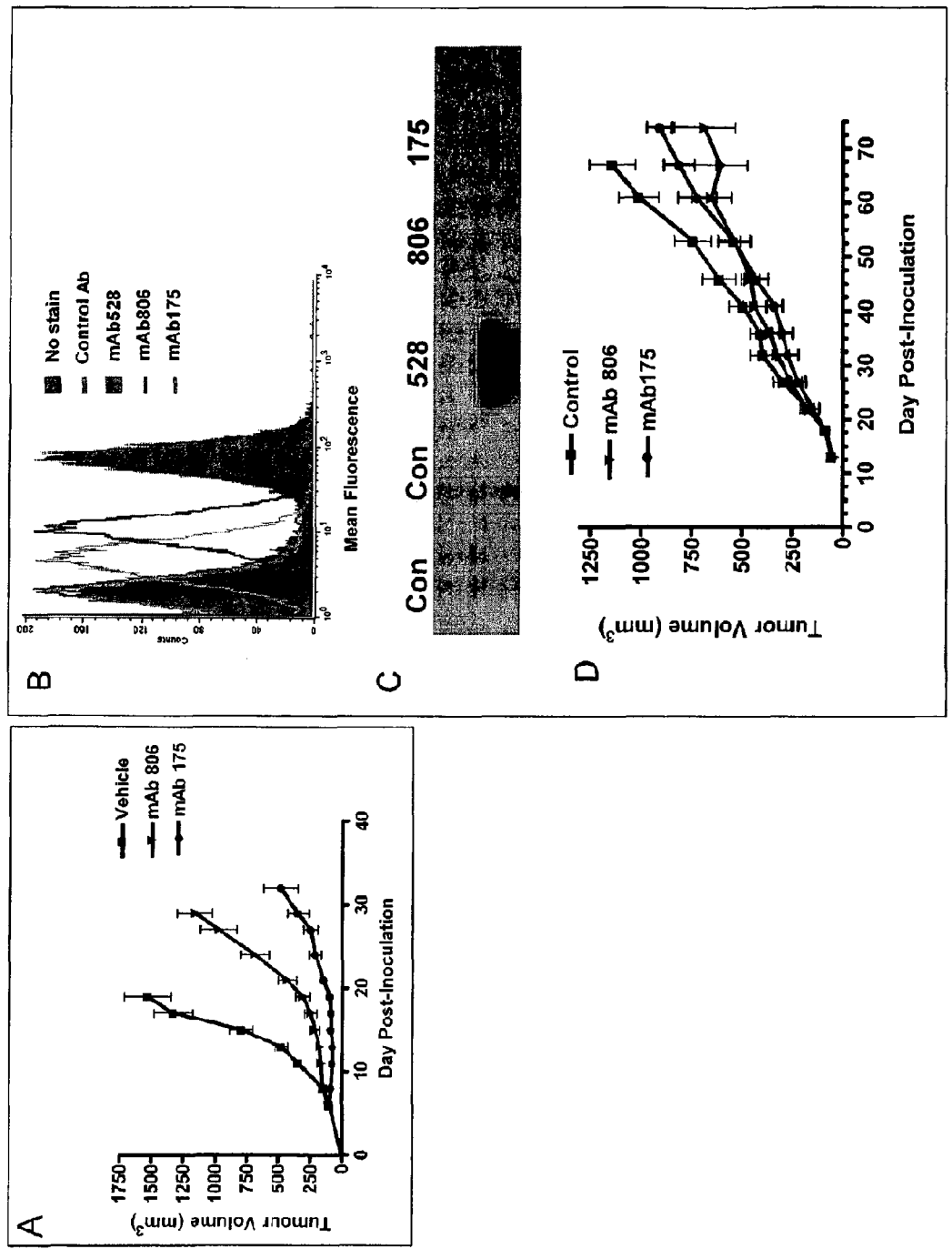
FIG. 4: Antitumor effects of mAb175 on brain and prostate cancer xenografts. A: Mice (n=5) bearing U87MG.Δ2-7 xenografts were injected i.p. with PBS, 1 mg of mAb175 or mAb806 (positive control), three times weekly for two weeks on days 6, 8, 10, 13, 15 and 17 when the starting tumor volume was 100 mm$^3$. Data are expressed as mean tumor volume±SE. B: Cells were stained with two irrelevant antibodies (blue, solid and green, hollow), mAb 528 for total EGFR (pink, solid), mAb806 (light blue, hollow) and mAb175 (orange, hollow) and then analyzed by FACS. C: DU145 cells were lysed, subjected to IP with mAb 528, mAb806, mAb175 or two independent irrelevant antibodies and then immunoblotted for EGFR. D: Mice (n=5) bearing DU145 xenografts were injected i.p. with PBS, 1 mg of mAb175 or mAb806, daily on days 18-22, 25-29 and 39-43 when the starting tumor volume was 85 mm$^3$. Data are expressed as mean tumor volume±SE.

Even though U87MG cells express approximately $1×10^5$ EGFR per cell, mAb 806 is not able to recognize any of the surface EGFR, and not surprisingly, does not inhibit U87MG in vivo growth. Furthermore these cells do not co-express any EGFR ligand. To test whether the EGFR epitope is transiently exposed and hence able to be recognized by mAb806 and mAb175 in cells containing an EGFR autocrine loop. The prostate cell line DU145 expresses the wtEGFR at levels similar to that observed in U87MG cells, however unlike the U87MG cells, the DU145 cells contain an amplification of the TGF-α gene and thus exhibit an EGFR/TGF-α autocrine loop. Both mAb175 and 806 bind to DU145 cells as determined by FACS analysis (FIG. 4B) and both are able to immunoprecipitate a small proportion of the EGFR extracted from these cells (FIG. 4C). Both techniques showed greater binding of mAb175, however, when compared to mAb 528, which binds to the L2 domain, mAb175 and mAb806 only bind a subset of EGFR on the surface of these cells (FIGS. 4B and 4C). Similar observations were seen with a second prostate cell line (LnCap); (data not shown) and a colon line (LIM1215) both of which also contain EGFR autocrine loops (22;48). Clearly, mAb806 and mAb175 can recognize only a small proportion of the EGFR on cells in the presence of an autocrine stimulation loop.

Since mAb175 and mAb806 bind more effectively to the EGFR expressed in DU145 cells than U87MG cells, we conducted a study to analyse the anti-tumor activity of these antibodies in DU145 xenografts grown in nude mice. Xenografts were allowed to establish for 18 days before therapy commenced (3 times a week for 3 weeks on days indicated). At this time the average tumor volume was 90 mm³ (FIG. 4D). Both mAb175 and mAb806 inhibited the growth of DU145 xenografts. The control group was sacrificed on day 67 and had a mean tumor volume of 1145 mm³ compared with 605 and 815 mm³ for the mAb806 and mAb175 groups respectively (p<0.007 and 0.02 respectively) (FIG. 4D).

3D-Structure of $EGFR_{287-302}$ in Contact with the Fab Fragments of mAb806 and mAb175

Figure 5:
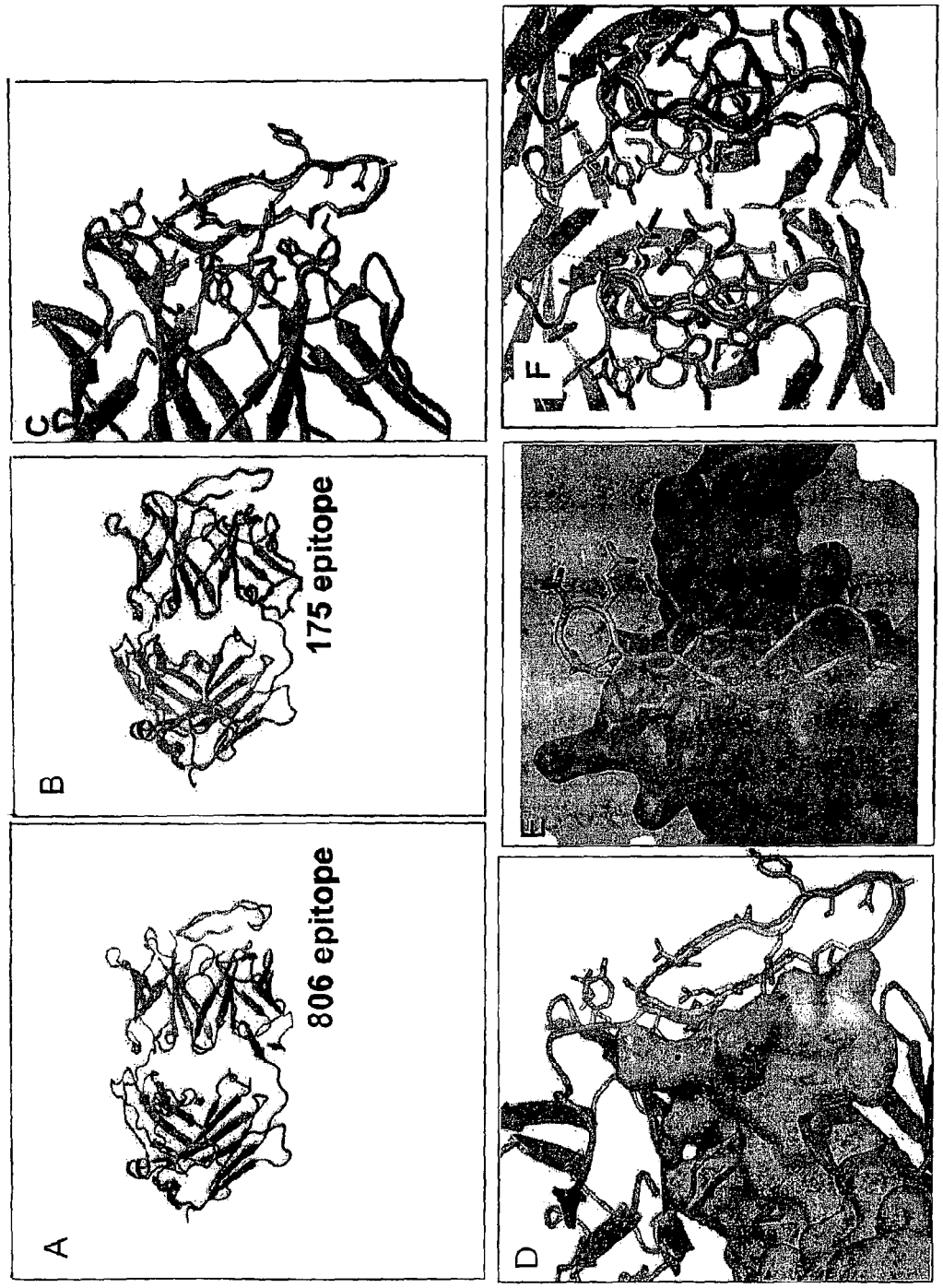
FIG. 5: Crystal structures of EGFR peptide 287-302 bound to the Fab fragments (A) Cartoon of Fab 806, with the light chain, red; heavy chain, blue; bound peptide, yellow; and the superposed $EGFR_{287-302}$ from EGFR, purple. (B) Cartoon of Fab 175 with the light chain, yellow; heavy chain, green; bound peptide, lilac; and $EGFR_{287-302}$ from EGFR (D1-3), purple. (C) Detail from (B) showing the similarity of $EGFR_{287-302}$ in the receptor to the peptide bound to FAb175. Peptides backbones are shown as Cα traces and the interacting side chains as sticks. O atoms are coloured red; N, blue; S, orange and C, as for the main chain. (D) Superposition of EGFR with the Fab175:peptide complex showing spacial overlap. Colouring as in (C) with the surface of EGFR187-286 colored turquoise. (E) Orthogonal view to (D) with EGFR187-286 shown in opaque blue and the surface of the light (orange) and heavy (green) chains transparent. (F) Detailed stereoview of 175 Fab complex looking into the antigen-binding site. Colouring as in (C) and side chain hydrogen bonds dotted in black. Water molecules buried upon complex formation are shown as red spheres.

In order to understand the molecular details of how mAb806 and mAb175 could recognise EGFR in some, but not all conformations, the crystal structures of Fab fragments for both antibodies were determined in complex with the oxidized $EGFR_{287-302}$ epitope (at 2.0 and 1.59 Å resolution respectively, FIGS. 5A & 5B) and alone (at 2.3 Å and 2.8 Å resolution, respectively). In both cases, the free and complexed Fab structures were essentially the same and the conformations of the peptide and CDR loops of the antibodies were well defined (FIG. 5). The epitope adopts a β-ribbon structure, with one edge of the ribbon pointing towards the Fab and V299 buried at the centre of the antigen-binding site (FIG. 5C-E). Both ends of the epitope are exposed to solvent, consistent with these antibodies binding much longer polypeptides.

Of the 20 antibody residues in contact with the epitope, there are only two substitutions between mAb806 and mAb175 (FIG. 1). mAb175 contact residues are: light-chain S30, S31, N32, Y49, H50, Y91, F94, W96 and heavy-chain D32, Y33, A34, Y51, S53, Y54, S55, N57, R59, A99, G100, R101; the mAb806 contact residues are the same, with sequence differences for the light-chain, N30 and heavy-chain, F33. $EGFR_{287-302}$ binds to the Fab through close contacts between peptide residues 293-302, with most of the contacts being between residues 297 and 302. The only hydrogen bonds between main chain atoms of $EGFR_{287-302}$ and the Fab are for residues 300 and 302 (FIG. 5F). Recognition of the epitope sequence occurs through side-chain hydrogen bonds to residues E293 (to H50 and R101 of the Fab), D297 (to Y51 and N57), R300 (to D32) and K301 (via water molecules to Y51 and W96). Hydrophobic contacts are made at G298, V299 and C302.

The conformation of the epitope backbone between 293 and 302 was essentially identical in the Fab806 and Fab175 crystals (rms deviation=0.4 Å, for Cα atoms in these residues). Although constrained by the disulfide bond, the N-terminus of the peptide (287-292) does not make significant contact in either antibody structure and conformations in this region differ. However, this segment in the Fab806 complex appears rather disordered. More interestingly, the conformation of the $EGFR_{287-302}$ peptide in contact with the antibodies is quite closely related to the $EGFR_{287-302}$ conformation observed in the backbone of the tethered or untethered EGFR structures (Li et al., 2005; Garrett et al., 2002). For $EGFR_{287-302}$ from the Fab175 complex, the rms deviations in Cα positions are 0.66 and 0.75 Å, respectively (FIG. 5).

To gain further insight into the recognition of EGFR by mAb806 and mAb175, the conformation of $^{15}N$ labelled oxidized peptide $EGFR_{287-302}$ was studied by NMR spectroscopy in solution, free and in the presence of 806 Fab (see Supplemental Data for details). For the free peptide, resonances were assigned and compared to those for random coil. Essentially, the free peptide adopted a random coil structure, not the beta ribbon as seen in the native EGFR (14). Upon addition of the Fab, resonance shifts were observed. However, due to the weak signal arising from significant line broadening upon addition of the Fab and successful crystallisation of the complexes, the solution structure of the Fab806-epitope complex was not pursued further. Clearly though, when the peptide binds to the Fab fragment of mAb806 (or mAb175) it appears that the Fab selects or induces the conformation of the peptide which matches that peptide in the native receptor.

Why do mAb806 and mAb175 recognise only some conformations of EGFR? We docked the Fab fragment of mAb175 onto an extra-cellular domain of EGFR (tethered and untethered monomers) by superimposing $EGFR_{287-302}$. For a Δ2-7-like fragment there were no significant steric clashes with the receptor. In the untethered form there was substantially more accessible surface area of the Fab buried (920 Å² compared with 550 Å² in the tethered form). Therefore, this antigen may make additional contacts with non-CDR regions of the antibody, as has been indicated by yeast expression mutants (45). Conversely, docking the whole EGFR ectodomain onto the Fab, there is substantial spatial overlap with the part of the CR1 domain preceding the epitope (residues 187-286) and running through the centre of the Fab (FIG. 5D, E). Hence, as the CR1 domain has essentially the same structure in tethered or untethered conformations, mAb806 or mAb175 will be unable to bind to either form of EGFR. Clearly, there must be a difference between the orientation of the epitope with respect to the CR1 domain in either known conformations of the wtEGFR and the orientation that permits epitope binding. Inspection of the CR1 domain indicated that the disulfide bond (271-283) preceding $EGFR_{287-302}$ constrains the polypeptide which blocks access to the epitope; disruption of this disulfide, even though it is not involved in direct binding to the antibodies, would be expected to allow partial unfolding of the CR1 domain so that mAb175 or mAb806 could gain access to the epitope.

Breaking of the EGFR 271-283 Disulfide Bond Increases mAb806 Binding

Disulfide bonds in proteins provide increased structural rigidity but in some cell surface receptors, particularly those for cytokines and growth factors, transient breaking of disulfide bonds and disulfide exchange can control the receptor's function (49). As this was one mechanism by which mAb806 and mAb175 could gain access to their binding site, we attempted to increase the accessibility of the epitope by mutating either or both of the cysteine residues at positions 271 and 283 to alanine residues (C271A/C283A). The vectors capable of expressing full length C271A-, C283A- or C271A/C283A-EGFR were transfected into the IL-3 dependent Ba/F3 cell line. Stable Ba/F3 clones, which expressed the C271A- and C271A/C283A-EGFR mutant at levels equivalent to the wtEGFR were selected (FIG. 6A). Ba/F3 cells expressing high levels of mutant C283A-EGFR were not observed. As previously described, the wtEGFR reacts poorly with mAb806; however, the mutant receptors reacted equally strongly with mAb528, mAb806 and the anti-FLAG antibody, suggesting that the receptor is expressed at the cell surface, is folded correctly and that the epitope for mAb806 is completely accessible in such cases. To confirm that mAb806 recognizes the C271A/C283A mutant more efficiently than the wtEGFR, we determined the ratio of mAb806 binding to the binding of mAb528. Since both the wt and C271A/C283A EGFR were N-terminally FLAG-tagged, we also determined the ratio of mAb806 and mAb528 binding to the M2 antibody. As reported previously, mAb806 only recognized a small proportion of the total wtEGFR expressed on the surface of Ba/F3 cells (the mAb806/528 binding ratio is 0.08) (Table 3). In contrast, mAb806 recognized virtually all of the C271A/C283A mutant EGFR expressed on the cell surface (an mAb806/528 binding ratio of 1.01) (FIG. 6A and Table 3).

TABLE 3 mAb806 reactivity with cells expressing the wt or C271A/C283A EGFR

| Cell Line | Ratios of antibody binding | | |
| --- | --- | --- | --- |
| | mAb 528/M2 | mAb806/M2 | mAb806/mAb 528 |
| wtEGFR-FLAG | 1.37 | 0.11 | 0.08 |
| wt-EGFR | — | — | 0.07 |
| C271/283A* | 1.08 ± 0.10 | 1.09 ± 0.38 | 1.01 ± 0.13 |

*Average of four independent clones.

Mutation of the two cysteines did not compromise EGF binding or receptor function. BaF3 cells expressing the C271A/C283A EGFR mutant proliferate in the presence of EGF (FIG. 6B). We have reproducibly observed a left-shift in the dose response curve for EGF in cells expressing the C271A/C283A mutations, suggesting either higher affinity for the ligand, or enhanced signaling potential for the mutant receptor. Western blotting analysis confirmed that the C271A/C283A mutant is expressed at similar levels to the wtEGFR and is tyrosine phosphorylated in response to EGF stimulation (FIG. 6C). Consistent with previous studies in other cell lines, mAb806 has no effect on the in vitro EGF-induced proliferation of Ba/F3 cells expressing the wtEGFR, while the ligand blocking mAb 528 completely inhibits the EGF-induced proliferation of these cells (FIG. 6D, left panel). In contrast, mAb806 totally ablated the EGF-induced proliferation in BaF3 cells expressing the C271/283A mutant (FIG. 6D, right panel). When the 271-283 cysteine loop is disrupted, not only does mAb806 bind more effectively, but once bound, mAb806 prevents ligand induced proliferation.

Phase I Imaging Study in Head and Neck Cancer

Figure 7:
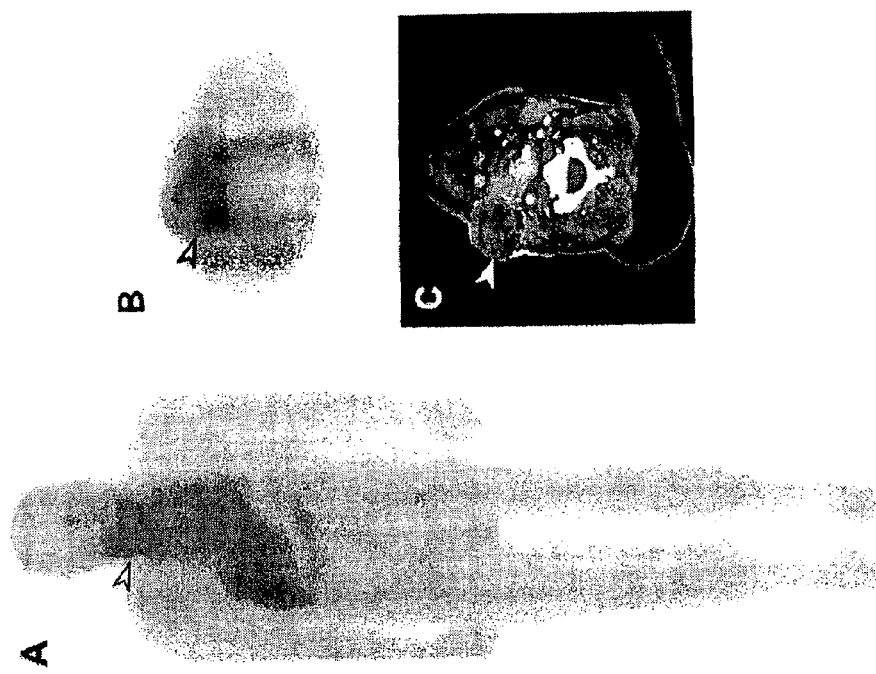
FIG. 7: A) Whole body gamma camera image of the biodistribution of $^{111}$In-ch806 in a patient with metastatic squamous cell carcinoma of the vocal cord, showing quantitative high uptake in tumour in the right neck (arrow). Blood pool activity, and minor catabolism of free $^{111}$In in liver, is also seen. B) Single Photon Computed Tomography (SPECT) image of the neck of this patient, showing uptake of $^{111}$In-ch806 in viable tumor (arrow), with reduced central uptake indicating necrosis. C) Corresponding CT scan of the neck demonstrating a large right neck tumour mass (arrow) with central necrosis.

Eight patients [1 female and 7 male; mean age of 61 years (range 44-75)] completed this phase 1 trial as reported (44). All patients fulfilled inclusion criteria and, except for Patient 8 (who had a primary brain tumor), all had metastatic disease at study entry. Ab uptake by the tumor was seen in all patients, and $^{111}$In-ch806, the chermerized version of mAb806, demonstrated prompt and high level uptake in tumor (FIG. 7). The clearance of $^{111}$In-ch806 from normal organs (liver, lungs, kidney and spleen) showed no difference between dose levels (44). In particular, liver clearance showed no difference between dose levels, indicating no saturable antigen compartment in the liver for ch806. Total liver uptake was a maximum of 14.45±2.43% ID immediately post infusion, and declined to 8.45±1.63% ID by 72 hours, and 3.18±0.87% ID by one week post infusion. This is in marked contrast to the uptake of antibodies to wtEGFR (eg 225), which have been shown to reach over 30% ID in liver (for a 40 mg dose) for over 3 days post infusion (50).

The measured peak tumor uptake of $^{111}$In-ch806 occurred 5-7 days post infusion. Calculation of quantitative tumor uptake in Patients 1 and 3 could not be accurately performed due to proximity of target lesion to cardiac blood pool and patient movement. Peak ch806 uptake in tumor ranged from 5.21 to 13.73×10$^{-3}$% ID/gm tumor tissue. Calculation of actual ch806 concentration in tumor showed peak values of (mean±SD) 0.85±0 µg/gm (5 mg/m$^2$), 0.92±0 µg/gm (10 mg/m$^2$), 3.80±1.10 µg/gm (20 mg/m$^2$), and 7.05±1.40 µg/gm (40 mg/m$^2$).

Discussion

When the levels or activity of the EGFR or the related erbB2 are perturbed, antibodies such as cetuximab and herceptin, that target EGFR family members, are important options for treating cancer. Determining the binding sites for these antibodies, the 3D-structures of both the target receptors and more recently, the antibody:receptor complexes, has improved our understanding of how these antibodies interfere with receptor activation. These studies have also suggested that targeting other epitopes on this receptor family may produce a new opportunities for using combinations of antibodies to improve cancer treatment.

Unfortunately, all of the currently available therapeutic anti-EGFR antibodies recognize the wtEGFR, which is expressed in virtually all normal tissues. Not only do the EGFR expressed in normal tissues represent a large sink for the antibodies, they are likely to be critical in the dose limiting toxicity (such as skin rash) observed and make use of antibody/cytotoxic conjugates impossible. Despite these problems, it should be noted that most normal tissues appear to lack activated EGFR, thus neutralizing anti-EGFR antibodies appear not have a profound effect on vital homeostatic signaling. In contrast, many tumors contain activated EGFR, either through autocrine/paracrine mechanisms, truncation, mutation, gene amplification and/or over-expression. Importantly, activated EGFR seems to contribute to tumorgenicity by enhancing cell movement, proliferation, invasion, angiogenesis and survival of tumour cells. Consequently, the administration of anti-EGFR antibodies or EGFR kinase inhibitors can decrease the growth and survival of the tumor cells. Antibodies directed to the unique junctional peptide in the Δ2-7 EGFR have the potential to target several tumors (51) without the difficulties associated with normal tissue uptake. In glioma, the expression of the Δ2-7 EGFR is accompanied by over-expression of the wtEGFR which would not be inhibited by other Δ2-7 EGFR antibodies, but should be inhibited by mAb806 or mAb175.

Previously, we described an antibody, mAb806, which was raised against cells expressing Δ2-7 EGFR. Not only does mAb806 bind this truncated receptor, but also binds to over-expressed wtEGFR. Mab806 recognizes an epitope contained within a cysteine loop (amino acids 287-302) that is accessible in the Δ2-7 EGFR, but not in the wtEGFR when expressed at low to moderate levels on cells and in the absence of ligands. Similarly, purified, full-length extracellular domain of EGFR (EGFR$_{1-621}$). The epitope for this antibody was found to be near the hinge region of the EGFR extracellular domain that undergoes at change conformation during the formation of the active state. Furthermore, not only is the epitope buried in the inactive conformation, it also appeared to be inaccessible in the ligand bound back-to-back, untethered EGFR dimer. The intriguing properties of mAb806 prompted us to reanalyze other hybridomas expressing the monoclonal antibodies isolated from the initial fusion (38). In preliminary screens, one of these mAb175, appeared to have similar EGFR binding properties to mAb806. The amino acid sequences within their CDR loops are remarkably similar (90% sequence identity), and these differences preserve the size and charge of the relevant side chain. Like mAb806 the mAb175 stains tumor cells which over-express the EGFR or which express the Δ2-7 EGFR, but not cells with moderate levels of the wtEGFR, e.g. human liver. Detailed epitope mapping showed that not only does mAb175 bind the same cysteine loop as mAb806, but it also has a near identical binding profile to a series of mutants containing point mutations in this loop. Furthermore, neither antibody required the epitope disulfide bond to be intact for binding.

Both mAb806 and mAb175 possess anti-tumor activity against human glioma xenografts that express the Δ2-7 EGFR and both induce a significant delay in tumor growth, although mAb175 appeared slightly more potent in this model. Interestingly, mAb806 and mAb175 bind to the EGFR expressed on DU145 prostate cells, a cell line that expresses modest levels of EGFR but secretes significant amount of TGF-α(52) in an autocrine fashion. As with cell lines which over-express the EGFR, both antibodies only bind a small proportion of the surface EGFR on DU145 cells. However, both antibodies inhibit the growth of DU145 xenografts in nude mice. Thus, it appears that the presence of ligand under physiological conditions increases the availability of the transitional form of the EGFR recognized by these antibodies and targeting this form is sufficient to downregulate EGFR driven cell growth.

This class of anti-EGFR antibodies may well have even wider anti-tumor action than first envisaged. Furthermore, the synergistic activity of mAb806, when used in combination with other EGFR therapeutics (41), suggests an immediate therapeutic role for antibodies of this class. mAb806 also binds to tumor cells that contain cancer-associated mutations which activate the EGFR kinase. mAb806 and mAb175 selectively bind cells that have an activated EGFR and may be useful reagents for identifying and/or monitoring patients likely to respond to currently approved EGFR therapeutics.

Figure 8:
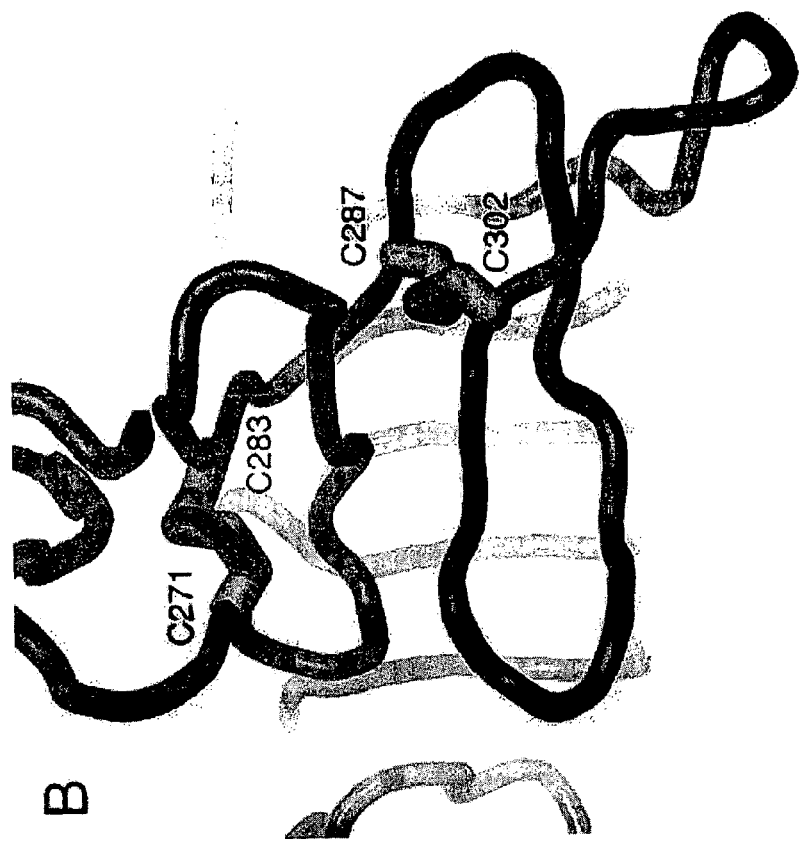
FIG. 8: A stereo model of the structure of the untethered EGFR1-621. The receptor backbone is traced in blue and the ligand TGF-α in red. The mAb806/175 epitope is drawn in turquoise and the disulfide bonds in yellow. The atoms of the disulfide bond which ties the epitope back into the receptor are shown in space-filling format. The model was constructed by docking the EGFR-ECD CR2 domain from the tethered conformation (13) onto the structure of an untethered EGFR monomer in the presence of its ligand (14).
Figure 8:
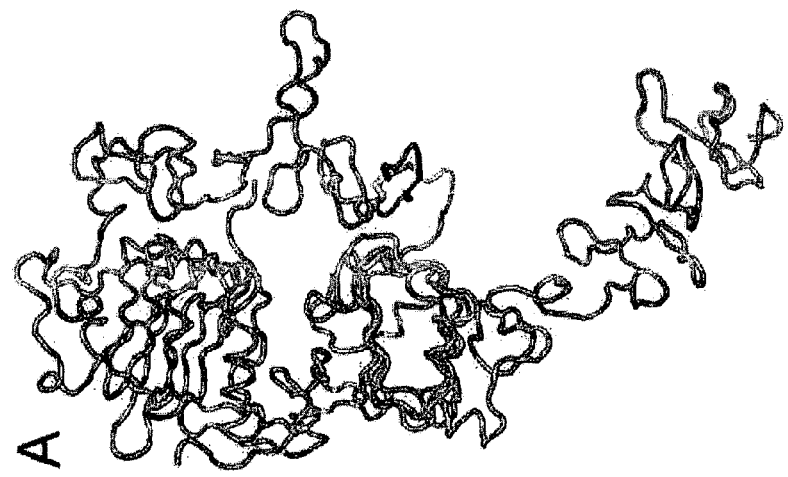

Our structural studies with the EGFR$_{287-302}$ epitope indicate that both mAb806 and mAb175 recognized the same 3D structural motif. The peptide residues in contact with mAb806 and mAb175 exhibited almost identical structures in both cases, suggesting that this is the conformation of these amino acid, found in Δ2-7 EGFR, the generating antigen. Indeed, the peptide backbone of EGFR$_{287-302}$ seen in the antibody/peptide structures closely matches that occurring in both known conformations of EGFR structure. However, the orientation of the epitope in these structures would prevent antibody access to the relevant amino acids: which is consistent with the experimental observation that antibody 806 does not bind wtEGFR. Detailed inspection of the EGFR structure raised another intriguing possibility. The EGFR$_{287-302}$ epitope hangs from a second disulfide bonded loop (amino acids 271-283) and disruption of this disulfide bond should allow access to the EGFR$_{287-302}$ loop without changing the backbone conformation of the epitope (see FIG. 8). Our results with the C271A/C283A EGFR mutant indicate that the CR1 domain must open up to allow mAb806 and 175 to bind stoichiometrically to the mutant receptor. This mutant receptor can still adopt a native conformation as it is fully responsive to EGF stimulation but, unlike the wtEGFR, is fully inhibited by mAb806.

On the surface of cells over-expressing the wtEGFR, there is clearly a sub-population of receptors in which the EGFR$_{287-302}$ epitope is accessible for mAb806 or mAb175 binding. While access most readily occurs during receptor activation, it is not yet clear whether this sub-population of receptors are those in conformational transition to the untethered form, those in transition from the untethered form to the ligated activated state, or whether there is incomplete oxidation in a sub-set of the EGFR in which the disulfide bond between 271 and 283 has been damaged (reduced). If a reduced form of EGFR does exist on the surface of cancer cells, our data clearly shows it is likely to be active and capable of initiating cell signaling. The ability of mAb806 to inhibit the growth of xenografts over-expressing the wtEGFR, despite only binding a small sub-population of receptors and not inhibiting signaling downstream of the EGFR, remains an enigma. For this reason the concept that mAb806 binds a unique sub-set of EGFR that has unusual signaling properties has always been appealing, especially given its tremendous synergy with other EGFR therapeutics. If it exists on the cell surface of cancer cells, an EGFR reduced at the 271-283 disulfide could represent this unique form of the EGFR. Finally, it should be remembered that while the deletion in the Δ2-7EGFR is very large, it does end at amino acid 273. The Δ2-7 EGFR lacks this disulfide bond and is known to have different signaling properties to the wtEGFR. On the other hand, activating kinase mutations, autocrine loops and under-glycosylation of the EGFR also enhance mAb806 reactivity by increasing activation of the receptor, presumably without the need of breaking the 271-283 disulfide. These observations support the concept that the CR1 domain can kink to allow access to EGFR$_{287-302}$ at some point during EGFR activation, but is protected from kinking in the tethered and ligand-bound states. We are currently conducting on-going studies to determine if the EGFR recognized by mAb806 contains a reduced 271-283 disulfide bond.

The analysis of the results of our Phase I trial of chimerized 806 (ch806) confirmed that the epitope targeted by mAb806 is tumor specific. Quantitative biodistribution analysis clearly demonstrates the rapid and specific uptake of ch806 in tumor. These data are consistent with the highest quantitative targeting of antibodies to antigens expressed on cancer cells and markedly superior to values of wtEGFR antibodies at equivalent doses (44;50). The uptake of ch806 in all normal tissues (including liver) was low, indicating no evidence of binding to wtEGFR in normal tissue, and in liver represented only blood pool activity and minor catabolism of free $^{111}$In-chelate. This is in marked distinction to antibodies that target wtEGFR (eg 225; Cetuximab), which have been shown to have very high uptake (20-30% ID) in liver retained for over 72 hours post infusion, despite large protein doses being administered (up to 300 mg)(50). In addition, antibodies to wtEGFR require large loading doses to saturate normal tissue before tumour uptake is evident (50), and also have dose limiting toxicity from antibody binding to wtEGFR in skin and gut (53). These results indicate that mAb806 does not target normal tissue in human, and quantitative analysis of biodistribution confirms the tumor specificity of the EGFR epitope targeted by mAb806 invivo.

Targeting the $EGFR_{287-302}$ epitope with antibodies derived from mAb806 or mAb175 is a way of attacking the activated EGFR in cancer cells with minimal uptake in normal tissue. Activation of the receptor can result from many of the mechanisms associated with cancer. Also, and possibly most importantly, these antibodies may be used to target cytotoxics, therapeutic nanoparticle, siRNA and radioisotopes directly to the tumor site. Finally, these studies confirm that mAb806 and mAb175 are valuable tools for helping map those events associated with EGFR activation on the cell surface.

In understanding, at a molecular level, how an antibody can recognise aberrant and activated forms of a growth factor receptor but not inactive wild-type receptor, this work can be used to generate antibodies to other targets for cancer therapeutics, for instance other members of the EGFR family. One method could use the disulfide mutant EGFR-C227A/C283A which binds antibodies mAb806 and mAb175 stoichiometrically. If conformational perturbations seen for EGFR also occur when erbB2, erbB3 or erbB4 are overexpressed or activated continuously, then homologous disulfide mutants of these receptors may act as immunogens for creating other EGFR family member targeting antibodies with selectivity for tumors. Furthermore, when tumor cells overexpress other receptors, particularly those with disulfide rich domains such as Trk, a proportion of these receptors may be partially misfolded due to underglycosylation or transiently broken disulfide bonds. It is conceivable that disulfide mutant or truncated receptors could be used similarly as immunogens to potentially generate antibodies which recognise other aberrantly expressed receptors.

Experimental Procedures
Cell Lines

The Δ2-7 EGFR transfected U87MG.Δ2-7(54) and the A431 cell lines (2) have been described previously. The hormone-independent prostate cell line DU145(55) was obtained from the ATCC (atcc.org). See Supplemental Data for growth conditions of the cell lines.

Antibodies, Fabs and peptides mAb806 and mAb175 were produced and purified in the Biological Production Facility (Ludwig Institute for Cancer Research, Melbourne). For preparation and characterization of the antibodies, antibody fragments and peptide epitope see Supplemental Data Mapping of mAb175 Using EGFR Fragments Expressed in Mammalian Cells and Yeast The mapping was performed as described in the Supplemental Data.

Surface Plasmon Resonance (BIAcore)

A BIAcore 3000 was used for all experiments. The peptides containing the putative mAb806 epitope were immobilized on a CM5 sensor chip using amine, thiol or Pms coupling at a flow rate of 5 μl/min(47). The mAb806 and mAb175 were passed over the sensor surface at a flow rate of 5 μl/min at 25° C. The surfaces were regenerated between runs by injecting 10 mM HCl at a flow rate of 10 μl/min.

Immunoprecipitation and Western Blotting

Cells were lysed with lysis buffer (1% Triton X-100, 30 mM HEPES, 150 mM NaCl, 500 mM 4-(2-aminoethyl)benzenesulfonylfluoride, 150 nM aprotinin, 1 mM E-64 protease inhibitor, 0.5 mM EDTA, and 1 mM leupeptin, pH 7.4) for 20 minutes, clarified by centrifugation at 14,000×g for 30 minutes, immunoprecipitated with the relevant antibodies at a final concentration of 5 μg/ml for 60 minutes and captured by Sepharose-A beads overnight. Samples were then eluted with 2× NuPAGE SDS Sample Buffer (Invitrogen), resolved on NuPAGE gels (either 3-8% or 4-12%), electro-transferred onto Immobilon-P transfer membrane (Millipore) then probed with the relevant antibodies before detection by chemoluminescence radiography.

Immunohistochemistry

Frozen sections were stained with 5 μg/ml mAb175 or irrelevant isotype control for 60 min at room temperature. Bound antibody was detected using the Dako Envision+ HRP detection system as per manufacturer's instructions. Sections were finally rinsed with water, counterstained with hematoxylin and mounted.

Xenograft Models

U87MG.Δ2-7 cells (($3\times10^6$) in 100 μL PBS were inoculated s.c. into both flanks of 4- to 6-week-old, female Balb/c nude mice (Animal Research Centre, Perth, Australia). All studies were conducted using established tumor models as reported previously (41). Treatment commenced once tumors had reached the mean volume indicated in the appropriate figure legend. Tumor volume in $mm^3$ was determined using the formula (length×width$^2$)/2, where length was the longest axis and width was the perpendicular measurement. Data are expressed as mean tumor volume±SE for each treatment group. All data was analyzed for significance by one-sided Student's t test where p<0.05 was considered statistically significant. This research project was approved by the Animal Ethics Committee of the Austin Hospital.

Generation and Characterization of Stable Cell Lines Expressing EGFR Mutant Constructs Mutations of the (wt) EGFR were generated using a site-directed mutagenesis kit (Stratagene, La Jolla, Calif.). The template for each mutagenesis was the human EGFR cDNA (accession number x00588)(2). Automated nucleotide sequencing of each construct was performed to confirm the integrity of the EGFR mutations. Wild type and mutant (C173A/C281A) EGFR were transfected into BaF/3 cells by electroporation. Further details on the characterization of the cell lines are presented in the Supplemental Data.

Crystal Structure Determinations of Fab 175, and Fab 806, Fab-Peptide Complexes and the NMR Structure of the 806 Peptide Epitope in Solution Crystallographic procedures for preparing and analyzing the Fab 806, Fab 175 and the individual Fab-peptide complexes and details on NMR studies of the $^{15}$N-labelled 806 epitope peptide in solution are described in the Supplemental Data. Structures were determined by molecular replacement and refinement converged with R=0.225/Rfree=0.289 for Fab806 and R=0.226/Rfree=0.279 for Fab806:peptide; R=0.210/Rfree=0.305 for Fab806 and R=0.203/Rfree=0.257 for Fab806:peptide.

Biodistribution of chAb 806 Tumor in Patients

To demonstrate the tumor specificity of mAb806 invivo, a chimeric version (ch806) was engineered and produced under cGMP conditions (56). A Phase I first-in-man trial was conducted to evaluate the safety, biodistribution and immune response of ch806 in patients with 806 positive tumors, and the results of safety, biodistribution and pharmacokinetics have been reported previously (44). To define the specificity of ch806 in tumor compared to normal tissue (ie liver) in patients, the quantitative uptake of ch806 in tumor and liver was performed by calculation of % injected dose (ID) of $^{111}$In-ch806 from whole body gamma camera images obtained over one week following injection of 5-7mCi (200-

280 MBq) $^{111}$In-ch806. Liver and tumor dosimetry calculations were performed based on regions of interest in each individual patient $^{111}$In-ch806 infusion image dataset, corrected for background and attenuation, allowing calculation of cumulated activity. Dosimetry calculation was performed to derive the concentration of $^{111}$In-ch806 in tumor and liver over a one week period post injection.

REFERENCES

1. Holbro, T. and Hynes, N. E. (2004) *Annu. Rev. Pharmacol. Toxicol.* 44:195-217, 195-217.
2. Ullrich, A., Coussens, L., Hayflick, J. S., Dull, T. J., Gray, A., Tam, A. W., Lee, J., Yarden, Y., Libermann, T. A., Schlessinger, J., and (1984) *Nature.* 309, 418-425.
3. Yen, L., Benlimame, N., Nie, Z. R., Xiao, D., Wang, T., Al Moustafa, A. E., Esumi, H., Milanini, J., Hynes, N. E., Pages, G., and Alaoui-Jamali, M. A. (2002) *Mol. Biol. Cell.* 13, 4029-4044.
4. Clayton, A. H., Walker, F., Orchard, S. G., Henderson, C., Fuchs, D., Rothacker, J., Nice, E. C., and Burgess, A. W. (2005) *J. Biol. Chem.* 280, 30392-30399.
5. Gadella, T. W. J. and Jovin, T. M. (1995) *Journal of Cell Biology* 129, 1543-1558.
6. Schlessinger, J. (2002) *Cell %20;* 110, 669-672.
7. Yarden, Y. and Schlessinger, J. (1987) *Biochemistry.* 26, 1443-1451.
8. Yarden, Y. and Sliwkowski, M. X. (2001) *Nat. Rev. Mol. Cell. Biol.* 2, 127-137.
9. Bouyain, S., Longo, P. A., L1, S., Ferguson, K. M., and Leahy, D. J. (2005) *Proc. Natl. Acad. Sci. U.S.A.* 102, 15024-15029.
10. Burgess, A. W., Cho, H. S., Eigenbrot, C., Ferguson, K. M., Garrett, T. P., Leahy, D. J., Lemmon, M. A., Sliwkowski, M. X., Ward, C. W., and Yokoyama, S. (2003) *Mol. Cell.* 12, 541-552.
11. Cho, H. S, and Leahy, D. J. (2002) *Science* 297, 1330-1333.
12. Cho, H. S., Mason, K., Ramyar, K. X., Stanley, A. M., Gabelli, S. B., Denney, D. W., Jr., and Leahy, D. J. (2003) *Nature* 421, 756-760.
13. Ferguson, K. M., Berger, M. B., Mendrola, J. M., Cho, H. S., Leahy, D. J., and Lemmon, M. A. (2003) *Mol Cell* 11, 507-517.
14. Garrett, T. P., i, N. M., Lou, M., Elleman, T. C., Adams, T. E., Lovrecz, G. O., Zhu, H. J., Walker, F., Frenkel, M. J., Hoyne, P. A., Jorissen, R. N., Nice, E. C., Burgess, A. W., and Ward, C. W. (2002) *Cell %20;* 110, 763-773.
15. Garrett, T. P., McKern, N. M., Lou, M., Elleman, T. C., Adams, T. E., Lovrecz, G. O., Kofler, M., Jorissen, R. N., Nice, E. C., Burgess, A. W., and Ward, C. W. (2003) *Mol Cell* 11, 495-505.
16. Jorissen, R. N., Walker, F. W., Pouliot, N., Garrett, T. P. J., Ward, C. W., and Burgess, A. W. Epidermal growth factor receptor: mechanisms of activation and signalling. Exp Cell Res 284, 31-53.2003.
17. Stamos, J., Sliwkowski, M. X., and Eigenbrot, C. (2002) *J Biol. Chem.* 277, 46265-46272.
18. Zhang, X., Gureasko, J., Shen, K., Cole, P. A., and Kuriyan, J. (2006) *Cell.* 125, 1137-1149.
19. de Larco, J. E. and Todaro, G. J. (1978) *J Cell Physiol* 94, 335-342.
20. Todaro, G. J., Delarco, J. E., and Cohen, S. (1976) *Nature* 264, 26-31.
21. de Larco, J. E., Reynolds, R., Carlberg, K., Engle, C., and Todaro, G. J. (1980) *J. Biol. Chem.* 255, 3685-3690.
22. Sizeland, A. M. and Burgess, A. W. (1992) *Mol. Biol. Cell* 3, 1235-1243.
23. Ekstrand, A. J., James, C. D., Cavenee, W. K., Seliger, B., Pettersson, R. F., and Collins, V. P. (1991) *Cancer Res.* 51, 2164-2172.
24. Humphrey, P. A., Wong, A. J., Vogelstein, B., Zalutsky, M. R., Fuller, G. N., Archer, G. E., Friedman, H. S., Kwatra, M. M., Bigner, S. H., and Bigner, D. D. (1990) *Proc. Natl. Acad. Sci. U.S.A.* 87, 4207-4211.
25. Aboud-Pirak, E., Hurwitz, E., Pirak, M. E., Bellot, F., Schlessinger, J., and Sela, M. (1988) *J. Natl. Cancer Inst.* 80, 1605-1611.
26. Aboud-Pirak, E., Hurwitz, E., Bellot, F., Schlessinger, J., and Sela, M. (1989) *Proc. Natl. Acad. Sci. U.S.A.* 86, 3778-3781.
27. Johns, T. G., Luwor, R. B., Murone, C., Walker, F., Weinstock, J., Vitali, A. A., Perera, R. M., Jungbluth, A. A., Stockert, E., Old, L. J., Nice, E. C., Burgess, A. W., and Scott, A. M. (2003) *Proc. Natl. Acad. Sci. U.S.A.* 100, 15871-15876.
28. Luwor, R. B., Johns, T. G., Murone, C., Huang, H. J., Cavenee, W. K., Ritter, G., Old, L. J., Burgess, A. W., and Scott, A. M. (2001) *Cancer Res.* 61, 5355-5361.
29. Perera, R. M., Narita, Y., Furnari, F. B., Gan, H. K., Murone, C., Ahlkvist, M., Luwor, R. B., Burgess, A. W., Stockert, E., Jungbluth, A. A., Old, L. J., Cavenee, W. K., Scott, A. M., and Johns, T. G. (2005) *Clin. Cancer Res.* 11, 6390-6399.
30. Arteaga, C. L. and Baselga, J. (2004) *Cancer Cell.* 5, 525-531.
31. Baselga, J. (2006) *Science.* 312, 1175-1178.
32. Bernier, J. (2006) *Expert. Rev Anticancer Ther.* 6, 1539-1552.
33. Mellinghoff, I. K., Cloughesy, T. F., and Mischel, P. S. (2007) *Clin. Cancer Res.* 13, 378-381.
34. Humphrey, P. A., Wong, A. J., Vogelstein, B., Zalutsky, M. R., Fuller, G. N., Archer, G. E., Friedman, H. S., Kwatra, M. M., Bigner, S. H., and Bigner, D. D. (1990) *Proc Natl Acad Sci USA* 87, 4207-4211.
35. Nishikawa, R., Ji, X. D., Harmon, R. C., Lazar, C. S., Gill, G. N., Cavenee, W. K., and Huang, H. J. (1994) *Proc. Natl. Acad. Sci. U.S.A.* 91, 7727-7731.
36. Sok, J. C., Coppelli, F. M., Thomas, S. M., Lango, M. N., Xi, S., Hunt, J. L., Freilino, M. L., Graner, M. W., Wikstrand, C. J., Bigner, D. D., Gooding, W. E., Furnari, F. B., and Grandis, J. R. (2006) *Clin Cancer Res.* 12, 5064-5073.
37. Johns, T. G., Stockert, E., Ritter, G., Jungbluth, A. A., Huang, H. J., Cavenee, W. K., Smyth, F. E., Hall, C. M., Watson, N., Nice, E. C., Gullick, W. J., Old, L. J., Burgess, A. W., and Scott, A. M. (2002) *Int J Cancer. %20;* 98, 398-408.
38. Jungbluth, A. A., Stockert, E., Huang, H. J., Collins, V. P., Coplan, K., Iversen, K., Kolb, D., Johns, T. J., Scott, A. M., Gullick, W. J., Ritter, G., Cohen, L., Scanlan, M. J., Cavanee, W. K., and Old, L. J. (2003) *Proc Natl Acad Sci USA* 100, 639-644.
39. Johns, T. G., Mellman, I., Cartwright, G. A., Ritter, G., Old, L. J., Burgess, A. W., and Scott, A. M. (2005) *FASEB J.* 19, 780-782.
40. Johns, T. G., Perera, R. M., Vernes, S. C., Vitali, A. A., Cao, D. X., Cavenee, W. K., Scott, A. M., and Furnari, F. B. (2007) *Clin Cancer Res.* 13, 1911-1925.
41. Perera, R. M., Narita, Y., Furnari, F. B., Gan, H. K., Murone, C., Ahlkvist, M., Luwor, R. B., Burgess, A. W., Stockert, E., Jungbluth, A. A., Old, L. J., Cavenee, W. K., Scott, A. M., and Johns, T. G. (2005) *Clin Cancer Res.* 11, 6390-6399.

42. Ogiso, H., Ishitani, R., Nureki, O., Fukai, S., Yamanaka, M., Kim, J. H., Saito, K., Sakamoto, A., Inoue, M., Shirouzu, M., and Yokoyama, S. (2002) *Cell* %20; 110, 775-787.

43. Walker, F., Orchard, S. G., Jorissen, R. N., Hall, N. E., Zhang, H. H., Hoyne, P. A., Adams, T. E., Johns, T. G., Ward, C., Garrett, T. P., Zhu, H. J., Nerrie, M., Scott, A. M., Nice, E. C., and Burgess, A. W. (2004) *J Biol. Chem.* 279, 22387-22398.

44. Scott, A. M., Lee, F. T., Tebbutt, N., Herbertson, R., Gill, S. S., Liu, Z., Skrinos, E., Murone, C., Saunder, T. H., Chappell, B., Papenfuss, A. T., Poon, A. M., Hopkins, W., Smyth, F. E., MacGregor, D., Chem., L. M., Jungbluth, A. A., Brechbiel, M. W., Murphy, R., Burgess, A. W., Hoffman, E. W., Johns, T. G., and Old, L. J. (2007) *Proc Natl Acad Sci USA.* 104, 4071-4076.

45. Chao, G., Cochran, J. R., and Wittrup, K. D. (2004) *J Mol Biol.* 342, 539-550.

46. Johns, T. G., Adams, T. E., Cochran, J. R., Hall, N. E., Hoyne, P. A., Olsen, M. J., Kim, Y. S., Rothacker, J., Nice, E. C., Walker, F., Ritter, G., Jungbluth, A. A., Old, L. J., Ward, C. W., Burgess, A. W., Wittrup, K. D., and Scott, A. M. (2004) *J Biol. Chem.* 279, 30375-30384.

47. Wade, J. D., Hojo, K., Kawasaki, K., Johns, T. G., Catimel, B., Rothacker, J., and Nice, E. C. (2006) *Anal Biochem.* 348, 315-317.

48. Sizeland, A. M. and Burgess, A. W. (1991) *Mol Cell Biol.* 11, 4005-4014.

49. Hogg, P. J. (2003) *Trends in biochemical sciences* 28, 210-214.

50. Divgi, C. R., Welt, S., Kris, M., Real, F. X., Yeh, S. D., Gralla, R., Merchant, B., Schweighart, S., Unger, M., Larson, S. M., and (1991) *J Natl Cancer Inst.* 83, 97-104.

51. Sampson, J. H., Crotty, L. E., Lee, S., Archer, G. E., Ashley, D. M., Wikstrand, C. J., Hale, L. P., Small, C., Dranoff, G., Friedman, A. H., Friedman, H. S., and Bigner, D. D. (2000) *Proc Natl Acad Sci USA.* %20; 97, 7503-7508.

52. MacDonald, A., Chisholm, G. D., and Habib, F. K. (1990) *Br. J. Cancer.* 62, 579-584.

53. Baselga, J. and Arteaga, C. L. (2005) *J Clin Oncol.* 23, 2445-2459.

54. Huang, H. S., Nagane, M., Klingbeil, C. K., Lin, H., Nishikawa, R., Ji, X. D., Huang, C. M., Gill, G. N., Wiley, H. S., and Cavenee, W. K. (1997) *J Biol Chem.* 272, 2927-2935.

55. Mickey, D. D., Stone, K. R., Wunderli, H., Mickey, G. H., Vollmer, R. T., and Paulson, D. F. (1977) *Cancer Res.* 37, 4049-4058.

56. Panousis, C., Rayzman, V. M., Johns, T. G., Renner, C., Liu, Z., Cartwright, G., Lee, F. T., Wang, D., Gan, H., Cao, D., Kypridis, A., Smyth, F. E., Brechbiel, M. W., Burgess, A. W., Old, L. J., and Scott, A. M. (2005) *Br. J. Cancer.* 92, 1069-1077.

Example 2

Supplemental Data

Experimental Procedures
Cell Lines

All cell lines were maintained in DMEM (Life Technologies, Grand Island, N.Y.) containing 10% FCS (CSL, Melbourne), 2 mM glutamine (Sigma Chemical Co, St. Louis), and penicillin/streptomycin (Life Technologies, Grand Island). In addition, the U87MG.Δ2-7 cell line was maintained in 400 mg/ml of Geneticin (Life Technologies, Inc, Grand Island). BaF/3(1) and BaF/3 cell lines expressing different EGF receptors (2) were maintained routinely in RPMI 1640 (GIBCO BRL) supplemented with 10% foetal calf serum (GIBCO BRL) and 10% WEHI-3B conditioned medium (3) as a source of IL-3. All cell lines were grown at 37° C. in an air/$CO_2$ (95%-5%) atmosphere.

Antibodies and Peptides

Antibody generation. The murine fibroblast line $NR6_{\Delta EGFR}$ was used as immunogen. Mouse hybridomas were generated by immunizing BALB/c mice five times subcutaneously at 2- to 3-week intervals, with $5 \times 10^5$-$2 \times 10^6$ cells in adjuvant. Complete Freund's adjuvant was used for the first injection. Thereafter, incomplete Freund's adjuvant (Difco) was used. Spleen cells from immunized mice were fused with mouse myeloma cell line SP2/0. Supernatants of newly generated clones were screened in hemadsorption assays for reactivity with cell line NR6, $NR6_{wtEGFR}$, and $NR6_{\Delta EGFR}$ and then analyzed by hemadsorption assays with human glioblastoma cell lines U87MG, $U87MG_{wtEGFR}$, and $U87MG_{\Delta EGFR}$.

Intact mAb's (50 mg) were digested in PBS with activated papain for 2-3 h at 37° C. at a ratio of 1:20 and the papain was inactivated with iodoacetamide. The digestion was then passed over a column of Protein-A sepharose (Amersham) in 20 mM sodium phosphate buffer pH 8.0, with the flow-through further purified by cation exchange using on a Mono-S column (Amersham). Protein was then concentrated using a 10,000 MWCO centrifugal concentrator (Millipore). For Fab-peptide complexes a molar excess of lyophilised peptide was added directly to the Fab and incubated for 2 hours at 4° C. before setting up crystallisation trials.

Mapping of mAb 175 Using EGFR Fragments Expressed in Mammalian Cells

The day prior to transfection with these fragments, human 293T embryonic kidney fibroblasts were seeded at $8 \times 10^5$ per well in 6-well tissue culture plates containing 2 ml of media. Cells were transfected with 3-4 μg of plasmid DNA complexed with Lipofectamine 2000 (Invitrogen) according to the manufacturer's instructions. 24 to 48 h after transfection, cell cultures were aspirated and cell monolayers lysed in 250 μl of lysis buffer (1% Triton X-100, 10% glycerol, 150 mM NaCl, 50 mM HEPES pH 7.4, 1 mM EGTA and Complete Protease Inhibitor mix (Roche). Aliquots of cell lysate (10-15 μl) were mixed with SDS sample buffer containing 1.5% β-mercaptoethanol, denatured by heating for 5 min at 100° C. and electrophoresed on 10% NuPAGE Bis-Tris polyacrylamide gels (Invitrogen). Samples were then electro-transferred to nitrocellulose membranes that were rinsed in TBST buffer (10 mM Tris-HCl, pH 8.0, 100 mM NaCl and 0.1% Tween-20) and blocked in TBST containing 2.5% skim milk for 30 min at room temperature. Membranes were incubated overnight at 4° C. with 0.5 μg/ml of mAb 175 in blocking buffer. Parallel membranes were probed overnight with mAb 9B11 (1:5000, Cell Signaling Technology, Danvers, Massachusetts) to detect the c-myc epitope. Membranes were washed in TBST, and incubated in blocking buffer containing horseradish peroxidase-conjugated rabbit anti-mouse IgG (Biorad) at a 1:5000 dilution for 2 h at room temperature. Blots were then washed in TBST, and developed using autoradiographic film following incubation with Western Pico Chemiluminescent Substrate (Pierce, Rockford, Ill.).

Mapping of mAb 175 Using EGFR Fragments Expressed in Mammalian Cells and Yeast

A series of overlapping c-myc-tagged EGFR ectodomain fragments, starting at residues 274, 282, 290 and 298 and all terminating at amino acid 501 and fused to growth hormone have been described previously (6).

Expression of EGFR proteins on the yeast cell surface was performed as previously described (7). Briefly, transformed colonies were grown at 30° C. in minimal media containing yeast nitrogen base, casein hydrolysate, dextrose, and phosphate buffer pH 7.4, on a shaking platform for approximately one day until an $OD_{600}$ of 5-6 was reached. Yeast cells were then induced for protein display by transferring to minimal media containing galactose, and incubated with shaking at 30° C. for 24 h. Cultures were then stored at 4° C. until analysis. Raw ascites fluid containing the c-myc monoclonal antibody 9E10 was obtained from Covance (Richmond, Calif.). $1 \times 10^6$ yeast cells were washed with ice-cold FACS buffer (PBS containing 1 mg/ml BSA) and incubated with either anti-c-myc ascites (1:50 dilution), or human EGFR monoclonal antibody (10 µg/ml) in a final volume of 50 µl, for 1 hr at 4° C. The cells were then washed with ice cold FACS buffer and incubated with phycoerythrin-labelled anti-mouse IgG (1:25 dilution), in a final volume of 50 µl for 1 h at 4° C., protected from light. After washing the yeast cells with ice-cold FACS buffer, fluorescence data was obtained with a Coulter Epics XL flow cytometer (Beckman-Coulter), and analyzed with WinMDI cytometry software (J. Trotter, Scripps University). For determination of linear versus conformational epitopes, yeast cells were heated at 80° C. for 30 min, then chilled on ice 20 min prior to labelling with antibodies. The series of EGFR mutants listed in Table 2 have been described previously (8).

Generation and Characterization of Stable Cell Lines Expressing EGFR Mutant Constructs Generation of Cell Lines Expressing EGFR Mutants Stable cell lines expressing the mutant EGFR were obtained by selection in neomycin-containing medium. After final selection, mRNA was isolated from each cell line, reverse transcribed and the EGFR sequence amplified by PCR. All mutations in the expressed EGFR were confirmed by sequencing the PCR products. The level of EGFR expression was determined by FACS analysis on a FACStar (Becton and Dickinson, Franklin Lakes, N.J.) using the anti-EGFR antibody mAb528(9; 10) at 10 µg/ml in PBS, 5% FCS, 5 mM EDTA followed by Alexa 488-labeled anti-mouse Ig (1:400 final dilution). Background fluorescence was determined by incubating the cells with an irrelevant, class-matched primary antibody. All cells were routinely passaged in RPMI, 10% FCS, 10% WEHI3B conditioned medium and 1.5 mg/ml G418.

EGF-Dependent Activation of Mutant EGFR

Cells expressing the wtEGFR or C271A/C283A-EGFR were washed and incubated for 3 hr in medium without serum or IL-3. Cells were collected by centrifugation and resuspended in medium containing EGF (100 ng/ml) or an equivalent volume of PBS. Cells were harvested after 15 min, pelleted and lysed directly in SDS/PAGE sample buffer containing (3-mercaptoethanol. Samples were separated on NuPAGE 4-12% gradient gels, transferred to Immobilon PVDF membrane and probed with anti-phosphotyrosine (4G10, Upstate Biotechnologies) or anti-EGFR antibodies (mAb806, produced at the LICR). Reactive bands were detected using chemiluminescence.

Effect of EGF and Antibodies on Cell Proliferation

Cells growing in log phase were harvested and washed twice with PBS to remove residual IL-3. Cells were resuspended in RPMI 1640 plus 10% FCS and seeded into 96-well plates at $10^5$ cells/well with carrier only or with increasing concentrations of EGF. Where appropriate, a fixed concentration of mAb528 or mAb806 (2 µg/well) was also added to the cultures. Proliferation was determined using the MTT assay (11).

Reactivity with Conformation-Specific Antibodies

Cells were collected by centrifugation and stained with the control or test antibodies (all at 10 µg/ml in FACS buffer for 40 min on ice, washed in FACS buffer) followed by Alexa 488-labeled anti-mouse Ig (1:400 final dilution, 20 min on ice). The cells were washed with ice-cold FACS buffer, collected by centrifugation, and analyzed on a FACScan; peak fluorescence channel and median fluorescence were determined for each sample using the statistical tool in CellQuest (Becton and Dickinson). Background (negative control) fluorescence was deducted from all measurements. The median fluorescence values were chosen as most representative of peak shape and fluorescence intensity and were used to derive the ratio of mAb 806 to mAb 528 binding.

Crystal Structure Determinations of 175, and 806 Fab, Fab-Peptide Complexes and the NMR Structure of the 806 Peptide Epitope in Solution Crystals of native 806 Fab were grown by hanging drop vapour diffusion using 10 mg/ml Fab and a reservoir containing 0.1M Sodium acetate buffer pH 4.6, 6-8% PEG6000 and 15-20% (Isopropanol. For data collection crystals were transferred to a cryoprotectant solution containing 0.1M Sodium acetate buffer pH 4.6, 10% PEG6000, 15-20% Isopropanol and 10% glycerol. Crystals were then mounted in a nylon loop and flash frozen directly into liquid nitrogen.

Crystals of 806 Fab-peptide complex were grown by hanging drop vapour diffusion using 10 mg/ml Fab-peptide complex and a reservoir containing 0.2M ammonium acetate 16-18% PEG 5,000 monomethylether, crystals quality was then improved through seeding techniques. For data collection crystals were transferred to a cryoprotectant solution consisting of reservoir supplemented with 25% glycerol. Crystals were then mounted in a nylon loop and flash frozen directly into liquid nitrogen.

Crystals of 175 Fab-peptide complex were initially grown by free interface diffusion using a Topaz crystallisation system (Fluidigm, San Francisco). Microcrystals were grown by hanging drop vapour diffusion using 7 mg/ml Fab with similar conditions 0.1M Bis-tris propane buffer, 0.2M ammonium acetate and 18% PEG 10,000. Microcrystals were then improved by streak seeding into 0.15 m Sodium formate and 15% PEG 1500 to yield small plate shaped crystals. For data collection crystals were transferred to a cryoprotectant solution consisting of reservoir supplemented with 25% glycerol. Crystals were then mounted in a nylon loop and flash frozen directly into liquid nitrogen.

Diffraction data on 806 Fab and 175 Fab complex crystals were collected in-house using a R-AXIS IV detector on a Rigaku micromax-007 generator fitted with AXCO optics, these data were then processed using CrystalClear. 806 Fab-peptide complex data were collected on an ADSC quantum315 CCD detector at beamline X29, Brookhaven National Laboratory, these data were processed with HKL2000(12) (data collection statistics are shown in Table 1). Native 806 Fab was solved by molecular replacement using the program MOLREP (13) using the coordinates of the Fab structure 2E8 refinement of the structure was performed in REFMAC5(14) and model building in Coot (15). Both 806-peptide and 175 Fab-peptide structures were solved by molecular replacement using the program MOLREP using the coordinates of the 806 Fab structure, refinement and rebuilding were again performed in REFMAC5, and COOT and O. Validation of the final structures were performed with PROCHECK (16) and WHATCHECK (17).

NMR Studies

For NMR studies, $^{15}$N-labelled peptide was produced recombinantly as a fusion to the SH2 domain of SHP2 using the method previously described by Fairlie et al.(18), except that the E. coli were grown in Neidhardt's minimal medium supplemented with $^{15}NH_4Cl$ (19). The peptide was cleaved from the fusion partner using CNBr, purified by reversed-phase HPLC and its identity confirmed by MALDI-TOF mass spectrometry and N-terminal sequencing. The methionine residue within the 806 antibody-binding sequence was mutated to leucine to enable cleavage from the fusion partner, but not within the peptide itself.

Samples used for NMR studies were prepared in $H_2O$ solution containing 5% $^2H_2O$, 70 mM NaCl and 50 mM $NaPO_4$ at pH 6.8. All spectra were acquired at 298K on a Bruker Avance500 spectrometer using a cryoprobe. Sequential assignments of the peptide in the absence of m806Fab were established using standard 2D TOCSY and NOESY as well as $^{15}N$-edited TOCSY and NOESY spectra. Interaction between the peptide and fAb806 was examined by monitoring $^{15}N$ HSQC spectra of the peptide in the absence and presence of fAb806. Spectral perturbation of $^{15}N$ HSQC spectra of the peptide in the presence of fAb806 clearly indicates the peptide was able to bind to the fAb806 under the presence solution conditions. Detailed conformation of the peptide in the complex form was, however, not determined.

SUPPLEMENTAL TABLE 1

Data Collection and Refinement Statistics

| | 806(native) | 806(peptide) | 175(native) | 175(peptide) |
|---|---|---|---|---|
| Data Collection | | | | |
| Space Group | $P2_12_12$ | $P2_1$ | $P2_12_12_1$ | $P2_12_12$ |
| Cell Dimensions (Å) | | | | |
| a | 140.37 | 35.92 | 36.37 | 83.17 |
| b | 74.62 | 83.16 | 94.80 | 69.26 |
| c | 83.87 | 72.21 β = 92.43 | 108.90 | 71.47 |
| Source | in-house | BNL X29 | in-house | in-house |
| Wavelength (Å) | 1.542 | 1.1 | 1.542 | 1.542 |
| Resolution range (Å) | 29.7-2.2 | 50-2.0 | 50-2.8 | 14.18-1.59 |
| | (2.27-2.20) | (2.07-2.0) | (2.87-2.80) | (1.65-1.59) |
| $R_{merge}$ (%) | 6.4 (26.7) | 6.6 (28.2) | | 8.6 (30.0) |
| I/σI | 12.2 (3.2) | 22 (3.15) | | 10.2 (2.2) |
| Completeness (%) | 98.3 (91.3) | 96.6 (79.2) | 98.4 (90.5) | 78.8 (11.8) |
| | | | | 98.1 at 1.89 Å |
| Total Reflections | 156497 | 98374 | | 205401 |
| Unique reflections | 44905 | 27692 | 9171 | 43879 |
| Refinement | | | | |
| Resolution range (Å) | 20-2.3 | 72.17-2.00 | 50-2.6 | 14.18-1.6 |
| Reflections | 37397 | 26284 | 9171 | 41611 |
| $R_{cryst}$ | 0.225 | 0.226 | 0.210 | 0.203 |
| $R_{free}$ | 0.289 | 0.279 | 0.305 | 0.257 |
| Protein Atoms | 6580 | 3294 | 3276 | 3390 |
| Solvent Atoms | 208 | 199 | 46 | 247 |
| r.m.s.d bond length (Å) | 0.022 | 0.007 | 0.015 | 0.014 |
| r.m.s.d bond angle (°) | 1.70 | 1.12 | 1.77 | 1.48 |
| Average B-factor (Å$^2$) | 40.3 | 33.6 | 37.5 | 20.7 |
| Overall anisotropic B-factors (Å$^2$) | | | | |
| B11 | -1.52 | 2.42 | 0.20 | 1.13 |
| B22 | 2.22 | -0.26 | -1.022 | -0.38 |
| B33 | -0.70 | -2.11 | 1.03 | -0.74 |

Numbers in parentheses ar for the highest resolution shell.

REFERENCES

1. Palacios, R., Henson, G., Steinmetz, M., and McKearn, J. P. (1984) Nature. 309, 126-131.
2. Walker, F., Orchard, S. G., Jorissen, R. N., Hall, N. E., Zhang, H. H., Hoyne, P. A., Adams, T. E., Johns, T. G., Ward, C., Garrett, T. P., Zhu, H. J., Nerrie, M., Scott, A. M., Nice, E. C., and Burgess, A. W. (2004) J Biol. Chem. 279, 22387-22398.
3. Ymer, S., Tucker, W. Q., Sanderson, C. J., Hapel, A. J., Campbell, H. D., and Young, I. G. (1985) Nature. %19-25; 317, 255-258.
4. Panousis, C., Rayzman, V. M., Johns, T. G., Renner, C., Liu, Z., Cartwright, G., Lee, F. T., Wang, D., Gan, H., Cao, D., Kypridis, A., Smyth, F. E., Brechbiel, M. W., Burgess, A. W., Old, L. J., and Scott, A. M. (2005) Br. J. Cancer. 92, 1069-1077.
5. Johns, T. G., Adams, T. E., Cochran, J. R., Hall, N. E., Hoyne, P. A., Olsen, M. J., Kim, Y. S., Rothacker, J., Nice, E. C., Walker, F., Ritter, G., Jungbluth, A. A., Old, L. J., Ward, C. W., Burgess, A. W., Wittrup, K. D., and Scott, A. M. (2004) J Biol. Chem. 279, 30375-30384.
6. Johns, T. G., Adams, T. E., Cochran, J. R., Hall, N. E., Hoyne, P. A., Olsen, M. J., Kim, Y. S., Rothacker, J., Nice, E. C., Walker, F., Ritter, G., Jungbluth, A. A., Old, L. J., Ward, C. W., Burgess, A. W., Wittrup, K. D., and Scott, A. M. (2004) J Biol. Chem. 279, 30375-30384.
7. Johns, T. G., Adams, T. E., Cochran, J. R., Hall, N. E., Hoyne, P. A., Olsen, M. J., Kim, Y. S., Rothacker, J., Nice, E. C., Walker, F., Ritter, G., Jungbluth, A. A., Old, L. J., Ward, C. W., Burgess, A. W., Wittrup, K. D., and Scott, A. M. (2004) J Biol. Chem. 279, 30375-30384.
8. Johns, T. G., Adams, T. E., Cochran, J. R., Hall, N. E., Hoyne, P. A., Olsen, M. J., Kim, Y. S., Rothacker, J., Nice, E. C., Walker, F., Ritter, G., Jungbluth, A. A., Old, L. J., Ward, C. W., Burgess, A. W., Wittrup, K. D., and Scott, A. M. (2004) *J Biol. Chem.* 279, 30375-30384.
9. Masui, H., Kawamoto, T., Sato, J. D., Wolf, B., Sato, G., and Mendelsohn, J. (1984) *Cancer Res.* 44, 1002-1007.
10. Gill, G. N., Kawamoto, T., Cochet, C., Le, A., Sato, J. D., Masui, H., McLeod, C., and Mendelsohn, J. (1984) *J Biol. Chem.* 259, 7755-7760.
11. van de Loosdrecht, A. A., Beelen, R. H., Ossenkoppele, G. J., Broekhoven, M. G., and Langenhuijsen, M. M. (1994) *J Immunol Methods.* 174, 311-320.
12. Otwinowski, Z. and Minor, W. (1997) *processing of X-ray diffraction data collected in oscillation mode* Academic Press (New York).
13. Vagin, A. and Teplyakov, A. (1997) *J. Appl. Cryst* 30, 1022-1025.
14. Murshudov, G. N., Vagin, A. A., and Dodson, E. J. (1997) *Acta crystallographica* 53, 240-255.
15. Emsley, P. and Cowtan, K. (2004) *Acta crystallographica* 60, 2126-2132.
16. Laskowski, R. A., MacArthur, M. W., Moss, D. S., and Thornton, J. M. (1993) *J. Appl. Cryst* 26, 283-291.
17. Hooft, R. W., Vriend, G., Sander, C., and Abola, E. E. (1996) *Nature* 381, 272.
18. Fairlie, W. D., Uboldi, A. D., De Souza, D. P., Hemmings, G. J., Nicola, N. A., and Baca, M. (2002) *Protein expression and purification* 26, 171-178.
19. Neidhardt, F. C., Bloch, P. L., and Smith, D. F. (1974) *Journal of bacteriology* 119, 736-747.

What is claimed is:

1. An isolated antibody or an antigen-binding fragment thereof which recognizes an EGFR epitope which is found in tumorigenic, hyperproliferative or abnormal cells and not detectable in normal cells, wherein said antibody or fragment thereof does not recognize the junctional peptide LEEKKGNYVVTDH (SEQ ID NO: 13), said antibody or fragment thereof having light chain variable region CDR 1, 2, and 3 sequences comprising SEQ ID NOs: 1-3, respectively, and heavy chain variable region CDR 1, 2, and 3 sequences comprising SEQ ID NOs: 4-6, respectively.

2. The antibody or fragment thereof according to claim 1 which recognizes the EGFR amino acid peptide epitope $_{287}$CGADSYEMEEDGVRKC$_{302}$ (SEQ ID NO: 14).

3. The antibody or fragment thereof according to claim 1 or 2 which is humanized or chimerized.

4. The isolated antibody or fragment thereof according to claim 1 or 2 further comprising a human antibody framework.

5. The antibody or fragment thereof according to claim 1 or 2, wherein the antibody or fragment thereof comprises a human IgG1 constant region.

6. The antibody or fragment thereof according to claim 1 or 2, wherein the antibody or fragment thereof comprises a human kappa constant region.

7. The antibody or fragment thereof according to claim 1 or 2 in the form of an antibody F(ab')$_2$, scFv fragment, diabody, triabody or tetrabody.

8. The antibody or fragment thereof according to claim 1 or 2, which carries a detectable or functional label.

9. The antibody or fragment thereof according to claim 8, wherein said label is a covalently attached drug.

10. The antibody or fragment thereof according to claim 8, wherein said label is a radiolabel.

11. The antibody or fragment thereof according to claim 1 or 2, wherein said antibody is pegylated.

12. A kit for the diagnosis of a tumor in which EGFR is aberrantly expressed or EGFR is amplified or is mutant, said kit comprising an antibody or fragment thereof of claim 1 or 2, optionally with reagents and/or instructions for use.

13. A pharmaceutical composition comprising an antibody or fragment thereof as defined in claim 1, and optionally, a pharmaceutically acceptable vehicle, carrier or diluent.

14. A kit for the treatment of a tumor in a human patient, comprising a pharmaceutical dosage form of the pharmaceutical composition of claim 13, and a separate pharmaceutical dosage form comprising an additional anti-cancer agent selected from the group consisting of chemotherapeutic agents, anti-EGFR antibodies, and radioimmunotherapeutic agents.

15. The kit of claim 14, wherein said chemotherapeutic agents are selected from the group consisting of tyrosine kinase inhibitors, phosphorylation cascade inhibitors, post-translational modulators, cell growth or division inhibitors, anti-mitotics, and signal transduction inhibitors.

16. The kit of claim 15, wherein said tyrosine kinase inhibitors are selected from the group consisting of AG1478, ZD1839, STI571, OSI-774, and SU-6668.

17. The kit of claim 14, wherein said anti-EGFR antibodies are selected from the group consisting of the anti-EGFR antibodies 528, 225, SC-03, and DH8.3.

18. An immunoconjugate or antibody fusion protein comprising the antibody or fragment thereof according to claim 1 conjugated to an agent selected from the group consisting of a chemical ablation agent, a toxin, an immunomodulator, a cytokine, a cytotoxic agent, a chemotherapeutic agent and a drug.

* * * * *